US012144251B2

(12) United States Patent
Uno

(10) Patent No.: US 12,144,251 B2
(45) Date of Patent: Nov. 12, 2024

(54) ORGANIC ELECTROLUMINESCENCE DEVICE AND CONDENSED CYCLIC COMPOUND FOR ORGANIC ELECTROLUMINESCENCE DEVICE

(71) Applicant: Samsung Display Co., Ltd., Yongin-Si (KR)

(72) Inventor: Takuya Uno, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 462 days.

(21) Appl. No.: 16/443,807

(22) Filed: Jun. 17, 2019

(65) Prior Publication Data

US 2020/0052224 A1 Feb. 13, 2020

(30) Foreign Application Priority Data

Aug. 10, 2018 (KR) ........................ 10-2018-0093700

(51) Int. Cl.
*H10K 85/60* (2023.01)
*C07D 487/04* (2006.01)
(Continued)

(52) U.S. Cl.
CPC ....... *H10K 85/6572* (2023.02); *C07D 487/04* (2013.01); *C07D 498/04* (2013.01);
(Continued)

(58) Field of Classification Search
CPC .. C07D 487/04; C07D 498/04; C07D 513/04; H01L 51/0052; H01L 51/0054; H01L 51/0059; H01L 51/006; H01L 51/0061; H01L 51/0067; H01L 51/0071; H01L 51/0072; H01L 51/0073; H01L 51/0074; H01L 51/5056; H10K 85/6572; H10K 85/622; H10K 85/633; H10K 85/636;
(Continued)

(56) References Cited

U.S. PATENT DOCUMENTS

| | | | |
|---|---|---|---|
| 4,720,432 | A | 1/1988 | Vanslyke et al. |
| 5,061,569 | A | 10/1991 | Vanslyke et al. |

(Continued)

FOREIGN PATENT DOCUMENTS

| | | | |
|---|---|---|---|
| CN | 103154005 | A | 6/2013 |
| CN | 105679946 | A | 6/2016 |

(Continued)

OTHER PUBLICATIONS

Lee et al., J. Mater. Chem. C, 2019, 7, pp. 5988-5994. (Year: 2019).*

(Continued)

*Primary Examiner* — Dawn L Garrett
(74) *Attorney, Agent, or Firm* — Lewis Roca Rothgerber Christie LLP

(57) ABSTRACT

Provided is an organic electroluminescence device including a first electrode, a hole transport region disposed on the first electrode, an emission layer disposed on the hole transport region, an electron transport region disposed on the emission layer, and a second electrode disposed on the electron transport region, in which the hole transport region includes a condensed cyclic compound, thereby securing high emission efficiency.

22 Claims, 2 Drawing Sheets

(51) Int. Cl.
*C07D 498/04* (2006.01)
*C07D 513/04* (2006.01)
*H10K 50/15* (2023.01)

(52) U.S. Cl.
CPC ......... *C07D 513/04* (2013.01); *H10K 85/622* (2023.02); *H10K 85/633* (2023.02); *H10K 85/636* (2023.02); *H10K 85/654* (2023.02); *H10K 85/6574* (2023.02); *H10K 85/6576* (2023.02); *H10K 50/15* (2023.02)

(58) Field of Classification Search
CPC ............. H10K 85/654; H10K 85/6574; H10K 85/6576; H10K 50/15; H10K 85/615; H10K 85/631; H10K 85/657; H10K 85/40; H10K 85/626; C07F 7/0816
See application file for complete search history.

(56) References Cited

U.S. PATENT DOCUMENTS

| | | | | |
|---|---|---|---|---|
| 6,242,115 | B1 | 6/2001 | Thomson et al. | |
| 8,766,248 | B2 | 7/2014 | Hotta et al. | |
| 8,766,249 | B2 | 7/2014 | Sawada et al. | |
| 8,987,462 | B2 | 3/2015 | Kim et al. | |
| 9,214,637 | B2 | 12/2015 | Suda et al. | |
| 9,564,598 | B2 | 2/2017 | Ito et al. | |
| 10,833,281 | B2 | 11/2020 | Kawakami et al. | |
| 11,450,811 | B2 * | 9/2022 | Jeong | H01L 51/006 |
| 2003/0118866 | A1 | 6/2003 | Oh et al. | |
| 2006/0186796 | A1 * | 8/2006 | Yabe | H01L 51/0058 313/504 |
| 2007/0138953 | A1 | 6/2007 | Tobise | |
| 2008/0241591 | A1 | 10/2008 | Kawamura et al. | |
| 2012/0273764 | A1 * | 11/2012 | Yu | H05B 33/14 257/40 |
| 2013/0150576 | A1 * | 6/2013 | Hotta | C07D 487/04 544/209 |
| 2013/0184458 | A1 | 7/2013 | Sawada et al. | |
| 2013/0207047 | A1 | 8/2013 | Suda et al. | |
| 2014/0306197 | A1 | 10/2014 | Kim et al. | |
| 2016/0072077 | A1 | 3/2016 | Ito et al. | |
| 2016/0163995 | A1 | 6/2016 | Kang et al. | |
| 2016/0315273 | A1 | 10/2016 | Kawabe et al. | |
| 2017/0229654 | A1 * | 8/2017 | Gao | H01L 51/0061 |
| 2018/0159047 | A1 | 6/2018 | Hwang et al. | |
| 2020/0388791 | A1 | 12/2020 | Zhang et al. | |

FOREIGN PATENT DOCUMENTS

| | | | | |
|---|---|---|---|---|
| EP | 2628743 | A1 | 8/2013 | |
| JP | 6-314594 | A | 11/1994 | |
| JP | 8-291115 | A | 11/1996 | |
| JP | 11-144873 | A | 5/1999 | |
| JP | 2000-302756 | A | 10/2000 | |
| JP | 2000-309566 | A | 11/2000 | |
| JP | 2006-151979 | A | 6/2006 | |
| JP | 2013-058560 | A | 3/2013 | |
| JP | 2012-035853 | A1 | 2/2014 | |
| JP | 2015-111624 | A | 6/2015 | |
| JP | 5887771 | B2 | 3/2016 | |
| JP | 5919726 | B2 | 5/2016 | |
| JP | 2014/050417 | A1 | 8/2016 | |
| JP | 2014/069637 | A1 | 9/2016 | |
| JP | 2014-091958 | A1 | 1/2017 | |
| JP | 2014/157618 | A1 | 2/2017 | |
| JP | 6264001 | B2 | 1/2018 | |
| KR | 2010-0131745 | A | 12/2010 | |
| KR | 10-2013-0139916 | A | 12/2013 | |
| KR | 10-2014-0086880 | A | 7/2014 | |
| KR | 10-2015-0042386 | A | 4/2015 | |
| KR | 10-2015-0058080 | A | 5/2015 | |
| KR | 10-2015-0066618 | A | 6/2015 | |
| KR | 10-2015-0124911 | A | 11/2015 | |
| KR | 10-1609027 | B1 | 4/2016 | |
| KR | 10-1634853 | B1 | 6/2016 | |
| KR | 10-2017-0076113 | A | 7/2017 | |
| KR | 10-1827067 | B1 | 3/2018 | |
| WO | 2011/055933 | A2 | 5/2011 | |
| WO | 2012/016630 | A1 | 2/2012 | |
| WO | 2012/050002 | A1 | 4/2012 | |
| WO | WO-2014050417 | A1 * | 4/2014 | C07D 209/86 |
| WO | WO-2014061960 | A1 * | 4/2014 | C07D 209/70 |
| WO | 2015/020217 | A1 | 2/2015 | |
| WO | 2017/170812 | A1 | 10/2017 | |
| WO | 2019/027163 | A1 | 2/2019 | |

OTHER PUBLICATIONS

Ai et al., ACS Appl. Mater. Interfaces, 2020, 12, pp. 6127-6136 . (Year: 2020).*
Machine translation of WO-2014050417-A1 (publication date: Apr. 2014). (Year: 2014).*
Translation for KR 20170076113 A (publication date: Jul. 2017). (Year: 2017).*
Translation for WO 2019/027163 A1 (publication date: Feb. 2019). (Year: 2019).*
Samsoniya, S.A. and Trapaidze, M.V., 76(4), 313-326 (2007). (Year: 2007).*
Translation for WO 2014061960 A1 (publication date Apr. 2014). (Year: 2014).*
Paul, D. and John, J., 2022. Recent Advances towards the Synthesis and Material Applications of Indoloindoles. Chemistry—An Asian Journal, 17(16), p. e202200460. (Year: 2022) (Year: 2022).*
Translation of KR 10-2010-0131745 (publication date Dec. 2010). (Year: 2010).*
European Communication corresponding to European Patent Application No. 19190330.1 dated Oct. 17, 2019 7 pages.
Machine translation of JP 2013-058560 A (publication date Mar. 2013). (Year: 2013).
Machine translation of WO 2019/027163 A1 (publication date Feb. 2019). (Year: 2019).
Machine translation of KR 2010-0131745 A (publication date Dec. 2010). (Year: 2010).
U.S. Office Action dated Aug. 16, 2021, issued in U.S. Appl. No. 16/357,527 (13 pages).
US Notice of Allowance dated May 9, 2022, issued in U.S. Appl. No. 16/357,527 (5 pages).
Ma, Changqi, et al., "Progress in Hole-Transport Materials for Use in Organic Light-Emitting Diodes," Progress in Chemistry, vol. 15, No. 6, Nov. 2003, 10 pages.
Chinese Office Action dated Feb. 24, 2023, issued in corresponding Chinese Patent Application No. 201910728480.6 (8 pages).

* cited by examiner

ORGANIC ELECTROLUMINESCENCE DEVICE AND CONDENSED CYCLIC COMPOUND FOR ORGANIC ELECTROLUMINESCENCE DEVICE

CROSS-REFERENCE TO RELATED APPLICATIONS

This U.S. non-provisional patent application claims priority under 35 U.S.C. § 119 of Korean Patent Application No. 10-2018-0093700 filed on Aug. 10, 2018, the entire content of which is hereby incorporated by reference.

BACKGROUND

The present disclosure herein relates to an organic electroluminescence device and a condensed cyclic compound used for the same.

Development of organic electroluminescence display as an image display is being actively conducted. An organic electroluminescence display is different from a liquid crystal display in that it is a self-luminescent display. An organic electroluminescence display achieves a display by recombining holes and electrons injected from a first electrode and a second electrode, respectively, in an emission layer. The combination of holes and electrons emits light from a luminescent material, which is an organic compound included in the emission layer.

In applying an organic electroluminescence device to a display, decrease of a driving voltage, increase of emission efficiency and extension of life for the organic electroluminescence device are desired. Hence, development of material that may allow stable implementation of these desired characteristics in the organic electroluminescence device is ongoing.

Furthermore, much effort has been directed to developing materials for a hole transport layer that implement an organic electroluminescence device with high efficiency.

SUMMARY

The present disclosure provides an organic electroluminescence device and a condensed cyclic compound used for the same.

An embodiment of the inventive concept provides an organic electroluminescence device including a first electrode, a hole transport region disposed on the first electrode, an emission layer disposed on the hole transport region, an electron transport region disposed on the emission layer, and a second electrode disposed on the electron transport region, wherein the hole transport region includes a condensed cyclic compound represented by the following Formula 1.

[Formula 1]

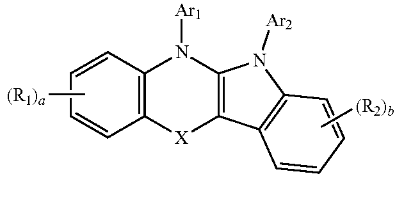

In Formula 1, X is a direct linkage, O, S, $NR_5$, or $SiR_6R_7$, $Ar_1$ and $Ar_2$ are each independently a substituted or unsubstituted aryl group having 6 to 40 carbon atoms for forming a ring, $R_1$ and $R_2$ are each independently a substituted or unsubstituted aryl group having 6 to 40 carbon atoms for forming a ring, or a substituted or unsubstituted alkyl group having 1 to 20 carbon atoms, and a and b are each independently an integer of 0 to 4.

In Formula 1, $R_5$ to $R_7$ are each independently a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring, and the substituted ones are substituted with a hydrogen atom, a deuterium atom, a halogen atom, a cyano group, a substituted or unsubstituted alkyl group having 1 to 40 carbon atoms, a substituted or unsubstituted aryl group having 6 to 40 carbon atoms for forming a ring, or a substituted or unsubstituted heteroaryl group having 2 to 40 carbon atoms for forming a ring, and any one of $Ar_1$, $R_1$ or $R_2$ is represented by the following Formula 2.

[Formula 2]

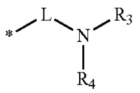

In Formula 2, L is a substituted or unsubstituted arylene group having 6 to 40 carbon atoms for forming a ring, and $R_3$ and $R_4$ are each independently a substituted or unsubstituted aryl group having 6 to 40 carbon atoms for forming a ring, or a substituted or unsubstituted heteroaryl group having 2 to 40 carbon atoms for forming a ring, and the substituted ones are substituted with a hydrogen atom, a deuterium atom, a halogen atom, a cyano group, a substituted or unsubstituted cycloalkyl group having 3 to 40 carbon atoms for forming a ring, a substituted or unsubstituted aryl group having 6 to 40 carbon atoms for forming a ring, or a substituted or unsubstituted heteroaryl group having 2 to 40 carbon atoms for forming a ring.

In an embodiment, the hole transport region may include a hole injection layer and a hole transport layer disposed between the hole injection layer and the emission layer, and the hole transport layer may include the condensed cyclic compound. In an embodiment, the hole transport layer may include a plurality of organic layers, and an organic layer adjacent to the emission layer among the plurality of organic layers may include the condensed cyclic compound.

In an embodiment, Formula 1 may be represented by any one of the following Formulae 1-1 to 1-5.

[Formula 1-1]

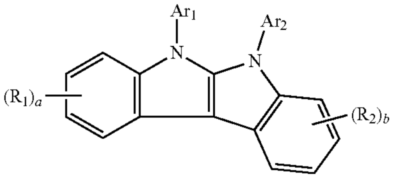

[Formula 1-2]

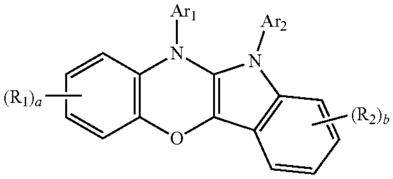

-continued

[Formula 1-3]

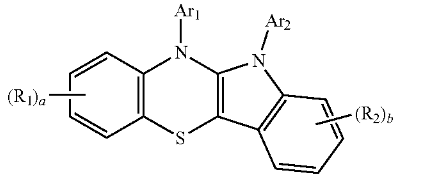

[Formula 1-4]

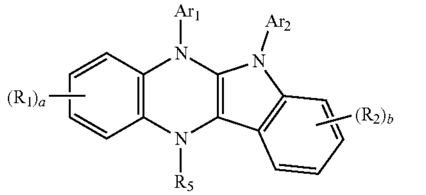

[Formula 1-5]

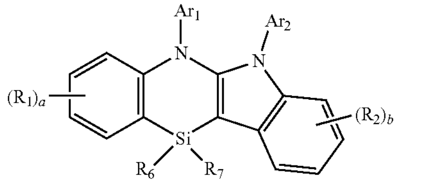

In Formulae 1-1 to 1-5, $Ar_1$, $Ar_2$, $R_1$, $R_2$, $R_5$ to $R_7$, a, and b are the same as defined in Formula 1.

In an embodiment, Formula 1 may be represented by any one of the following Formulae 3-1 to 3-3.

[Formula 3-1]

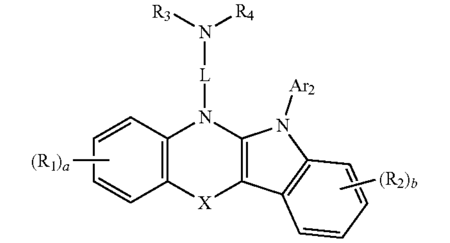

[Formula 3-2]

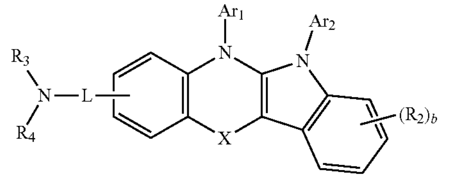

[Formula 3-3]

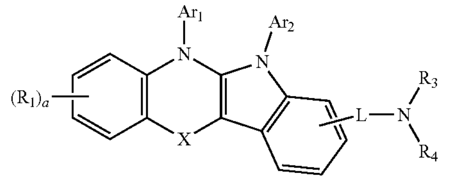

In Formulae 3-1 to 3-3, X, $Ar_1$, $Ar_2$, $R_1$ to $R_4$, L, a, and b are the same as defined in Formulae 1 and 2.

In an embodiment, $R_1$ and $R_2$ in Formula 1 may be each independently a substituted or unsubstituted phenyl group, a substituted or unsubstituted naphthyl group, a substituted or unsubstituted fluorenyl group, a substituted or unsubstituted anthracenyl group, a substituted or unsubstituted phenanthryl group, a substituted or unsubstituted biphenyl group, a substituted or unsubstituted terphenyl group, a substituted or unsubstituted quaterphenyl group, a substituted or unsubstituted quinqphenyl group, a substituted or unsubstituted sexiphenyl group, a substituted or unsubstituted triphenylenyl group, a substituted or unsubstituted pyrenyl group, a substituted or unsubstituted benzofluoranthenyl group, or a substituted or unsubstituted chrysenyl group.

In an embodiment, L in Formula 2 may be a substituted or unsubstituted phenylene group, a substituted or unsubstituted biphenylene group, a substituted or unsubstituted naphthylene group, a substituted or unsubstituted anthracenylene group, a substituted or unsubstituted phenanthrene group, or a substituted or unsubstituted fluorenylene group.

In an embodiment, $R_3$ and $R_4$ in Formula 2 may be each independently a substituted or unsubstituted phenyl group, a substituted or unsubstituted naphthyl group, a substituted or unsubstituted fluorenyl group, a substituted or unsubstituted anthracenyl group, a substituted or unsubstituted phenanthryl group, a substituted or unsubstituted biphenyl group, a substituted or unsubstituted terphenyl group, a substituted or unsubstituted quaterphenyl group, a substituted or unsubstituted thiophene group, a substituted or unsubstituted benzothiophene group, a substituted or unsubstituted dibenzothiophene group, a substituted or unsubstituted furan group, a substituted or unsubstituted benzofuranyl group, a substituted or unsubstituted dibenzofuranyl group, or a substituted or unsubstituted naphthobenzofuranyl group.

An embodiment of the inventive concept provides a condensed cyclic compound represented by the following Formula 1.

[Formula 1]

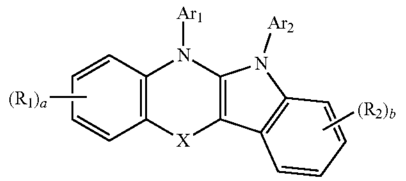

In Formula 1, X is a direct linkage, O, S, $NR_5$, or $SiR_6R_7$, $Ar_1$ and $Ar_2$ are each independently a substituted or unsubstituted aryl group having 6 to 40 carbon atoms for forming a ring, $R_1$ and $R_2$ are each independently a substituted or unsubstituted aryl group having 6 to 40 carbon atoms for forming a ring, or a substituted or unsubstituted alkyl group having 1 to 20 carbon atoms, and a and b are each independently an integer of 0 to 4.

In Formula 1, each of $R_5$, $R_6$, and $R_7$ is independently a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring, and the substituted ones are substituted with a hydrogen atom, a deuterium atom, a halogen atom, a cyano group, a substituted or unsubstituted alkyl group having 1 to 40 carbon atoms, a substituted or unsubstituted aryl group having 6 to 40 carbon atoms for forming a ring, or a substituted or unsubstituted heteroaryl group having 2 to 40 carbon atoms for forming a ring, and any one of $Ar_1$, $R_1$ or $R_2$ is represented by the following Formula 2.

[Formula 2]

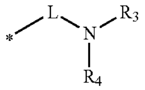

In Formula 2, L is a substituted or unsubstituted arylene group having 6 to 40 carbon atoms for forming a ring, and each of $R_3$ and $R_4$ is independently a substituted or unsubstituted aryl group having 6 to 40 carbon atoms for forming a ring, or a substituted or unsubstituted heteroaryl group having 2 to 40 carbon atoms for forming a ring, and the substituted ones are substituted with a hydrogen atom, a deuterium atom, a halogen atom, a cyano group, a substituted or unsubstituted cycloalkyl group having 3 to 40 carbon atoms for forming a ring, a substituted or unsubstituted aryl group having 6 to 40 carbon atoms for forming a ring, or a substituted or unsubstituted heteroaryl group having 2 to 40 carbon atoms for forming a ring.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
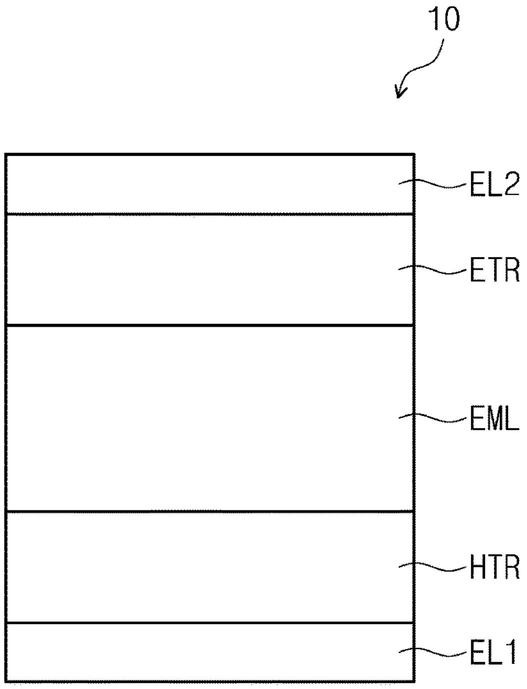
FIG. 1 is a schematic cross-sectional view of an organic electroluminescence device according to an embodiment of the inventive concept.

The above objects, other objects, features and advantages of the inventive concept will be easily understood from preferred exemplary embodiments with reference to the accompanying drawings. The inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art.

Like reference numerals refer to like elements for explaining each drawing. In the accompanying drawings, the sizes of elements may be enlarged for clarity of the inventive concept. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be understood that the terms "comprise" or "have," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening layers may also be present. On the contrary, when a layer, a film, a region, a plate, etc. is referred to as being "under" another part, it can be "directly under" the other part, or intervening layers may also be present.

In the present disclosure,-*means a part to be connected.

First of all, an organic electroluminescence device according to an embodiment of the inventive step will be explained referring to FIGS. 1 to 3.

Figure 2:
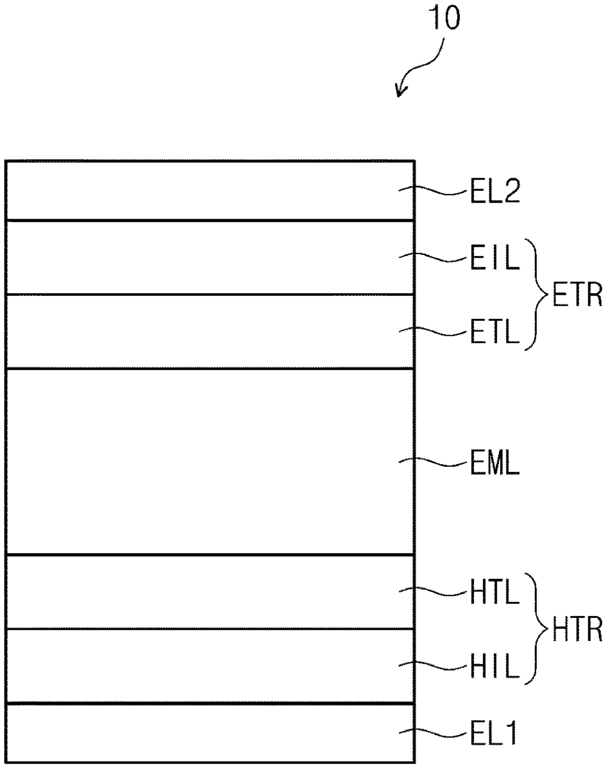
FIG. 2 is a schematic cross-sectional view of an organic electroluminescence device according to an embodiment of the inventive concept.
Figure 3:
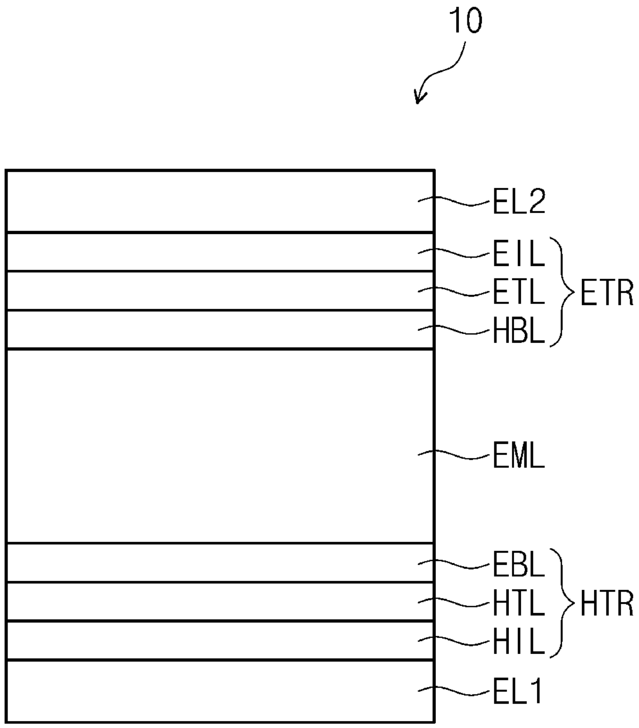
FIG. 3 is a schematic cross-sectional view of an organic electroluminescence device according to an embodiment of the inventive concept.

Referring to FIGS. 1 to 3, an organic electroluminescence device 10 according to an embodiment of the inventive concept may include a first electrode EL1, a hole transport region HTR, an emission layer EML, an electron transport region ETR, and a second electrode EL2, laminated in order.

The first electrode EL1 and the second electrode EL2 are disposed oppositely, and a plurality of organic layers may be disposed between the first electrode EL1 and the second electrode EL2. The plurality of organic layers may include a hole transport region HTR, an emission layer EML and an electron transport region ETR. An organic electroluminescence device 10 according to an embodiment of the inventive concept may include the condensed cyclic compound according to an embodiment of the inventive concept in the hole transport region HTR.

FIG. 2 shows a schematic cross-sectional view illustrating an organic electroluminescence device 10 according to an embodiment of the inventive concept, in which a hole transport region HTR includes a hole injection layer HIL and a hole transport layer HTL, and an electron transport region ETR includes an electron injection layer EIL and an electron transport layer ETL. Furthermore, FIG. 3 shows a schematic cross-sectional view illustrating an organic electroluminescence device 10 according to an embodiment of the inventive concept, in which a hole transport region HTR includes a hole injection layer HIL, a hole transport layer HTL and an electron blocking layer EBL, and an electron transport region ETR includes an electron injection layer EIL, an electron transport layer ETL and a hole blocking layer HBL.

The first electrode EL1 has conductivity. The first electrode EL1 may be a pixel electrode or an anode. The first electrode EL1 may be a transmissive electrode, a transflective electrode, or a reflective electrode. In case the first electrode EL1 is a transmissive electrode, the first electrode EL1 may include a transparent metal oxide such as indium tin oxide (ITO), indium zinc oxide (IZO), zinc oxide (ZnO), or indium tin zinc oxide (ITZO). In case the first electrode EL1 is a transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed using the above materials, and a transparent conductive layer formed using ITO, IZO, ZnO, or ITZO. For example, the first electrode EL1 may have a triple-layer structure of ITO/Ag/ITO. However, an embodiment of the inventive concept is not limited thereto.

The thickness of the first electrode EL1 may be from about 1,000 Å to about 10,000 Å, for example, from about 1,000 Å to about 3,000 Å.

A plurality of organic layers is disposed on the first electrode EL1. The organic layers may include a hole transport region HTR, an emission layer EML and an electron transport region ETR.

The hole transport region HTR is disposed on the first electrode EL1. The hole transport region HTR may include at least one of a hole injection layer HIL, a hole transport layer HTL, a hole buffer layer or an electron blocking layer. The thickness of the hole transport region HTR may be from about 1,000 Å to about 1,500 Å, for example.

In an embodiment of the inventive concept, the hole transport region HTR may include a condensed cyclic compound, which includes a core structure of indoloindole and a noncyclic tertiary amine group.

In the present disclosure, "substituted or unsubstituted" may mean unsubstituted or substituted with at least one substituent selected from the group consisting of deuterium, halogen, cyano, nitro, amino, silyl, boron, phosphine oxide, phosphine sulfide, alkyl, alkenyl, aryl and heterocyclic group. In addition, each of the substituent illustrated above may be substituted or unsubstituted. For example, biphenyl may be interpreted as aryl, or phenyl substituted with phenyl.

In the present disclosure, the terms "forming a ring by combining adjacent groups with each other" may mean forming a substituted or unsubstituted hydrocarbon ring, or a substituted or unsubstituted heterocycle by combining adjacent groups with each other. The hydrocarbon ring includes an aliphatic hydrocarbon ring and an aromatic hydrocarbon ring. The heterocycle includes an aliphatic heterocycle and an aromatic heterocycle. The hydrocarbon ring and heterocycle may be a monocycle or a polycycle. In addition, the ring formed by combining adjacent groups may be connected with another ring to form a spiro structure.

In the description, the term "an adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentane, two ethyl groups may be interpreted as "adjacent groups" to each other.

In the present disclosure, examples of a halogen atom are a fluorine atom, a chlorine atom, a bromine atom, or an iodine atom.

In the present disclosure, the alkyl group may have a linear, branched or cyclic form. The carbon number of the alkyl group may be 1 to 40, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group means any functional group or substituent derived from an aromatic hydrocarbon ring. The aryl group may be monocyclic aryl or polycyclic aryl. The carbon number of the aryl group for forming a ring may be 6 to 60, 6 to 40, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without limitation.

In the present disclosure, the fluorenyl group may be substituted, and two substituents may be combined with each other to form a spiro structure. Examples of the substituted fluorenyl group may include the following groups, without limitation.

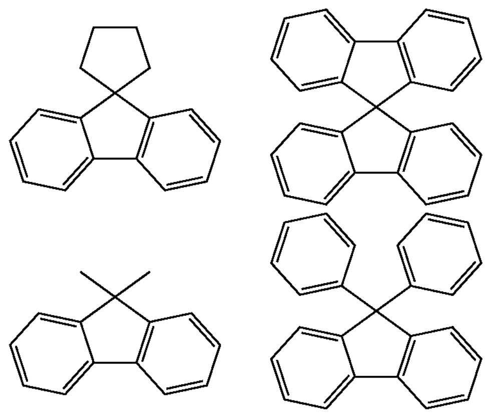

In the present disclosure, the heterocyclic group may be heterocycle including at least one of B, O, N, P, Si, or S as a heteroatom. When the heterocyclic group includes two or more heteroatoms, these heteroatoms may be the same or different from each other. The heterocyclic group may be monocyclic heterocycle or polycyclic heterocycle, and includes heteroaryl. The carbon number of the heterocyclic group for forming a ring may be 2 to 40, 2 to 30, 2 to 20, or 2 to 10. Examples of the heterocyclic group are thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-aryl carbazole, N-heteroaryl carbazole, N-alkyl carbazole, benzoxazole, benzoimidazole, benzothiazole, benzocarbazole, benzothiophene, dibenzothiophene, thienothiophene, benzofuran, phenanthroline, thiazole, isoxazole, oxadiazole, thiadiazole, phenothiazine, dibenzosilole, dibenzofuran, etc., without limitation.

In the present disclosure, the silyl group includes alkyl silyl and aryl silyl. Examples of the silyl group are trimethylsilyl, triethylsilyl, t-butyl dimethylsilyl, vinyl dimethylsilyl, propyl dimethylsilyl, triphenylsilyl, diphenylsilyl, phenylsilyl, etc., without limitation.

In the present disclosure, the carbon number of the amine group is not specifically limited, and may be 1 to 30. The amine group may include alkyl amine and aryl amine. Examples of the amine group are methylamine, dimethylamine, phenylamine, naphthylamine, 9-methyl-anthracenylamine, triphenylamine, etc., without limitation.

The above explanation on the aryl group may be applied to the arylene group, except that the arylene group is divalent.

The above explanation on the heteroaryl group may be applied to the heteroarylene group, except that the heteroarylene group is divalent.

In an embodiment of the inventive concept, the hole transport region HTR includes a condensed cyclic compound represented by the following Formula 1.

[Formula 1]

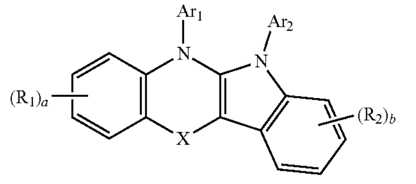

In Formula 1, X may be a direct linkage, O, S, $NR_5$, or $SiR_6R_7$.

In Formula 1, each of $Ar_1$ and $Ar_2$ may independently be a substituted or unsubstituted aryl group having 6 to 40 carbon atoms for forming a ring.

In an embodiment, $R_1$ and $R_2$ may be each independently a substituted or unsubstituted phenyl group, a substituted or unsubstituted naphthyl group, a substituted or unsubstituted fluorenyl group, a substituted or unsubstituted anthracenyl group, a substituted or unsubstituted phenanthryl group, a substituted or unsubstituted biphenyl group, a substituted or unsubstituted terphenyl group, a substituted or unsubstituted quaterphenyl group, a substituted or unsubstituted quinqphenyl group, a substituted or unsubstituted sexiphenyl group, a substituted or unsubstituted triphenylenyl group, a substituted or unsubstituted pyrenyl group, a substituted or unsubstituted benzofluoranthenyl group, or a substituted or unsubstituted chrysenyl group.

In Formula 1, each of $R_1$ and $R_2$ may independently be a substituted or unsubstituted aryl group having 6 to 40 carbon atoms for forming a ring, or a substituted or unsubstituted alkyl group having 1 to 20 carbon atoms.

In Formula 1, each of a and b may independently be an integer of 0 to 4. In case a is an integer of 2 or more, a plurality of $R_1$ may be the same or different from each other. In case b is an integer of 2 or more, a plurality of $R_2$ may be the same or different from each other.

In Formula 1, $R_5$ to $R_7$ may be each independently a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring.

In Formula 1, the substituted ones may be substituted with a hydrogen atom, a deuterium atom, a halogen atom, a cyano group, a substituted or unsubstituted alkyl group having 1 to 40 carbon atoms, a substituted or unsubstituted aryl group having 6 to 40 carbon atoms for forming a ring, or a substituted or unsubstituted heteroaryl group having 2 to 40 carbon atoms for forming a ring.

In Formula 1, any one of $Ar_1$, $R_1$ or $R_2$ is represented by the following Formula 2.

[Formula 2]

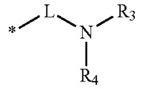

In Formula 2, L may be a substituted or unsubstituted arylene group having 6 to 40 carbon atoms for forming a ring.

In an embodiment, L may be a substituted or unsubstituted phenylene group, a substituted or unsubstituted biphenylene group, a substituted or unsubstituted naphthylene group, a substituted or unsubstituted anthracenylene group, a substituted or unsubstituted phenanthrene group, or a substituted or unsubstituted fluorenylene group.

In Formula 2, each of $R_3$ and $R_4$ may independently be a substituted or unsubstituted aryl group having 6 to 40 carbon atoms for forming a ring, or a substituted or unsubstituted heteroaryl group having 2 to 40 carbon atoms for forming a ring.

In $R_3$ and $R_4$, the substituted ones may be substituted with a hydrogen atom, a deuterium atom, a halogen atom, a cyano group, a substituted or unsubstituted cycloalkyl group having 3 to 40 carbon atoms for forming a ring, a substituted or unsubstituted aryl group having 6 to 40 carbon atoms for forming a ring, or a substituted or unsubstituted heteroaryl group having 2 to 40 carbon atoms for forming a ring.

In an embodiment, $R_3$ and $R_4$ may be each independently a substituted or unsubstituted phenyl group, a substituted or unsubstituted naphthyl group, a substituted or unsubstituted fluorenyl group, a substituted or unsubstituted anthracenyl group, a substituted or unsubstituted phenanthryl group, a substituted or unsubstituted biphenyl group, a substituted or unsubstituted terphenyl group, a substituted or unsubstituted quaterphenyl group, a substituted or unsubstituted thiophene group, a substituted or unsubstituted benzothiophene group, a substituted or unsubstituted dibenzothiophene group, a substituted or unsubstituted furan group, a substituted or unsubstituted benzofuranyl group, a substituted or unsubstituted dibenzofuranyl group, or a substituted or unsubstituted naphthobenzofuranyl group.

Meanwhile, $Ar_2$ in Formula 1 may not be represented by Formula 2. Especially in the case of the compound of Formula 1, in which X is O, S, $NR_5$ or $SiR_6R_7$, and $Ar_2$ is represented by Formula 2, degrades emission efficiency and life of the device employing the compound. That is, when X is O, S, $NR_5$ or $SiR_6R_7$ in Formula 1, the electron density of indoloindole ring is biased toward the state that the benzoxazine ring including X has relatively high electron density and the indole ring has relatively low electron density, and therefore, the indole ring with low electron density withdraws the electrons of the amine group with high electron density, and the strong electron resistance of the amine group may not be maintained.

For example, Formula 1 may be represented by any one of the following Formulae 1-1 to 1-5.

[Formula 1-1]

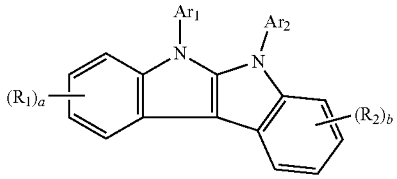

-continued

[Formula 1-2]

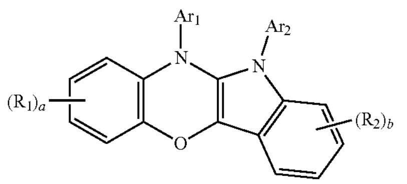

[Formula 1-3]

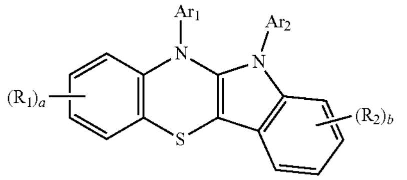

[Formula 1-4]

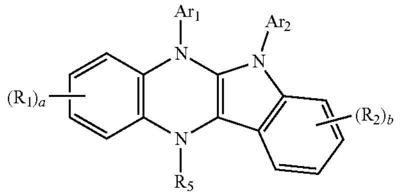

[Formula 1-5]

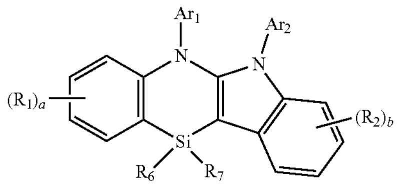

In Formulae 1-1 to 1-5, $Ar_1$, $Ar_2$, $R_1$, $R_2$, $R_5$ to $R_7$, a, and b are the same as defined in Formula 1.

Formula 1-1 is an embodiment of Formula 1 in which X is a direct linkage, Formula 1-2 is an embodiment of Formula 1 in which X is O, Formula 1-3 is an embodiment of Formula 1 in which X is S, Formula 1-4 is an embodiment of Formula 1 in which X is $NR_5$, and Formula 1-5 is an embodiment of Formula 1 in which X is $SiR_6R_7$.

For example, Formula 1 may be represented by any one of the following Formulae 3-1 to 3-3.

[Formula 3-1]

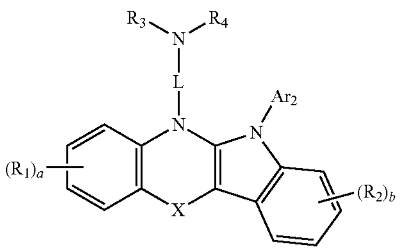

-continued

[Formula 3-2]

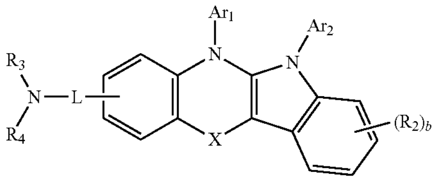

[Formula 3-3]

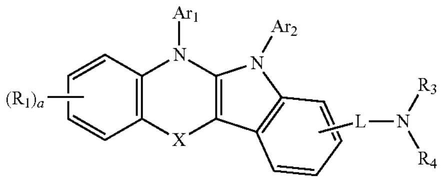

In Formulae 3-1 to 3-3, X, $Ar_1$, $Ar_2$, $R_1$ to $R_4$, L, a, and b are the same as defined in Formulae 1 and 2.

Formula 3-1 is an embodiment of Formula 1 in which $Ar_1$ is represented by Formula 2, Formula 3-2 is an embodiment of Formula 1 in which $R_1$ is represented by Formula 2, and Formula 3-3 is an embodiment of Formula 1 in which $R_2$ is represented by Formula 2.

For example, Formula 1-1 may be represented by the following Formula 4-1 or 4-2.

[Formula 4-1]

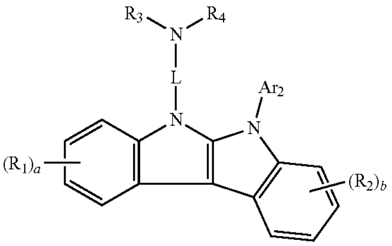

[Formula 4-2]

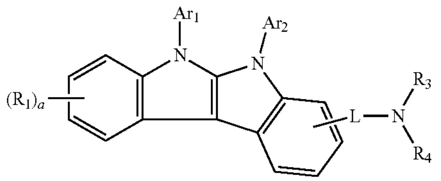

In Formulae 4-1 and 4-2, $Ar_1$, $Ar_2$, $R_1$ to $R_4$, L, a, and b are the same as defined in Formulae 1 and 2.

For example, Formula 1-2 may be represented by any one of the following Formulae 5-1 to 5-3.

[Formula 5-1]

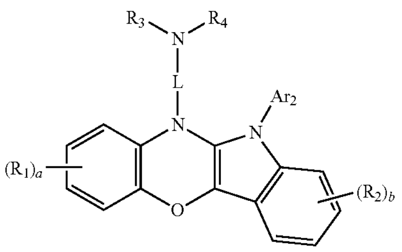

-continued

[Formula 5-2]

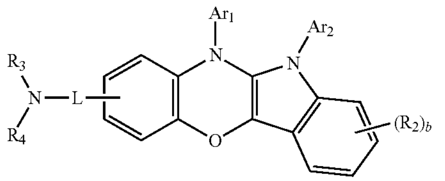

[Formula 5-3]

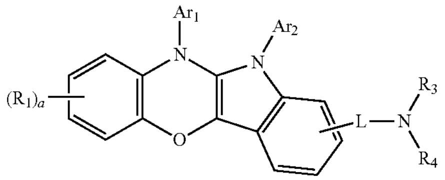

In Formulae 5-1 to 5-3, $Ar_1$, $Ar_2$, $R_1$ to $R_4$, L, a, and b are the same as defined in Formulae 1 and 2.

For example, Formula 1-3 may be represented by any one of the following Formulae 6-1 to 6-3.

[Formula 6-1]

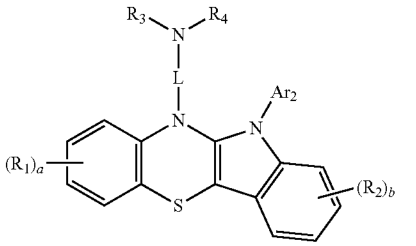

[Formula 6-2]

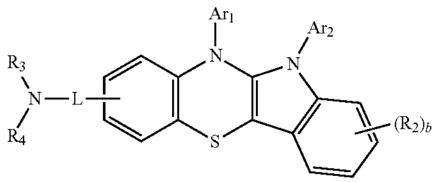

[Formula 6-3]

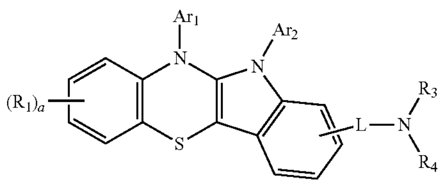

In Formulae 6-1 to 6-3, $Ar_1$, $Ar_2$, $R_1$ to $R_4$, L, a, and b are the same as defined in Formulae 1 and 2.

For example, Formula 1-4 may be represented by any one of the following Formulae 7-1 to 7-3.

[Formula 7-1]

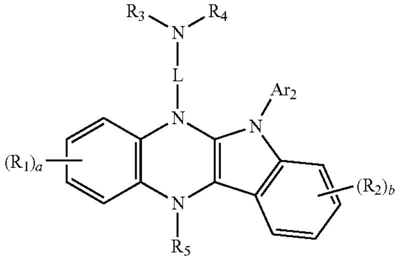

[Formula 7-2]

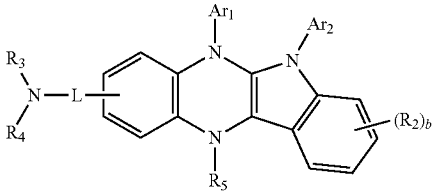

[Formula 7-3]

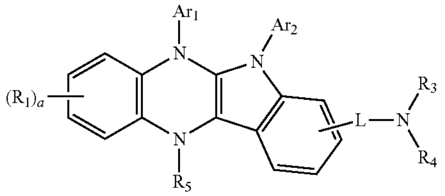

In Formulae 7-1 to 7-3, $Ar_1$, $Ar_2$, $R_1$ to $R_5$, L, a, and b are the same as defined in Formulae 1 and 2.

For example, Formula 1-5 may be represented by any one of the following Formulae 8-1 to 8-3.

[Formula 8-1]

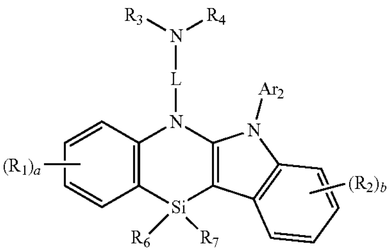

[Formula 8-2]

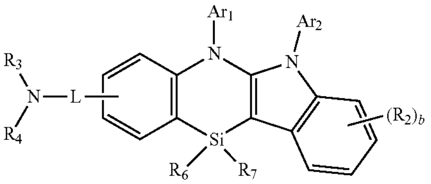

[Formula 8-3]

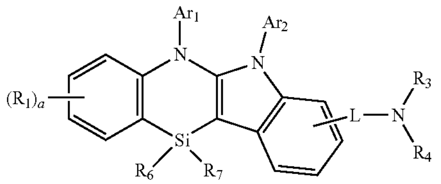

In Formulae 8-1 to 8-3, $Ar_1$, $Ar_2$, $R_1$ to $R_4$, $R_6$, $R_7$, L, a, and b are the same as defined in Formulae 1 and 2.

The condensed cyclic compound may be any one selected from the group consisting of compounds represented in the following Compound Groups 1 to 5. However, an embodiment of the inventive concept is not limited thereto.
[Compound Group 1]
A1
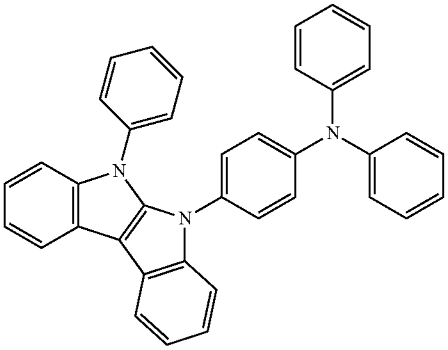
A2
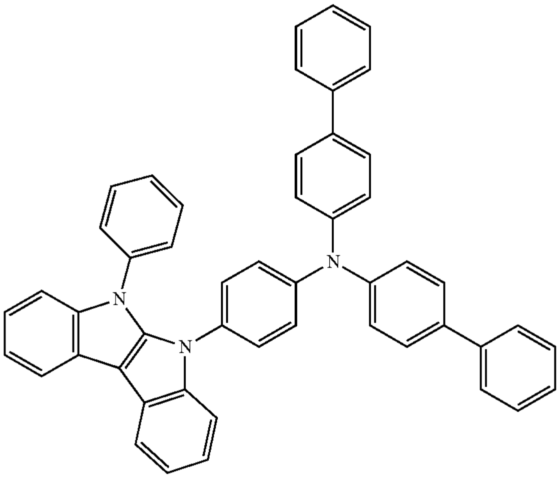
A3
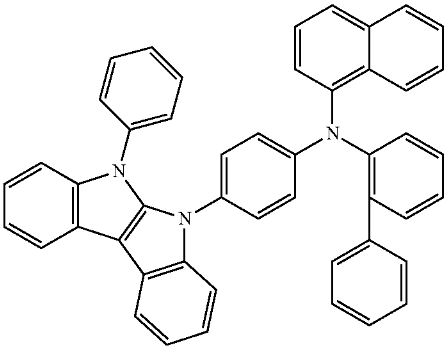
-continued
A4
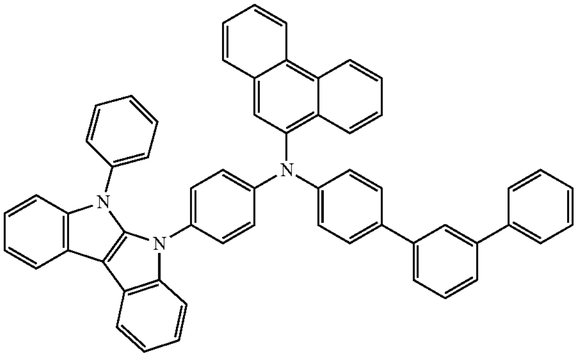
A5
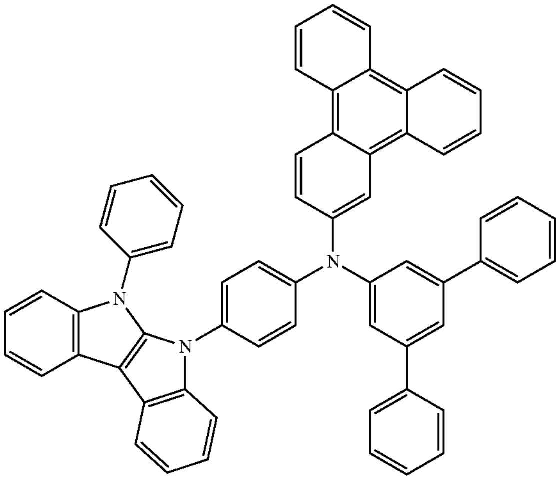
A6
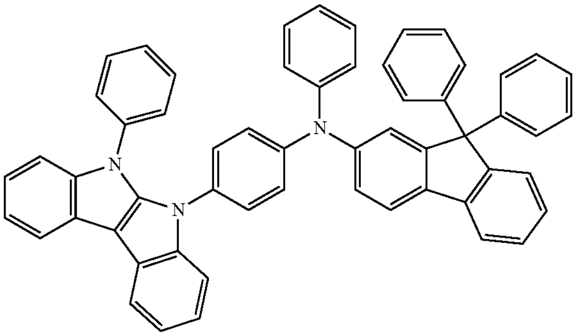
A7
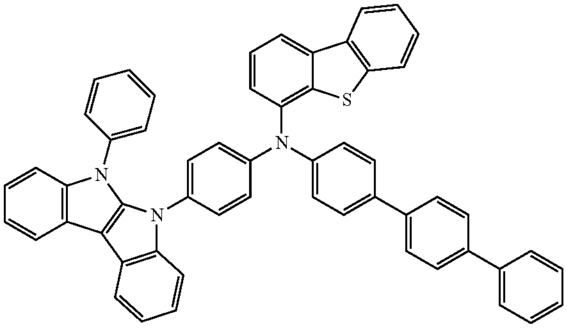

-continued
A8
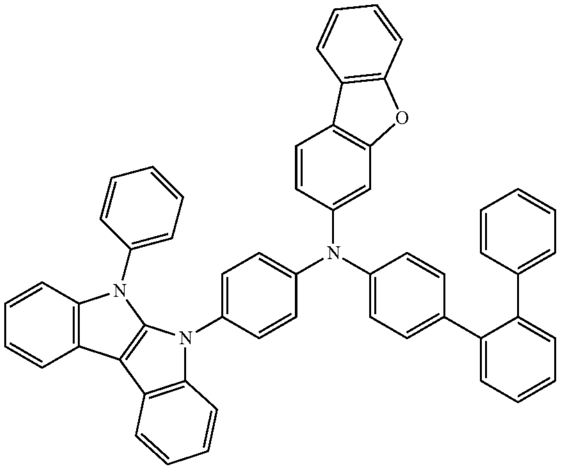
A9
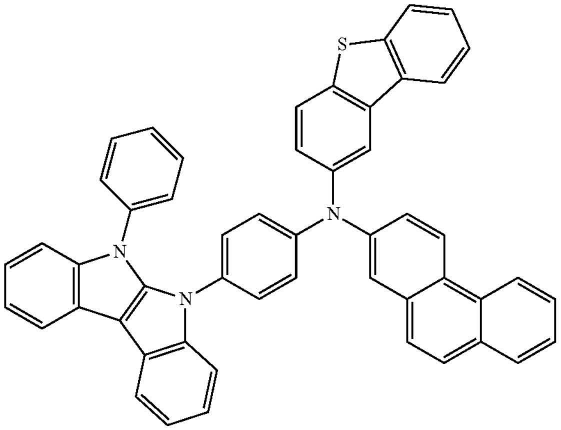
A10
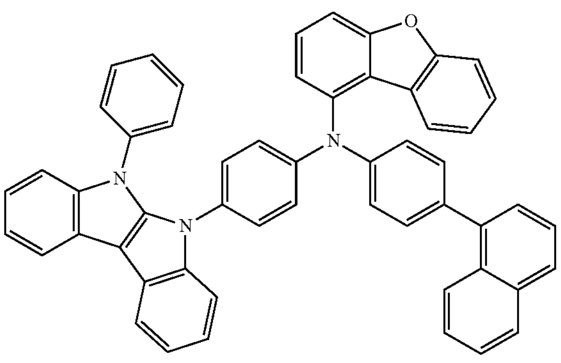
-continued
A11
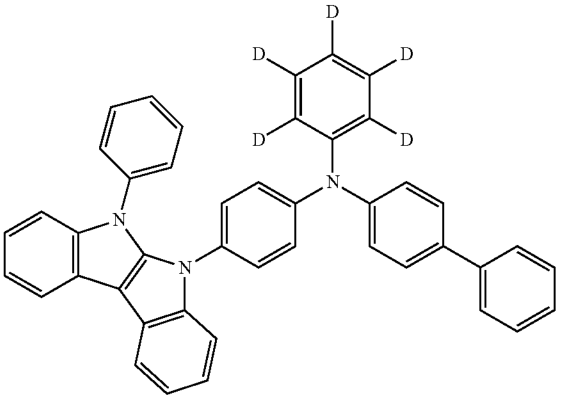
A12
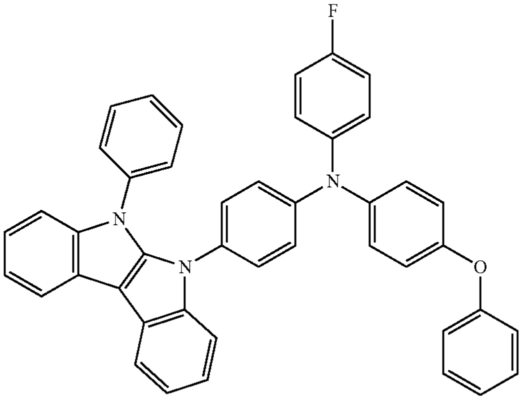
A13
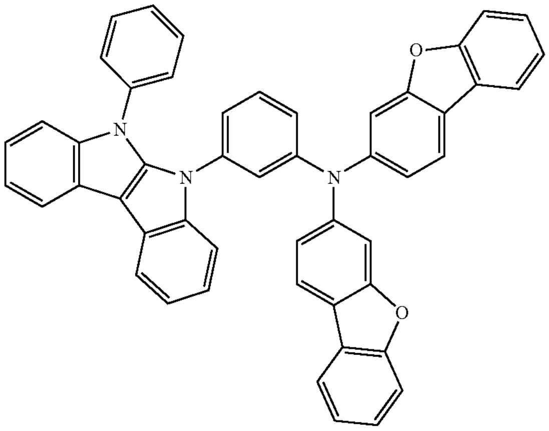

-continued
A14
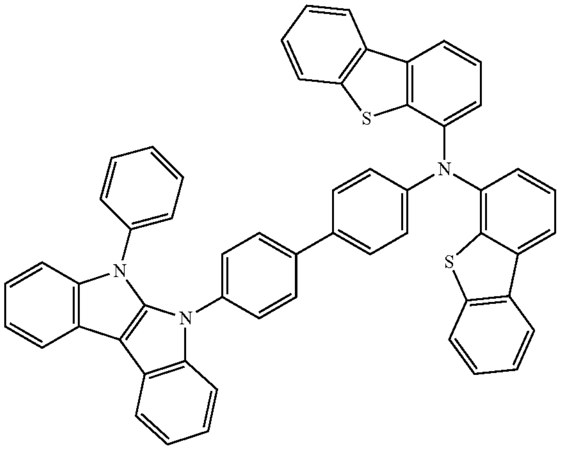
A15
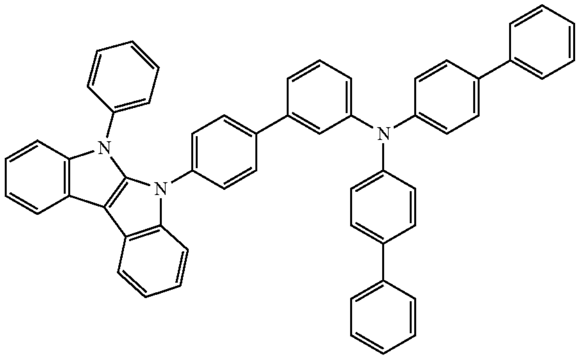
A16
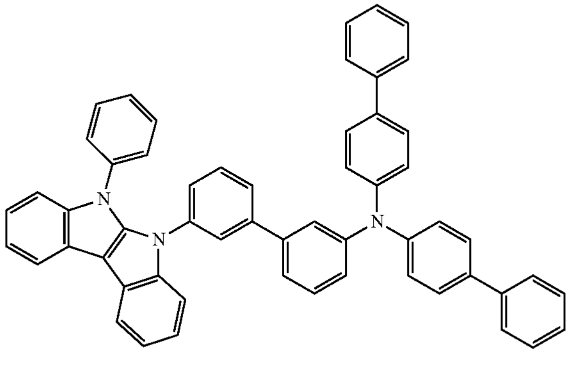
-continued
A17
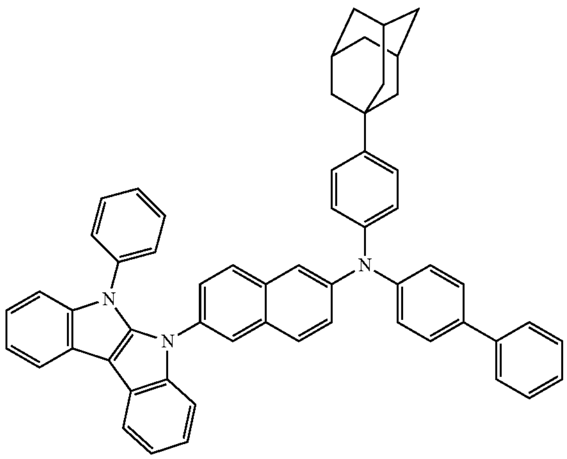
A18
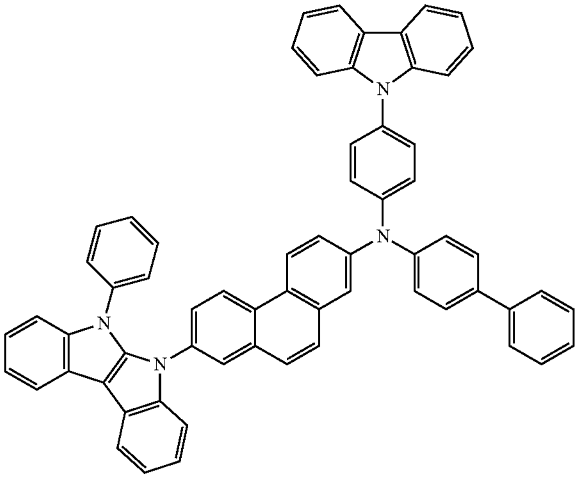
A19
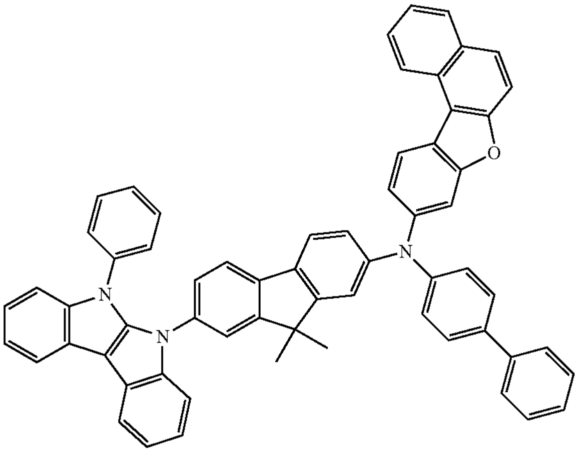

-continued
A20
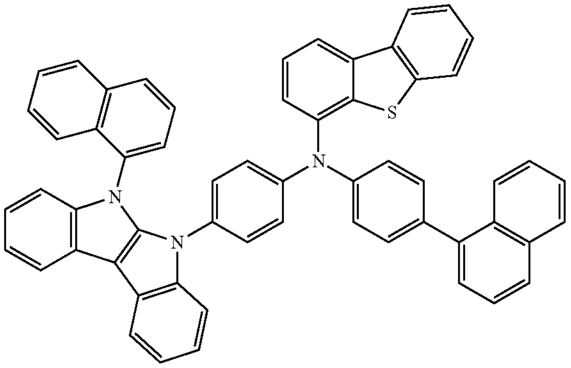
A21
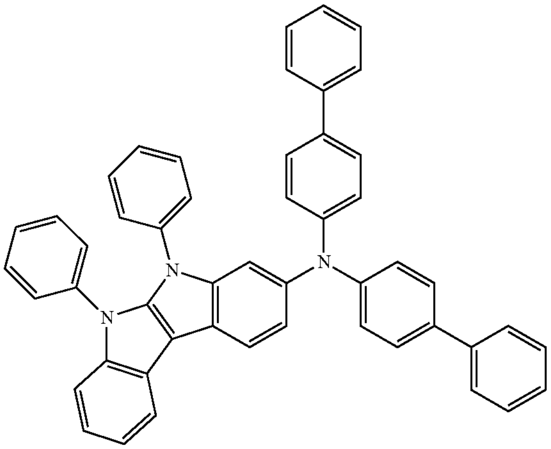
A22
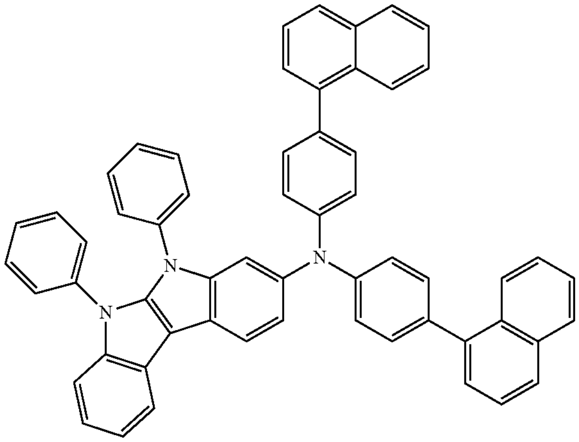
-continued
A23
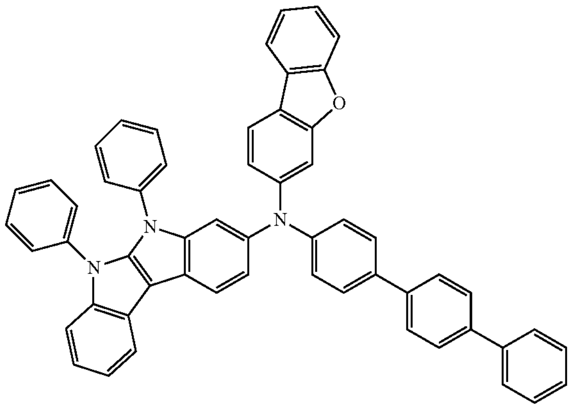
A24
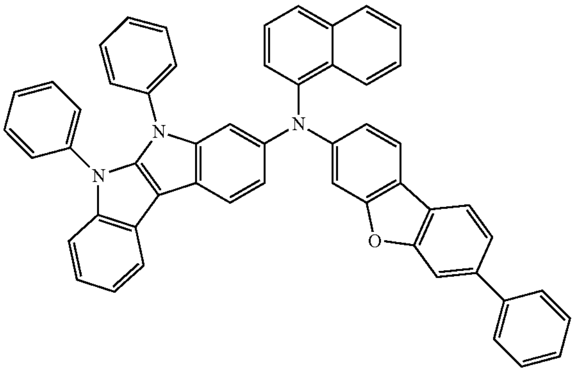
A25
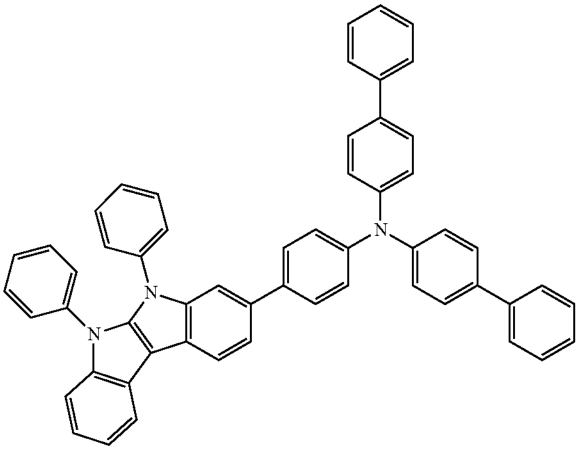

-continued
A26
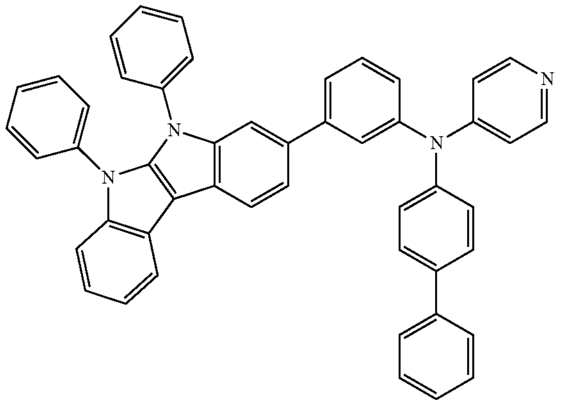
A27
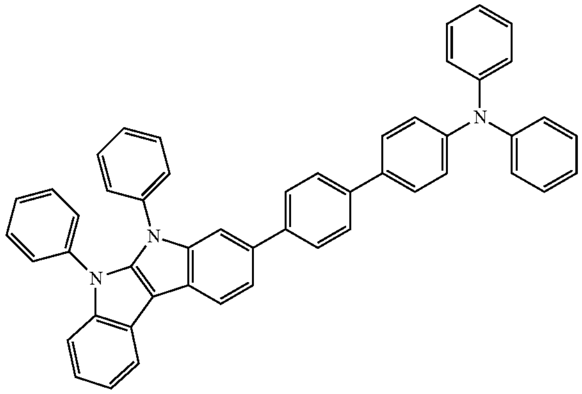
A28
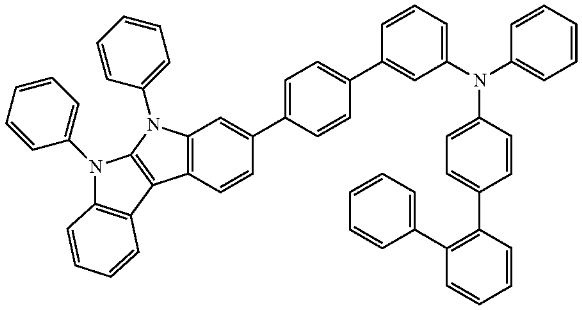
-continued
A29
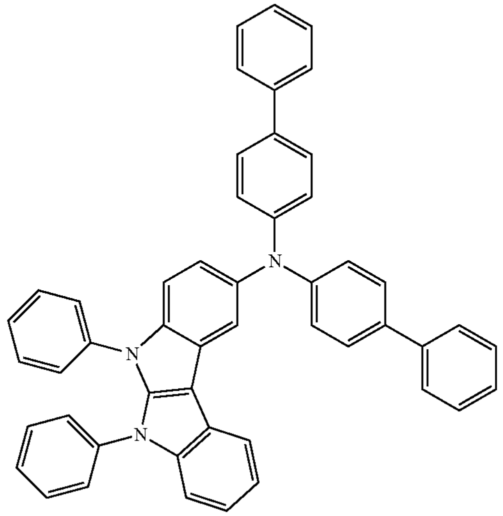
A30
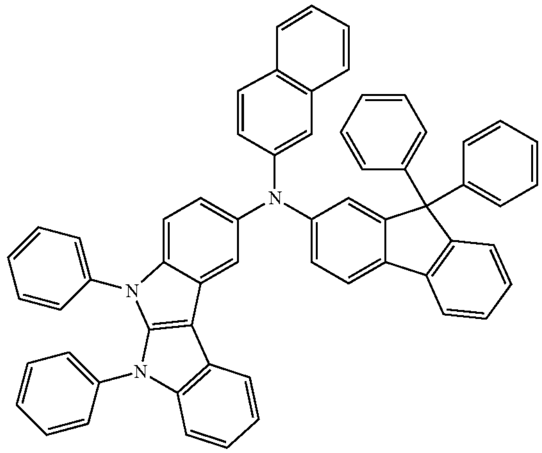
A31
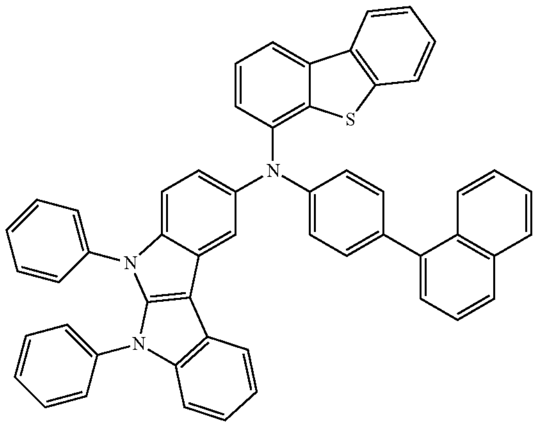

-continued
A32
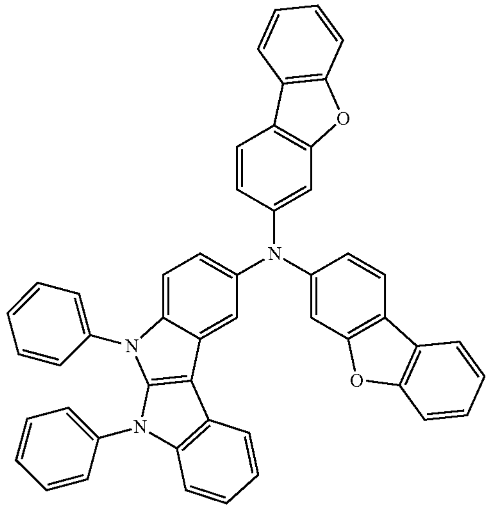
A33
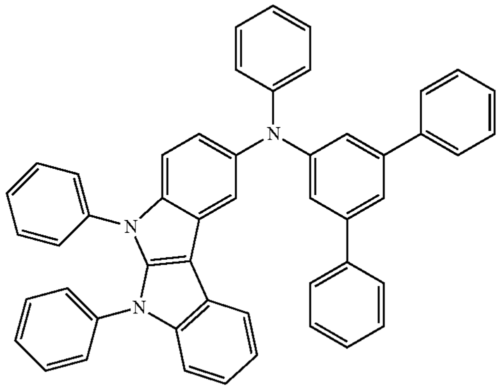
A34
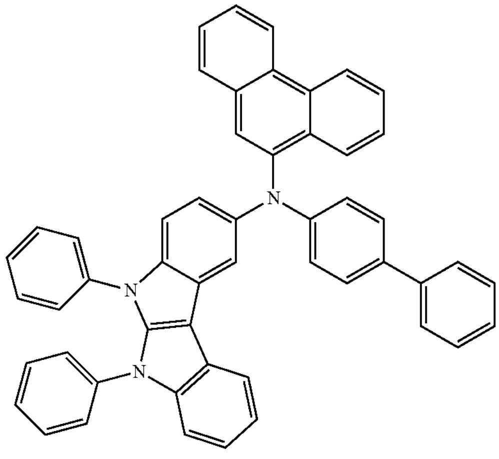
-continued
A35
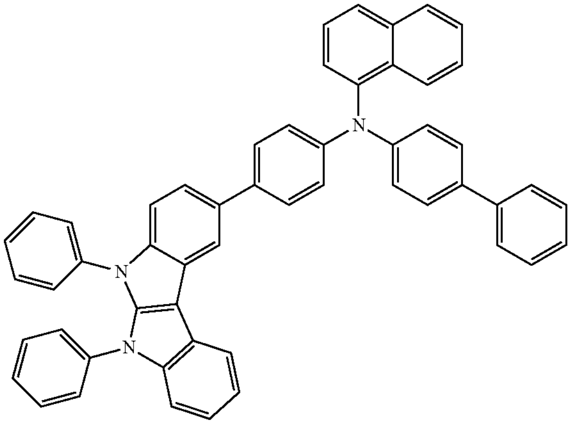
A36
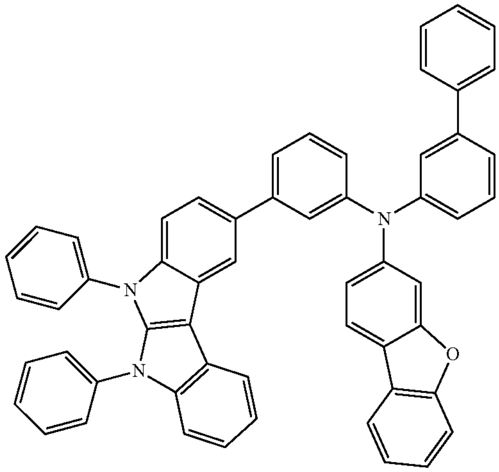
A37
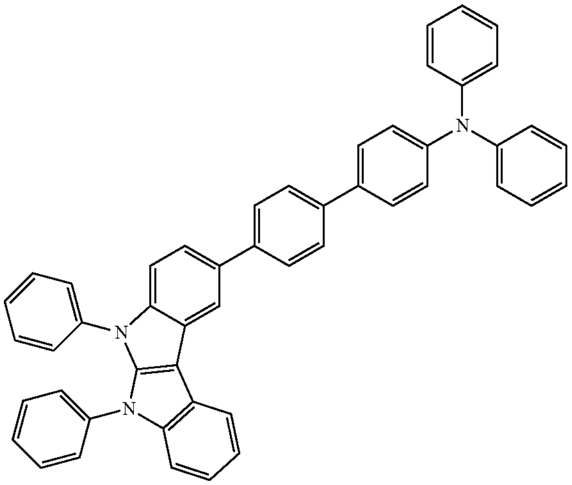

A38
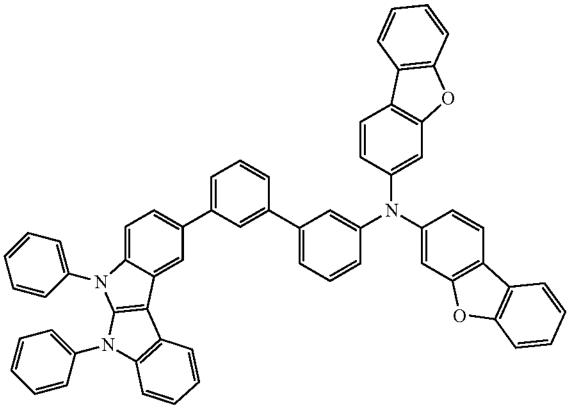
A39
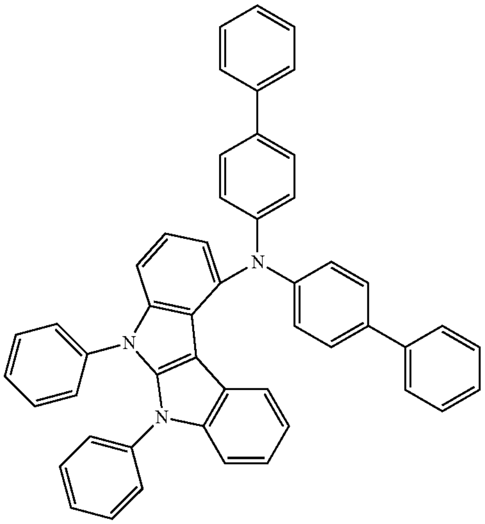
A40
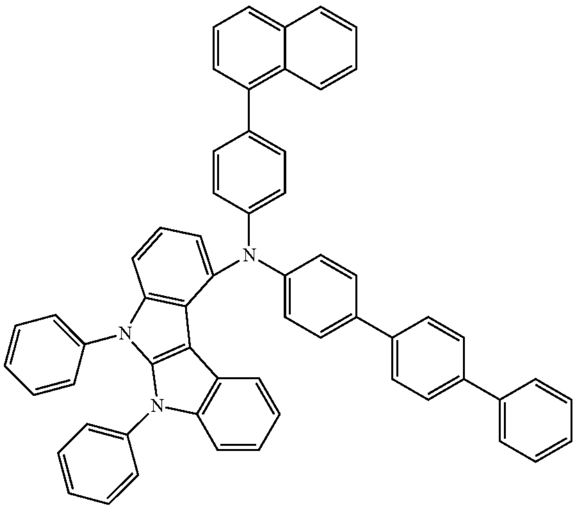
A41
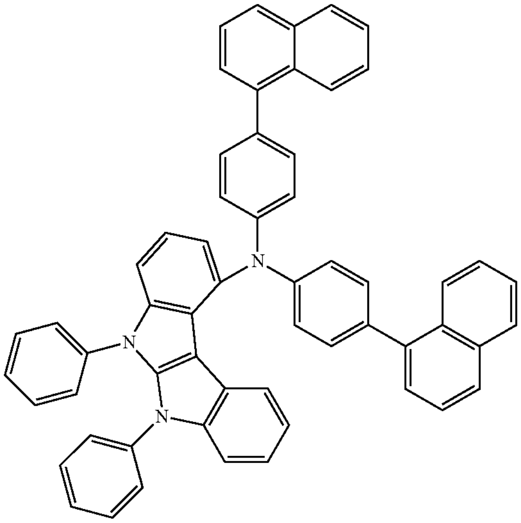
A42
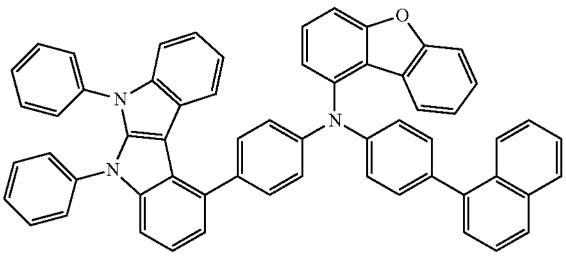
A43
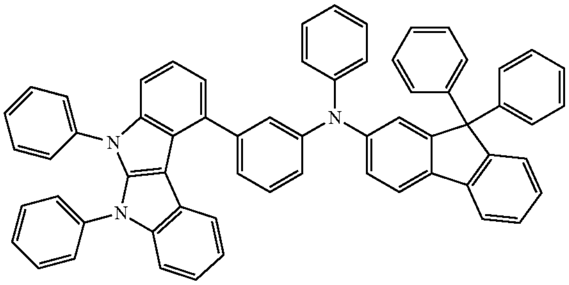
A44
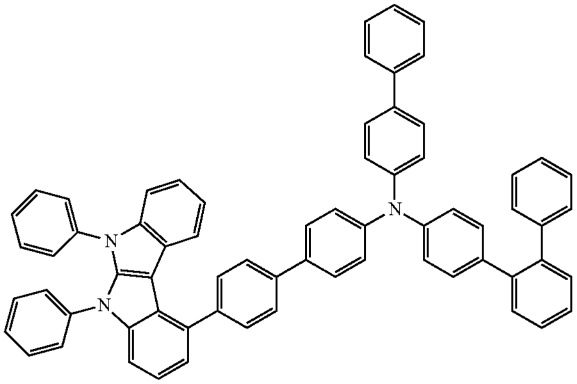

-continued
A45
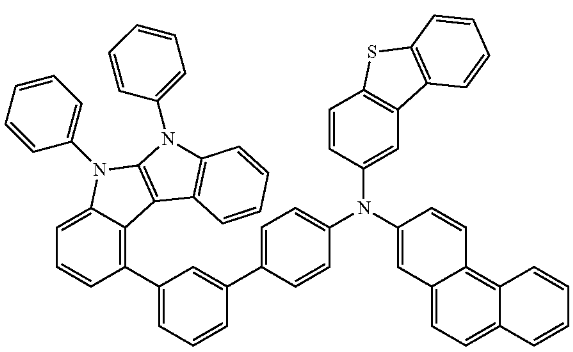
A46
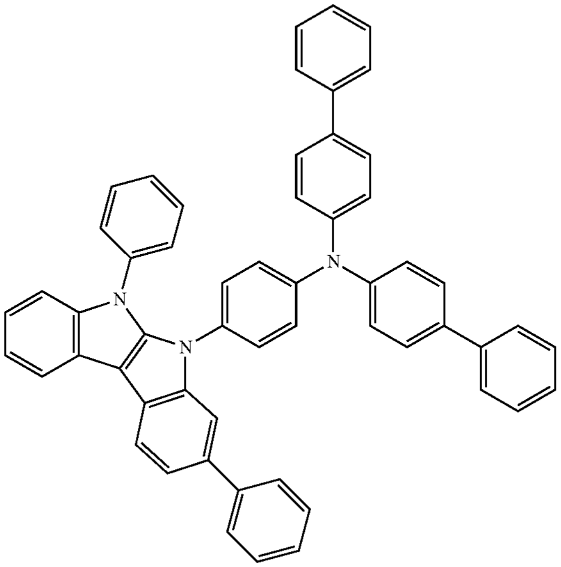
A47
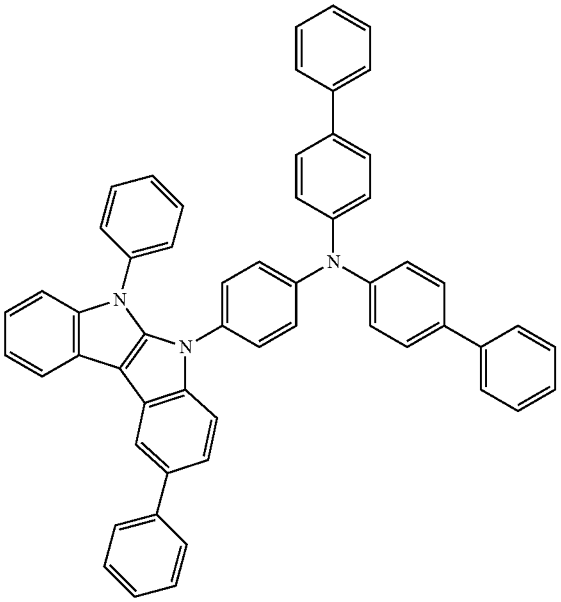
-continued
A48
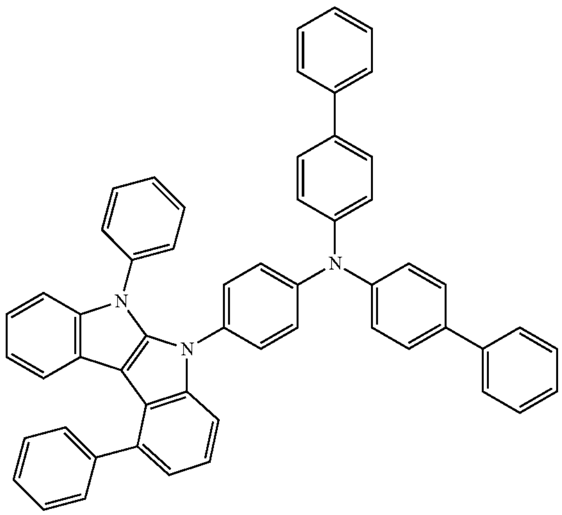
A49
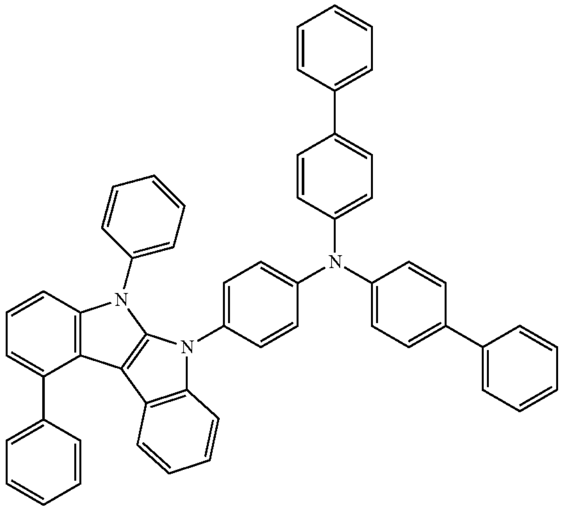
A50
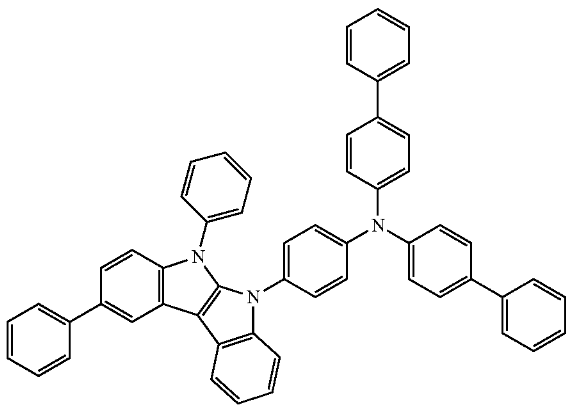

-continued
A51
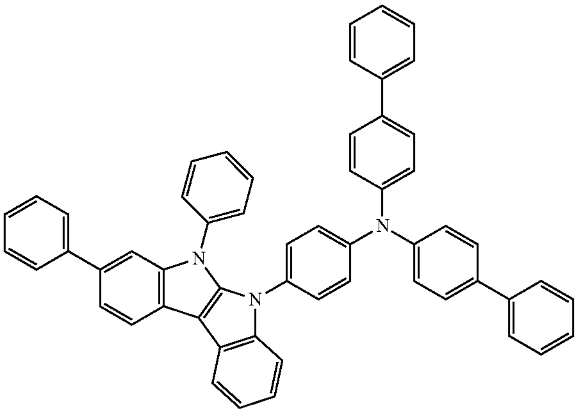
A52
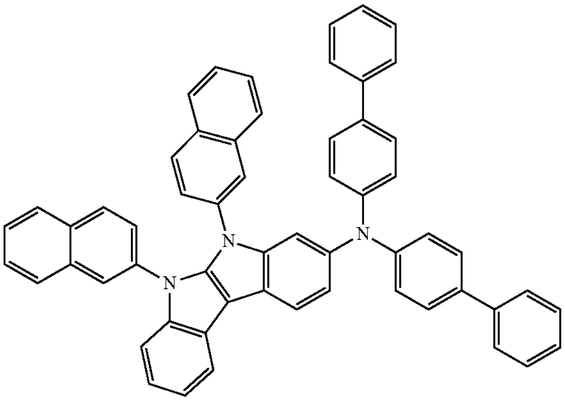
A53
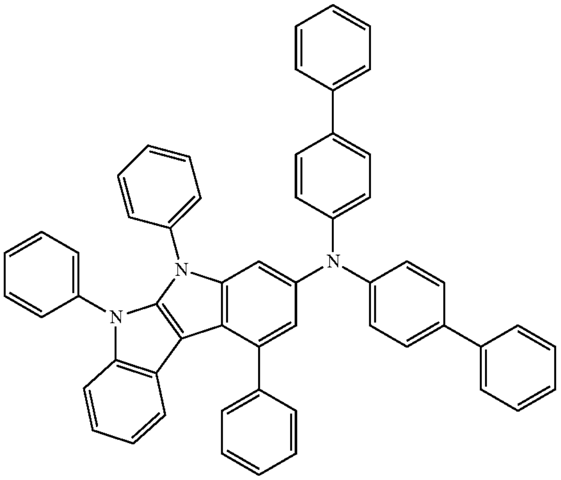
-continued
A54
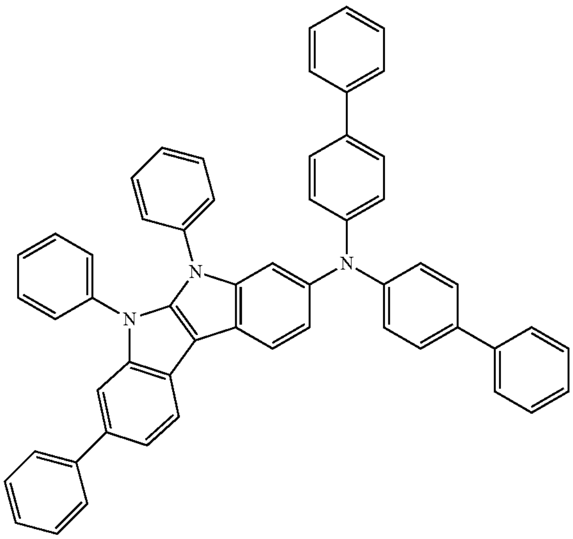
A55
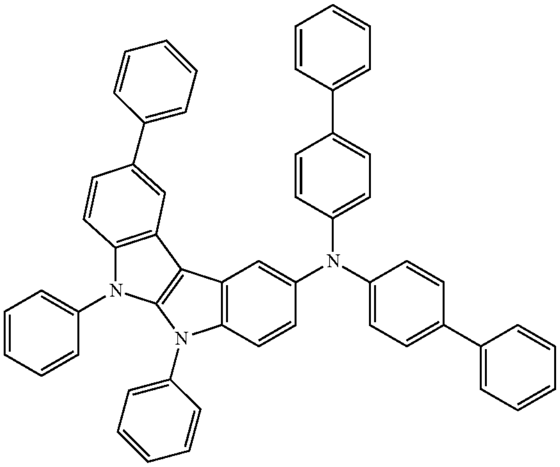
[Compound Group 2]
B1
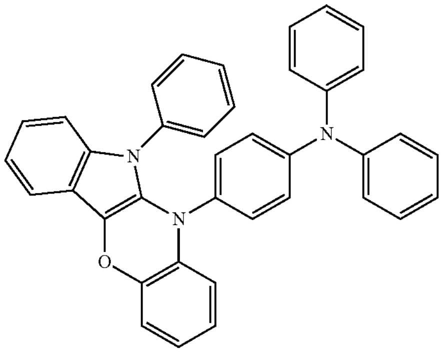

-continued
B2
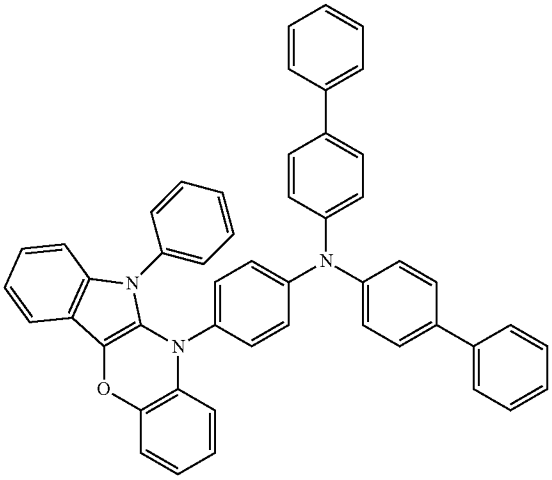
B3
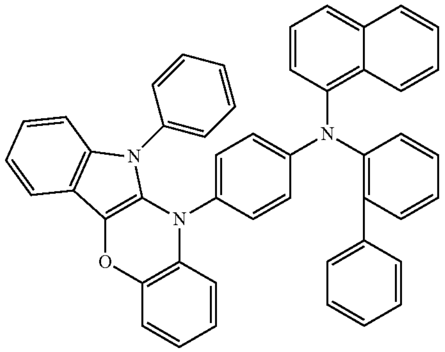
B4
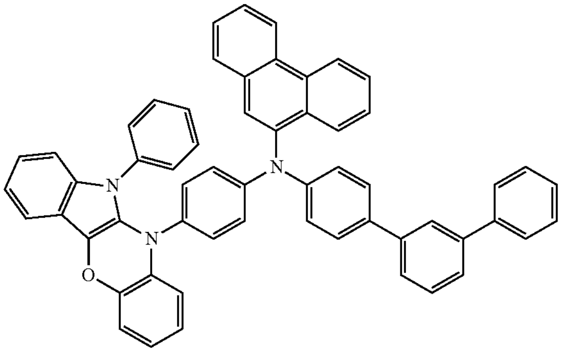
-continued
B5
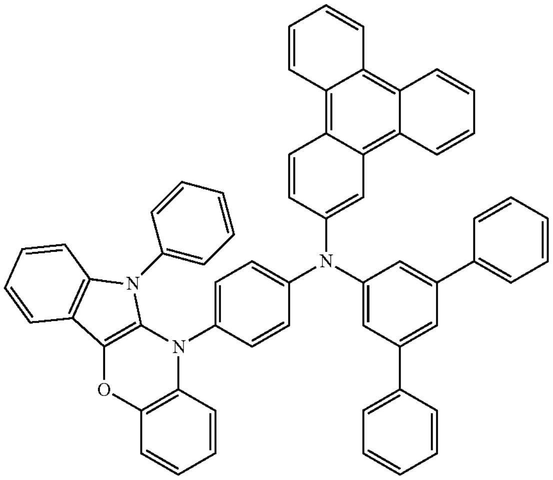
B6
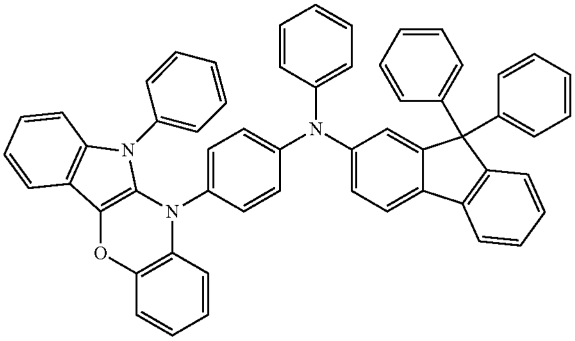
B7
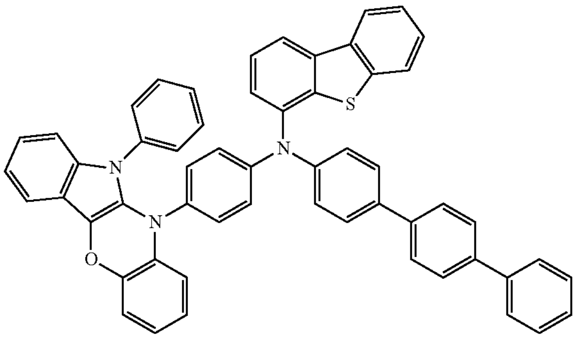

B8
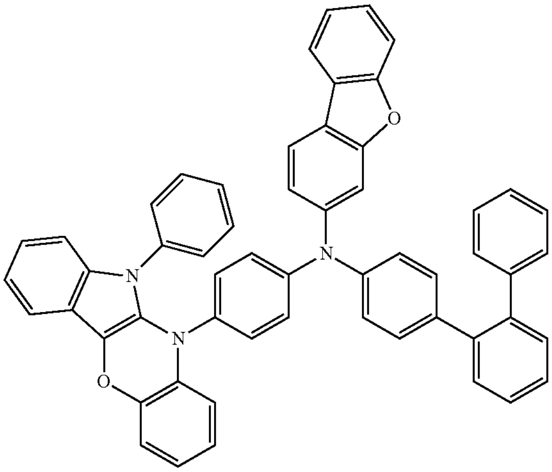
B9
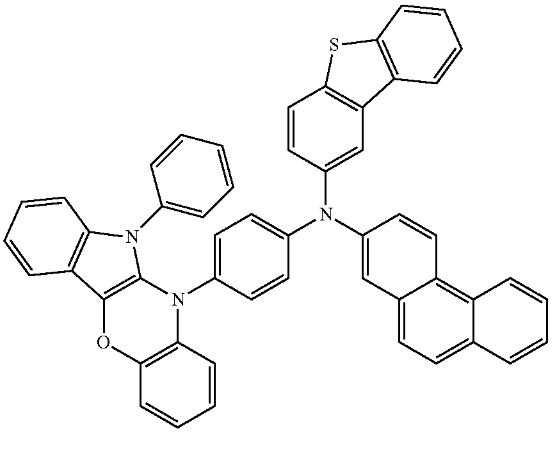
B10
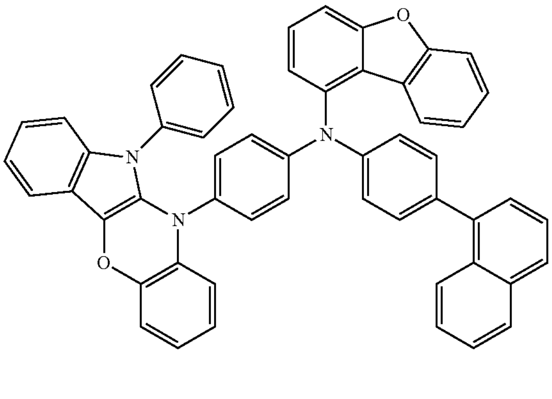
B11
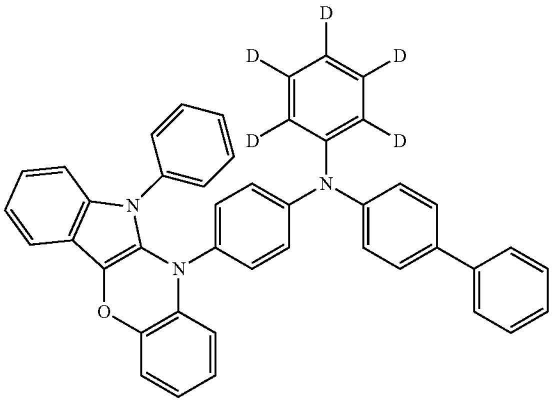
B12
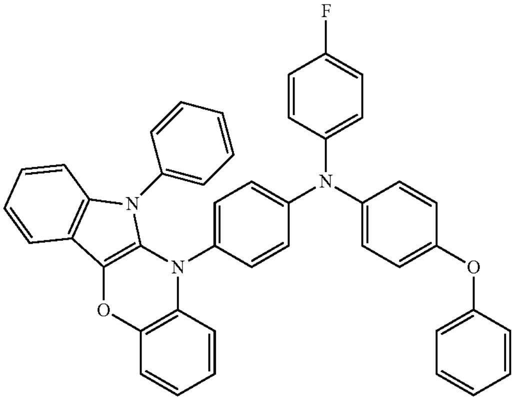
B13
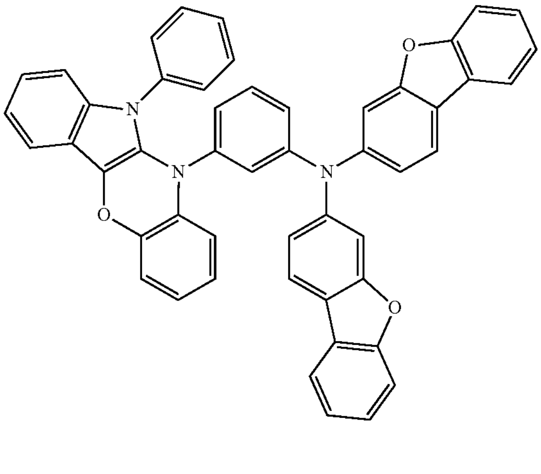

-continued
B14
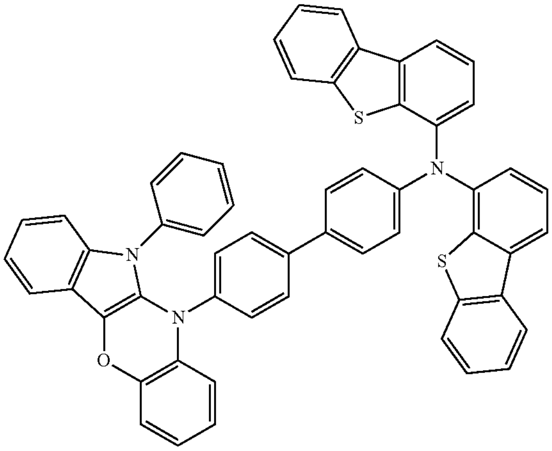
B15
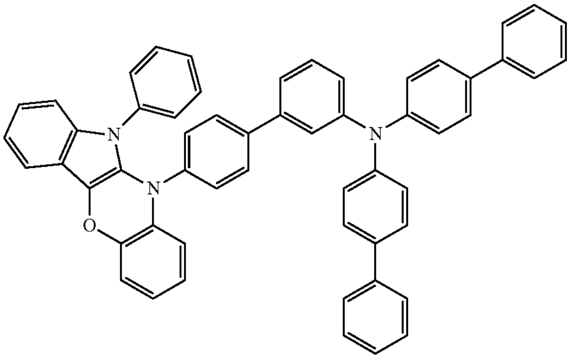
B16
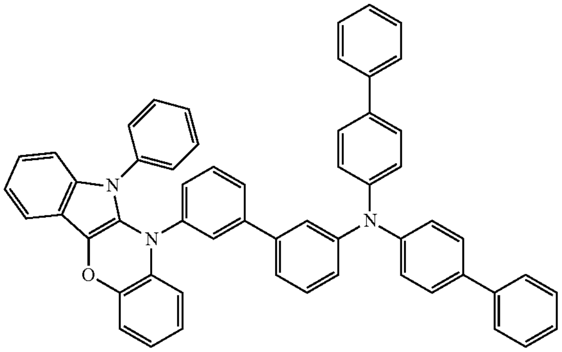
-continued
B17
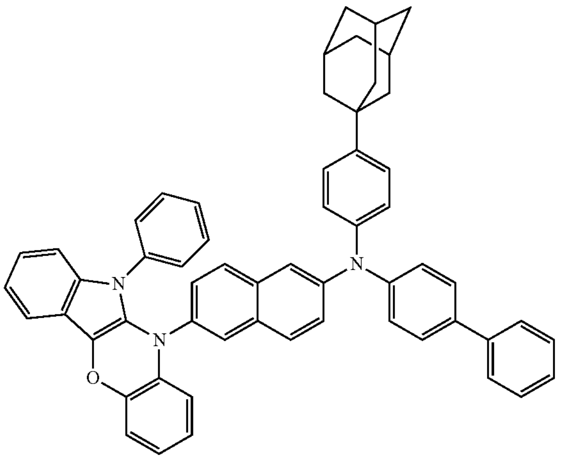
B18
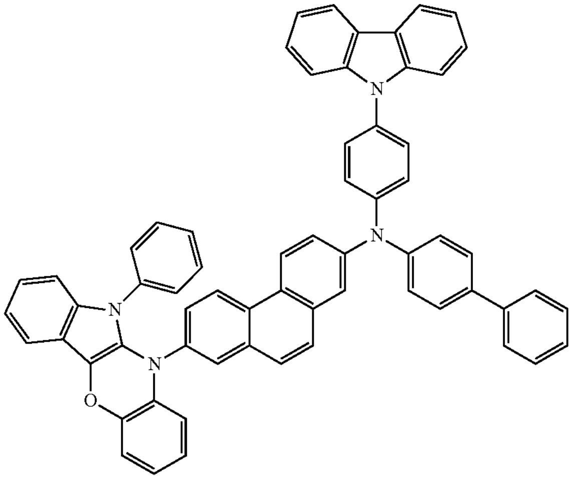
B19
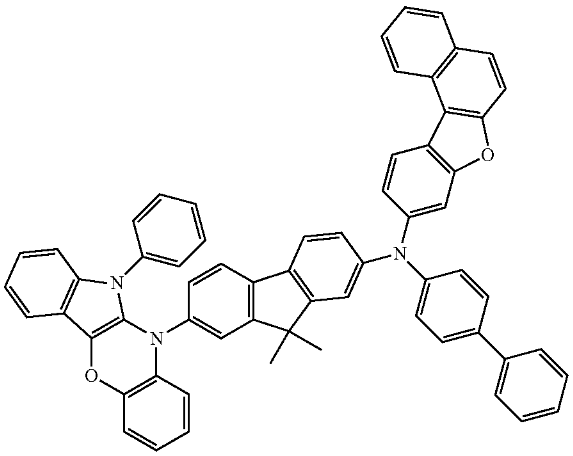

-continued
B20
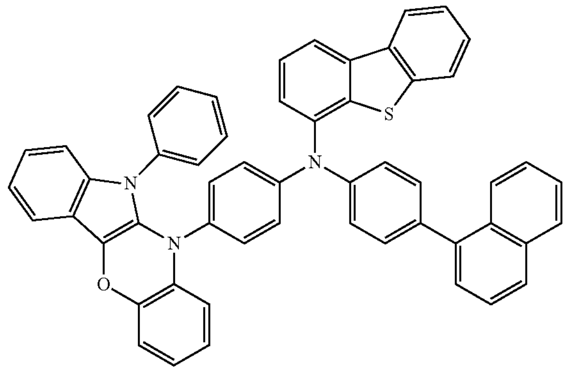
B21
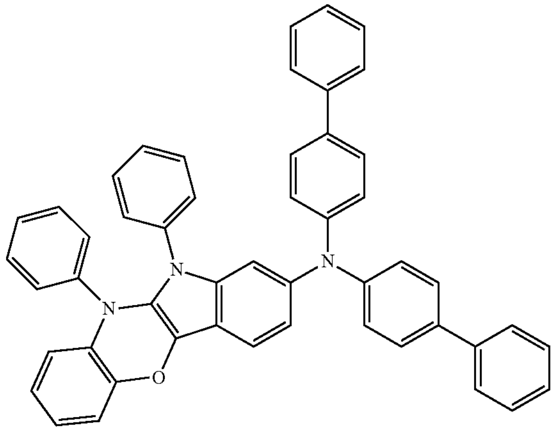
B22
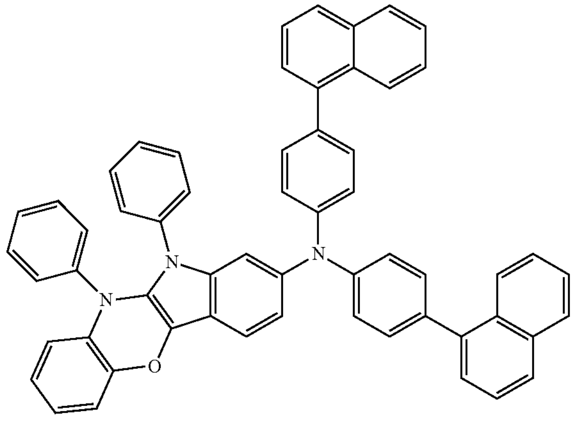
-continued
B23
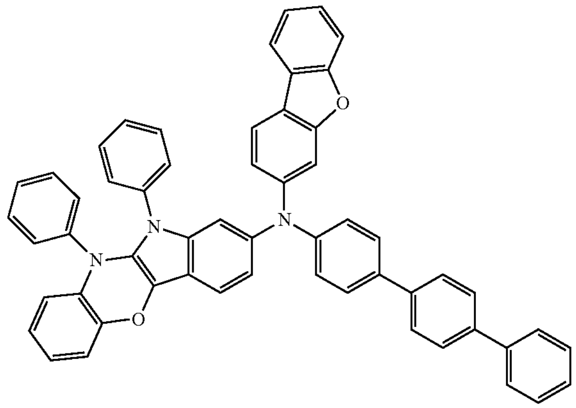
B24
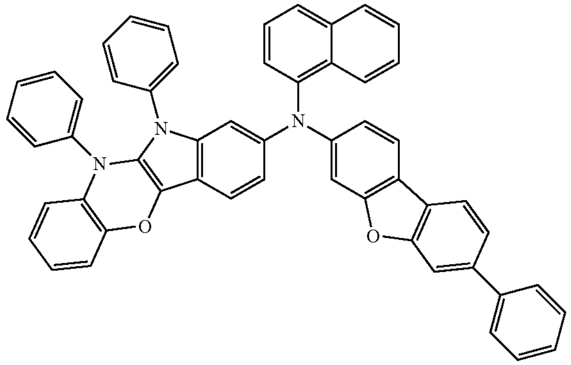
B25
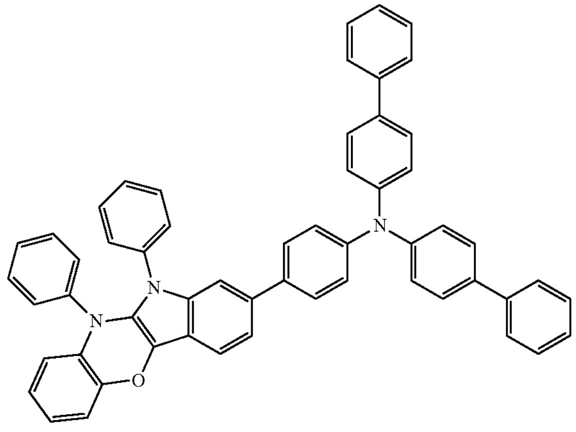

B26
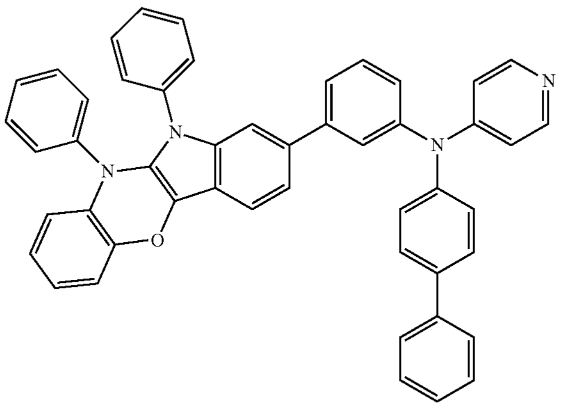
B27
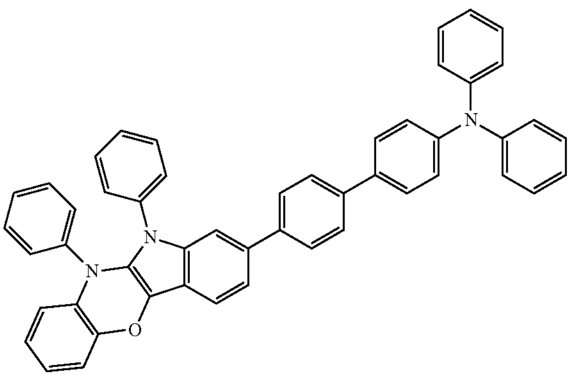
B28
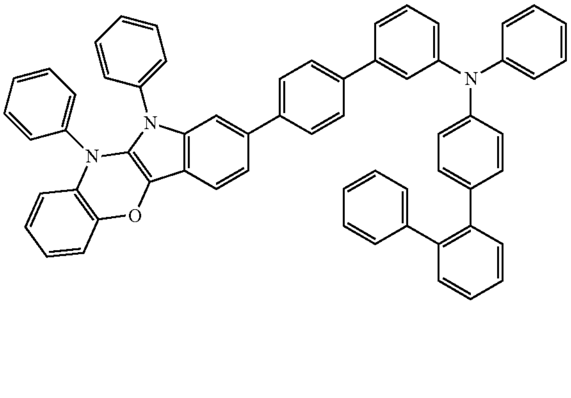
B29
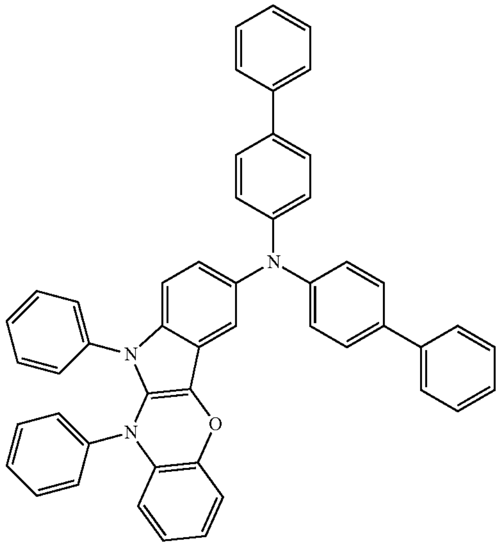
B30
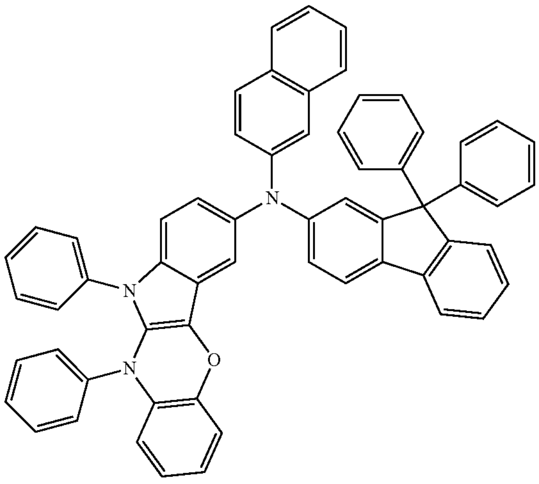
B31
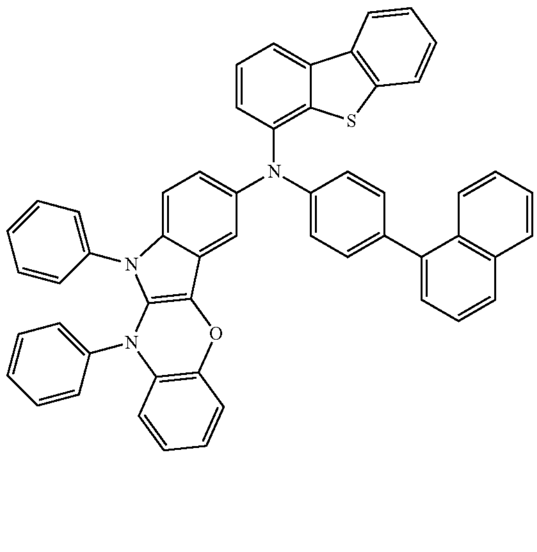

-continued
B32
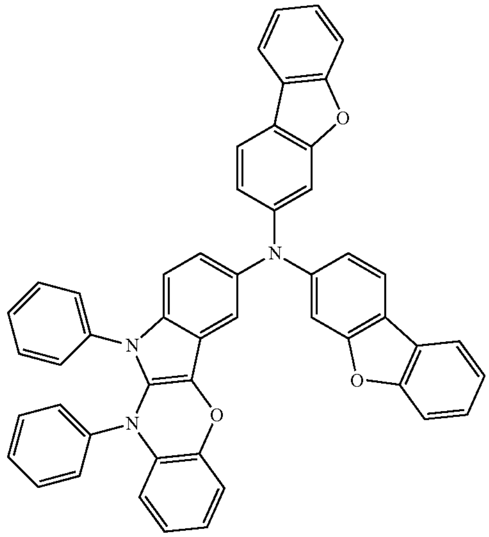
B33
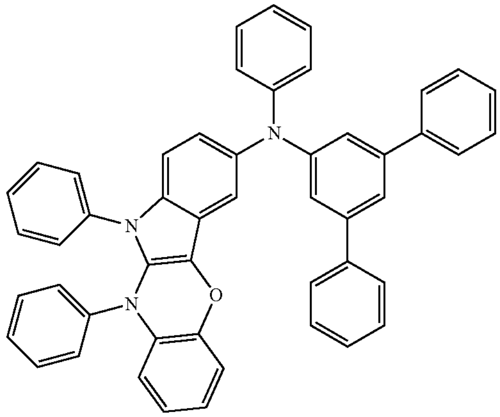
B34
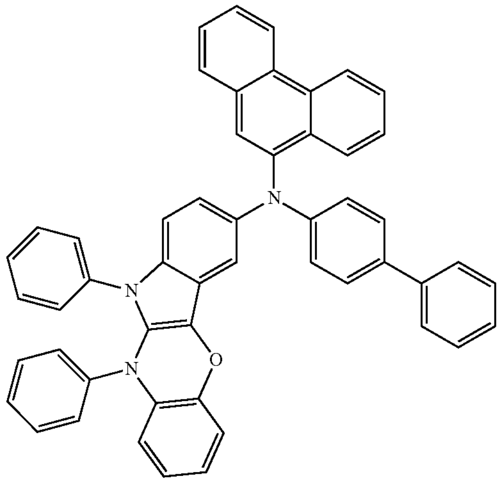
-continued
B35
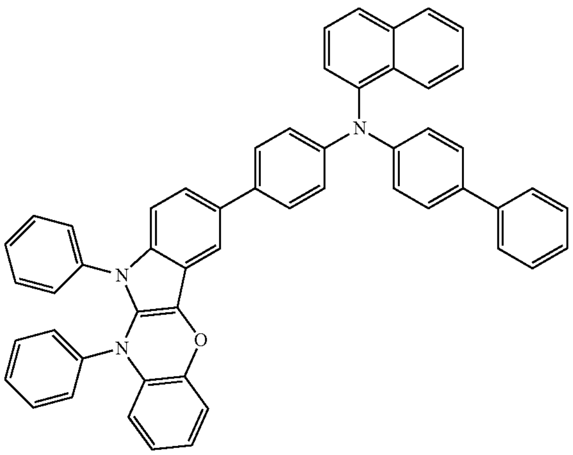
B36
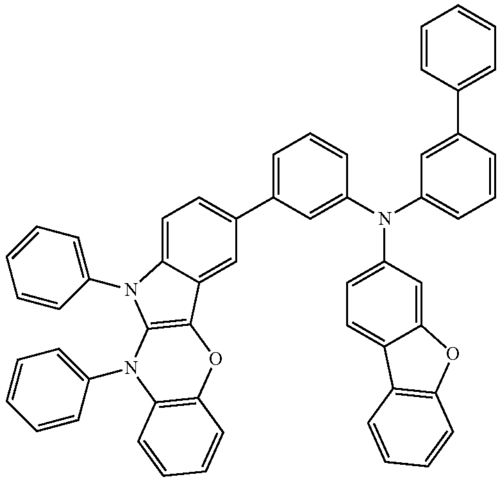
B37
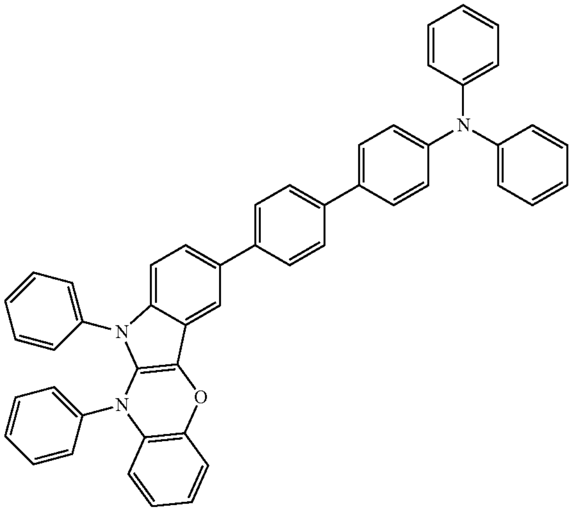

-continued
B38
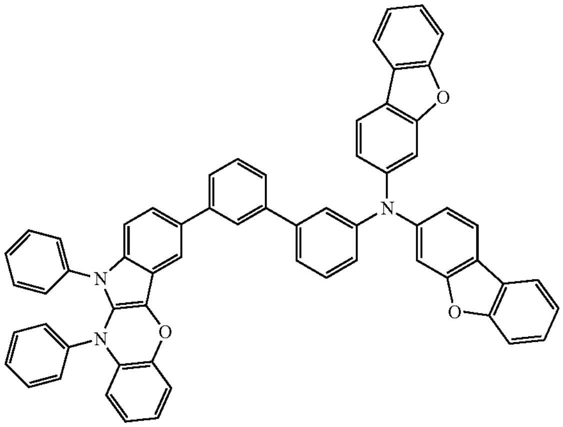
B39
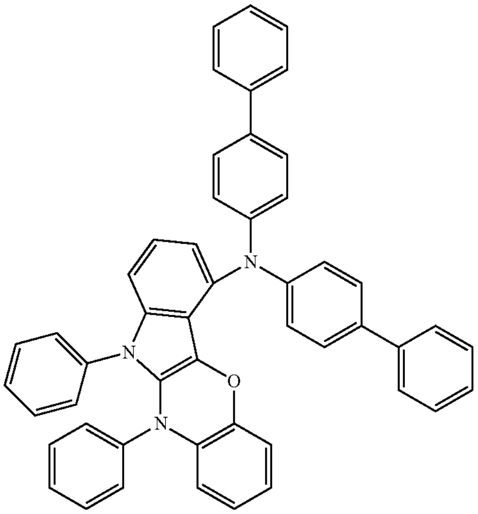
B40
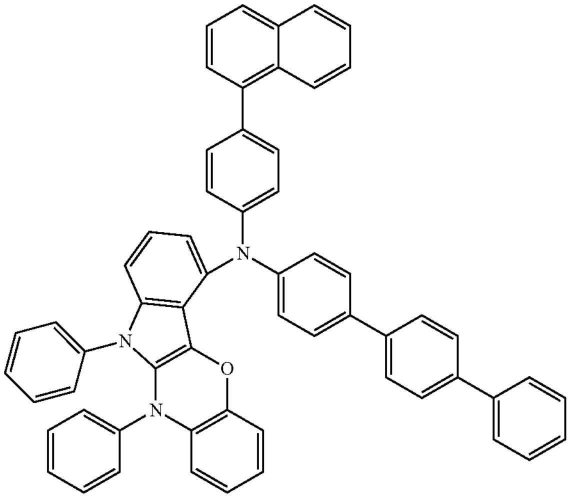
-continued
B41
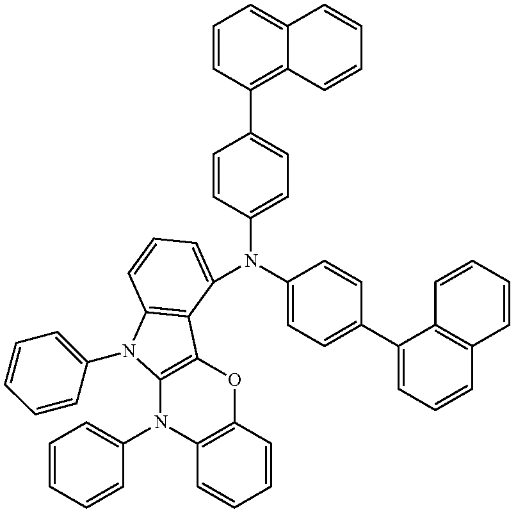
B42
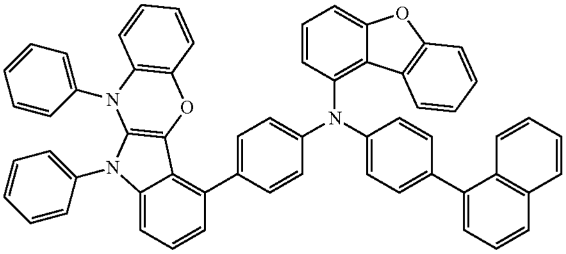
B43
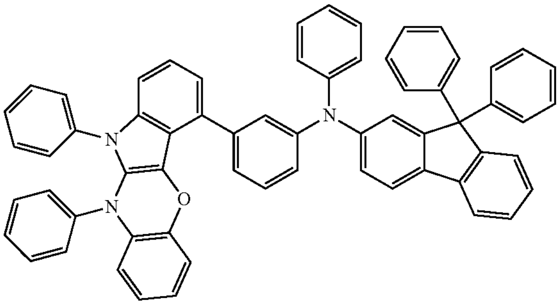
B44
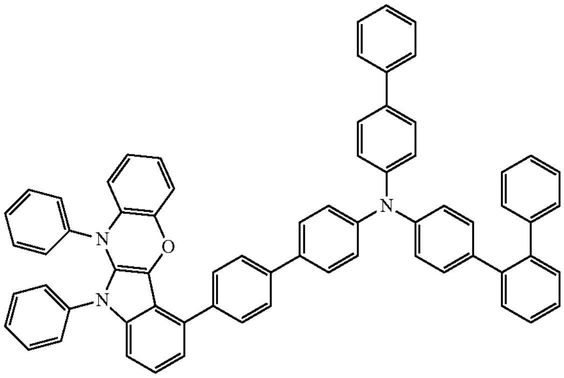

-continued
B45
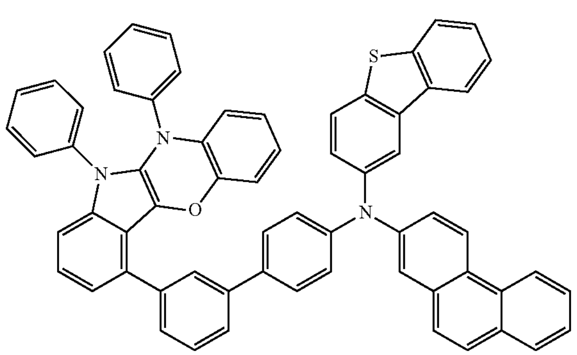
B46
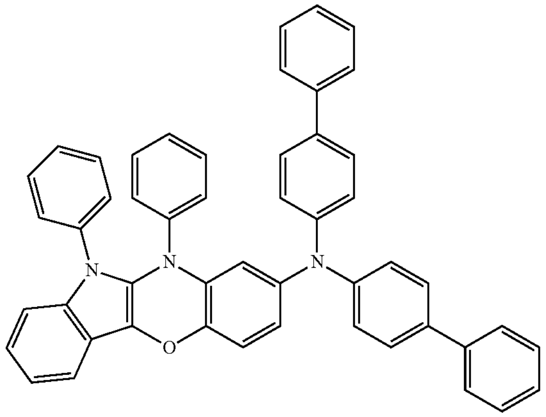
B47
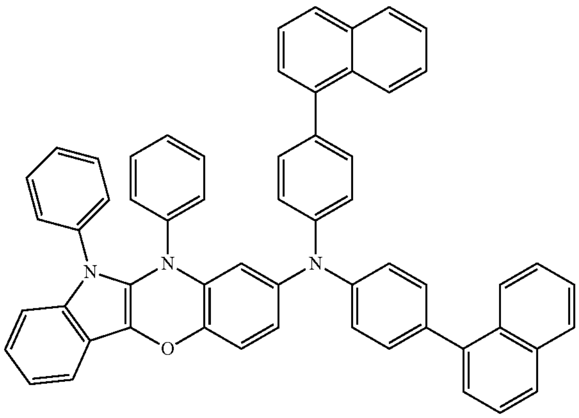
-continued
B48
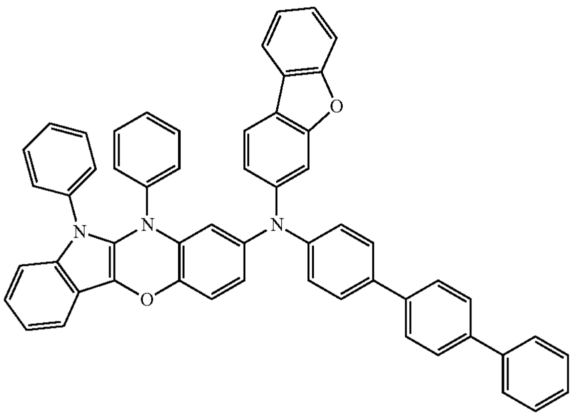
B49
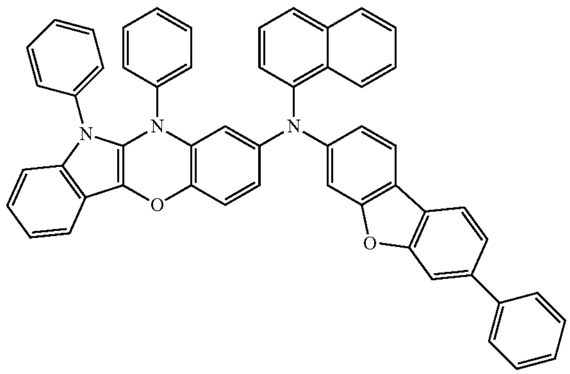
B50
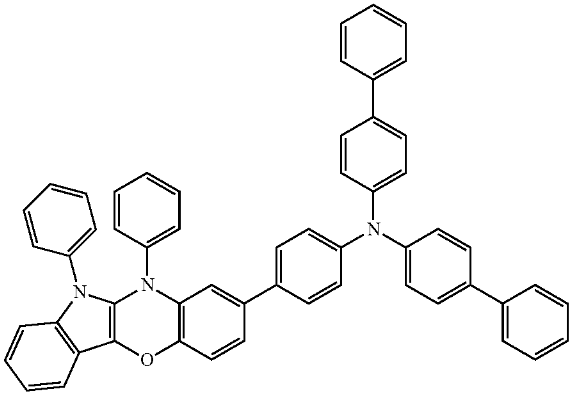

-continued
B51
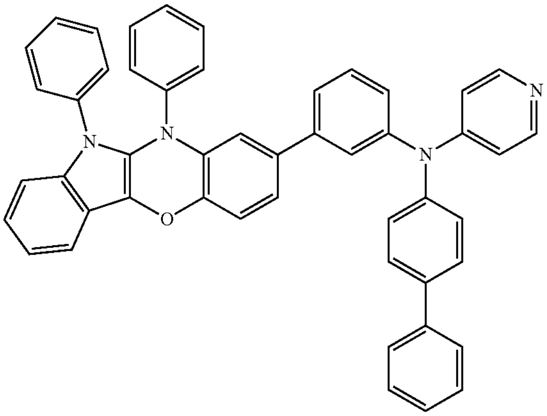
B52
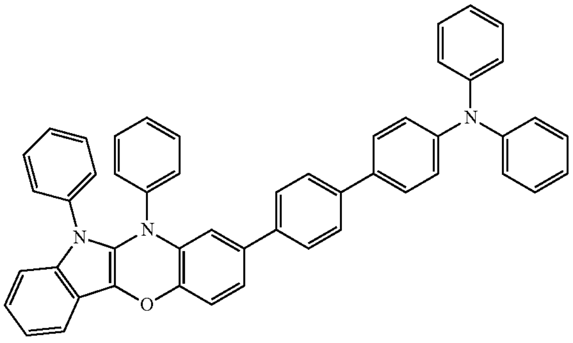
B53
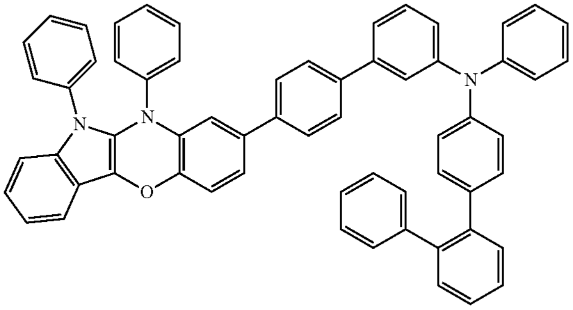
B54
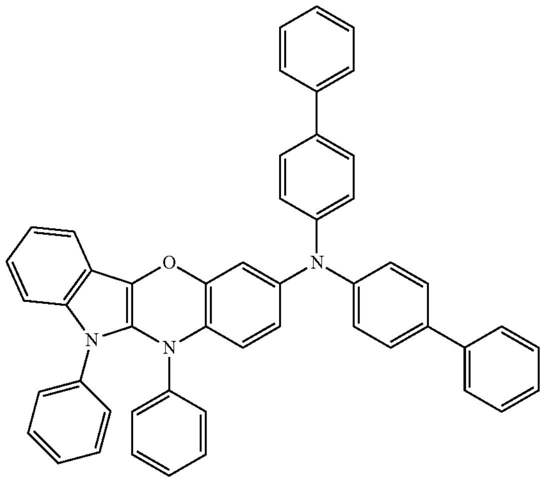
-continued
B55
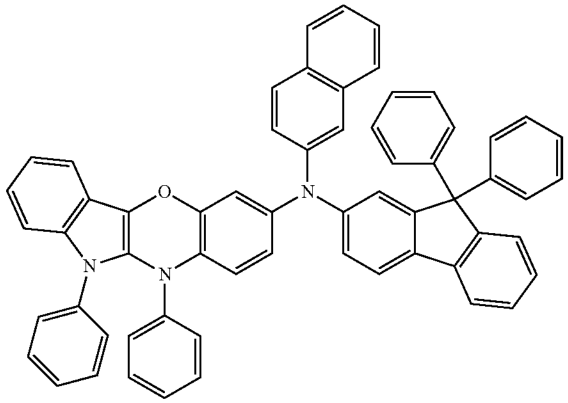
B56
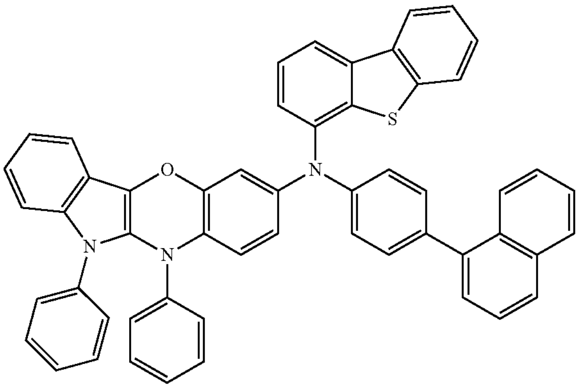
B57
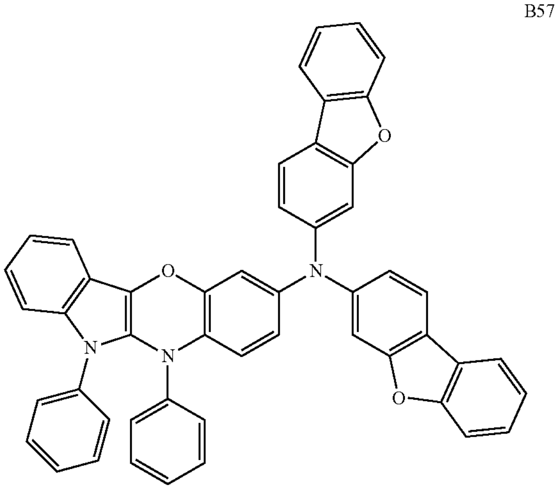

B58
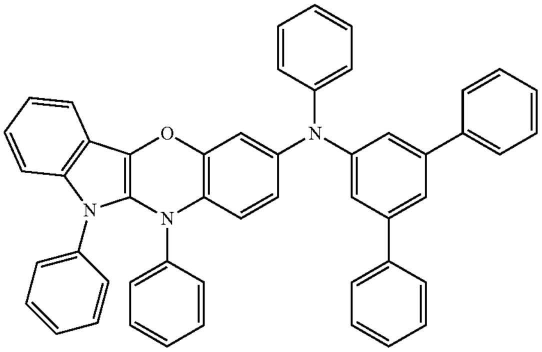
B59
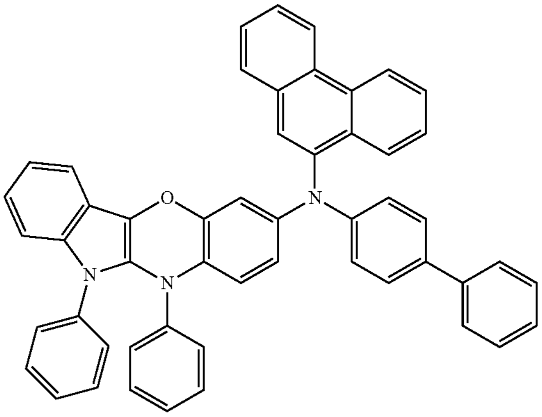
B60
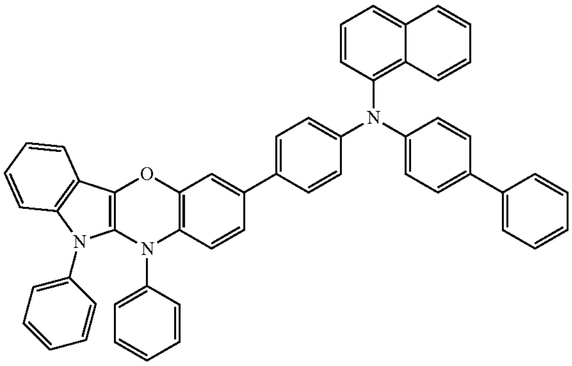
B61
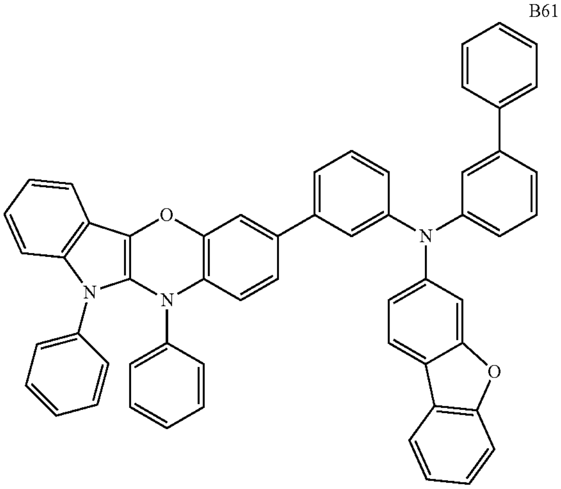
B62
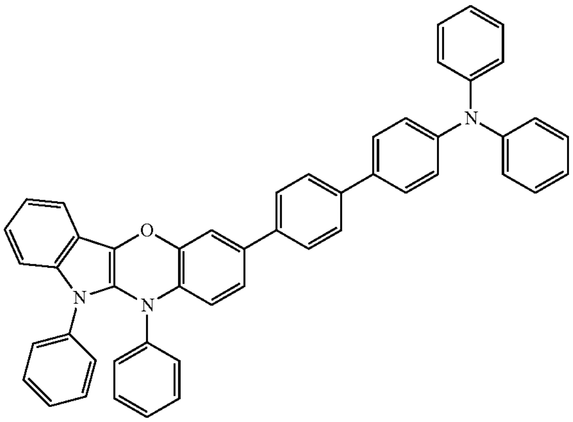
B63
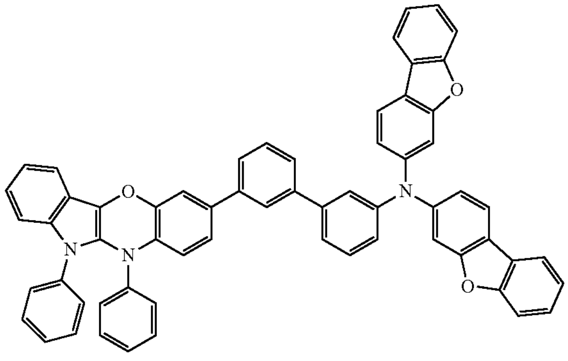

-continued
B64
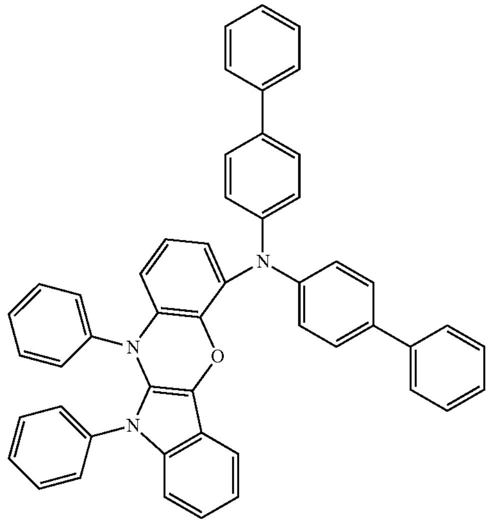
B65
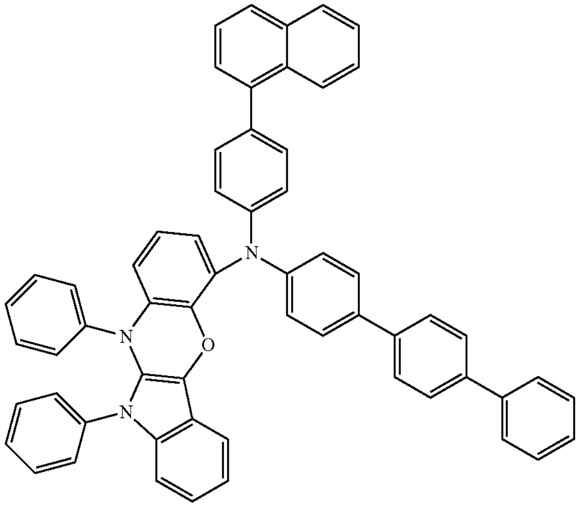
B66
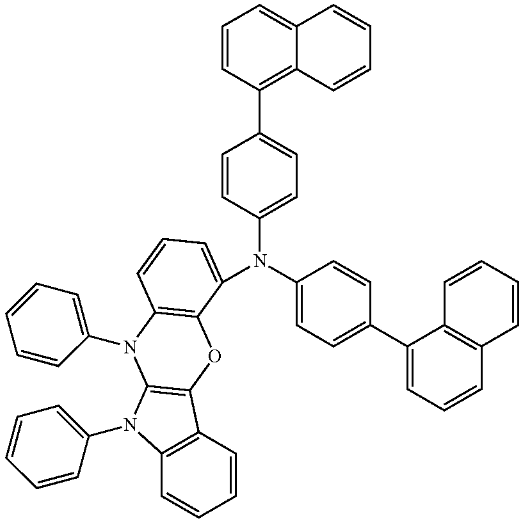
-continued
B67
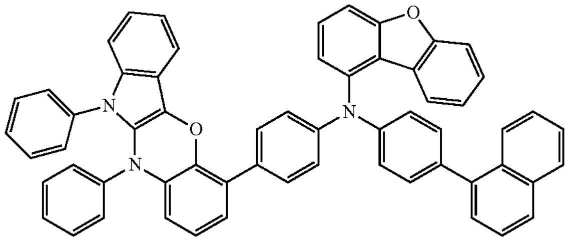
B68
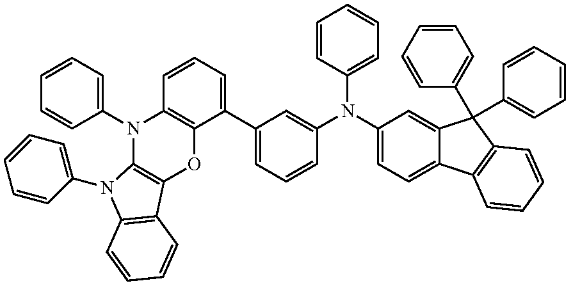
B69
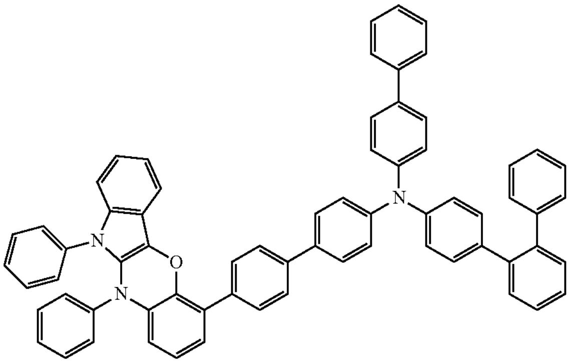
B70
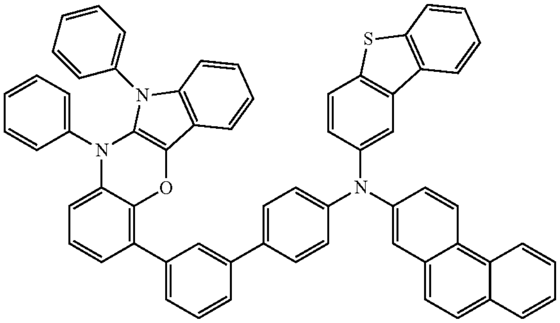

[Compound Group 3]
C1
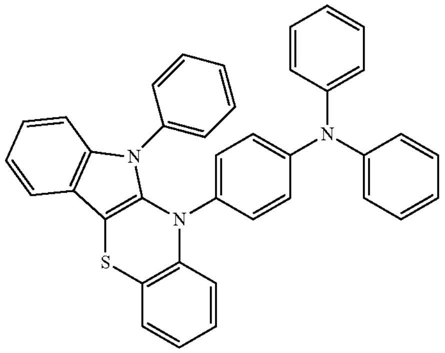
C2
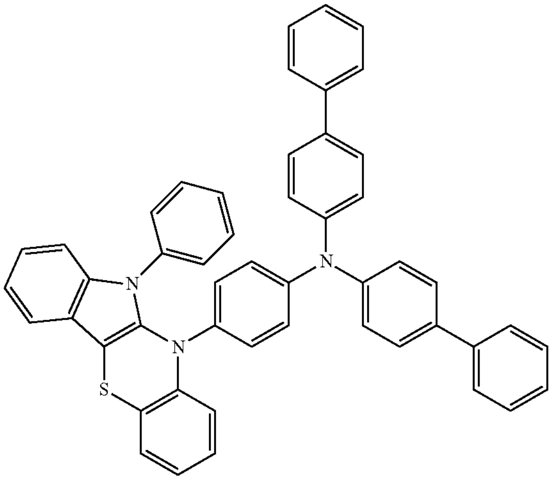
C3
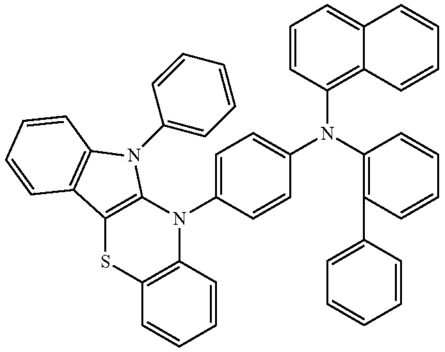
C4
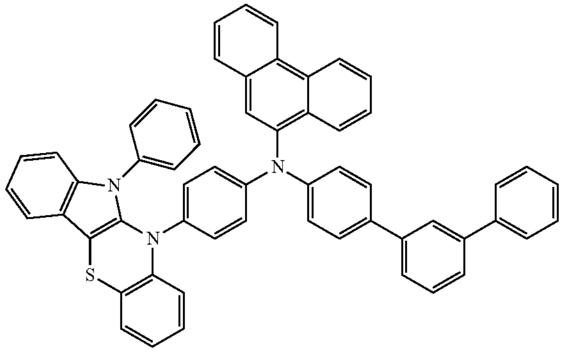
-continued
C5
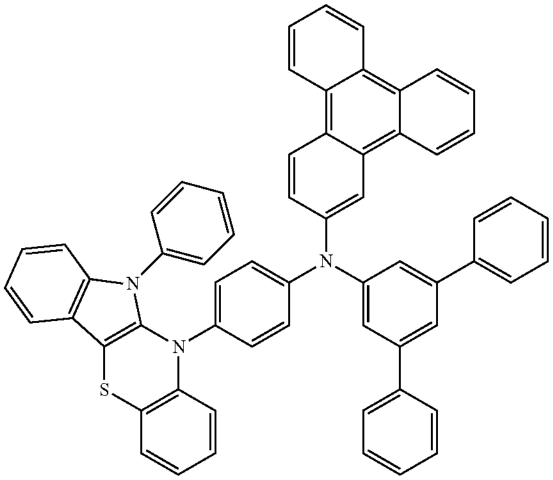
C6
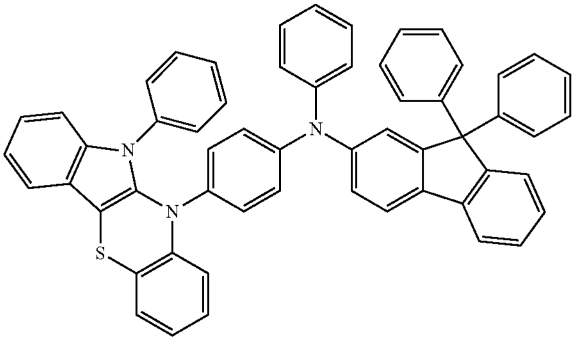
C7
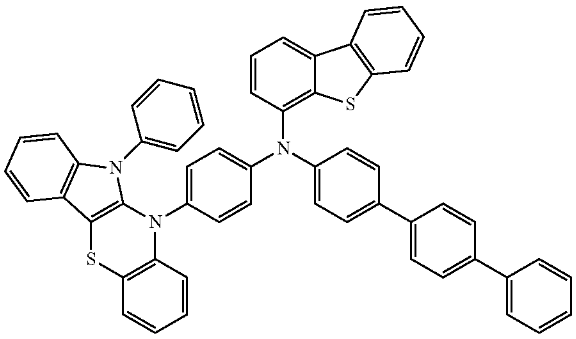

-continued
C8
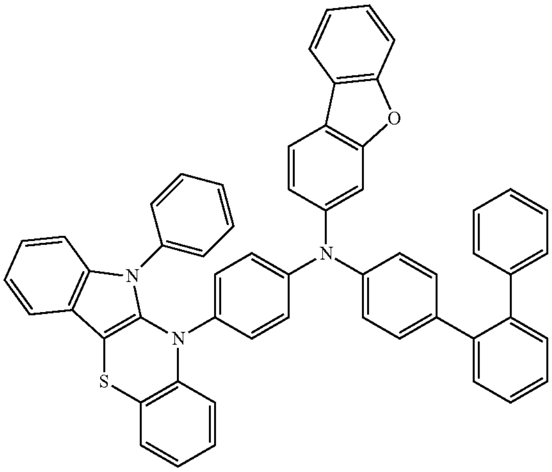
C9
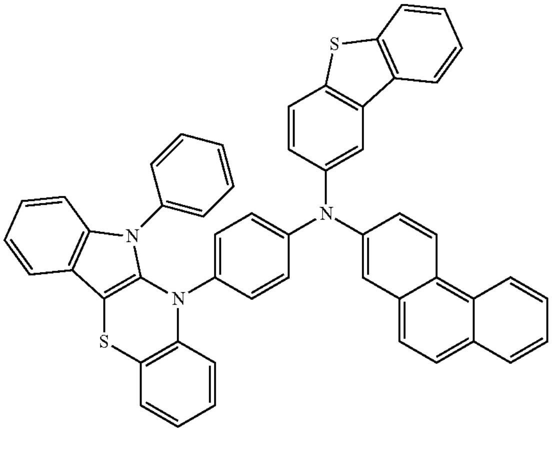
C10
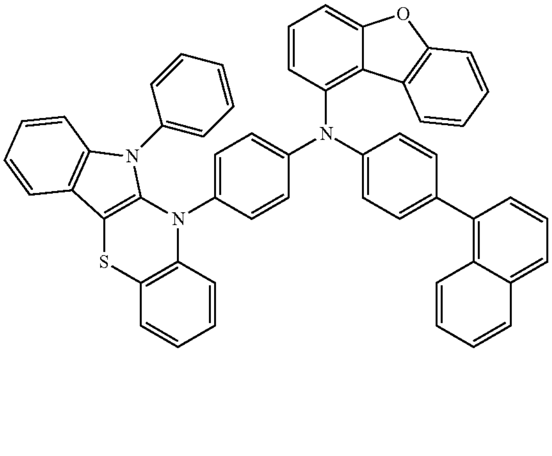
-continued
C11
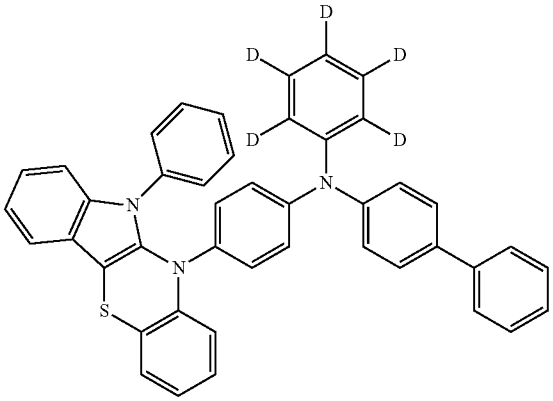
C12
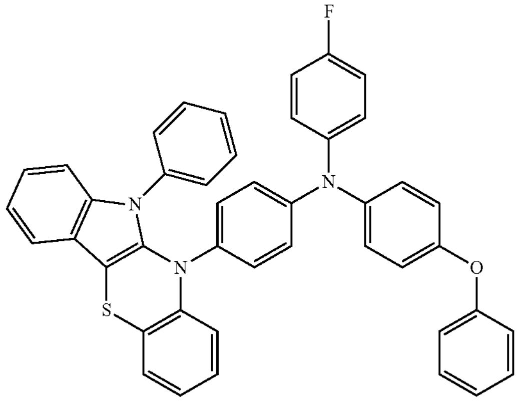
C13
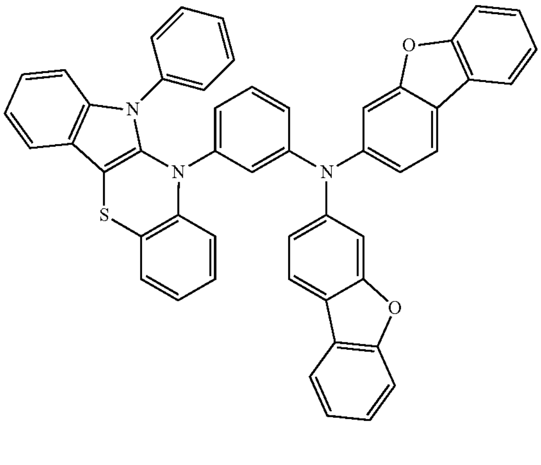

-continued
C14
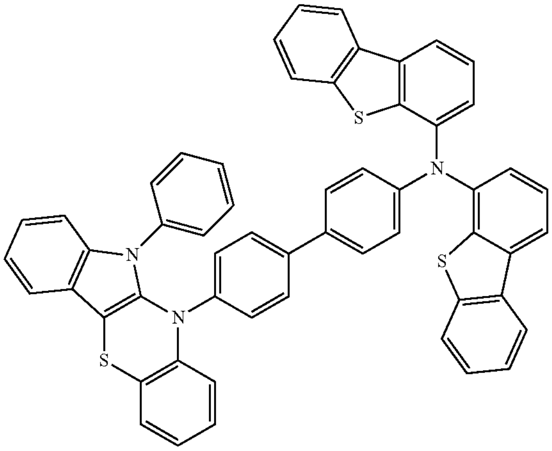
C15
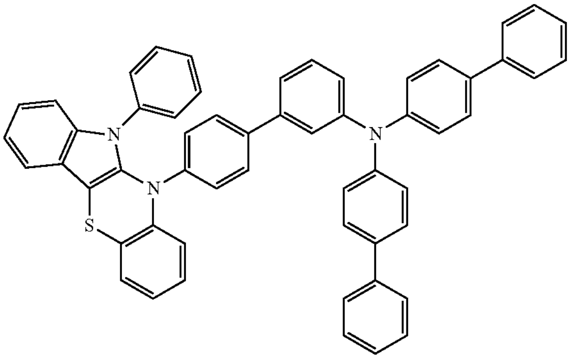
C16
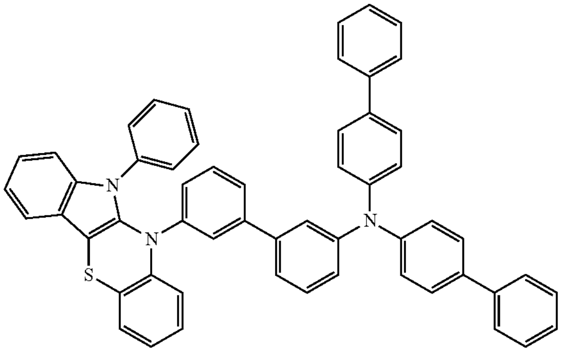
-continued
C17
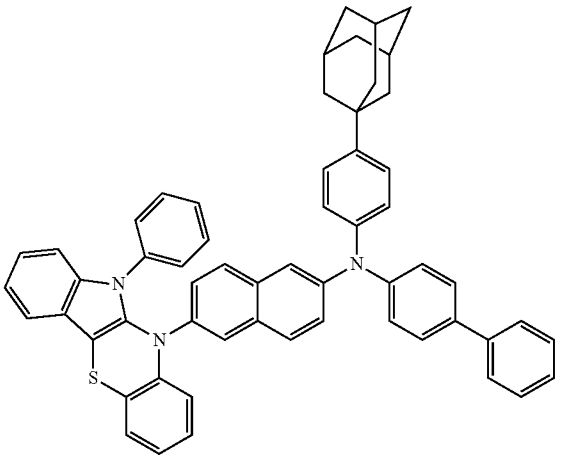
C18
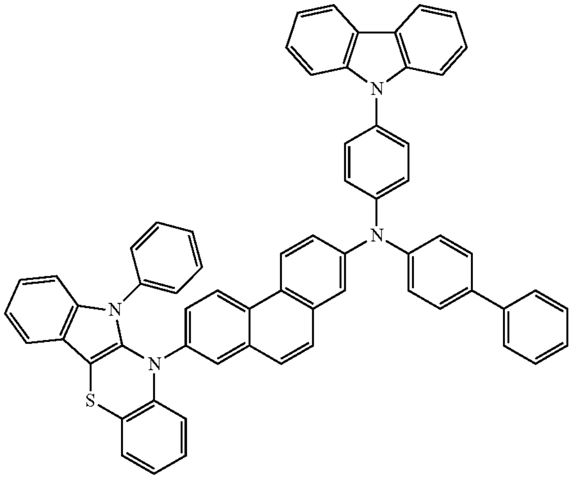
C19
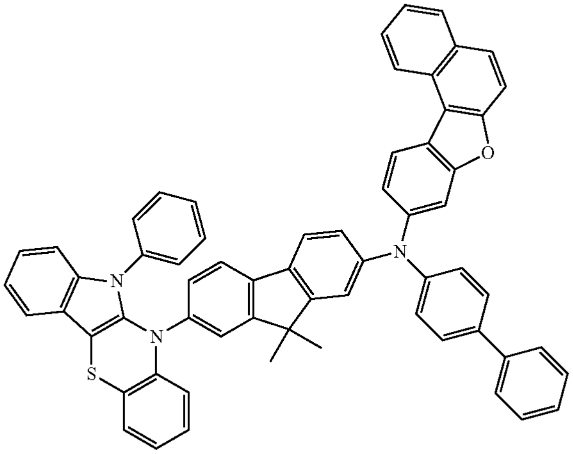

-continued
C20
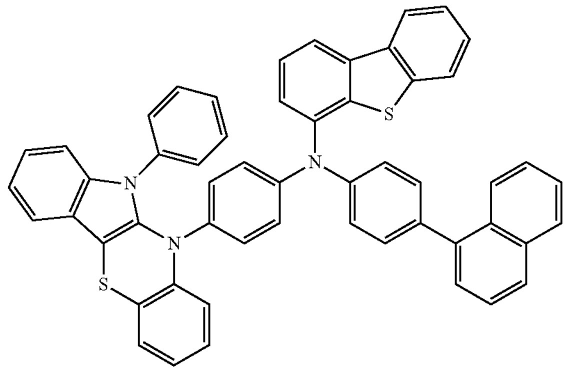
C21
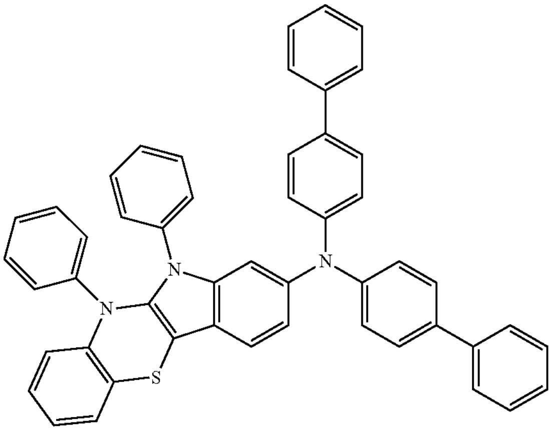
C22
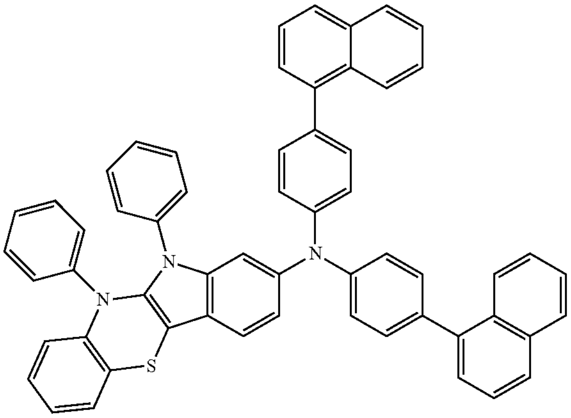
-continued
C23
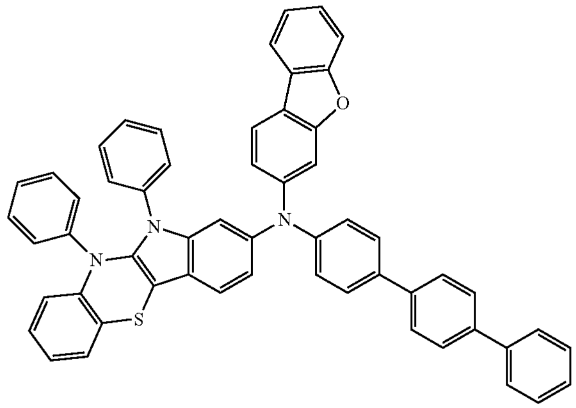
C24
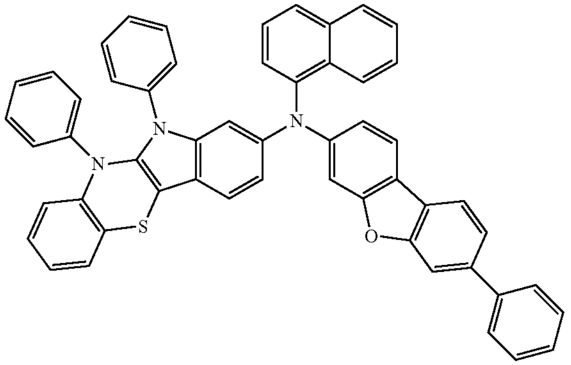
C25
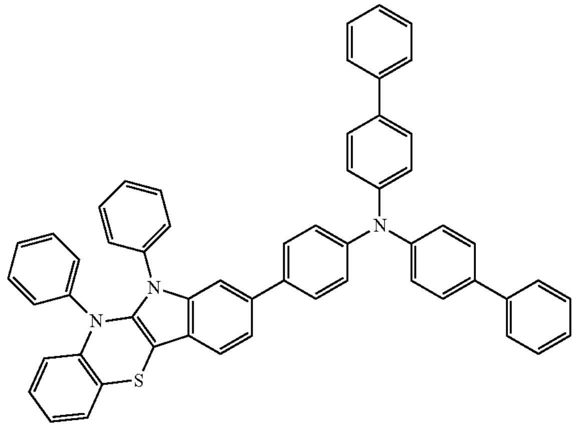

-continued
C26
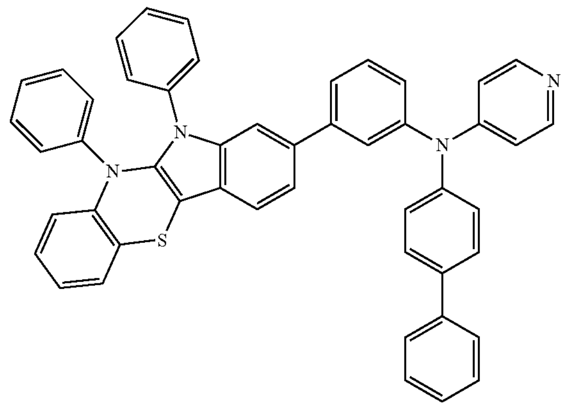
C27
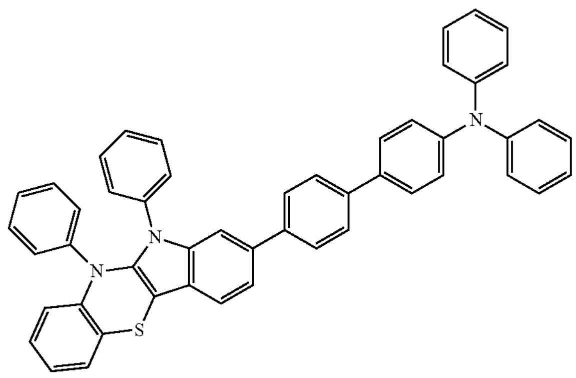
C28
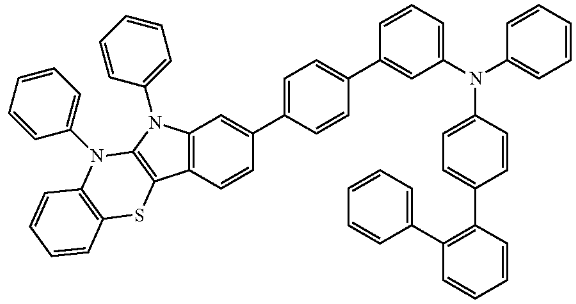
-continued
C29
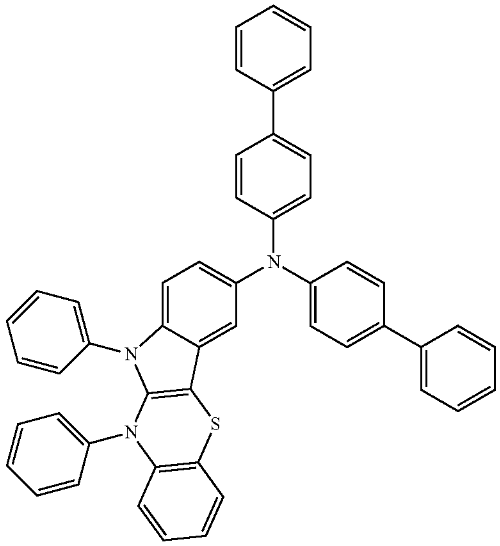
C30
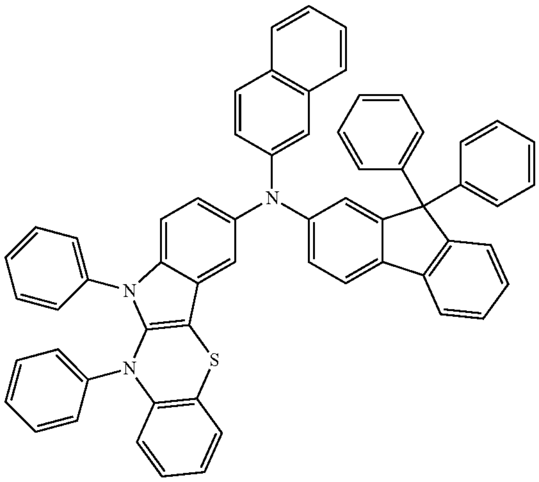
C31
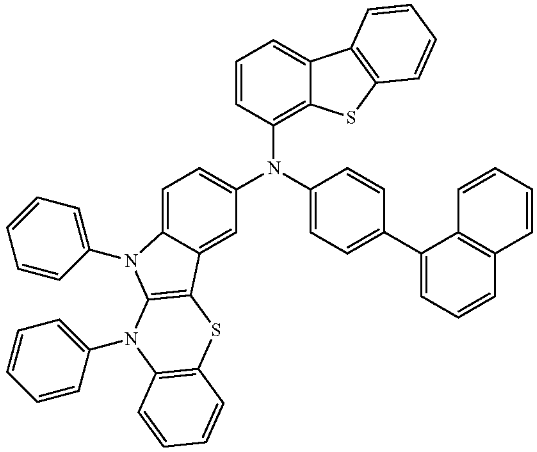

-continued
C32
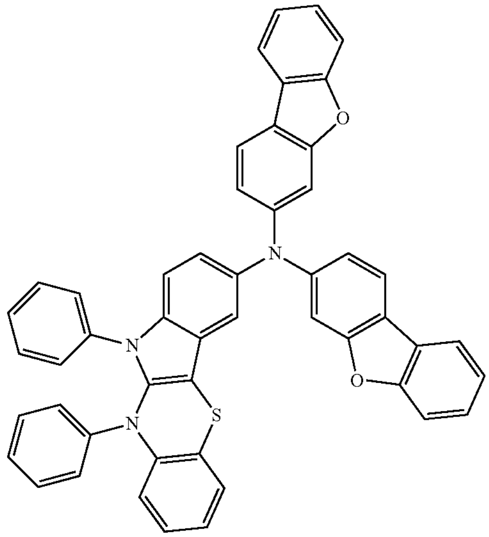
C33
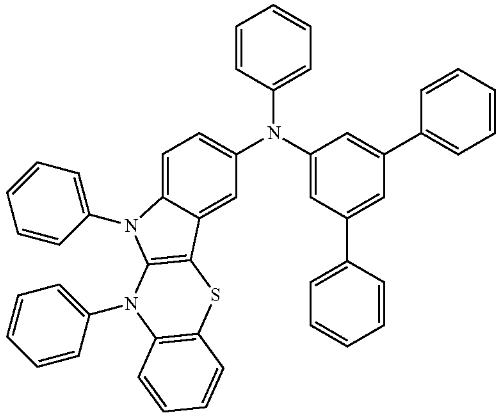
C34
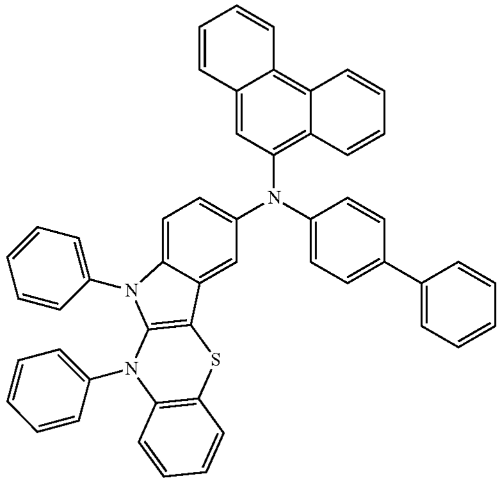
-continued
C35
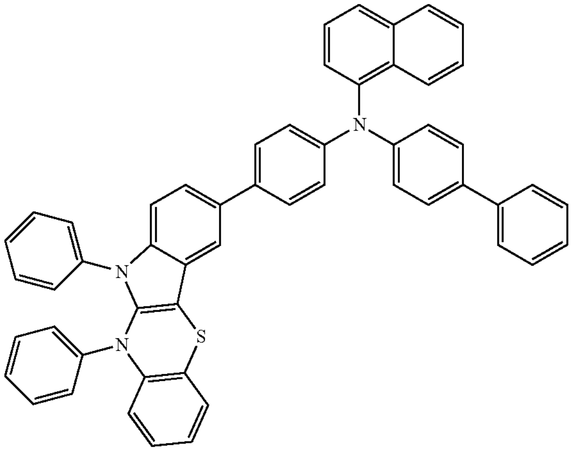
C36
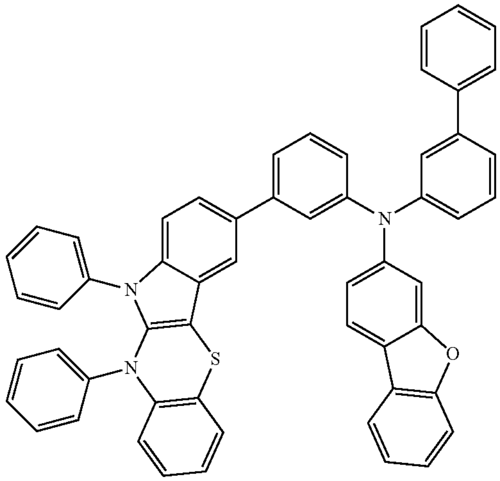
C37
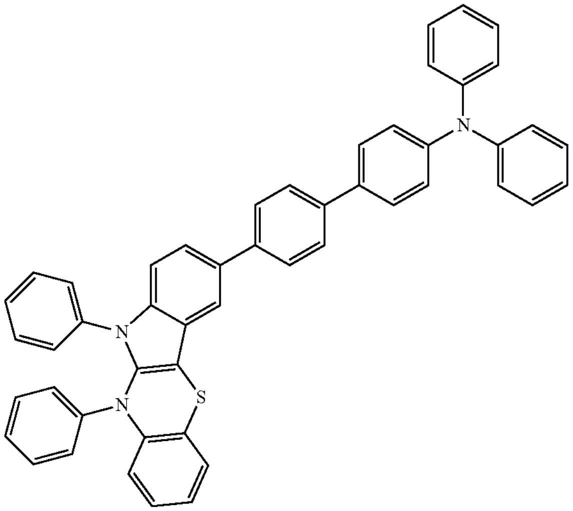

-continued
C38
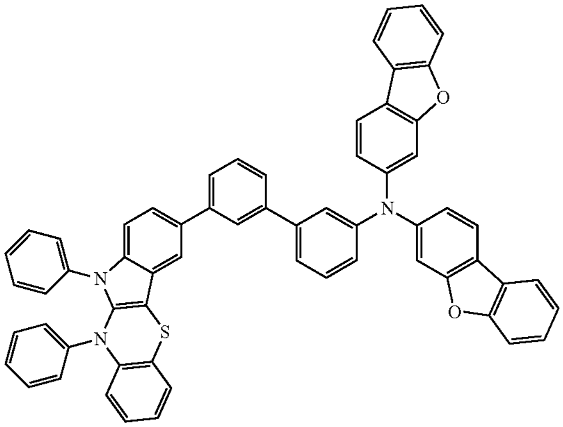
C39
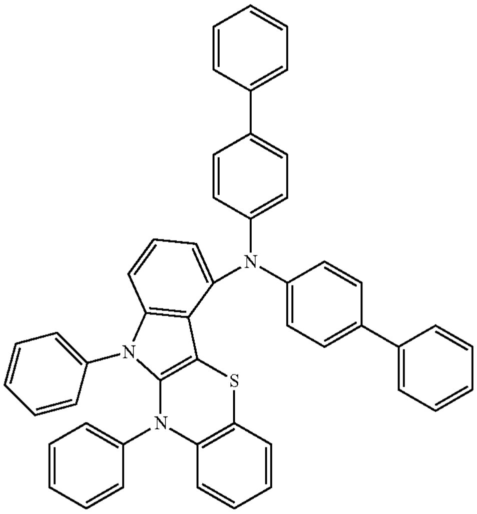
C40
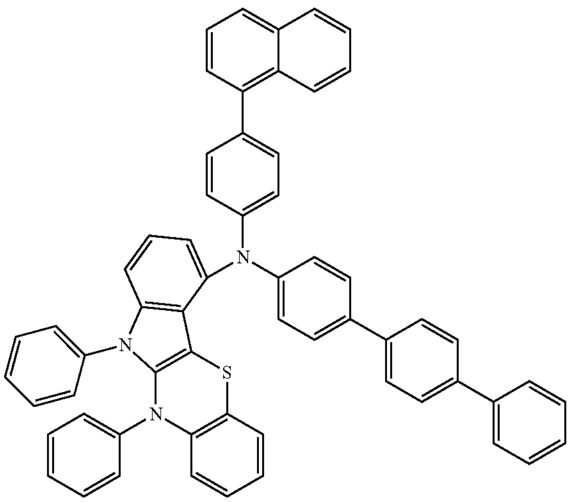
-continued
C41
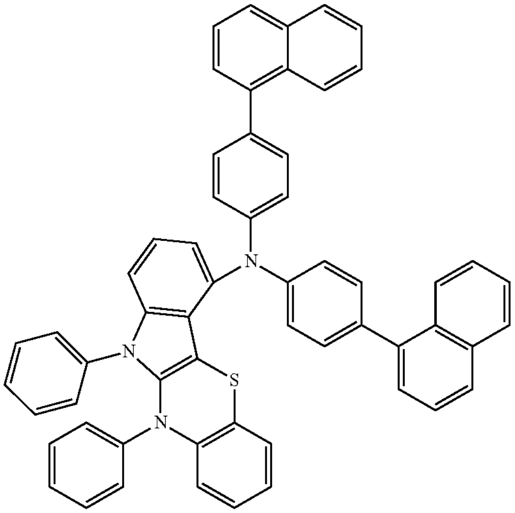
C42
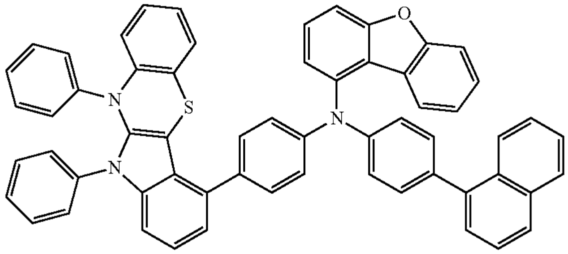
C43
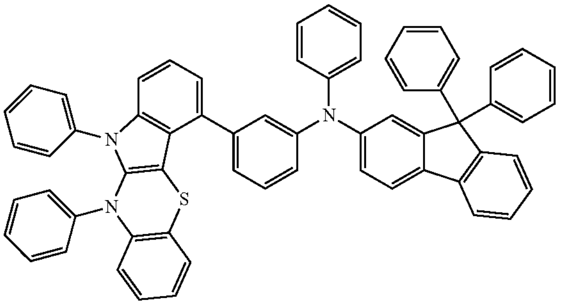
C44
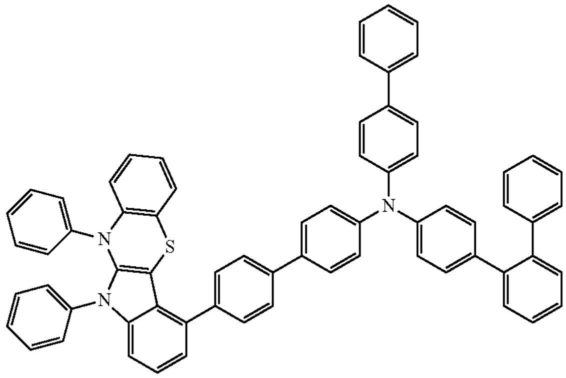

-continued
C45
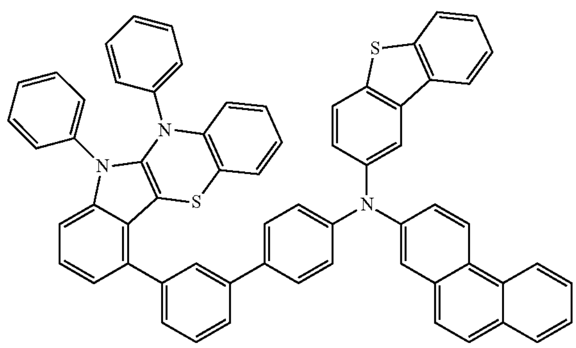
C46
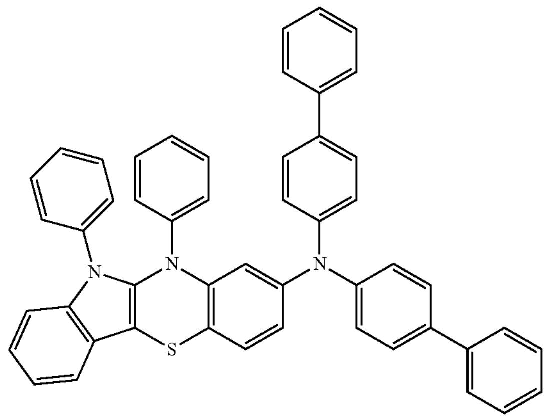
C47
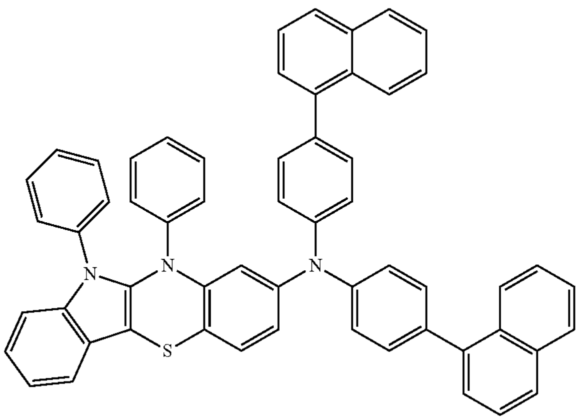
-continued
C48
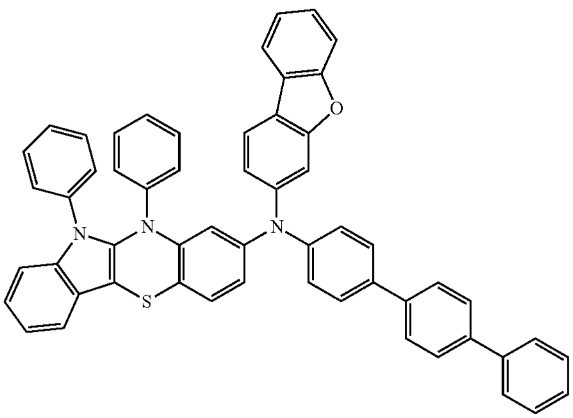
C49
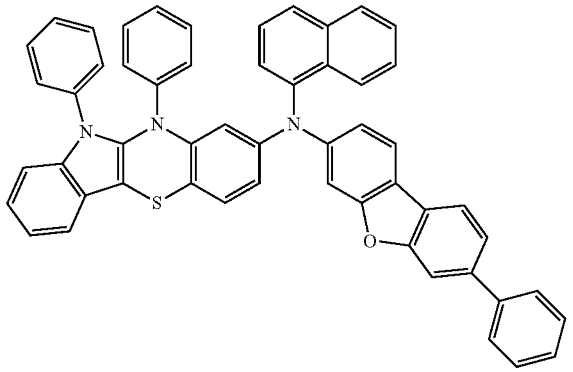
C50
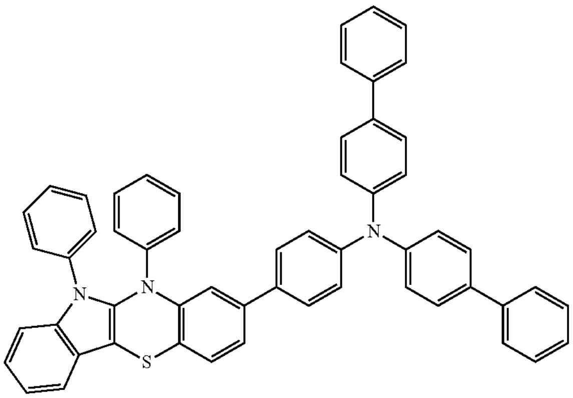

-continued
C51
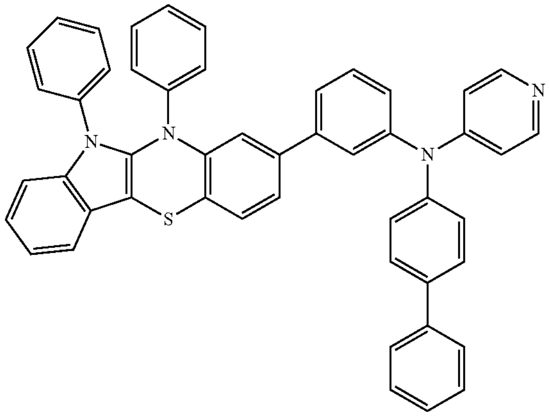
C52
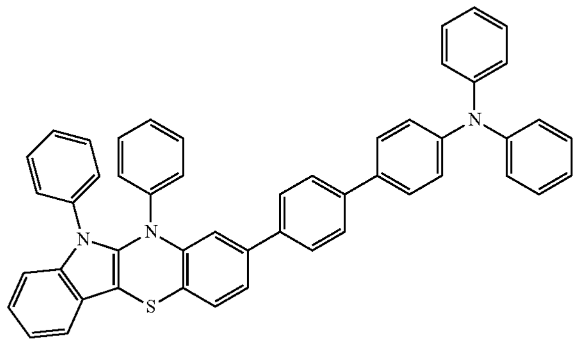
C53
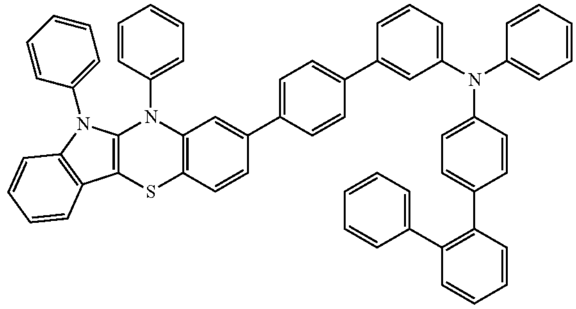
C54
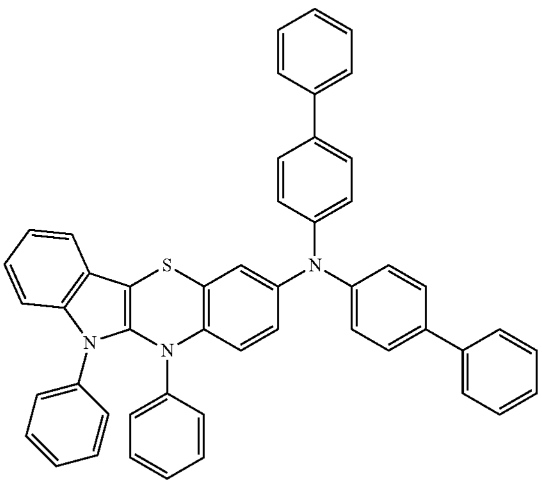
-continued
C55
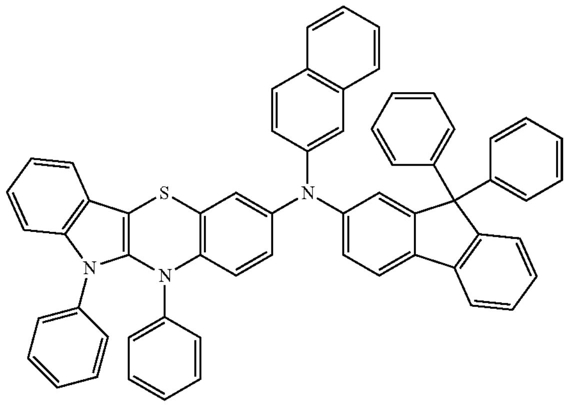
C56
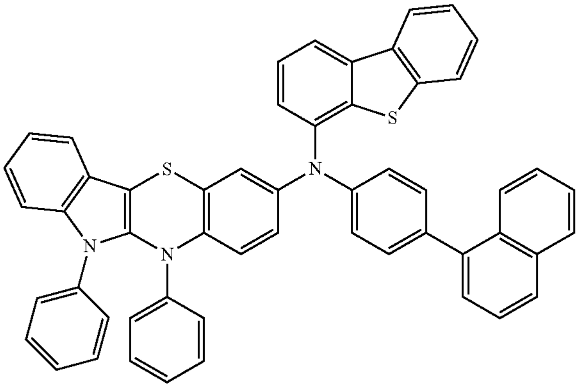
C57
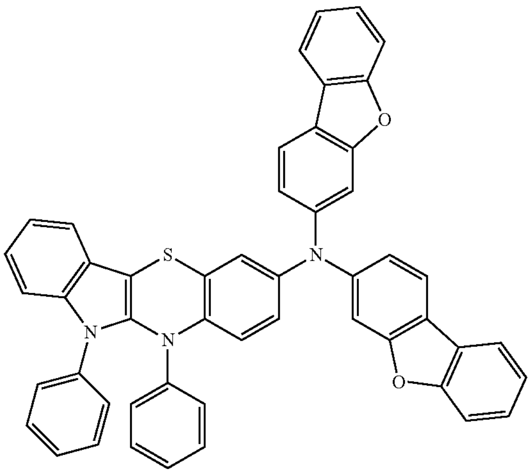

-continued
C58
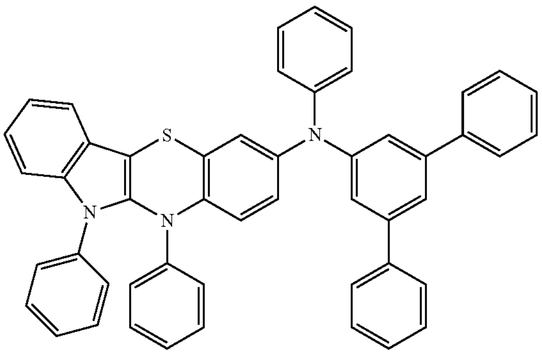
C59
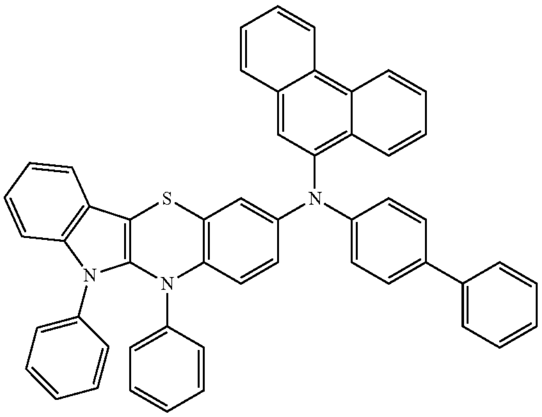
C60
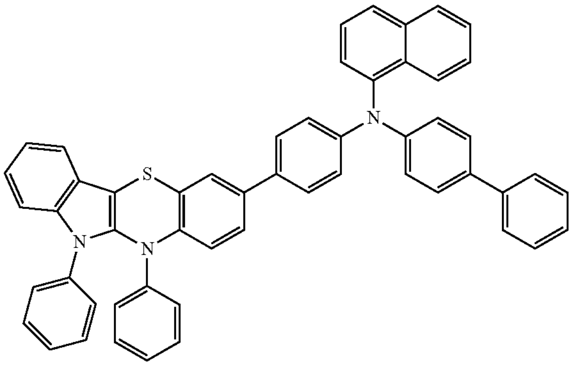
-continued
C61
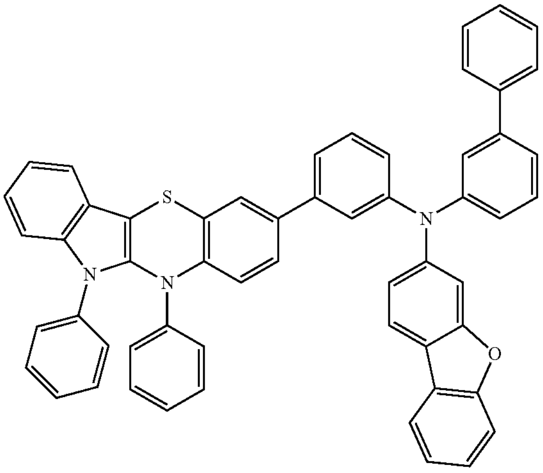
C62
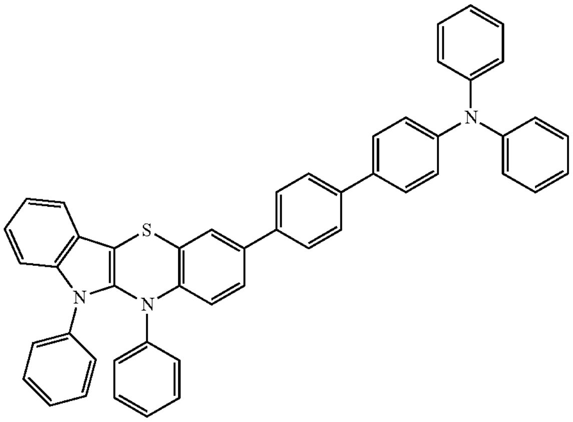
C63
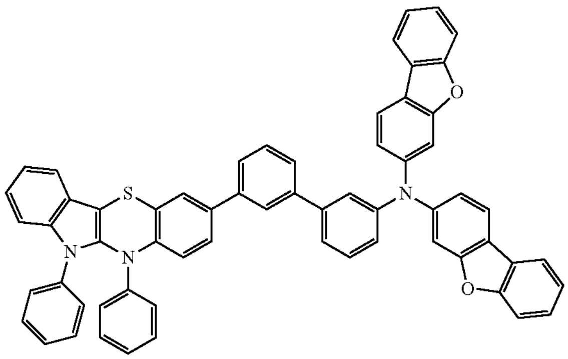

C64
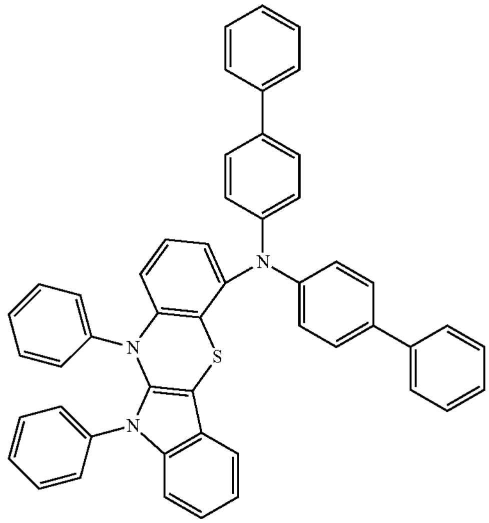
C65
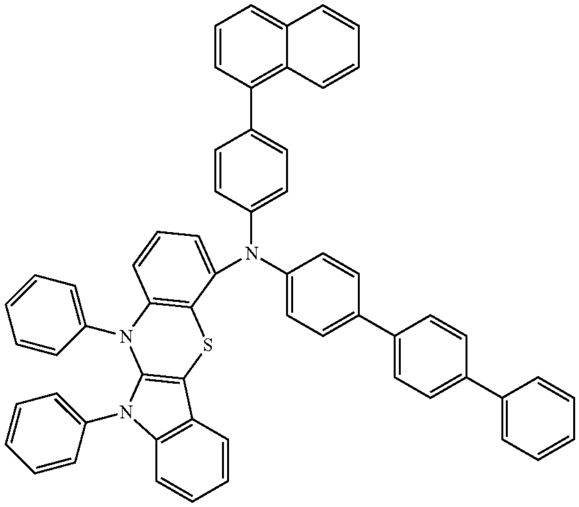
C66
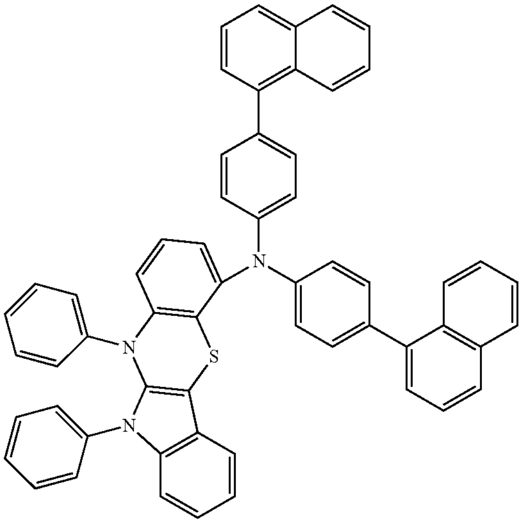
C67
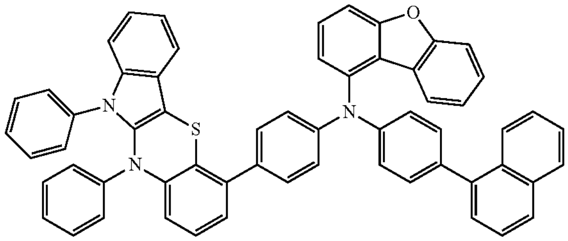
C68
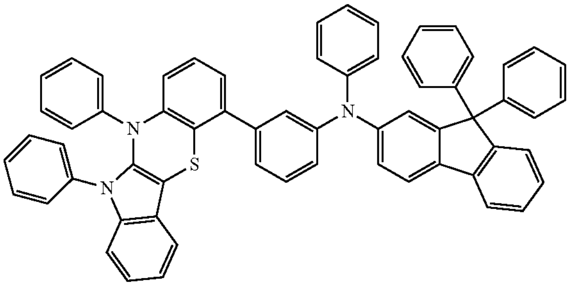
C69
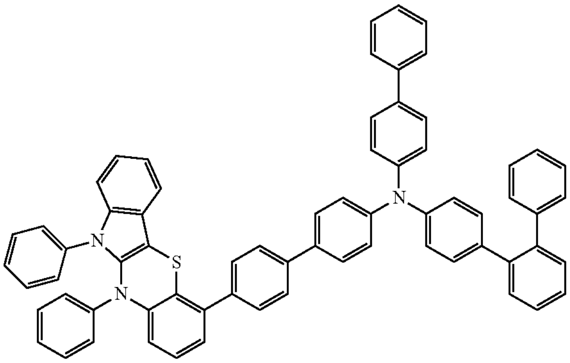
C70
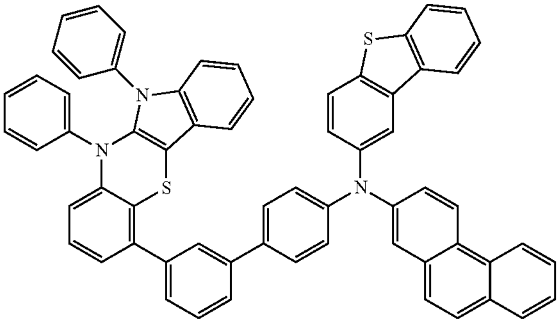

[Compound Group 4]
D1
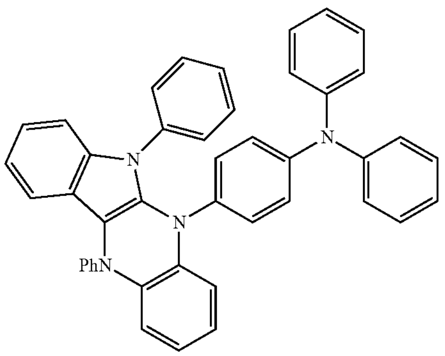
D2
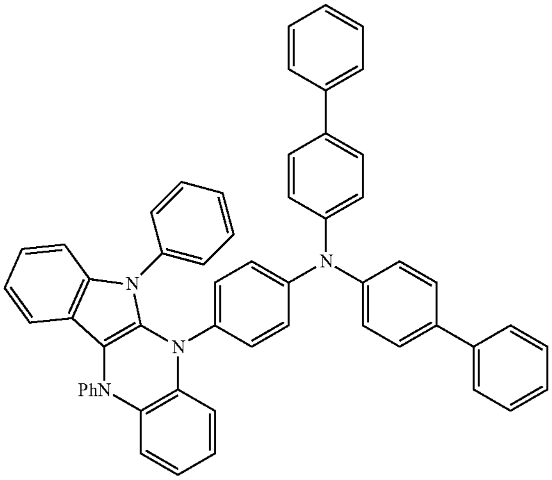
D3
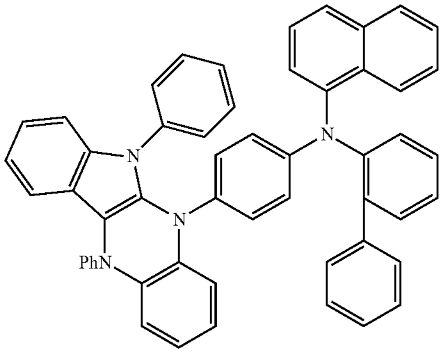
D4
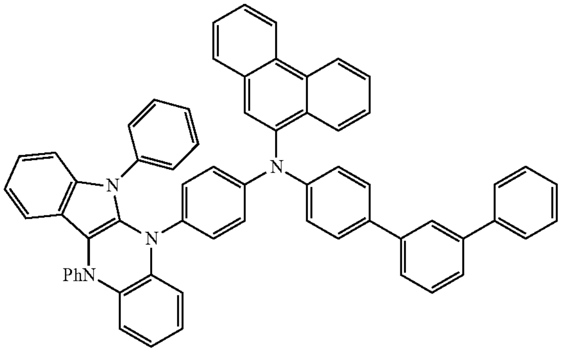
-continued
D5
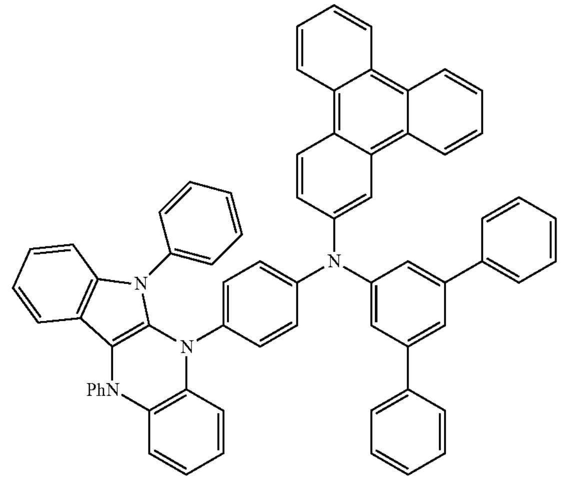
D6
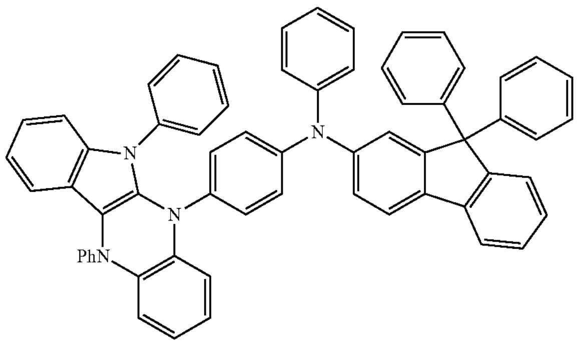
D7
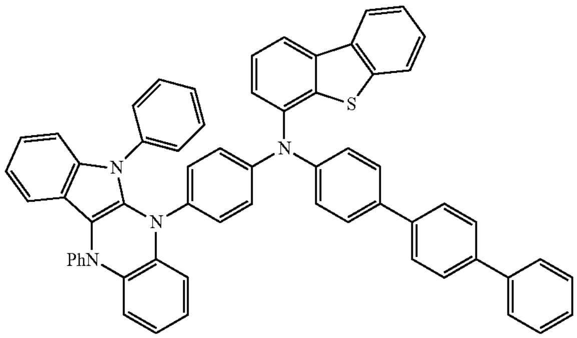

-continued
D8
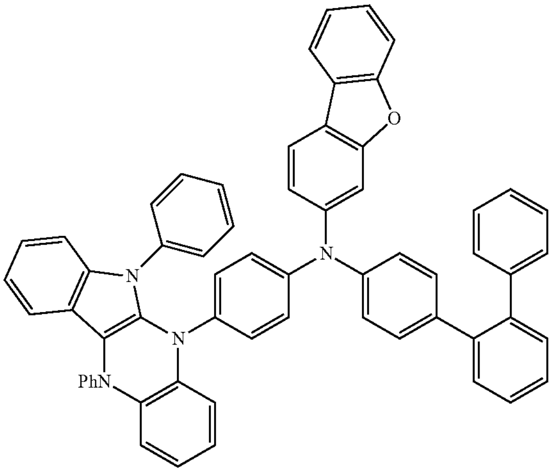
D9
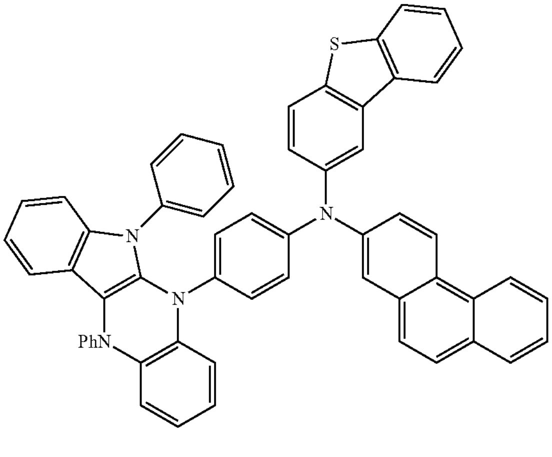
D10
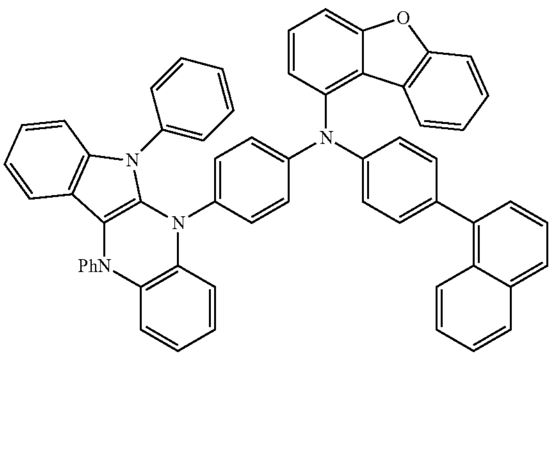
-continued
D11
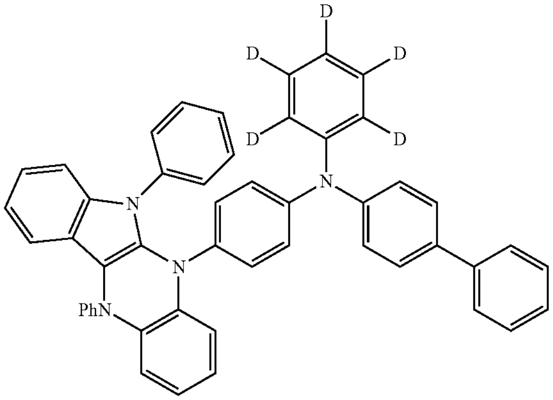
D12
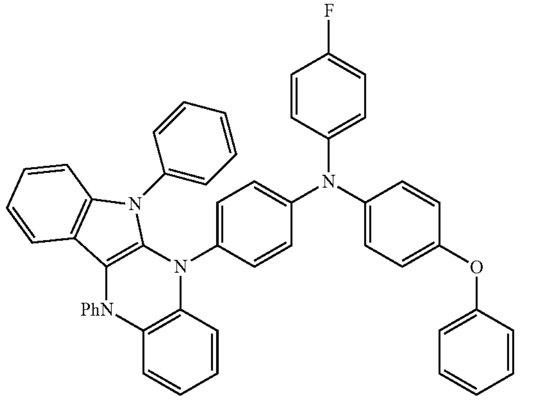
D13
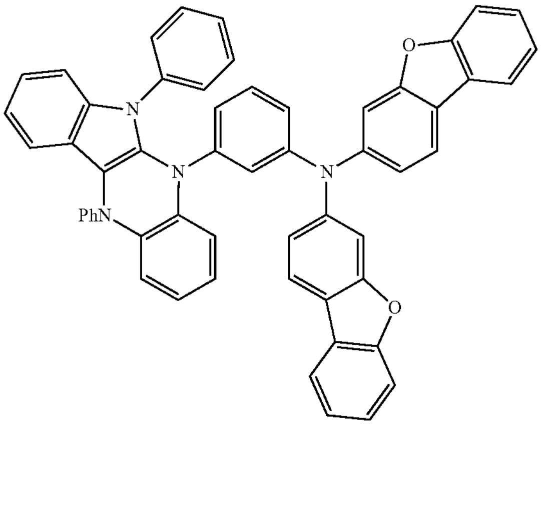

-continued
D14
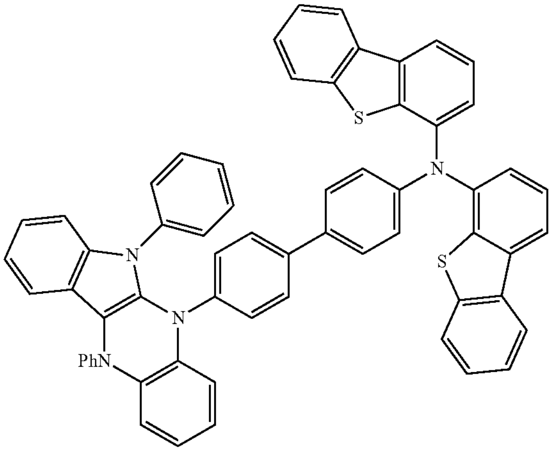
D15
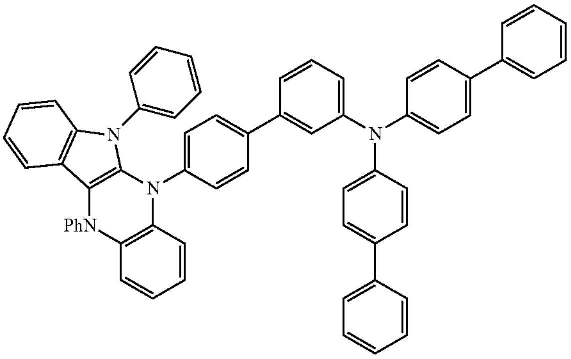
D16
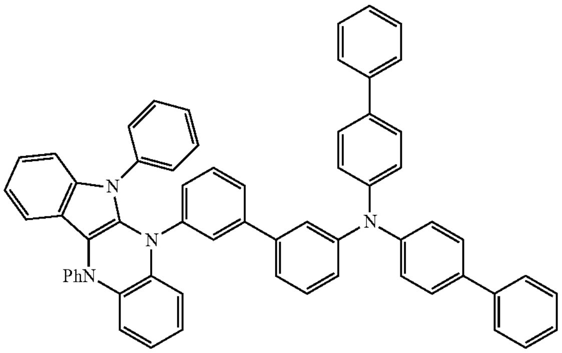
-continued
D17
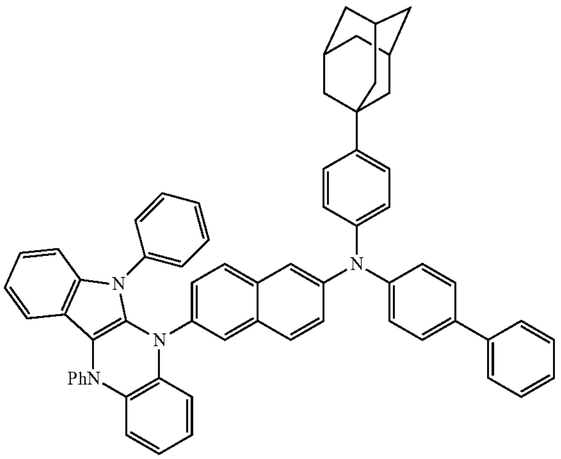
D18
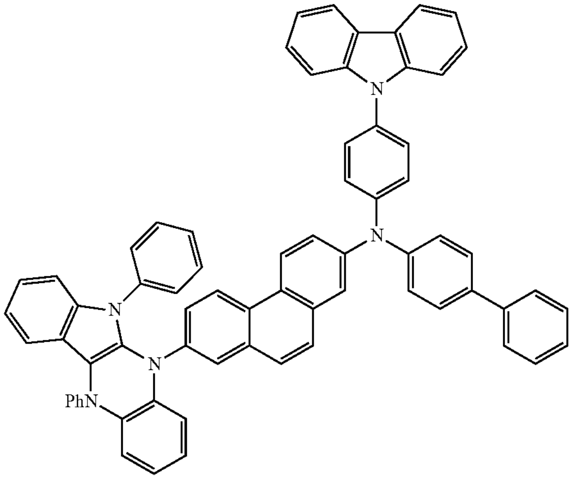
D19
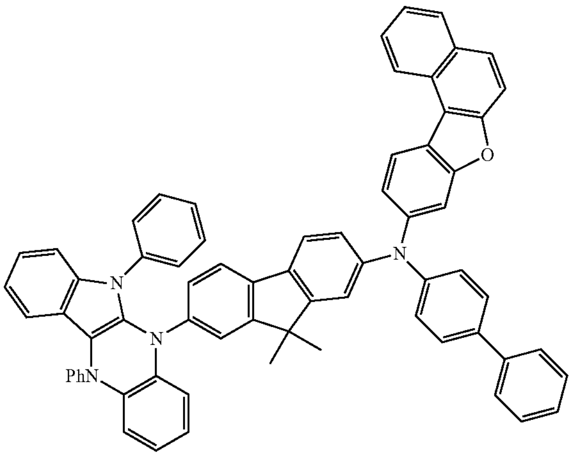

-continued
D20
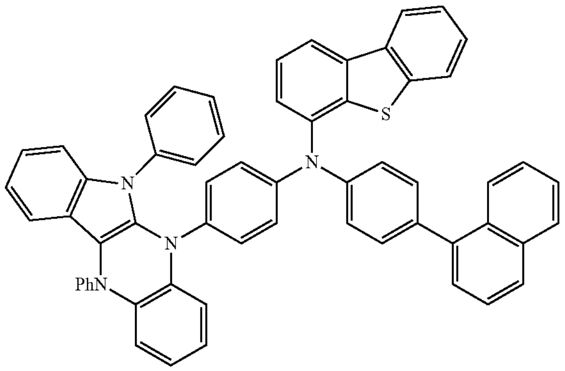
D21
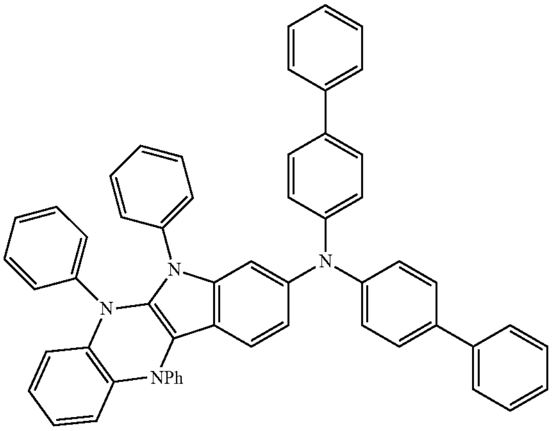
D22
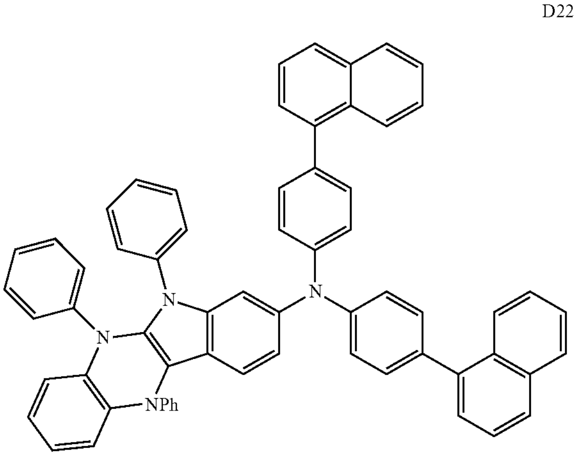
-continued
D23
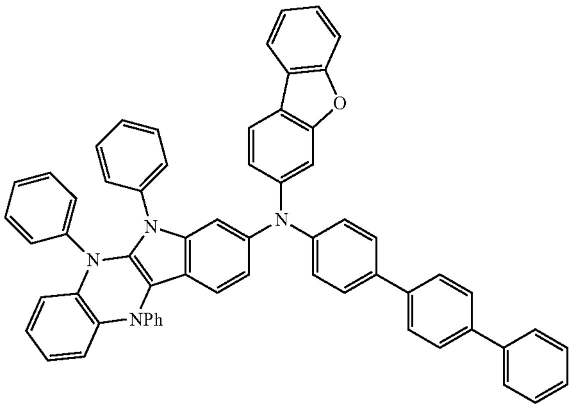
D24
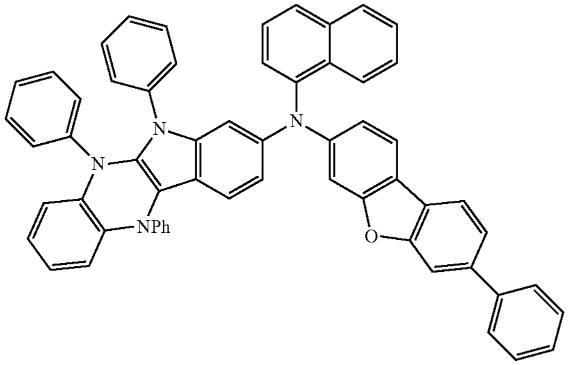
D25
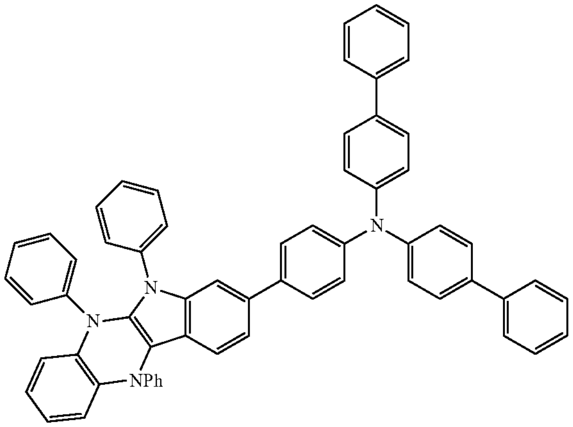

-continued
D26
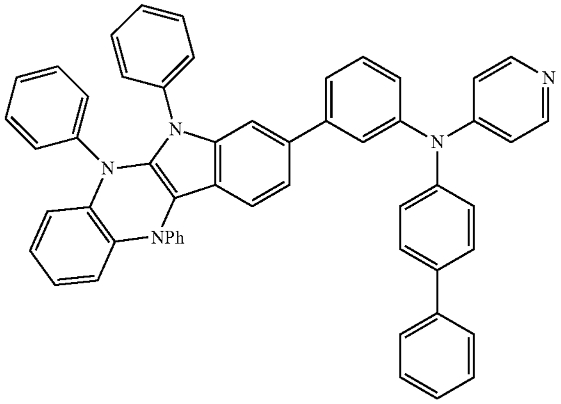
D27
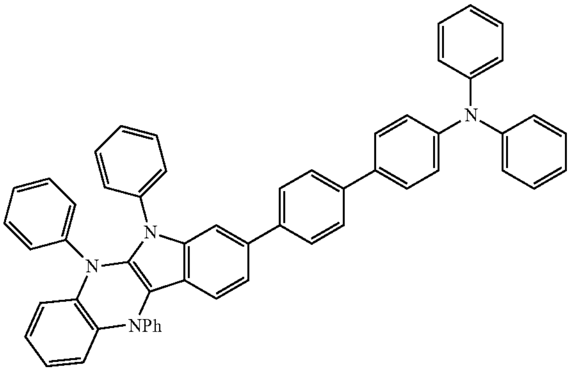
D28
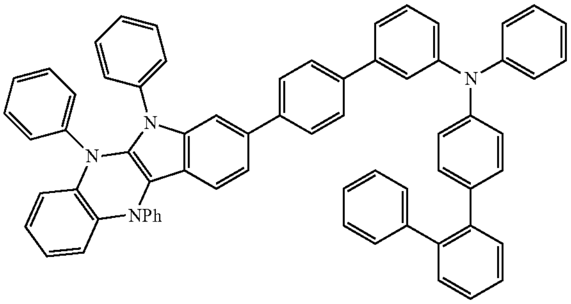
-continued
D29
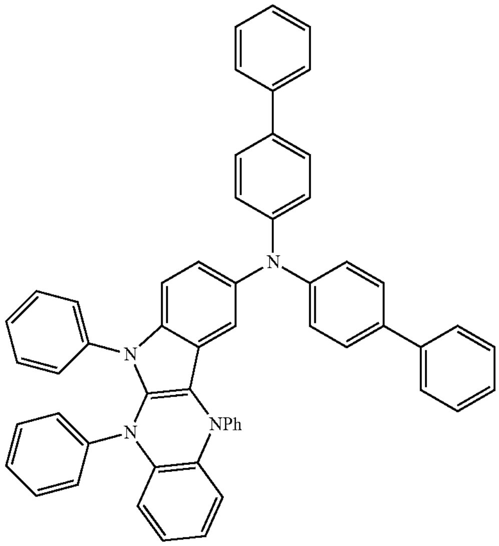
D30
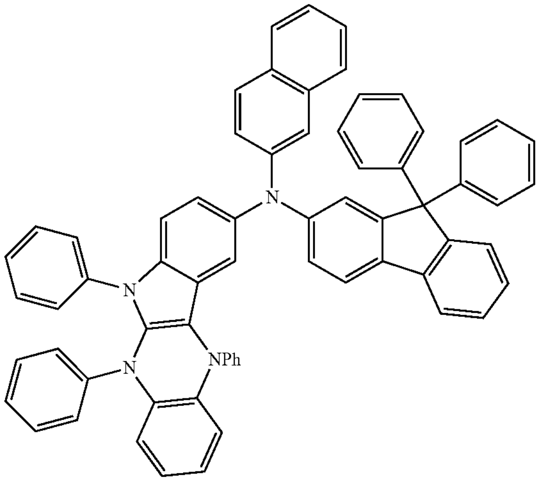
D31
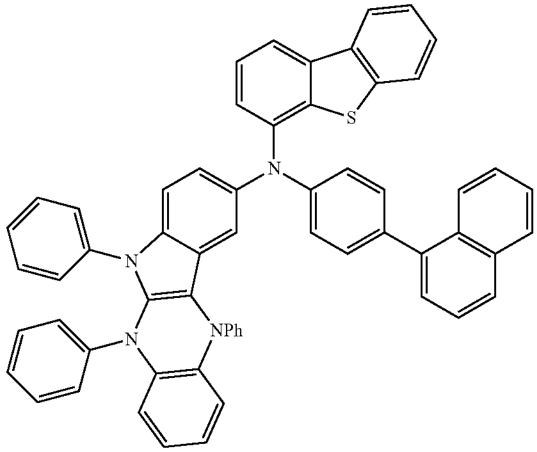

-continued
D32
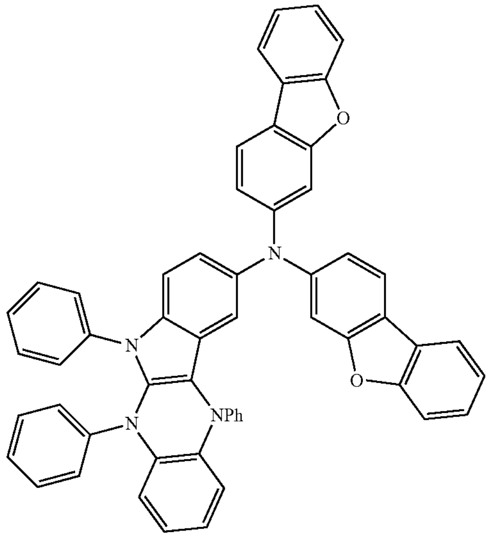
D33
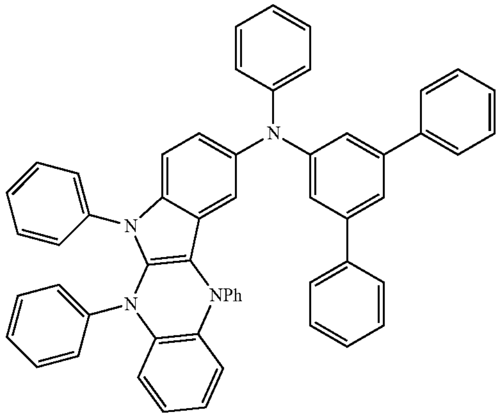
D34
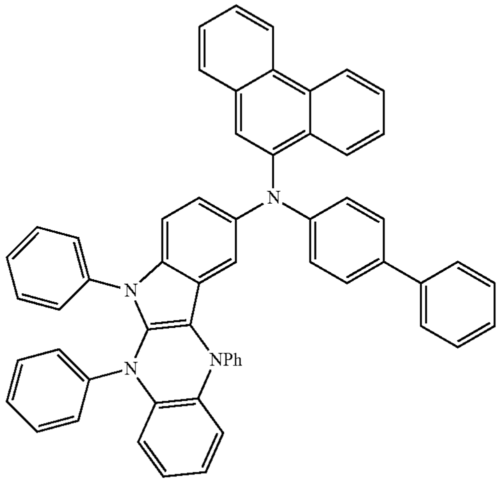
-continued
D35
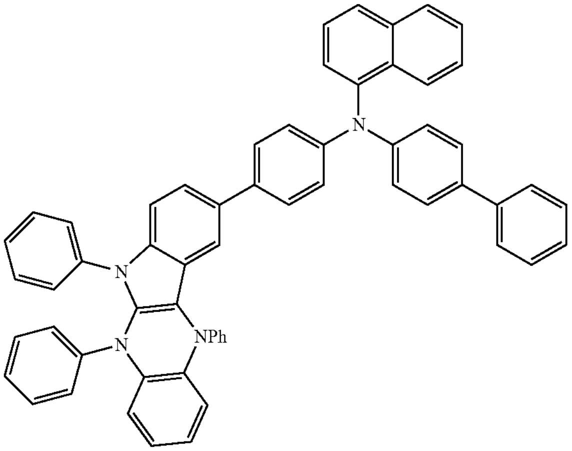
D36
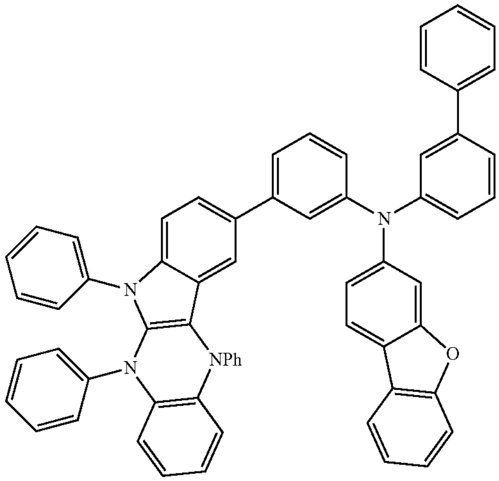
D37
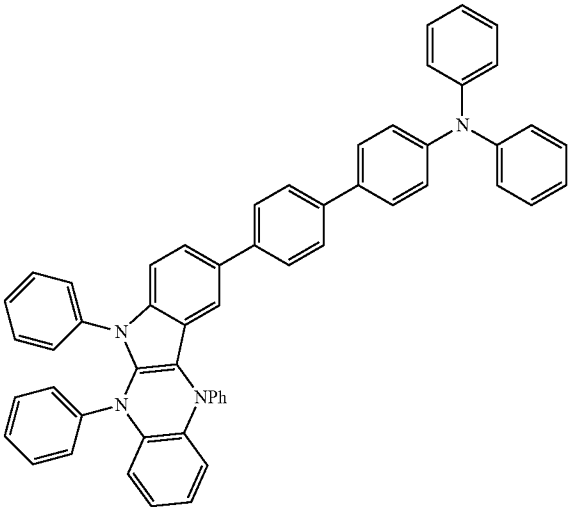

D38
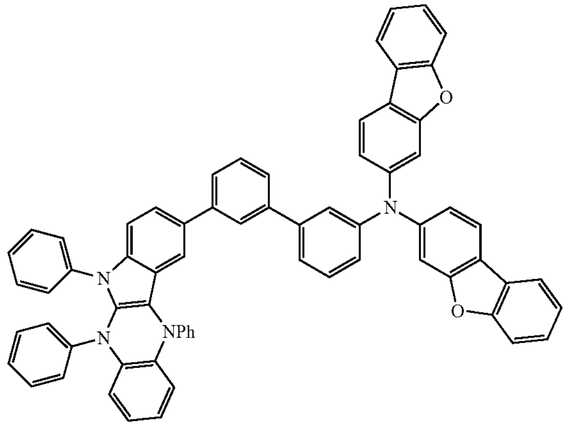
D39
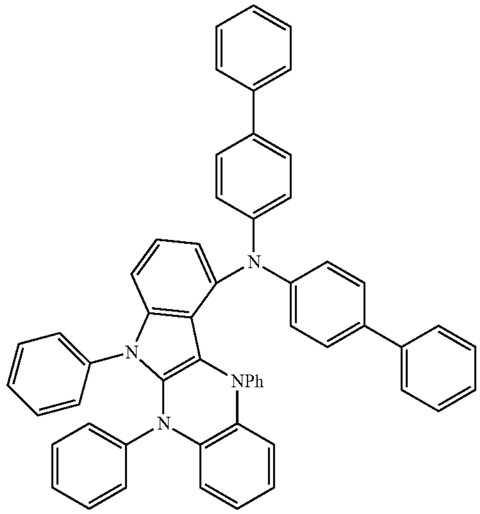
D40
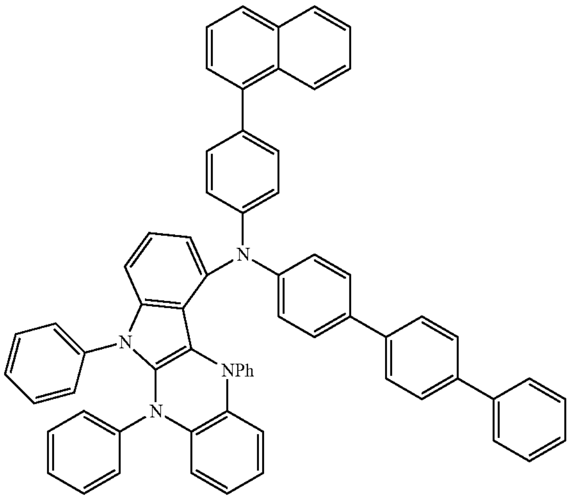
D41
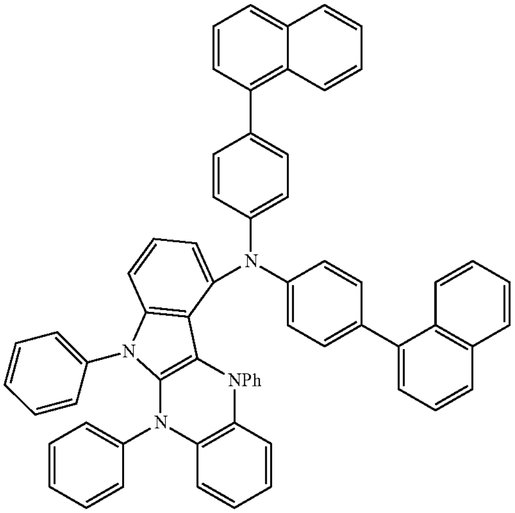
D42
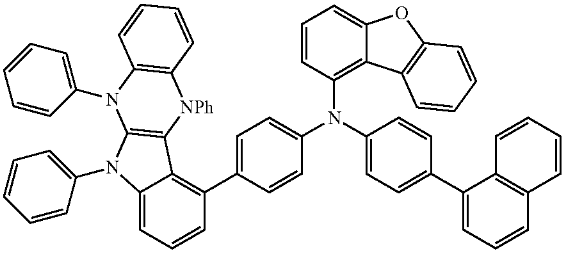
D43
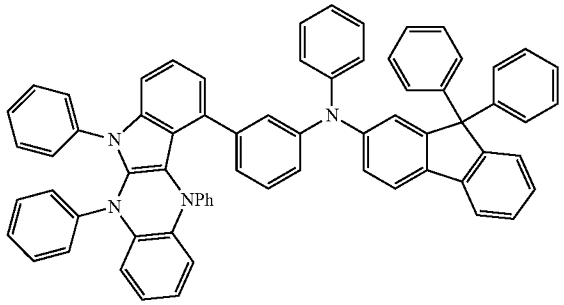
D44
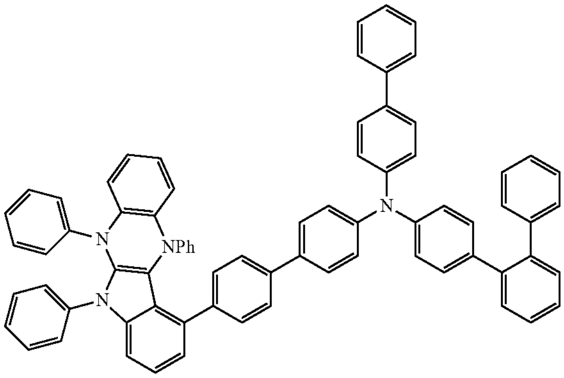

-continued
D45
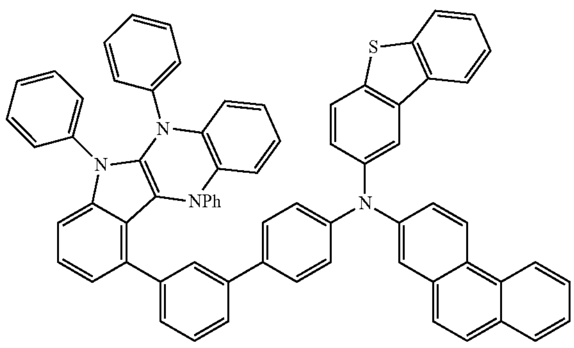
D46
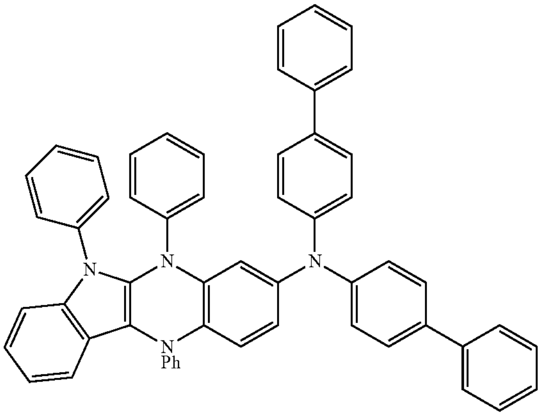
D47
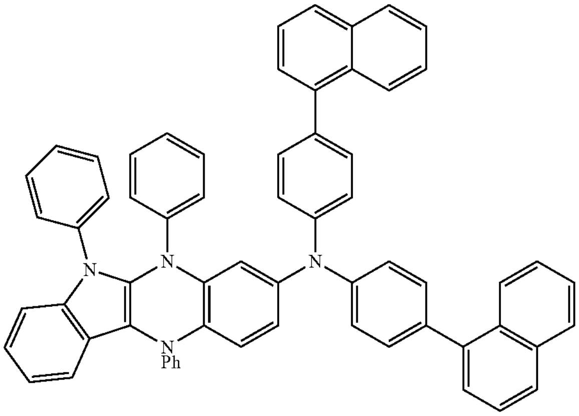
-continued
D48
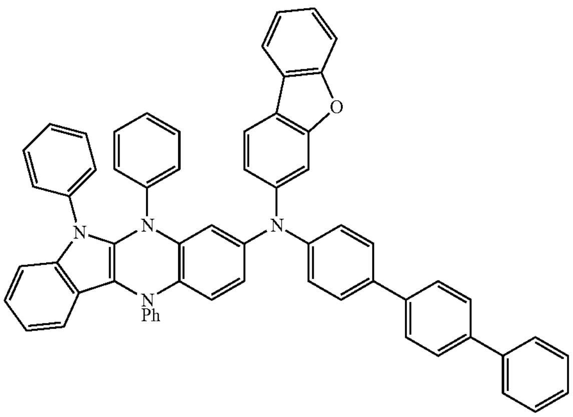
D49
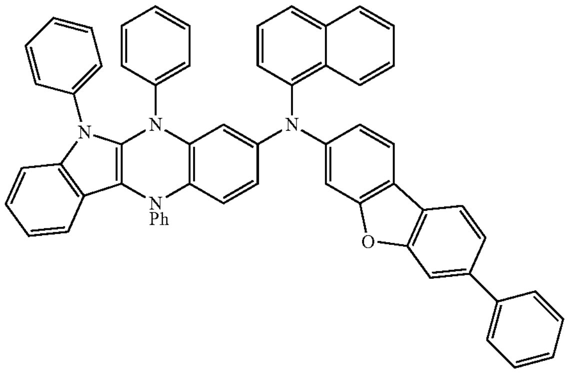
D50
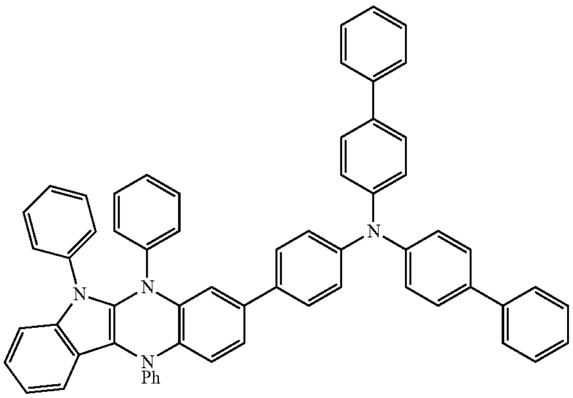

-continued
D51
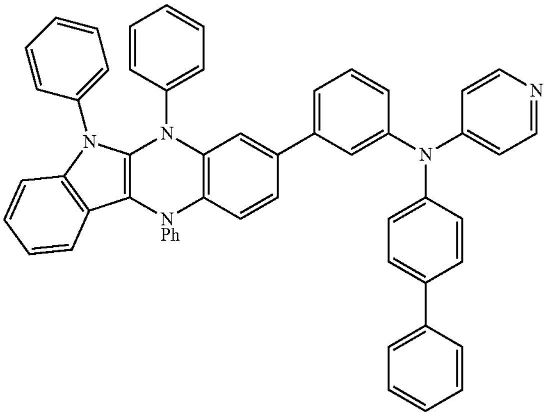
D52
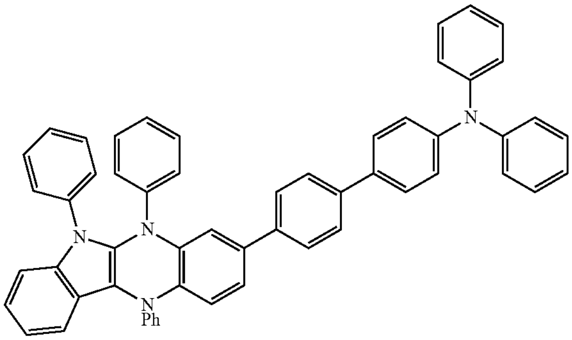
D53
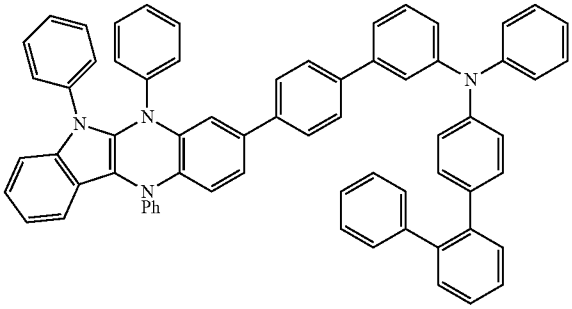
D54
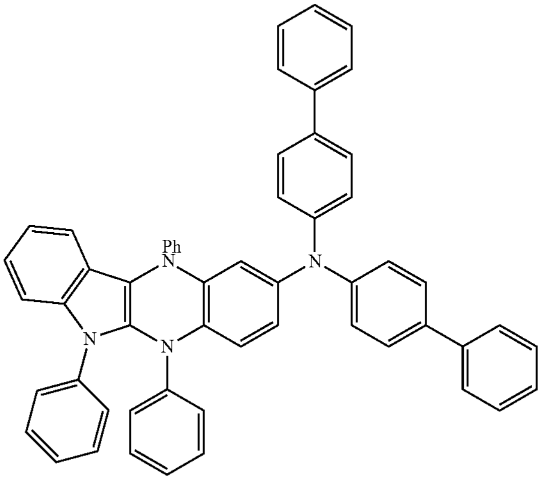
-continued
D55
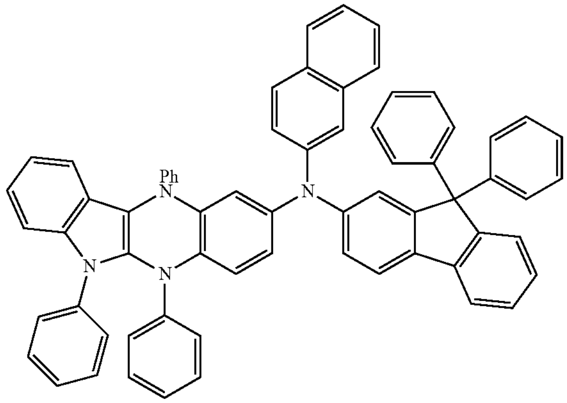
D56
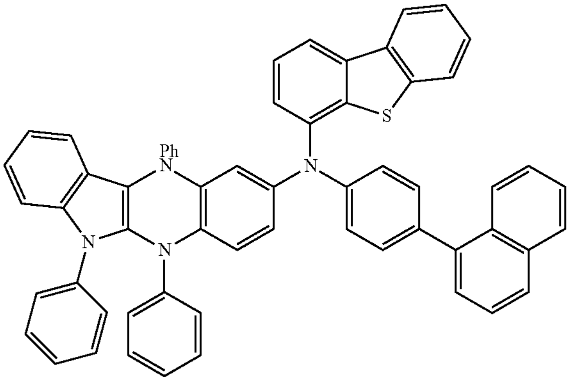
D57
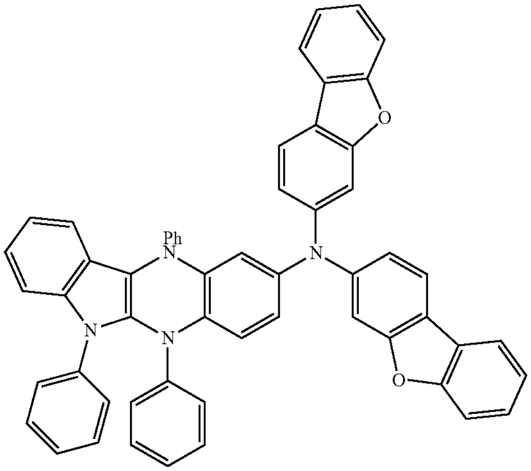

-continued
D58
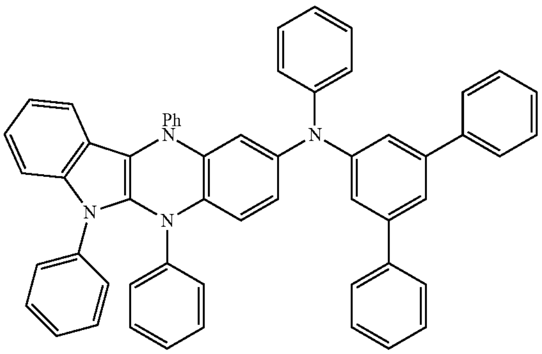
D59
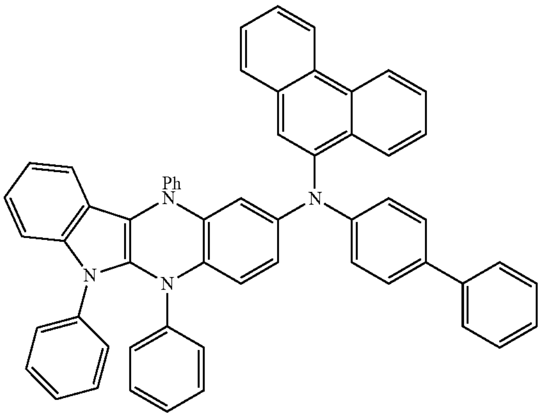
D60
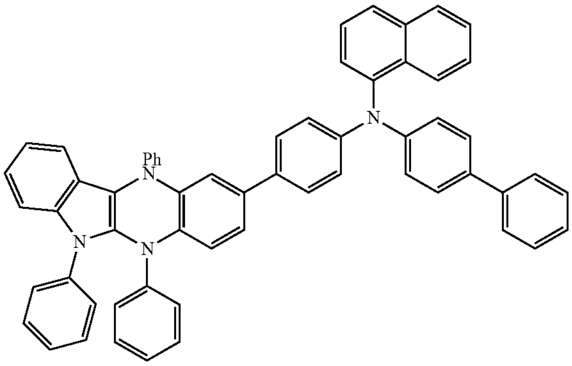
-continued
D61
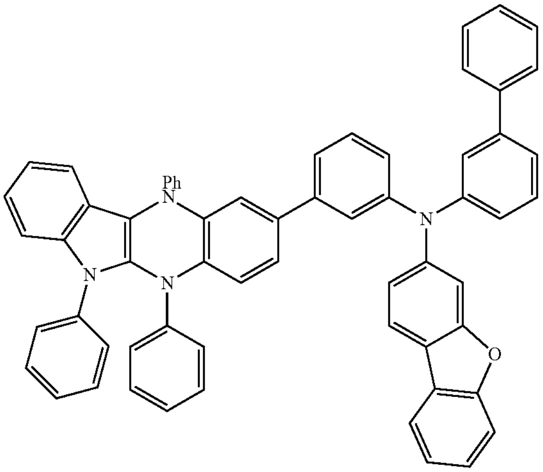
D62
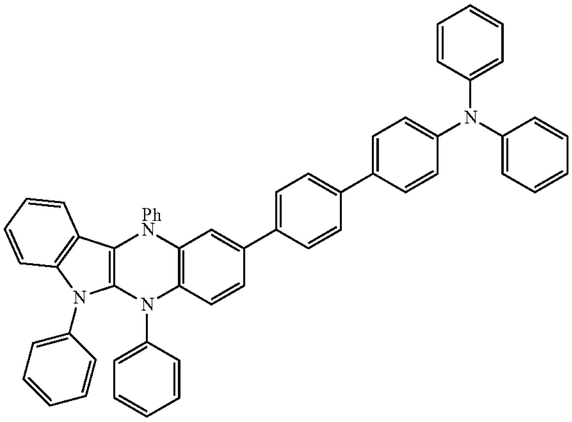
D63
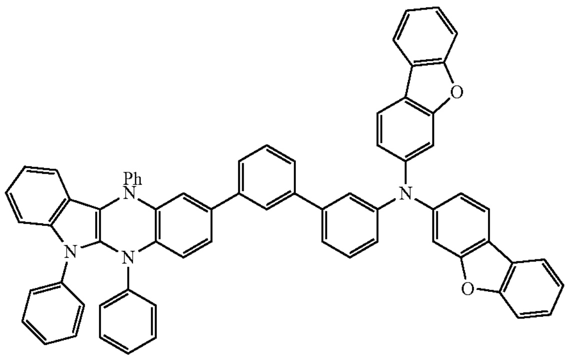

-continued
D64
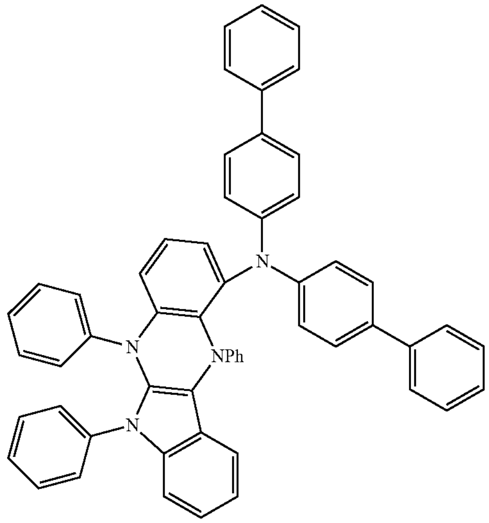
D65
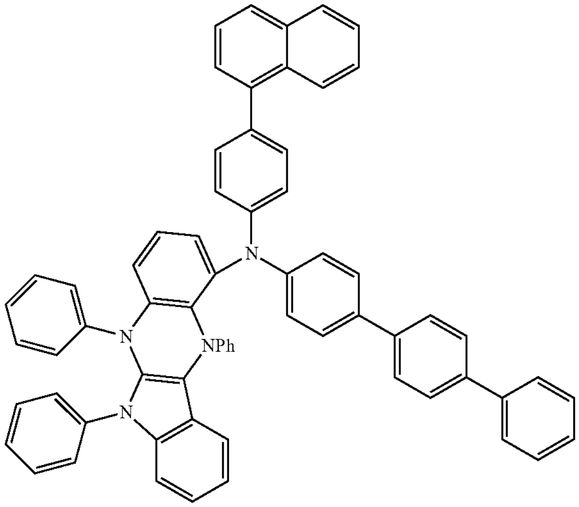
D66
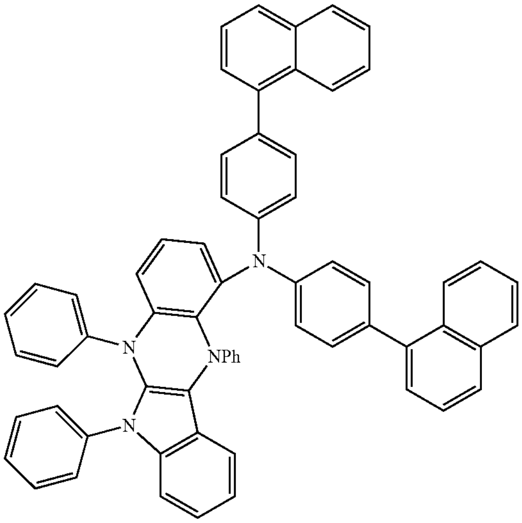
-continued
D67
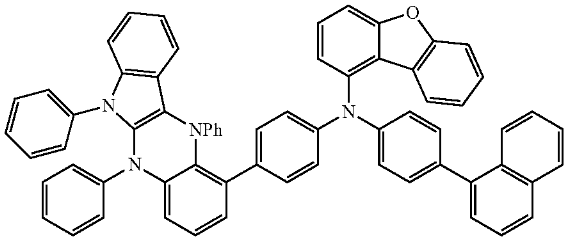
D68
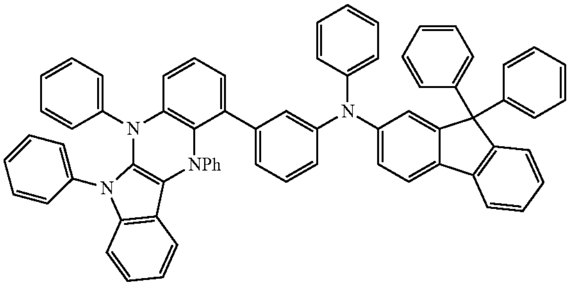
D69
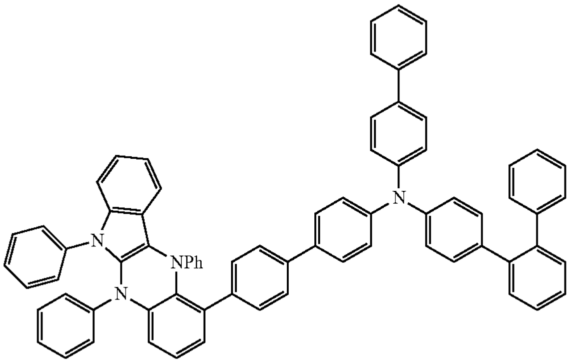
D70
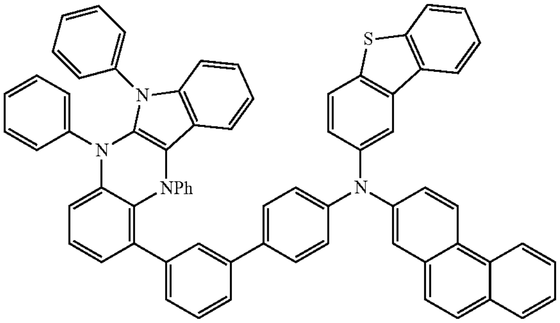

[Compound Group 5]
E1
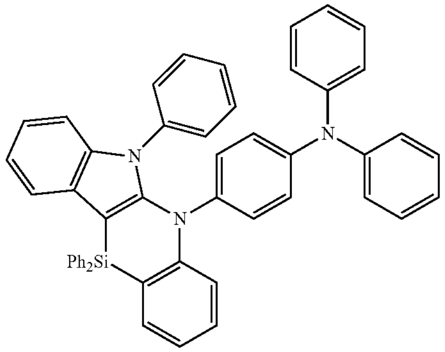
E2
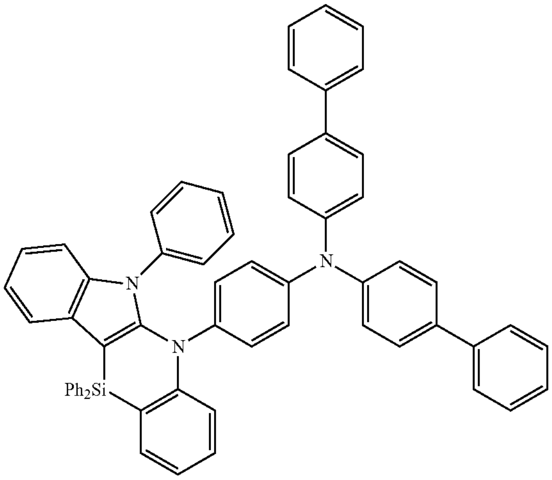
E3
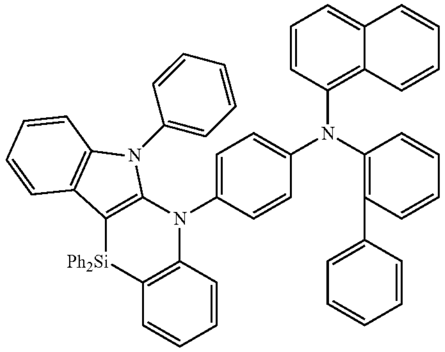
E4
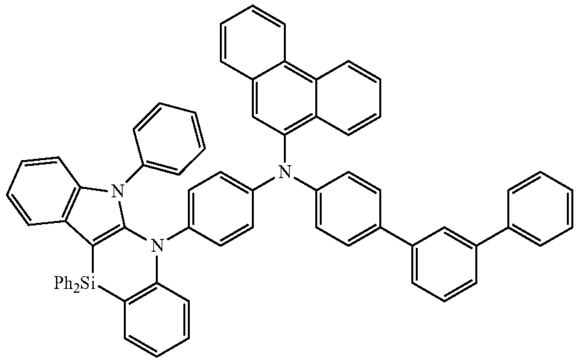
-continued
E5
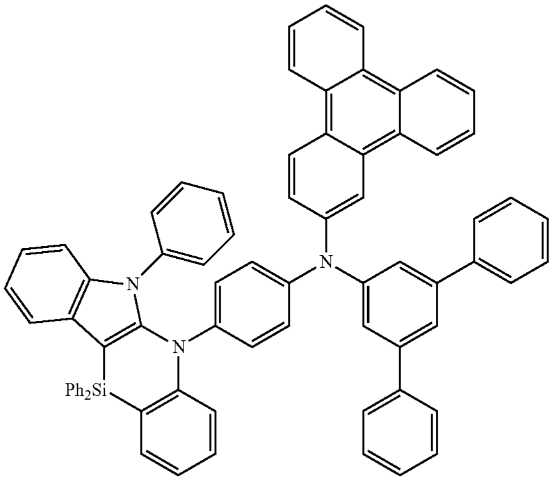
E6
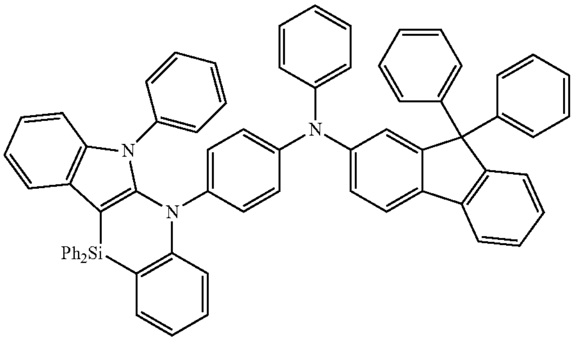
E7
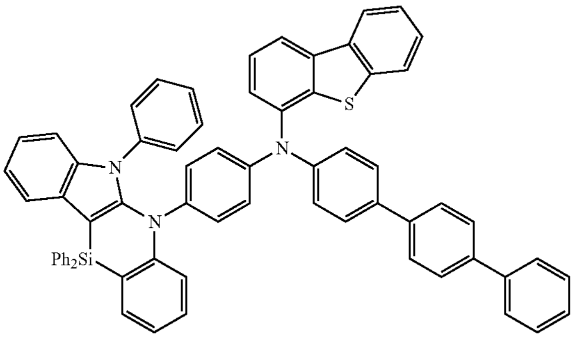

-continued
E8
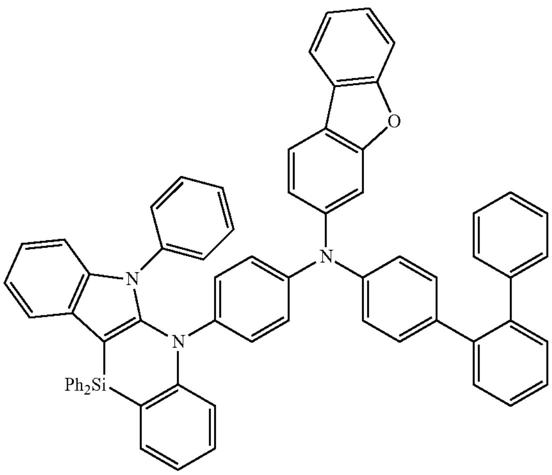
E9
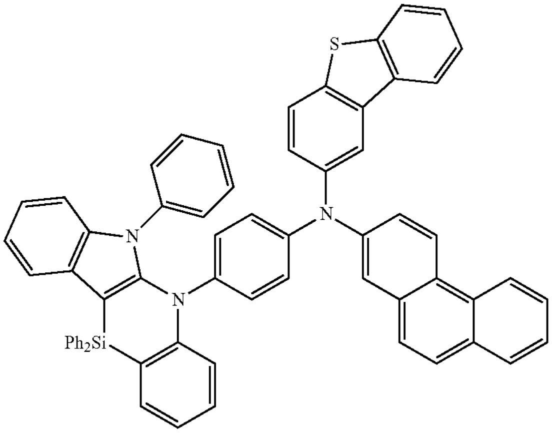
E10
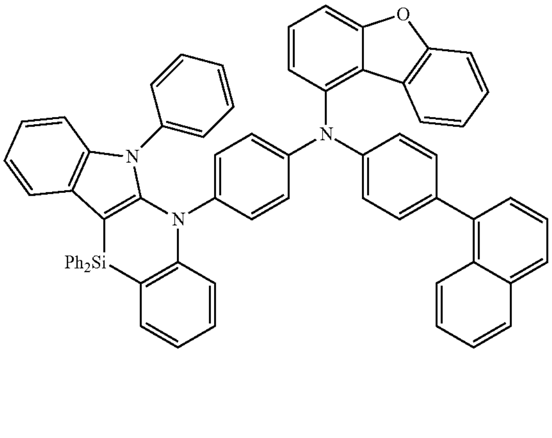
-continued
E11
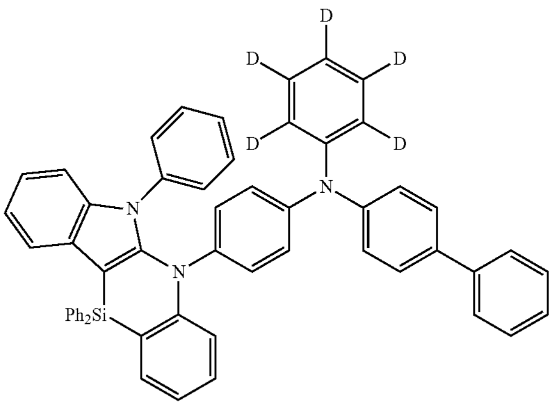
E12
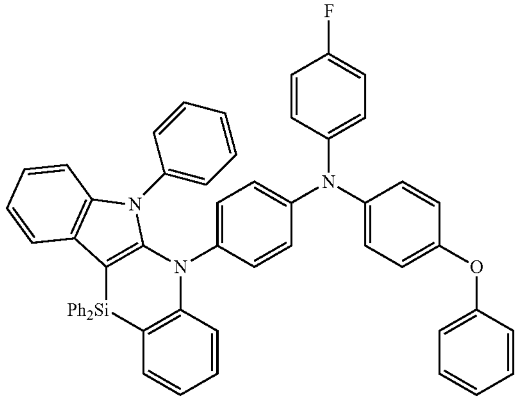
E13
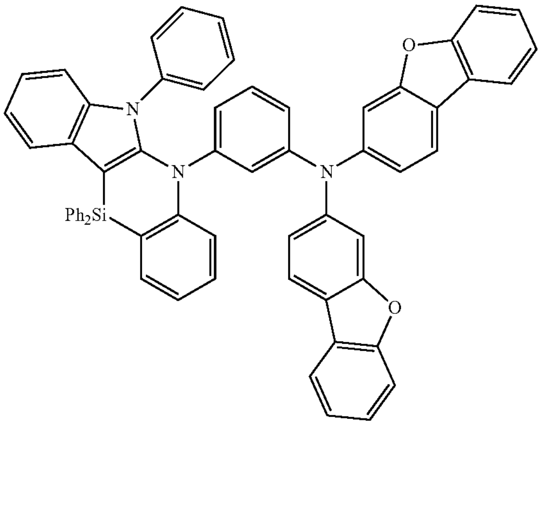

E14
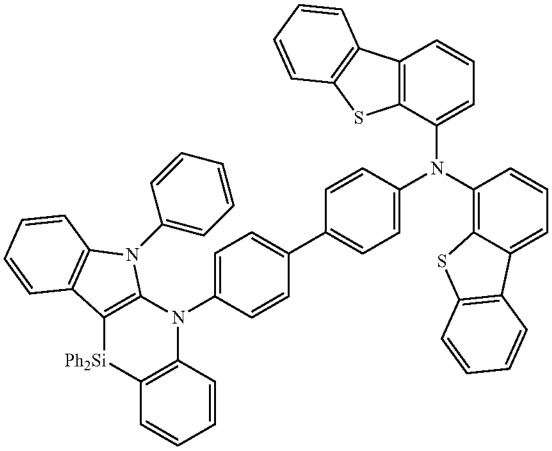
E15
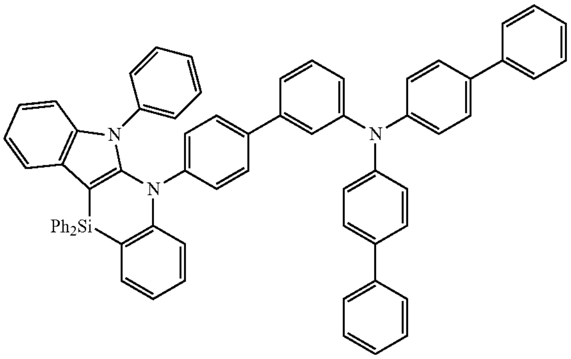
E16
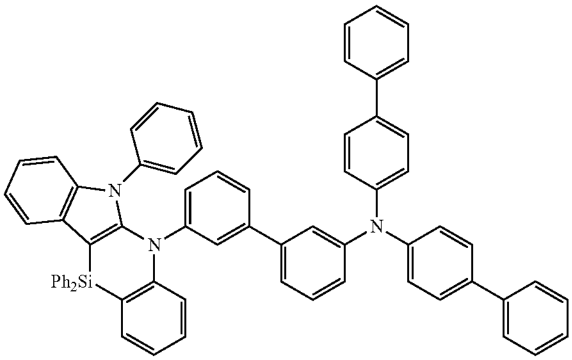
E17
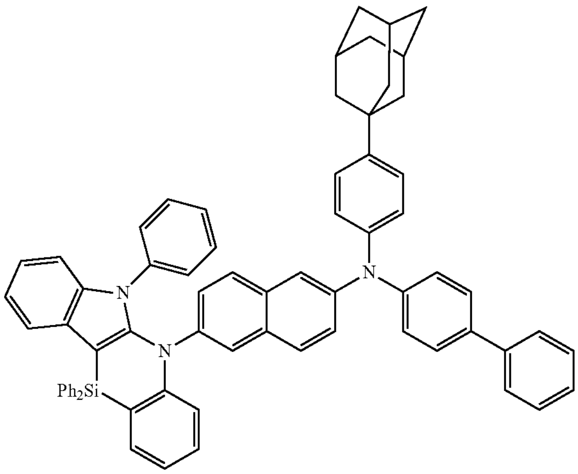
E18
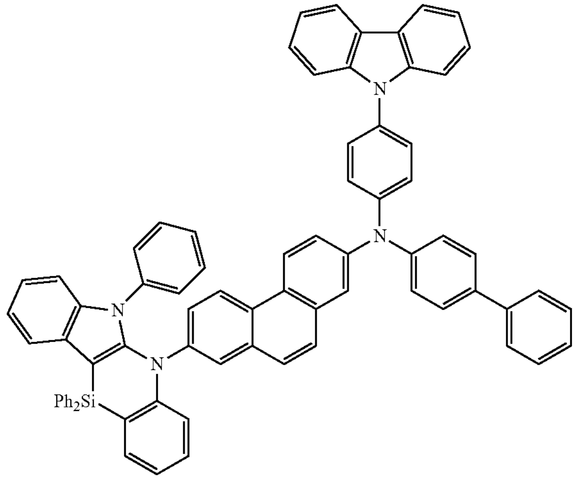
E19
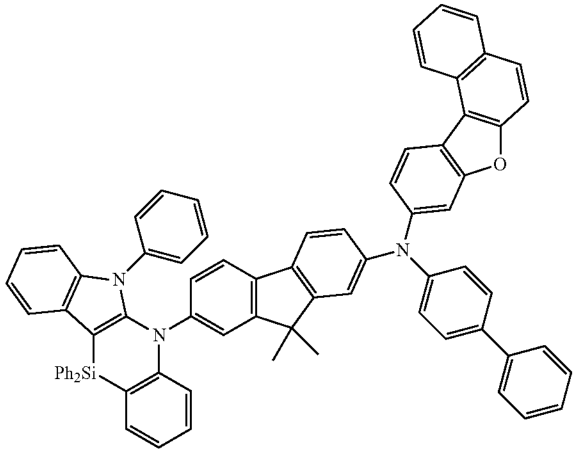

-continued
E20
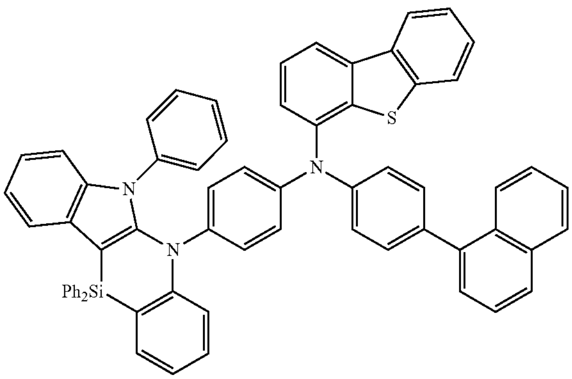
E21
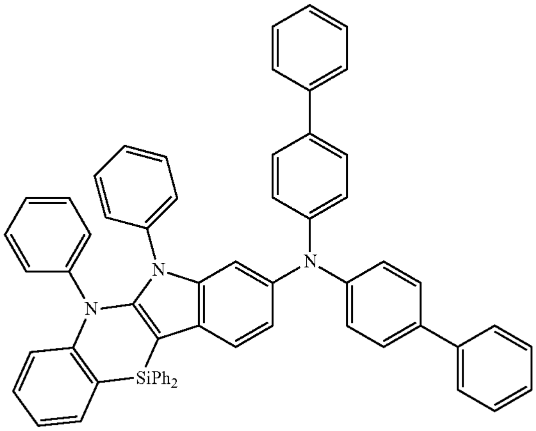
E22
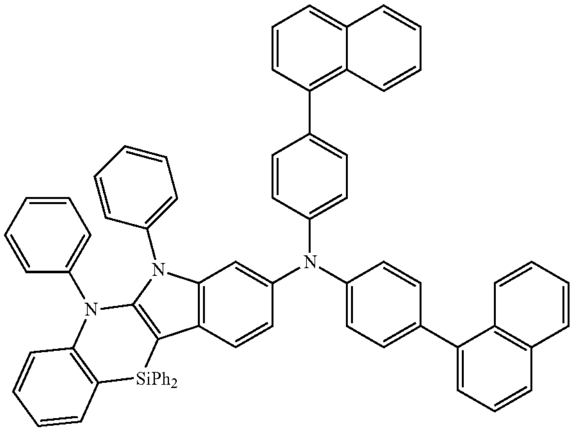
-continued
E23
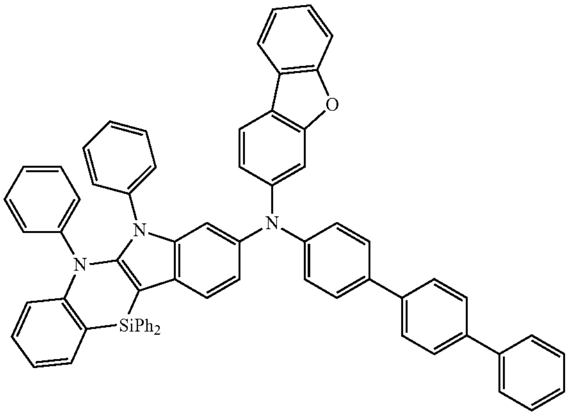
E24
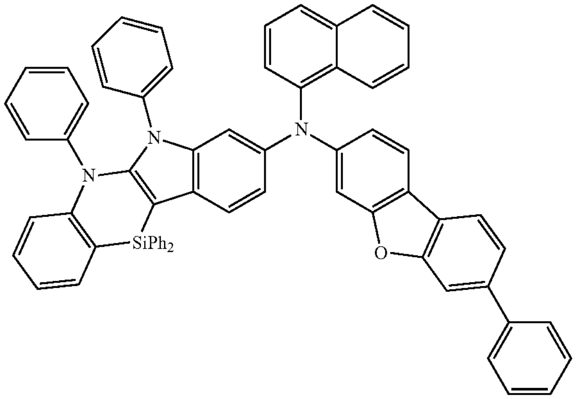
E25
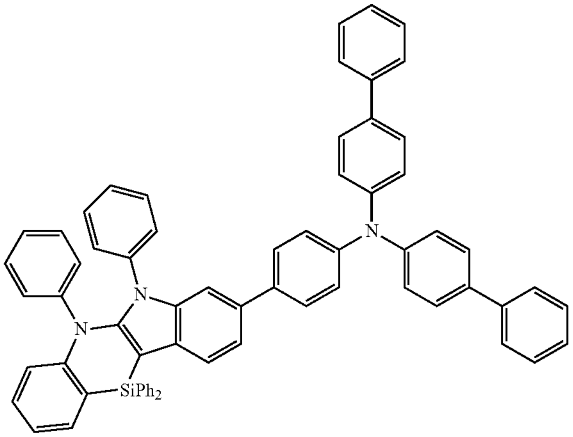

-continued
E26
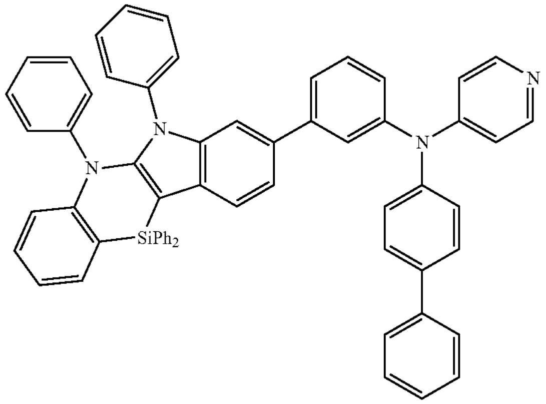
E27
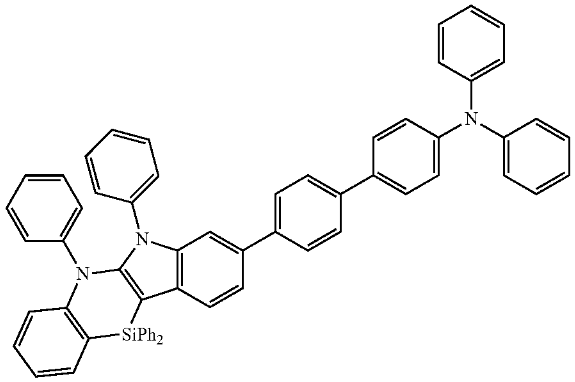
E28
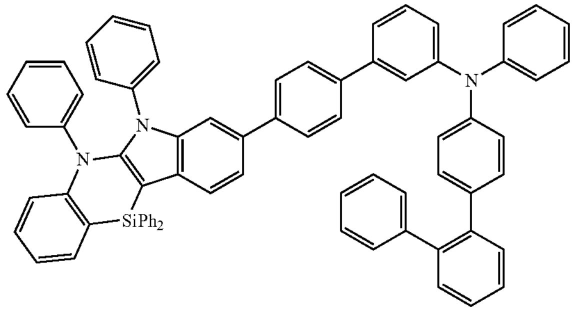
-continued
E29
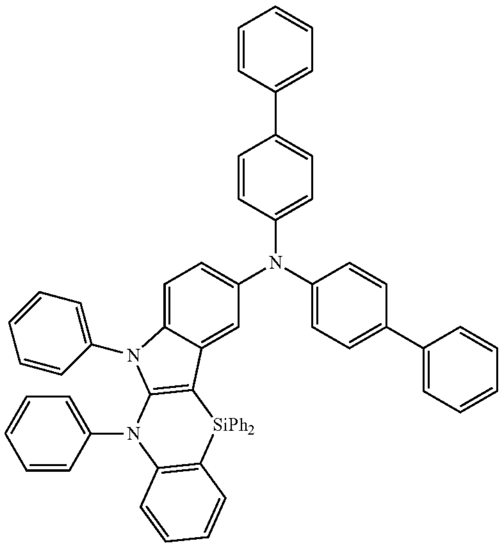
E30
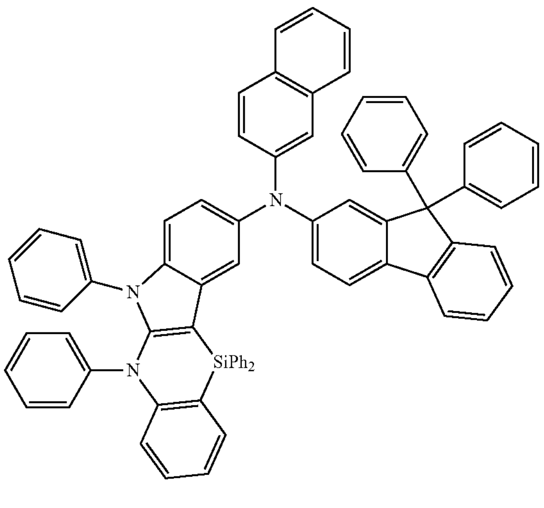
E31
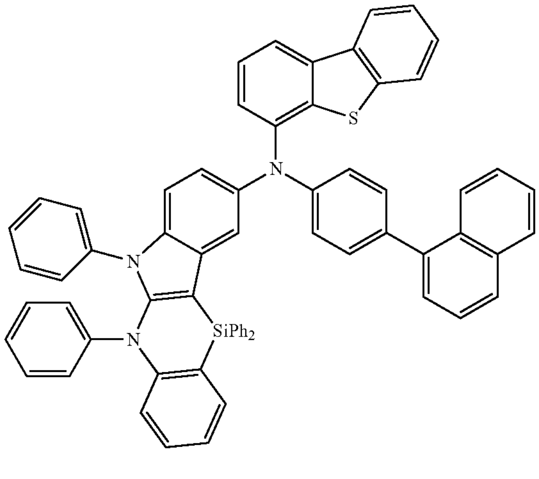

-continued
E32
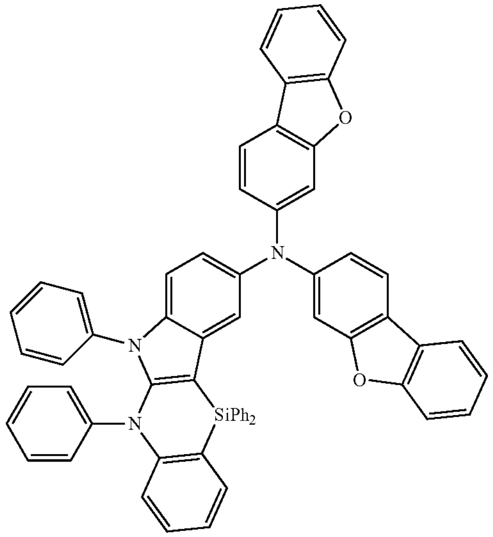
E33
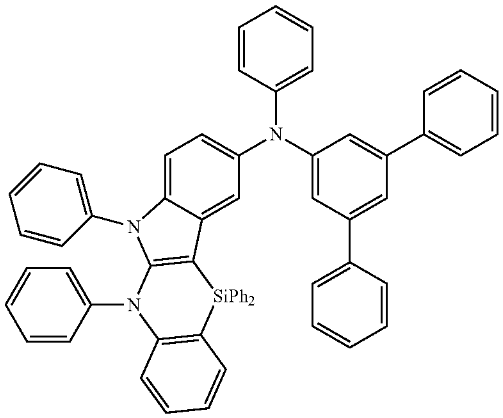
E34
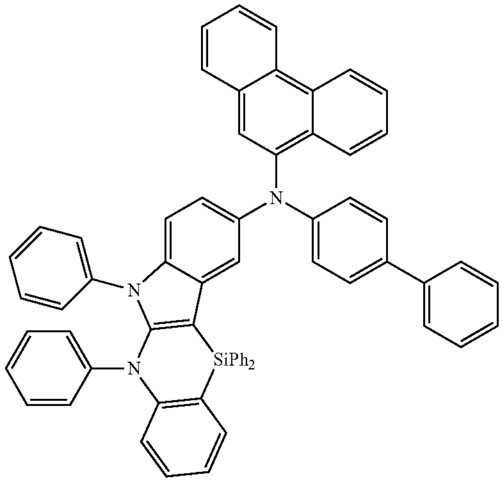
-continued
E35
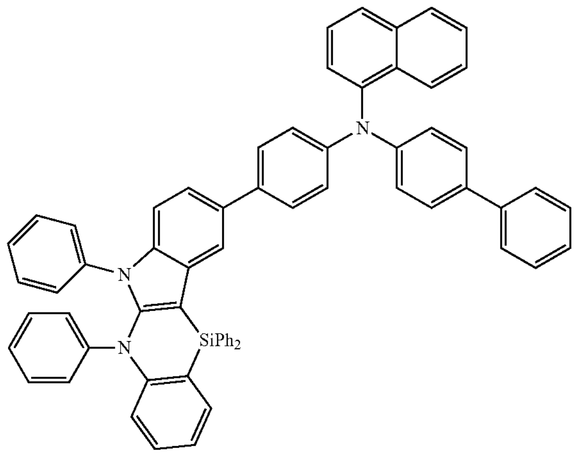
E36
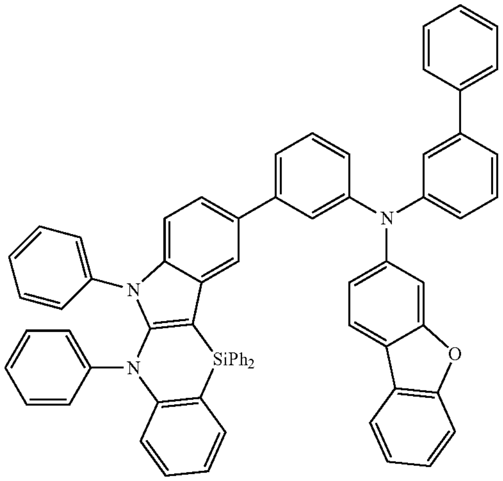
E37
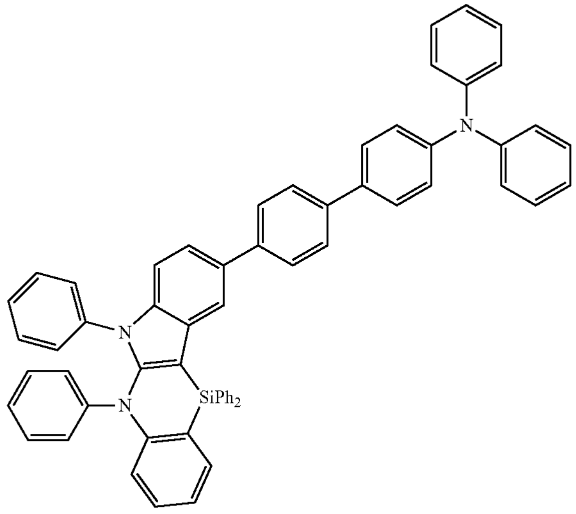

-continued
E38
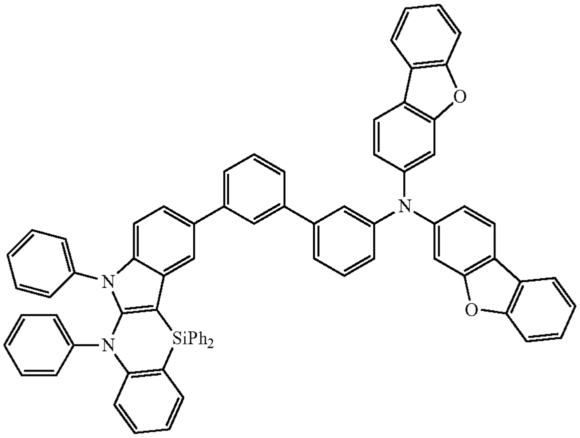
E39
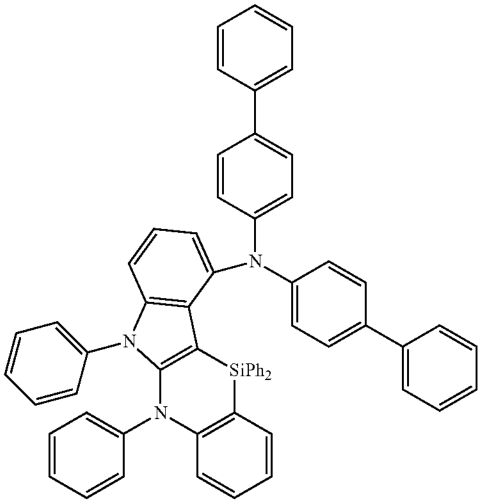
E40
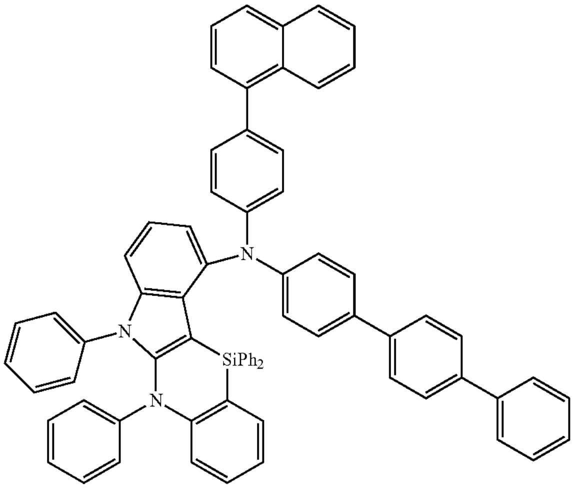
-continued
E41
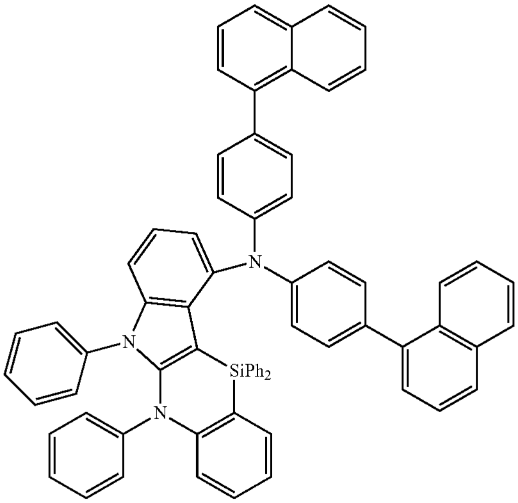
E42
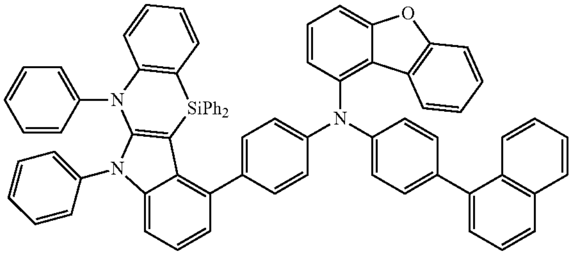
E43
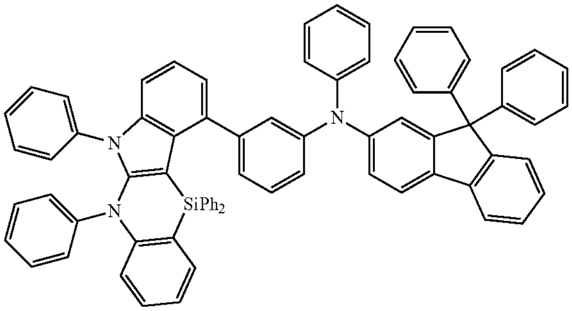
E44
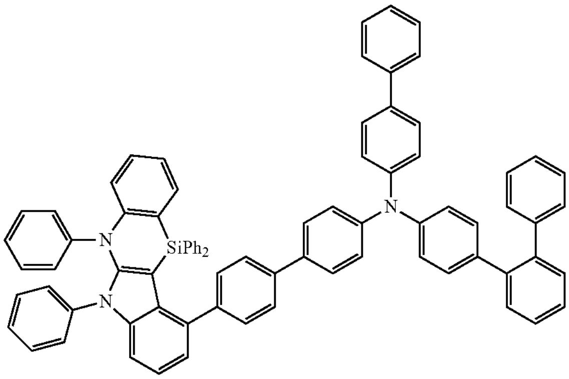

-continued
E45
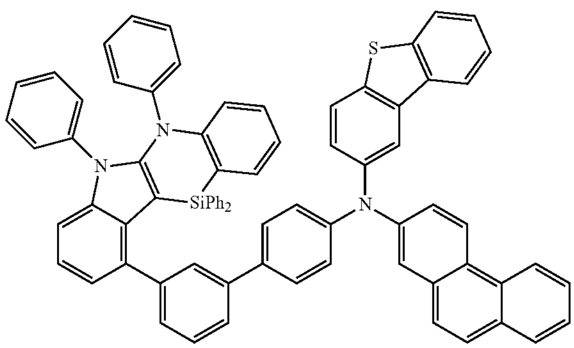
E46
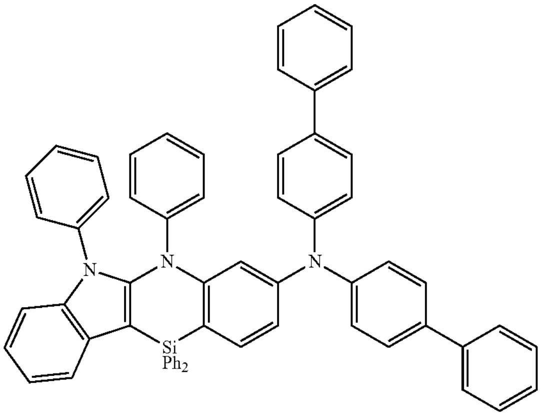
E47
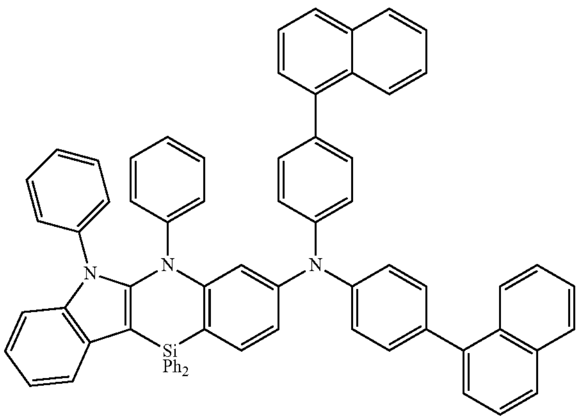
-continued
E48
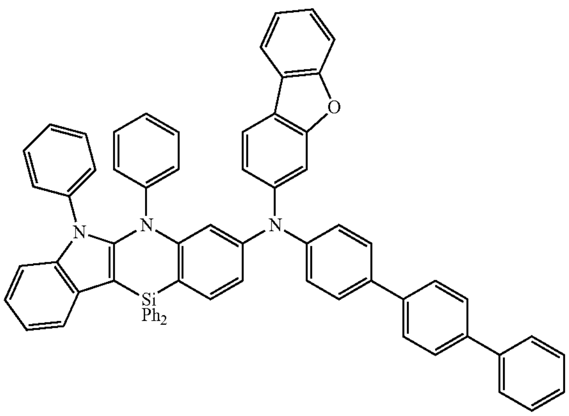
E49
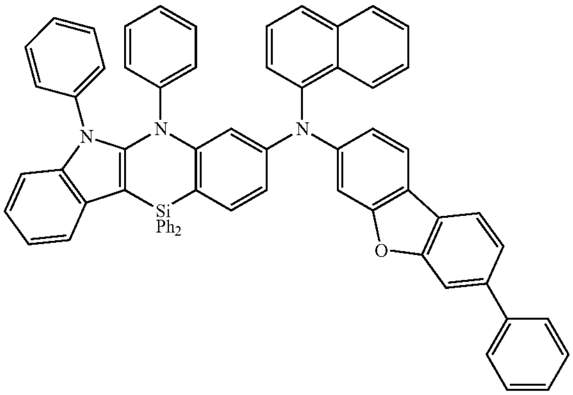
E50
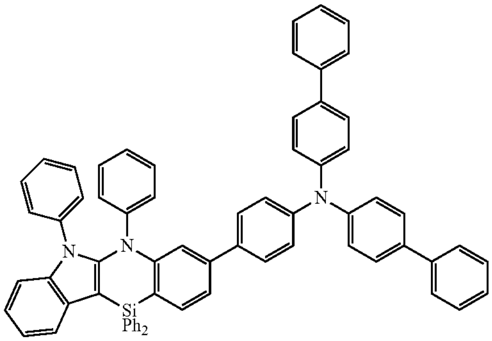
E51
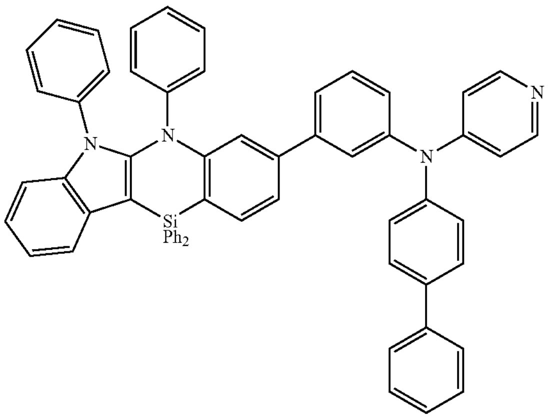

-continued
E52
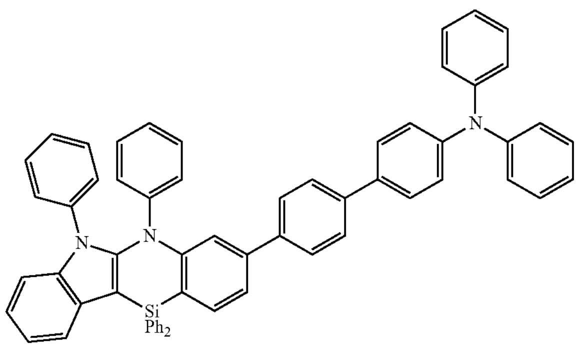
E53
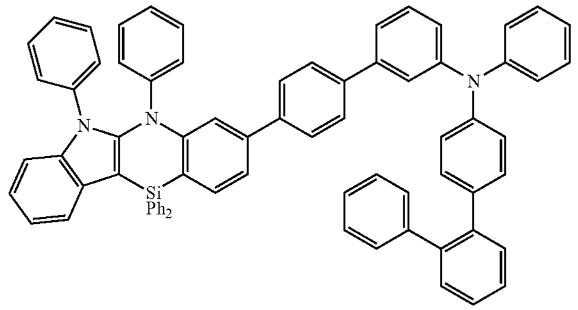
E54
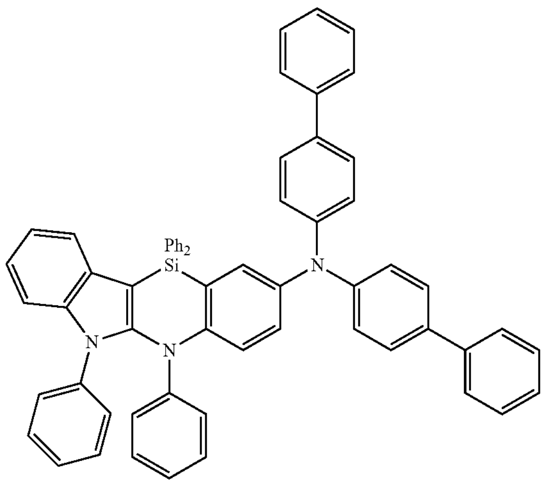
E55
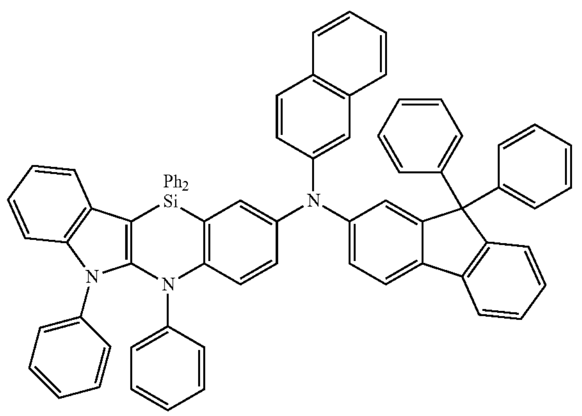
-continued
E56
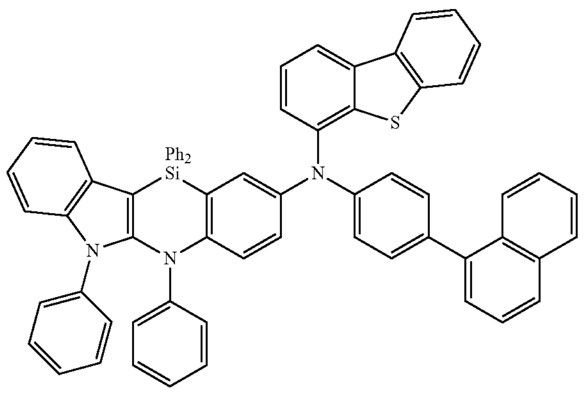
E57
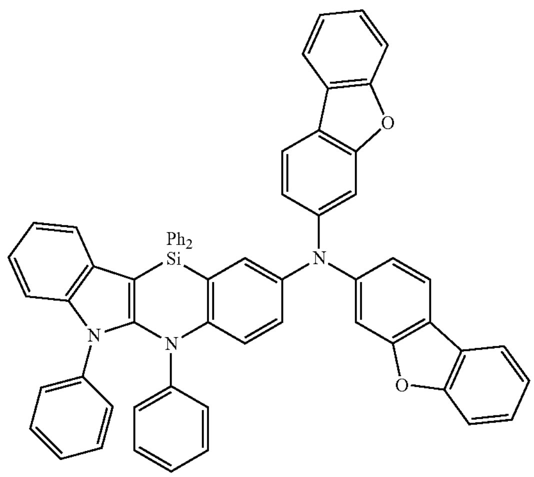
E58
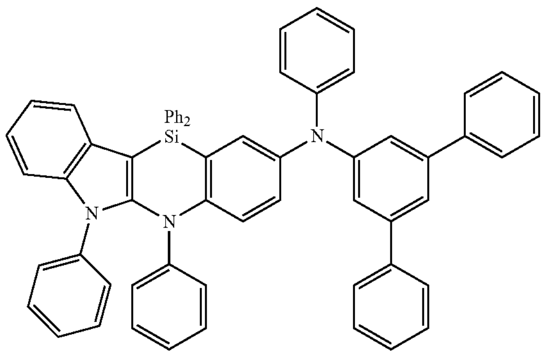

-continued
E59
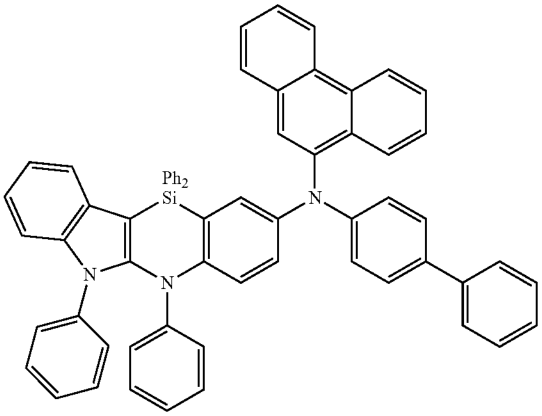
E60
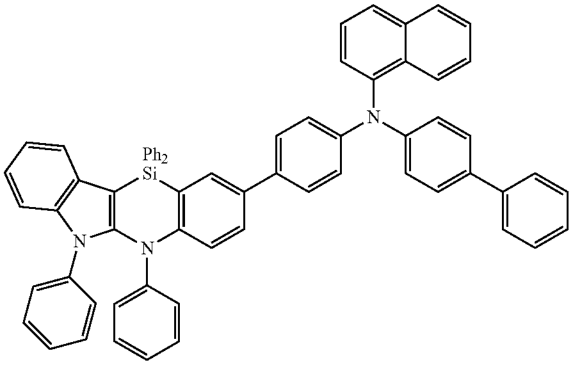
E61
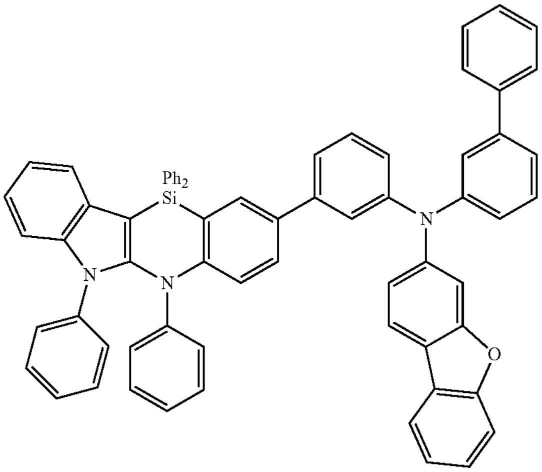
-continued
E62
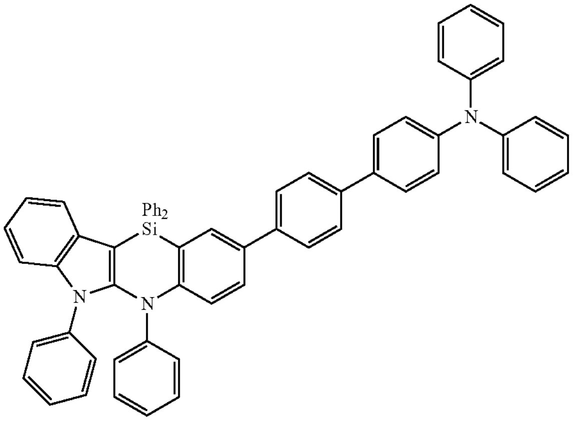
E63
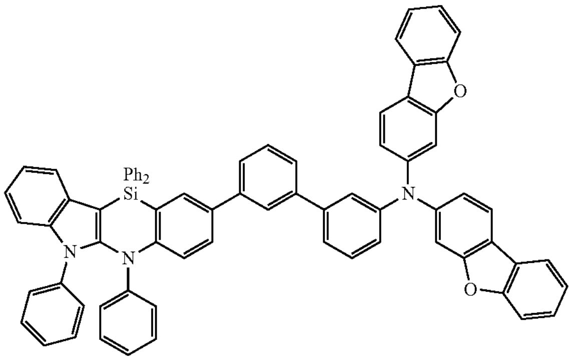
E64
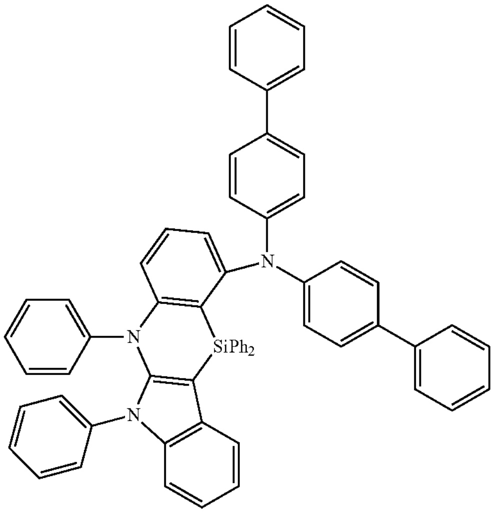

-continued

E65

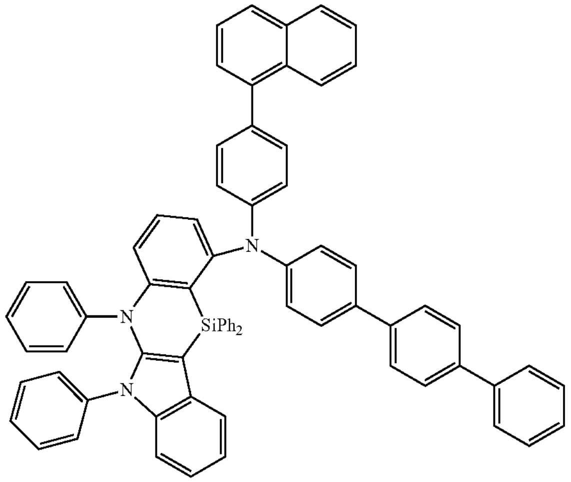

E66

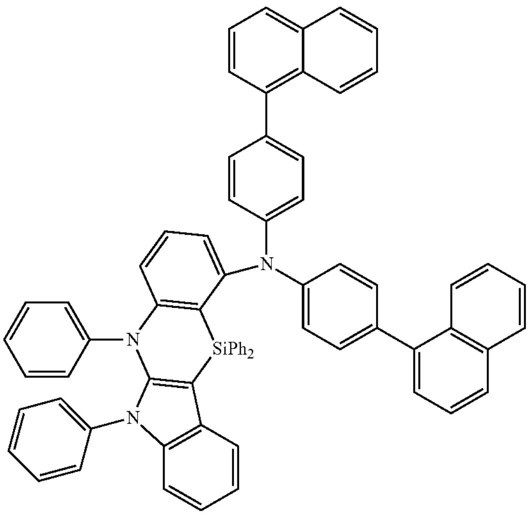

E67

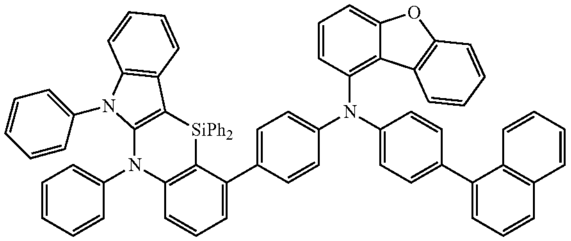

E68

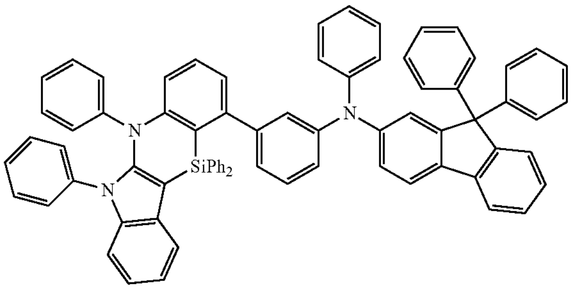

-continued

E69

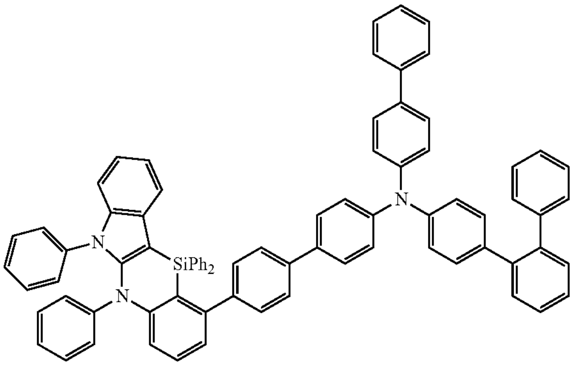

E70

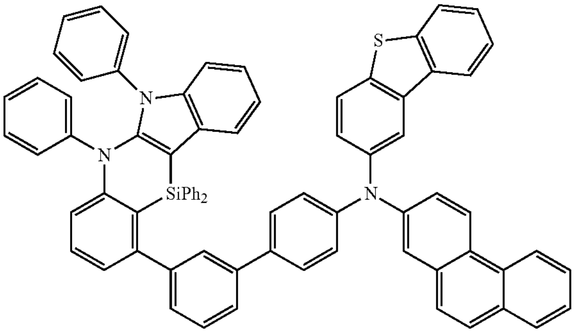

Referring to FIGS. 2 and 3 again, the hole transport region HTR may have a single layer formed using a single material, a single layer formed using a plurality of different materials, or a multilayer structure including a plurality of layers formed using a plurality of different materials.

The hole transport region HTR may have a single layer structure of a hole injection layer HIL or a hole transport layer HTL, or may have a single layer structure formed using a hole injection material and a hole transport material. In addition, the hole transport region HTR may have a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, laminated in order from the first electrode EL1, without limitation.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris {N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2, 3-f: 2',3'-h] quinoxaline-2,3,6,7,10,11-hexacarbonitrile (HAT-CN), etc.

The hole transport layer HTL may include, for example, carbazole derivatives such as N-phenyl carbazole, polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris (N-carbazolyl)triphenylamine (TCTA), N,N'-di(naphthalen-1-yl)-N,N'-diphenyl-benzidine (NPB), 4,4'-cyclohexylidene bis[N,N-bis(4-methylphenyl)benzenamine](TAPC), 4,4'-bis [N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, for example, from about 100 Å to about 1,000 Å. In case the hole transport region HTR includes both of the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. In case the thicknesses of the hole transport region HTR, the hole injection layer HIL and the hole transport layer HTL satisfy the above-described ranges, satisfactory hole transport properties may be obtained without substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide and molybdenum oxide, without limitation.

As described above, the hole transport region HTR may further include at least one of a hole buffer layer or an electron blocking layer in addition to the hole injection layer HIL and the hole transport layer HTL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer is a layer preventing electron injection from the electron transport region ETR into the hole transport region HTR.

In case the hole transport region HTR includes both of the hole injection layer HIL and the hole transport layer HTL, and also includes the above-described condensed cyclic compound, the condensed cyclic compound may be included in the hole transport layer HTL.

In case the hole transport layer HTL consists of a plurality of organic layers, the condensed cyclic compound may be included in an organic layer adjacent to the emission layer EML.

In case the hole transport region HTR includes the condensed cyclic compound, the hole transport region HTR may further include a known material in addition to the condensed cyclic compound.

The emission layer EML is disposed on the hole transport region HTR. The thickness of the emission layer EML may be, for example, from about 100 Å to about 1,000 Å, or from about 100 Å to about 300 Å. The emission layer EML may have a single layer formed using a single material, a single layer formed using a plurality of different materials, or a multilayer structure having a plurality of layers formed using a plurality of different materials.

The emission layer EML may be a fluorescence emission layer or a phosphorescence emission layer. The emission layer EML may include a host and a dopant.

The emission layer EML may employ any host material commonly used without specific limitation. For example, the emission layer EML may include at least one of bis[2-(diphenylphosphino)phenyl] ether oxide (DPEPO), 4,4'-bis (carbazol-9-yl)biphenyl (CBP), 1,3-bis(carbazol-9-yl)benzene (mCP), 2,8-bis(diphenylphosphoryl)dibenzo[b,d] furan (PPF), 4,4',4"-tris(carbazol-9-yl)-triphenylamine (TcTa) or 1,3,5-tris(N-phenylbenzimidazole-2-yl)benzene (TPBi). However, an embodiment of the inventive concept is not limited thereto. For example, the emission layer EML may include, as a host material, tris(8-hydroxyquinolino)aluminum (Alq3), 4,4'-bis(N-carbazolyl)-1,1'-biphenyl (CBP), poly(N-vinylcarbazole) (PVK), 9,10-di(naphthalen-2-yl)anthracene (ADN), 4,4',4"-tris(carbazol-9-yl)-triphenylamine (TCTA), 1,3,5-tris(N-phenylbenzimidazol-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino) phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), etc.

For example, the emission layer EML may further include, as a dopant material, at least one of N,N,N',N'-tetraphenyl-pyrene-1,6-diamine (TPD), 4,4'-bis(2-(9-ethyl-9H-carbazol-3-yl)vinyl)-1,1'-biphenyl (BCzVBi), 4,4'-bis (9-ethyl-3-carbazovinylene)-1,1'-biphenyl, 10-phenyl-10H, 10'H-spiro[acridine-9,9'-anthracene]-10'-one (ACRSA), 3,4, 5,6-tetra-9H-carbazol-9-yl-1,2-benzenedicarbonitrile (4CzPN), 2,4,5,6-tetra-9H-carbazol-9-yl-isophthalonitrile (4CzIPN), bis[4-(9,9-dimethyl-9,10-dihydroacridine)phenyl]sulfone (DMAC-DPS), or 2-phenoxazine-4,6-diphenyl-1,3,5-triazine (PSZ-TRZ). The emission layer EML may further include, as a known dopant material, styryl derivatives (for example, 1,4-bis[2-(3-N-ethylcarbazolyl)vinyl] benzene (BCzVB), 4-(di-p-tolylamino)-4'-[(di-p-tolylamino)styryl] stilbene (DPAVB), N-(4-((E)-2-(6-((E)-4-(diphenylamino)styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

The emission layer EML may emit blue light. The emission layer EML may emit light having a wavelength range of about 510 nm or shorter, or about 480 nm or shorter. The emission layer EML may be a phosphorescence emission layer emitting phosphorescence light.

The electron transport region ETR is disposed on the emission layer EML. The electron transport region ETR may include at least one of a hole blocking layer, an electron transport layer ETL or an electron injection layer EIL, without limitation.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In addition, the electron transport region ETR may have a single layer structure having a plurality of different materials, or a laminated structure of electron transport layer ETL/electron injection layer EIL, or hole blocking layer/electron transport layer ETL/electron injection layer EIL, laminated in order from the emission layer EML, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In case the electron transport region ETR includes the electron transport layer ETL, the electron transport region ETR may include anthracene derivatives. However, an embodiment of the inventive concept is not limited thereto. The electron transport region may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-Biphenyl-4-olato)aluminum (BAlq), berylliumbis (benzoquinolin-10-olate) ($Bebq_2$), 9,10-di(naphthalen-2-yl) anthracene (ADN) and a mixture thereof. The thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without substantial increase of a driving voltage.

When the electron transport region ETR includes the electron injection layer EIL, the electron transport region ETR may use LiF, lithium quinolate (LIQ), $Li_2O$, BaO, NaCl, CsF, a metal in lanthanoides such as Yb, or a metal halide such as RbCl and RbI. However, an embodiment of the inventive concept is not limited thereto. The electron injection layer EIL also may be formed using a mixture material of an electron transport material and an insulating organo metal salt. The organo metal salt may be a material having an energy band gap of about 4 eV or more. Particularly, the organo metal salt may include, for example, a metal acetate, a metal benzoate, a metal acetoacetate, a metal acetylacetonate, or a metal stearate. The thickness of the electron injection layer EIL may be from about 1 Å to about 100 Å, for example, from about 3 Å to about 90 Å. In case the thickness of the electron injection layer EIL satisfies the above described range, satisfactory electron injection properties may be obtained without inducing the substantial increase of a driving voltage.

The electron transport region ETR may include a hole blocking layer, as described above. The hole blocking layer may include, for example, at least one of 2,9-dimethyl-4,7-diphenyl-1,10-phenanthroline (BCP) or 4,7-diphenyl-1,10-phenanthroline (Bphen), without limitation.

The second electrode EL2 is disposed on the electron transport region ETR. The second electrode EL2 may be a common electrode or a cathode. The second electrode EL2 may be a transmissive electrode, a transflective electrode or a reflective electrode. In case the second electrode EL2 is the transmissive electrode, the second electrode EL2 may be formed using transparent metal oxides, for example, ITO, IZO, ZnO, ITZO, etc.

In case the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayer structure including a reflective layer or a transflective layer formed using the above-described materials and a transparent conductive layer formed using ITO, IZO, ZnO, ITZO, etc.

Even not shown, the second electrode EL2 may be connected with an auxiliary electrode. In case the second electrode EL2 is connected with the auxiliary electrode, the resistance of the second electrode EL2 may decrease.

In the organic electroluminescence device 10, according to the application of a voltage to each of the first electrode EL1 and the second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

In case the organic electroluminescence device 10 is a top emission type, the first electrode EL1 may be a reflective electrode, and the second electrode EL2 may be a transmissive electrode or a transflective electrode. In case the organic electroluminescence device 10 is a bottom emission type, the first electrode EL1 may be a transmissive electrode or a transflective electrode, and the second electrode EL2 may be a reflective electrode.

The organic electroluminescence device 10 according to an embodiment of the inventive concept includes the above-described condensed cyclic compound as a material for the hole transport region HTR, thereby securing enhanced efficiency and device life.

An embodiment of the inventive concept provides a condensed cyclic compound represented by the following Formula 1.

[Formula 1]

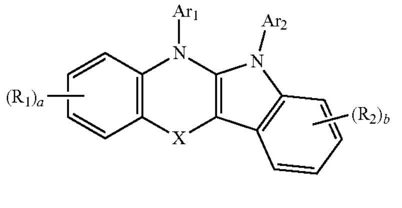

In Formula 1, X may be a direct linkage, O, S, $NR_5$, or $SiR_6R_7$.

In Formula 1, each of $Ar_1$ and $Ar_2$ may independently be a substituted or unsubstituted aryl group having 6 to 40 carbon atoms for forming a ring.

In Formula 1, each of $R_1$ and $R_2$ may independently be a substituted or unsubstituted aryl group having 6 to 40 carbon atoms for forming a ring, or a substituted or unsubstituted alkyl group having 1 to 20 carbon atoms.

In Formula 1, a and b may be each independently an integer of 0 to 4. In case a is an integer of 2 or more, a plurality of $R_1$ may be the same or different from each other. In case b is an integer of 2 or more, a plurality of $R_2$ may be the same or different from each other.

In Formula 1, each of $R_5$, $R_6$, and $R_7$ may independently be a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring.

In Formula 1, the substituted ones may be substituted with a hydrogen atom, a deuterium atom, a halogen atom, a cyano group, a substituted or unsubstituted alkyl group having 1 to 40 carbon atoms, a substituted or unsubstituted aryl group having 6 to 40 carbon atoms for forming a ring, or a substituted or unsubstituted heteroaryl group having 2 to 40 carbon atoms for forming a ring.

In Formula 1, any one of $Ar_1$, $R_1$ or $R_2$ is represented by the following Formula 2.

[Formula 2]

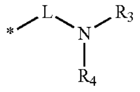

In Formula 2, L may be a substituted or unsubstituted arylene group having 6 to 40 carbon atoms for forming a ring.

In Formula 2, each of $R_3$ and $R_4$ may independently be a substituted or unsubstituted aryl group having 6 to 40 carbon atoms for forming a ring, or a substituted or unsubstituted heteroaryl group having 2 to 40 carbon atoms for forming a ring.

In $R_3$ and $R_4$, the substituted ones may be substituted with a hydrogen atom, a deuterium atom, a halogen atom, a cyano group, a substituted or unsubstituted cycloalkyl group having 3 to 40 carbon atoms for forming a ring, a substituted or unsubstituted aryl group having 6 to 40 carbon atoms for forming a ring, or a substituted or unsubstituted heteroaryl group having 2 to 40 carbon atoms for forming a ring.

The explanation on the condensed cyclic compound described in the above particular explanation on the organic electroluminescence device according to an embodiment of the inventive concept may be applied to the condensed cyclic compound represented by Formula 1 according to an embodiment of the inventive concept.

The condensed cyclic compound according to an embodiment of the inventive concept may be any one selected from the group consisting of compounds represented in the above Compound Groups 1 to 5.

Hereinafter, the inventive concept will be explained in more detail with reference to specific embodiments and comparative embodiments. The following embodiments are illustrated only for assisting the understanding of the inventive concept, and the scope of the inventive concept is not limited thereto.

Synthesis Examples

The condensed cyclic compound according to an embodiment of the inventive concept may be synthesized, for example, as follows. However, the synthetic method of the condensed cyclic compound according to an embodiment of the inventive concept is not limited thereto.

1. Synthesis of Compound A2

Compound A2, the condensed cyclic compound according to an embodiment of the inventive concept, may be synthesized, for example, as follows.

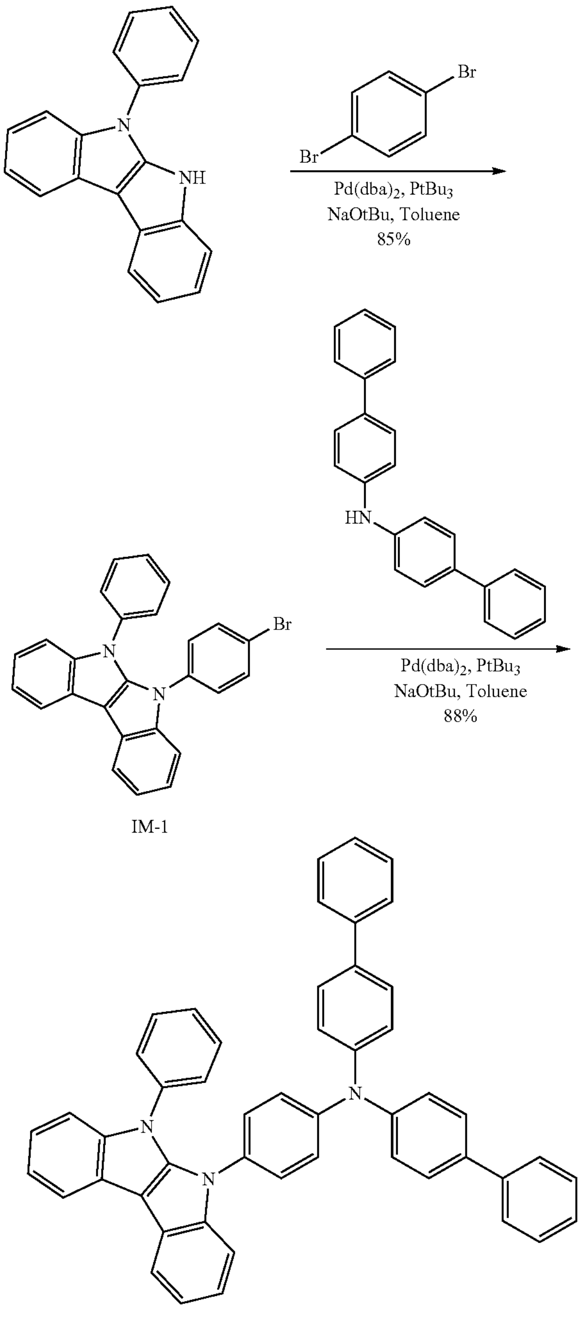

A2

Synthesis of Intermediate IM-1

In an Ar atmosphere, 5-phenyl-5,6-dihydroindolo[2,3-b]indole (5.00 g, 17.7 mmol), $Pd(dba)_2$ (0.31 g, 0.03 equiv, 0.5 mmol), NaOtBu (11.65 g, 1.0 equiv, 1.70 mmol), toluene (88 mL), 1,4-dibromobenzene (4.60 g, 1.1 equiv, 19.5 mmol) and $tBu_3P$ (0.36 g, 0.1 equiv, 1.8 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-1 (6.58 g, yield 85%).

Intermediate IM-1 was identified by measuring FAB-MS in which a molecular ion peak was observed at mass m/z=437.

Synthesis of Compound A2

In an Ar atmosphere, IM-1 (5.00 g, 11.4 mmol), $Pd(dba)_2$ (0.20 g, 0.03 equiv, 0.3 mmol), NaOtBu (2.20 g, 2.0 equiv, 22.8 mmol), toluene (57 mL), bis(4-biphenyl)amine (4.04 g, 1.1 equiv, 12.6 mmol) and $tBu_3P$ (0.23 g, 0.1 equiv, 1.1 mmol) were added sequentially into a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound A2 (6.82 g, yield 88%) as a solid.

Compound A2 was identified by measuring FAB-MS in which a molecular ion peak was observed at mass m/z=677.

2. Synthesis of Compound A13

Compound A13, the condensed cyclic compound according to an embodiment of the inventive concept, may be synthesized, for example, as follows.

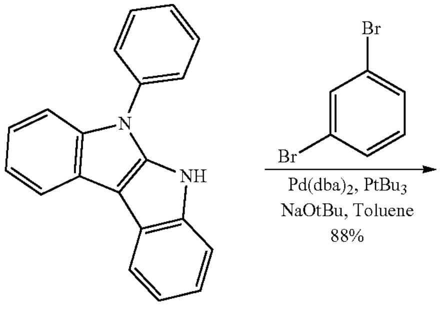

-continued

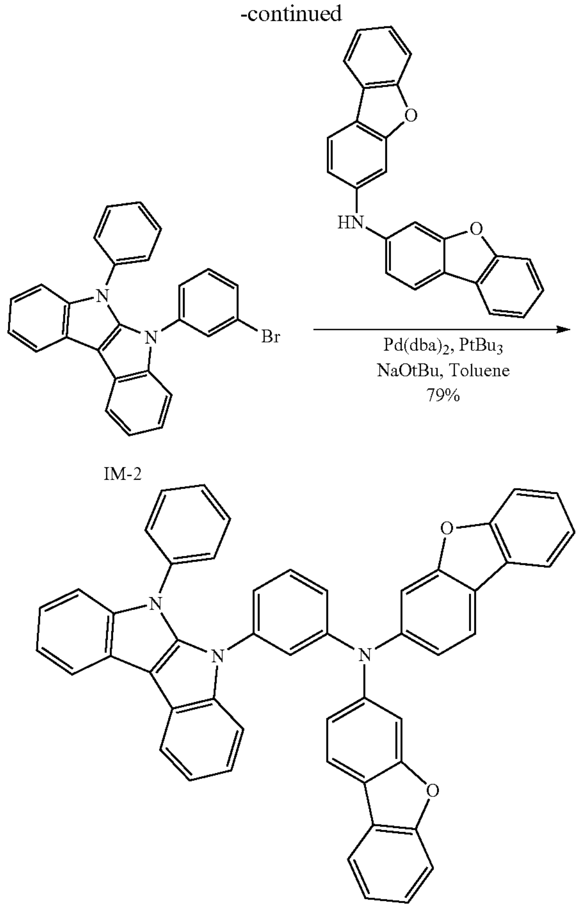

IM-2

A13

Synthesis of Intermediate IM-2

In an Ar atmosphere, 5-phenyl-5,6-dihydroindolo[2,3-b]indole (5.00 g, 17.7 mmol), $Pd(dba)_2$ (0.31 g, 0.03 equiv, 0.5 mmol), NaOtBu (11.65 g, 1.0 equiv, 1.70 mmol), toluene (88 mL), 1,3-dibromobenzene (4.60 g, 1.1 equiv, 19.5 mmol) and $tBu_3P$ (0.36 g, 0.1 equiv, 1.8 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-2 (6.82 g, yield 88%).

Intermediate IM-2 was identified by measuring FAB-MS in which a molecular ion peak was observed at mass m/z=437.

Synthesis of Compound A13

In an Ar atmosphere, IM-2 (5.00 g, 11.4 mmol), $Pd(dba)_2$ (0.20 g, 0.03 equiv, 0.3 mmol), NaOtBu (2.20 g, 2.0 equiv, 22.8 mmol), toluene (57 mL), bis(4-biphenyl-3-yl)amine (4.40 g, 1.1 equiv, 12.6 mmol) and $tBu_3P$ (0.23 g, 0.1 equiv, 1.1 mmol) were added sequentially into a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound A13 (6.37 g, yield 79%) as a solid.

Compound A13 was identified by measuring FAB-MS in which a molecular ion peak was observed at mass m/z=705.

3. Synthesis of Compound A22

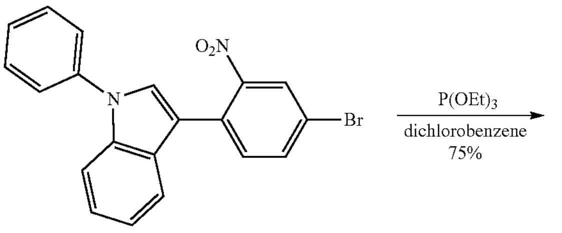

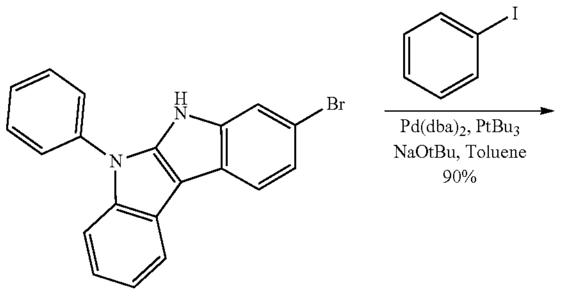

IM-3

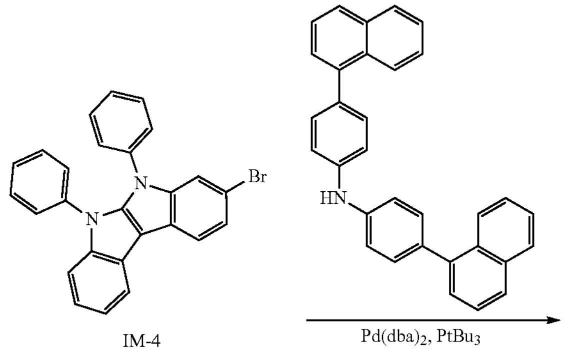

IM-4

Pd(dba)2, PtBu3
NaOtBu, Toluene
83%

-continued

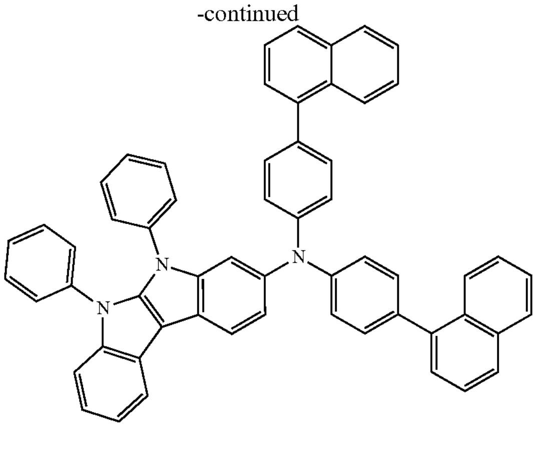

A22

Synthesis of Intermediate IM-3

In an Ar atmosphere, 3-(4-bromo-2-nitrophenyl)-1-phenyl-1H-indole (15.00 g, 38.1 mmol), o-dichlorobenzene (76.3 mL) and $P(OEt)_3$ (25.35 g, 4 equiv, 152.6 mmol) were added sequentially into a 300 mL three neck flask, and the mixture was stirred and heated at about 160° C. for about 24 hours. After cooling in the air to room temperature, reaction solvent was evaporated. The crude product thus obtained was purified by silica gel column chromatography (using a mixture of hexane and toluene as developing solvent) to obtain Intermediate IM-3 (10.33 g, yield 75%).

Intermediate IM-3 was identified by measuring FAB-MS in which a molecular ion peak was observed at mass m/z=361.

Synthesis of Intermediate IM-4

In an Ar atmosphere, IM-3 (7.00 g, 19.4 mmol), $Pd(dba)_2$ (0.33 g, 0.03 equiv, 0.6 mmol), NaOtBu (1.86 g, 1.0 equiv, 19.4 mmol), toluene (97 mL), iodobenzene (4.28 g, 1.1 equiv, 21.3 mmol) and $tBu_3P$ (0.39 g, 0.1 equiv, 1.9 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-4 (7.63 g, yield 90%).

Intermediate IM-4 was identified by measuring FAB-MS in which a molecular ion peak was observed at mass m/z=437.

Synthesis of Compound A22

In an Ar atmosphere, IM-4 (5.00 g, 11.4 mmol), $Pd(dba)_2$ (0.20 g, 0.03 equiv, 0.3 mmol), NaOtBu (2.20 g, 2.0 equiv, 22.8 mmol), toluene (57 mL), bis[4-(naphthalen-1-yl)phenyl]amine (5.30 g, 1.1 equiv, 12.6 mmol) and $tBu_3P$ (0.23 g, 0.1 equiv, 1.1 mmol) were added sequentially into a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound A22 (7.38 g, yield 83%) as a solid.

Compound A22 was identified by measuring FAB-MS in which a molecular ion peak was observed at mass m/z=777.

4. Synthesis of Compound A35

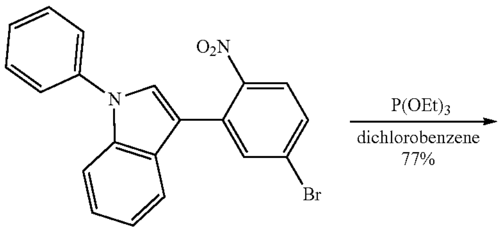

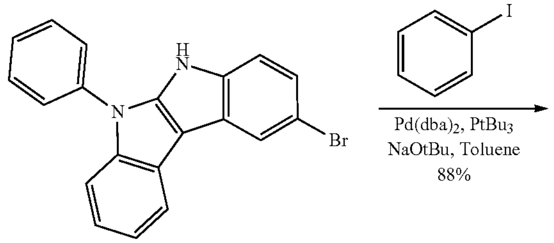

IM-5

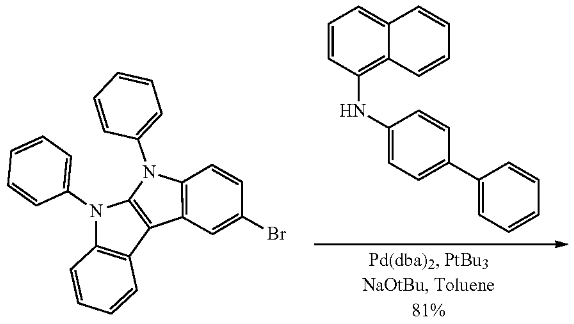

IM-6

-continued

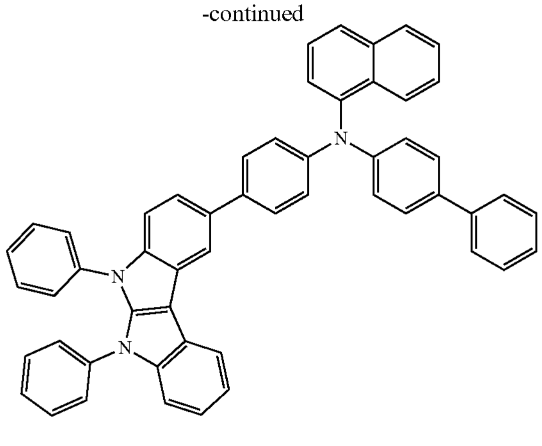

A35

Synthesis of Intermediate IM-5

In an Ar atmosphere, 3-(5-bromo-2-nitrophenyl)-1-phenyl-1H-indole (15.00 g, 38.1 mmol), o-dichlorobenzene (76.3 mL) and $P(OEt)_3$ (25.35 g, 4 equiv, 152.6 mmol) were added sequentially into a 300 mL three neck flask, and the mixture was stirred and heated at about 160° C. for about 24 hours. After cooling in the air to room temperature, reaction solvent was evaporated. The crude product thus obtained was purified by silica gel column chromatography (using a mixture of hexane and toluene as developing solvent) to obtain Intermediate IM-5 (10.61 g, yield 77%).

Intermediate IM-5 was identified by measuring FAB-MS in which a molecular ion peak was observed at mass m/z=361.

Synthesis of Intermediate IM-6

In an Ar atmosphere, IM-5 (7.00 g, 19.4 mmol), $Pd(dba)_2$ (0.33 g, 0.03 equiv, 0.6 mmol), NaOtBu (1.86 g, 1.0 equiv, 19.4 mmol), toluene (97 mL), iodobenzene (4.28 g, 1.1 equiv, 21.3 mmol) and $tBu_3P$ (0.39 g, 0.1 equiv, 1.9 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-6 (7.46 g, yield 88%).

Intermediate IM-6 was identified by measuring FAB-MS in which a molecular ion peak was observed at mass m/z=437.

Synthesis of Compound A35

In an Ar atmosphere, IM-6 (5.00 g, 11.4 mmol), $Pd(dba)_2$ (0.20 g, 0.03 equiv, 0.3 mmol), NaOtBu (2.20 g, 2.0 equiv, 22.8 mmol), toluene (57 mL), N-[(1,1'-biphenyl)-4-yl]naphthalen-1-amine (3.71 g, 1.1 equiv, 12.6 mmol) and $tBu_3P$ (0.23 g, 0.1 equiv, 1.1 mmol) were added sequentially to a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound A35 (6.74 g, yield 81%) as a solid.

Compound A35 was identified by measuring FAB-MS in which a molecular ion peak was observed at mass m/z=727.

5. Synthesis of Compound A42

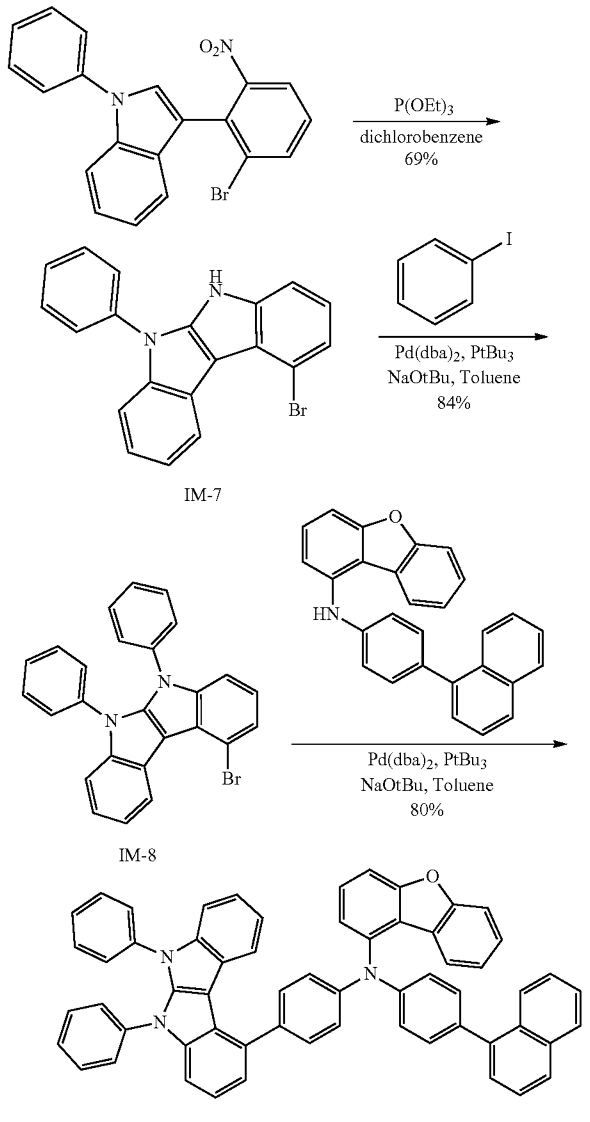

IM-7

IM-8

A42

Synthesis of Intermediate IM-7

In an Ar atmosphere, 3-(2-bromo-6-nitrophenyl)-1-phenyl-1H-indole (15.00 g, 38.1 mmol), o-dichlorobenzene (76.3 mL) and $P(OEt)_3$ (25.35 g, 4 equiv, 152.6 mmol) were added sequentially to a 300 mL three neck flask, and the mixture was stirred and heated at about 160° C. for about 24 hours. After cooling in the air to room temperature, reaction solvent was evaporated. The crude product thus obtained was purified by silica gel column chromatography (using a mixture of hexane and toluene as developing solvent) to obtain Intermediate IM-7 (9.51 g, yield 69%).

Intermediate IM-7 was identified by measuring FAB-MS in which a molecular ion peak was observed at mass m/z=361.

Synthesis of Intermediate IM-8

In an Ar atmosphere, IM-7 (7.00 g, 19.4 mmol), $Pd(dba)_2$ (0.33 g, 0.03 equiv, 0.6 mmol), NaOtBu (1.86 g, 1.0 equiv, 19.4 mmol), toluene (97 mL), iodobenzene (4.28 g, 1.1 equiv, 21.3 mmol) and $tBu_3P$ (0.39 g, 0.1 equiv, 1.9 mmol) were added sequentially to a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-8 (7.12 g, yield 84%).

Intermediate IM-8 was identified by measuring FAB-MS in which a molecular ion peak was observed at mass m/z=437.

Synthesis of Compound A42

In an Ar atmosphere, IM-8 (5.00 g, 11.4 mmol), $Pd(dba)_2$ (0.20 g, 0.03 equiv, 0.3 mmol), NaOtBu (2.20 g, 2.0 equiv, 22.8 mmol), toluene (57 mL), N-[4-(naphthalen-1-yl)phenyl]dibenzofuran-1-amine (4.85 g, 1.1 equiv, 12.6 mmol) and $tBu_3P$ (0.23 g, 0.1 equiv, 1.1 mmol) were added sequentially into a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound A42 (7.48 g, yield 80%) as a solid.

Compound A42 was identified by measuring FAB-MS in which a molecular ion peak was observed at mass m/z=817.

6. Synthesis of Compound B6

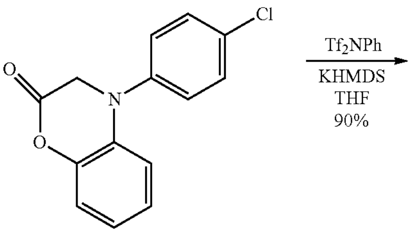

-continued

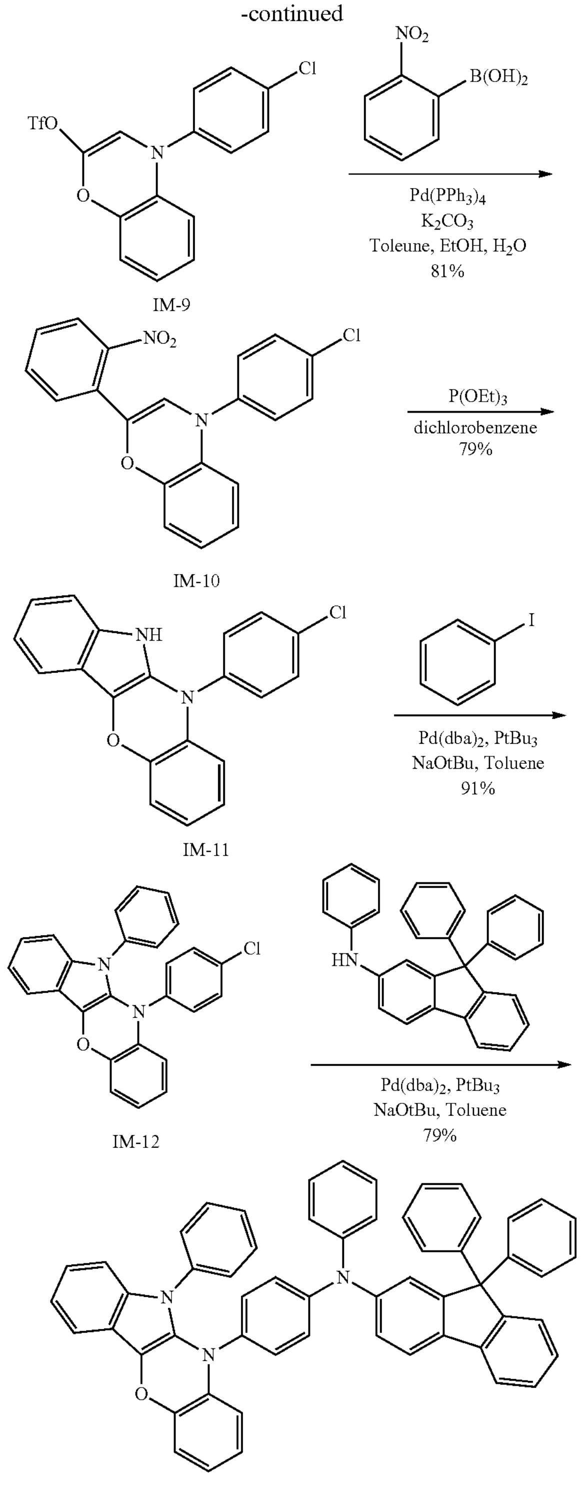

IM-9

IM-10

IM-11

IM-12

B6

Synthesis of Intermediate IM-9

In an Ar atmosphere, 4-(4-chlorophenyl)-3,4-dihydro-2H-benzoxazin-2-one (15.00 g, 57.8 mmol) and THF (193 mL, 0.3 M) were added to a 500 mL three neck flask. While stirring the resulting mixture at about −78° C., KHMDS/THF solution (63.5 mL, 1.1 equiv, 1.0 mol) was added dropwise thereto, followed by stirring at the same temperature for about 1 hour. N,N'-bis(trifluoromethanesulfonyl) aniline (24.76 g, 1.2 equiv, 69.3 mmol) and THF solution (17.3 mL, 1 mol/L) were added dropwise thereto, followed by stirring at the same temperature for about 30 minutes. The temperature was elevated to room temperature and the stirring was conducted for about 2 hours. 10% NaOH aqueous solution was added thereto, and then the reaction solution was extracted with AcOEt. After removing aqueous layer, an organic layer was washed with sodium bicarbonate aqueous solution and saturated saline in order, and then dried over $MgSO_4$. $MgSO_4$ was filtered out and organic layers were concentrated. The crude product IM-9 (20.37 g, yield 90%) thus obtained was used in the next step without purification.

Intermediate IM-9 was identified by measuring FAB-MS in which a molecular ion peak was observed at mass m/z=391.

Synthesis of Intermediate IM-10

In an Ar atmosphere, IM-9 (17.00 g, 43.4 mmol), 2-nitrophenylboronic acid (7.97 g, 1.1 equiv, 47.7 mmol), $K_2CO_3$ (17.99 g, 3.0 equiv, 130.2 mmol), $Pd(PPh_3)_4$ (2.51 g, 0.05 eq, 2.2 mmol), and a mixture solution of toluene/EtOH/$H_2O$ (4/2/1) (303 mL) were added sequentially into a 500 mL three neck flask, and the mixture was stirred and heated at about 80° C. for about 5 hours. After cooling in the air to room temperature, the reaction solution was extracted with toluene. After removing aqueous layer, an organic layer was washed with saturated saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-10 (12.82 g, yield 81%).

Intermediate IM-10 was identified by measuring FAB-MS in which a molecular ion peak was observed at mass m/z=364.

Synthesis of Intermediate IM-11

In an Ar atmosphere, IM-10 (12.00 g, 30.5 mmol), o-dichlorobenzene (66 mL) and $P(OEt)_3$ (21.86 g, 4 equiv, 131.6 mmol) were added sequentially into a 300 mL three neck flask, and the mixture was stirred and heated at about 160° C. for about 24 hours. After cooling in the air to room temperature, the reaction solution was evaporated. The crude product thus obtained was purified by silica gel column chromatography (using a mixture of hexane and toluene as developing solvent) to obtain Intermediate IM-11 (8.65 g, yield 79%).

Intermediate IM-11 was identified by measuring FAB-MS in which a molecular ion peak was observed at mass m/z=332.

Synthesis of Intermediate IM-12

In an Ar atmosphere, IM-11 (7.00 g, 21.0 mmol), $Pd(dba)_2$ (0.36 g, 0.03 equiv, 0.6 mmol), NaOtBu (4.04 g, 2.0 equiv, 42.1 mmol), toluene (105 mL), iodobenzene (4.72 g, 1.1 equiv, 23.1 mmol) and $tBu_3P$ (0.43 g, 0.1 equiv, 2.1 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer.

Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-12 (7.83 g, yield 91%).

Intermediate IM-12 was identified by measuring FAB-MS in which a molecular ion peak was observed at mass m/z=408.

Synthesis of Compound B6

In an Ar atmosphere, IM-12 (5.00 g, 12.2 mmol), $Pd(dba)_2$ (0.21 g, 0.03 equiv, 0.4 mmol), NaOtBu (2.35 g, 2.0 equiv, 24.5 mmol), toluene (61 mL), N,9,9-triphenyl-9H-fluoren-2-amine (5.51 g, 1.1 equiv, 13.5 mmol) and $tBu_3P$ (0.25 g, 0.1 equiv, 1.2 mmol) were added sequentially into a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound B6 (7.55 g, yield 79%) as a solid.

Compound B6 was identified by measuring FAB-MS in which a molecular ion peak was observed at mass m/z=781.

7. Synthesis of Compound B13

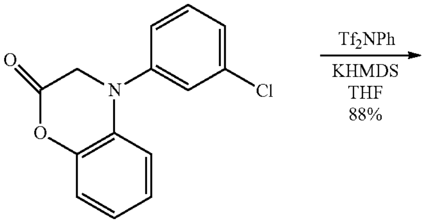

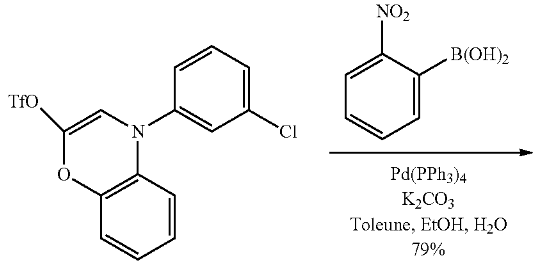

IM-13

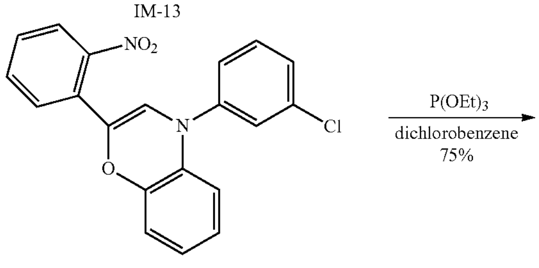

IM-14

-continued

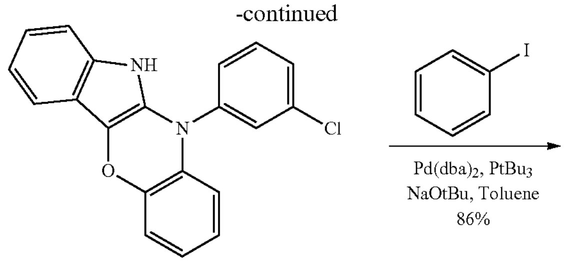

IM-15

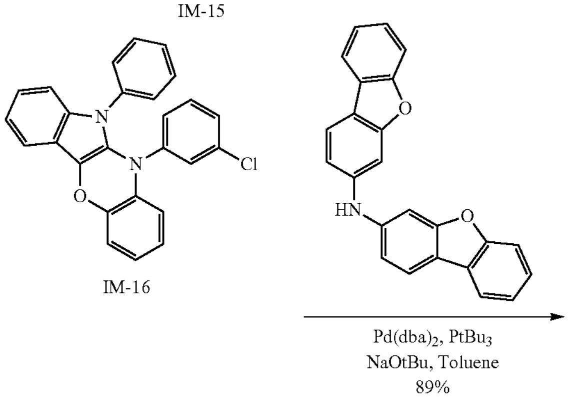

IM-16

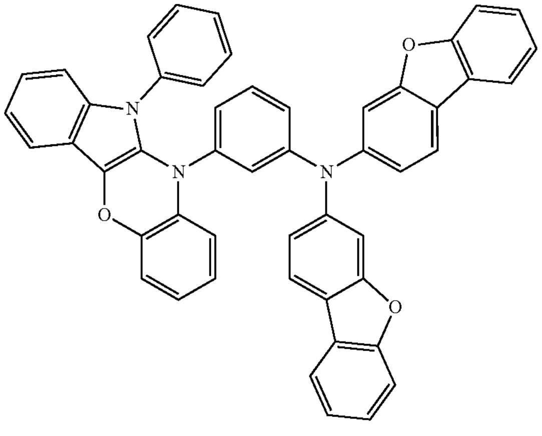

B13

Synthesis of Intermediate IM-13

Under an Ar atmosphere, 4-(3-chlorophenyl)-3,4-dihydro-2H-benzoxazin-2-one (15.00 g, 57.8 mmol) and THF (193 mL, 0.3 M) were added to a 500 mL three neck flask. While stirring the resulting mixture at about −78° C., KHMDS/THF solution (63.5 mL, 1.1 equiv, 1.0 mol) was added dropwisely thereto, followed by stirring at the same temperature for about 1 hour. N,N'-bis(trifluoromethanesulfonyl)aniline (24.76 g, 1.2 equiv, 69.3 mmol) and THF solution (17.3 mL, 1 mol/L) were added dropwise thereto, followed by stirring at the same temperature for about 30 minutes. The temperature was elevated to room temperature and the stirring was conducted for about 2 hours. 10% NaOH aqueous solution was added thereto, and then the reaction solution was extracted with AcOEt. After removing aqueous layer, an organic layer was washed with sodium bicarbonate aqueous solution and saturated saline in order, and then dried over $MgSO_4$. $MgSO_4$ was filtered out and organic layers were concentrated. The crude product IM-13 (19.91 g, yield 88%) thus obtained was used in the next step without purification.

Intermediate IM-13 was identified by measuring FAB-MS in which a molecular ion peak was observed at mass m/z=391.

Synthesis of Intermediate IM-14

In an Ar atmosphere, IM-13 (17.00 g, 43.4 mmol), 2-nitrophenylboronic acid (7.97 g, 1.1 equiv, 47.7 mmol), $K_2CO_3$ (17.99 g, 3.0 equiv, 130.2 mmol), $Pd(PPh_3)_4$ (2.51 g, 0.05 eq, 2.2 mmol), and a mixture solution of toluene/EtOH/$H_2O$ (4/2/1) (303 mL) were added sequentially into a 500 mL three neck flask, and the mixture was stirred and heated at about 80° C. for about 5 hours. After cooling in the air to room temperature, the reaction solution was extracted with toluene. After removing aqueous layer, an organic layer was washed with saturated saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-14 (12.50 g, yield 79%).

Intermediate IM-14 was identified by measuring FAB-MS in which a molecular ion peak was observed at mass m/z=364.

Synthesis of Intermediate IM-15

In an Ar atmosphere, IM-14 (12.00 g, 30.5 mmol), o-dichlorobenzene (66 mL) and $P(OEt)_3$ (21.86 g, 4 equiv, 131.6 mmol) were added sequentially into a 300 mL three neck flask, and the mixture was stirred and heated at about 160° C. for about 24 hours. After cooling in the air to room temperature, the reaction solution was evaporated. The crude product thus obtained was purified by silica gel column chromatography (using a mixture of hexane and toluene as developing solvent) to obtain Intermediate IM-15 (8.21 g, yield 75%).

Intermediate IM-15 was identified by measuring FAB-MS in which a molecular ion peak was observed at mass m/z=332.

Synthesis of Intermediate IM-16

In an Ar atmosphere, IM-15 (7.00 g, 21.0 mmol), $Pd(dba)_2$ (0.36 g, 0.03 equiv, 0.6 mmol), NaOtBu (4.04 g, 2.0 equiv, 42.1 mmol), toluene (105 mL), iodobenzene (4.72 g, 1.1 equiv, 23.1 mmol) and $tBu_3P$ (0.43 g, 0.1 equiv, 2.1 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-16 (7.40 g, yield 86%).

Intermediate IM-16 was identified by measuring FAB-MS in which a molecular ion peak was observed at mass m/z=408.

Synthesis of Compound B13

In an Ar atmosphere, IM-16 (5.00 g, 12.2 mmol), $Pd(dba)_2$ (0.21 g, 0.03 equiv, 0.4 mmol), NaOtBu (2.35 g, 2.0 equiv, 24.5 mmol), toluene (61 mL), bis(dibenzofuran-3-yl)amine (5.51 g, 1.1 equiv, 13.5 mmol) and $tBu_3P$ (0.25 g, 0.1 equiv, 1.2 mmol) were added sequentially into a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound B13 (7.76 g, yield 89%) as a solid.

Compound B13 was identified by measuring FAB-MS in which a molecular ion peak was observed at mass m/z=712.

8. Synthesis of Compound B23

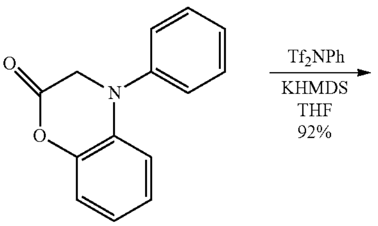

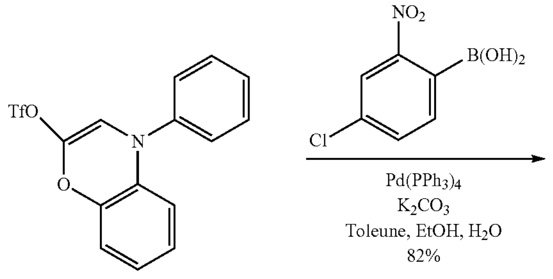

IM-17

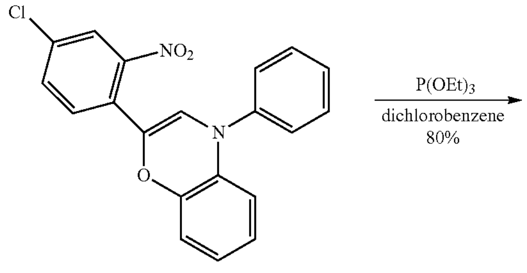

IM-18

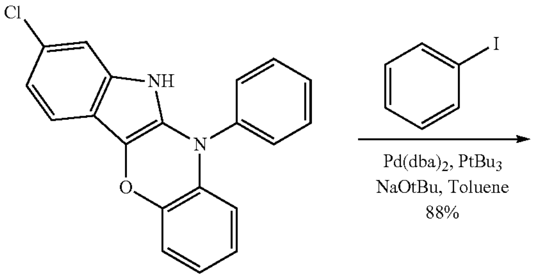

IM-19

-continued

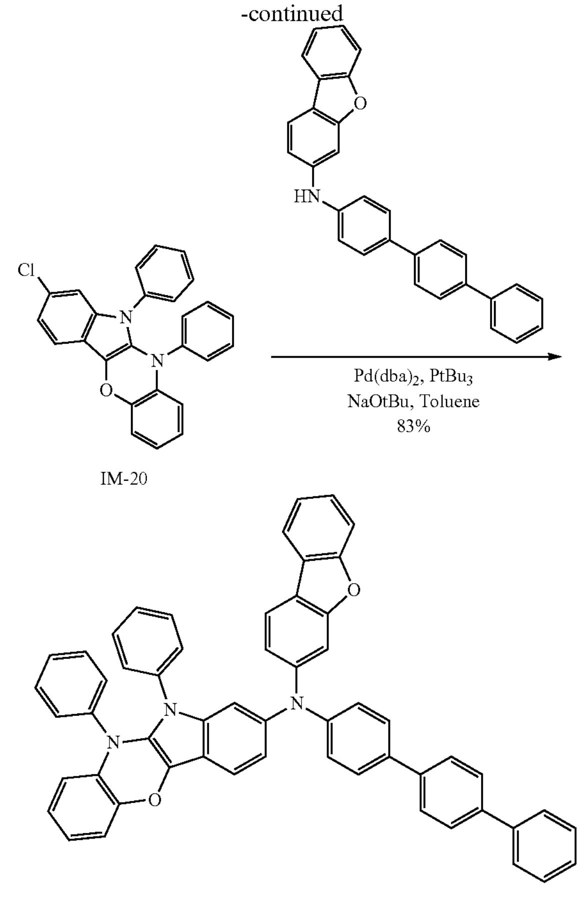

IM-20

B23

Synthesis of Intermediate IM-17

In an Ar atmosphere, 4-phenyl-3,4-dihydro-2H-benzoxazin-2-one (15.00 g, 66.6 mmol) and THF (222 mL, 0.3 M) were added to a 500 mL three neck flask. While stirring the resulting mixture at about −78° C., KHMDS/THF solution (73.3 mL, 1.1 equiv, 1.0 mol) was added dropwise thereto, followed by stirring at the same temperature for about 1 hour. N,N'-bis(trifluoromethanesulfonyl)aniline (28.55 g, 1.2 equiv, 79.9 mmol) and THF solution (20.0 mL, 1 mol/L) were added dropwise thereto, followed by stirring at the same temperature for about 30 minutes. The temperature was elevated to room temperature and the stirring was conducted for about 2 hours. 10% NaOH aqueous solution was added thereto, and then the reaction solution was extracted with AcOEt. After removing the aqueous layer, an organic layer was washed with sodium bicarbonate aqueous solution and saturated saline in order, and then dried over $MgSO_4$. $MgSO_4$ was filtered out and organic layers were concentrated. The crude product IM-17 (21.89 g, yield 92%) thus obtained was used in the next step without purification.

Intermediate IM-17 was identified by measuring FAB-MS in which a molecular ion peak was observed at mass m/z=357.

Synthesis of Intermediate IM-18

In an Ar atmosphere, IM-17 (17.00 g, 47.6 mmol), 4-chloro-2-nitrophenylboronic acid (10.54 g, 1.1 equiv, 52.3 mmol), $K_2CO_3$ (19.73 g, 3.0 equiv, 142.7 mmol), $Pd(PPh_3)_4$ (2.74 g, 0.05 eq, 2.4 mmol), and a mixture solution of toluene/EtOH/$H_2O$ (4/2/1) (333 mL) were added sequentially to a 500 mL three neck flask, and the mixture was stirred and heated at about 80° C. for about 5 hours. After cooling in the air to room temperature, the reaction solution was extracted with toluene. After removing aqueous layer, an organic layer was washed with saturated saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-18 (14.23 g, yield 82%).

Intermediate IM-18 was identified by measuring FAB-MS in which a molecular ion peak was observed at mass m/z=364.

Synthesis of Intermediate IM-19

In an Ar atmosphere, IM-18 (12.00 g, 32.9 mmol), o-dichlorobenzene (66 mL) and $P(OEt)_3$ (21.86 g, 4 equiv, 131.6 mmol) were added in order to a 300 mL three neck flask, and the mixture was stirred and heated at about 160° C. for about 24 hours. After cooling in the air to room temperature, the reaction solution was evaporated. The crude product thus obtained was purified by silica gel column chromatography (using a mixture of hexane and toluene as developing solvent) to obtain Intermediate IM-19 (8.76 g, yield 80%).

Intermediate IM-19 was identified by measuring FAB-MS in which a molecular ion peak was observed at mass m/z=332.

Synthesis of Intermediate IM-20

In an Ar atmosphere, IM-19 (7.00 g, 21.0 mmol), $Pd(dba)_2$ (0.36 g, 0.03 equiv, 0.6 mmol), NaOtBu (4.04 g, 2.0 equiv, 42.1 mmol), toluene (105 mL), iodobenzene (4.72 g, 1.1 equiv, 23.1 mmol) and $tBu_3P$ (0.43 g, 0.1 equiv, 2.1 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-20 (7.57 g, yield 88%).

Intermediate IM-20 was identified by measuring FAB-MS in which a molecular ion peak was observed at mass m/z=408.

Synthesis of Compound B23

In an Ar atmosphere, IM-20 (5.00 g, 12.2 mmol), $Pd(dba)_2$ (0.21 g, 0.03 equiv, 0.4 mmol), NaOtBu (2.35 g, 2.0 equiv, 24.5 mmol), toluene (61 mL), N-[(1,1':4',1"-terphenyl)-4-yl]dibenzofuran-3-amine (5.54 g, 1.1 equiv, 13.5 mmol) and $tBu_3P$ (0.25 g, 0.1 equiv, 1.2 mmol) were added sequentially to a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound B23 (7.96 g, yield 83%) as a solid.

Compound B23 was identified by measuring FAB-MS in which a molecular ion peak was observed at mass m/z=783.

9. Synthesis of Compound C66

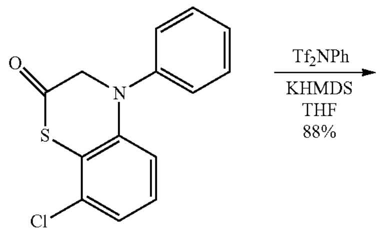

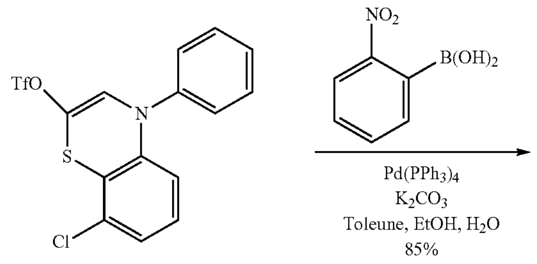

IM-21

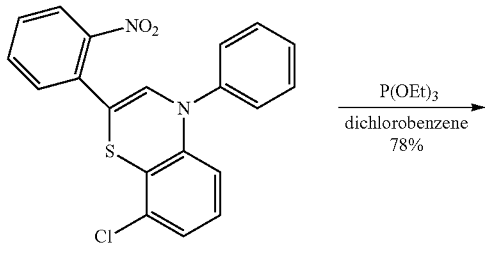

IM-22

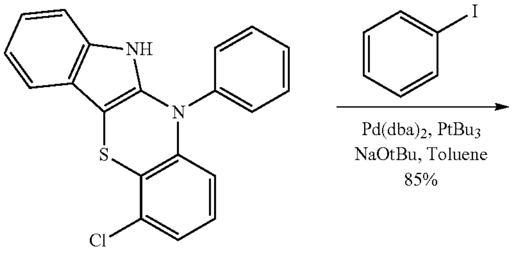

IM-23

-continued

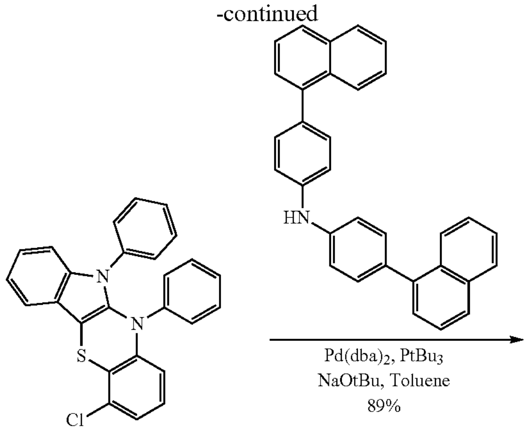

IM-24

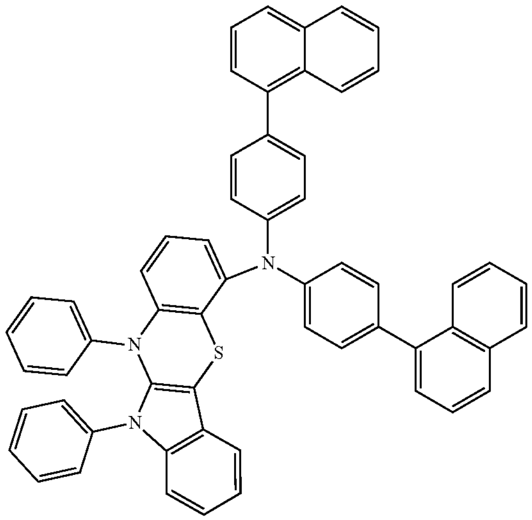

C66

Synthesis of Intermediate IM-21

In an Ar atmosphere, 8-chloro-4-phenyl-3,4-dihydro-2H-benzothiazin-2-one (15.00 g, 54.4 mmol) and THF (181 mL, 0.3 M) were added to a 500 mL three neck flask. While stirring the resulting mixture at about −78° C., KHMDS/THF solution (59.8 mL, 1.1 equiv, 1.0 mol) was added dropwise thereto, followed by stirring at the same temperature for about 1 hour. N,N'-bis(trifluoromethanesulfonyl) aniline (23.32 g, 1.2 equiv, 59.8 mmol) and THF solution (16.3 mL, 1 mol/L) were added dropwise thereto, followed by stirring at the same temperature for about 30 minutes. The temperature was elevated to room temperature and the stirring was conducted for about 2 hours. 10% NaOH aqueous solution was added thereto, and then the reaction solution was extracted with AcOEt. After removing aqueous layer, an organic layer was washed with sodium bicarbonate aqueous solution and saturated saline in that order, and then dried over $MgSO_4$. $MgSO_4$ was filtered out and organic layers were concentrated. The crude product IM-21 (19.52 g, yield 88%) thus obtained was used in the next step without purification.

Intermediate IM-21 was identified by measuring FAB-MS in which a molecular ion peak was observed at mass m/z=407.

Synthesis of Intermediate IM-22

In an Ar atmosphere, IM-21 (17.00 g, 41.7 mmol), 2-nitrophenylboronic acid (7.65 g, 1.1 equiv, 45.9 mmol), $K_2CO_3$ (17.28 g, 3.0 equiv, 125.1 mmol), $Pd(PPh_3)_4$ (2.41 g, 0.05 eq, 2.1 mmol) and a mixture solution of toluene/EtOH/$H_2O$ (4/2/1) (292 mL) were added sequentially into a 500 mL three neck flask, and the mixture was stirred and heated at about 80° C. for about 5 hours. After cooling in the air to room temperature, the reaction solution was extracted with toluene. After removing aqueous layer, an organic layer was washed with saturated saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-22 (13.49 g, yield 85%).

Intermediate IM-22 was identified by measuring FAB-MS in which a molecular ion peak was observed at mass m/z=380.

Synthesis of Intermediate IM-23

In an Ar atmosphere, IM-22 (12.00 g, 31.5 mmol), o-dichlorobenzene (63 mL) and $P(OEt)_3$ (20.94 g, 4 equiv, 126.0 mmol) were added sequentially into a 300 mL three neck flask, and the mixture was stirred and heated at about 160° C. for about 24 hours. After cooling in the air to room temperature, the reaction solution was evaporated. The crude product thus obtained was purified by silica gel column chromatography (using a mixture of hexane and toluene as developing solvent) to obtain Intermediate IM-23 (8.57 g, yield 78%).

Intermediate IM-23 was identified by measuring FAB-MS in which a molecular ion peak was observed at mass m/z=348.

Synthesis of Intermediate IM-24

In an Ar atmosphere, IM-23 (7.00 g, 20.1 mmol), $Pd(dba)_2$ (0.35 g, 0.03 equiv, 0.6 mmol), NaOtBu (3.86 g, 2.0 equiv, 40.1 mmol), toluene (100 mL), iodobenzene (4.50 g, 1.1 equiv, 22.1 mmol) and $tBu_3P$ (0.41 g, 0.1 equiv, 2.0 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-24 (7.25 g, yield 85%).

Intermediate IM-24 was identified by measuring FAB-MS in which a molecular ion peak was observed at mass m/z=408.

Synthesis of Compound C66

In an Ar atmosphere, IM-24 (5.00 g, 11.8 mmol), $Pd(dba)_2$ (0.20 g, 0.03 equiv, 0.4 mmol), NaOtBu (2.26 g, 2.0 equiv, 23.5 mmol), toluene (58 mL), bis[4-(naphthalen-1-yl)phenyl]amine (5.46 g, 1.1 equiv, 12.9 mmol) and $tBu_3P$ (0.24 g, 0.1 equiv, 1.2 mmol) were added sequentially into a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound C66 (8.48 g, yield 89%) as a solid.

Compound C66 was identified by measuring FAB-MS in which a molecular ion peak was observed at mass m/z=810.

10. Synthesis of Compound D34

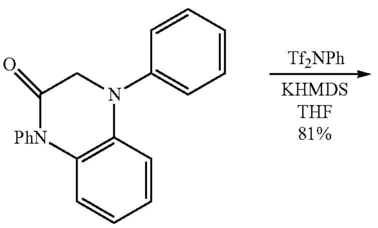

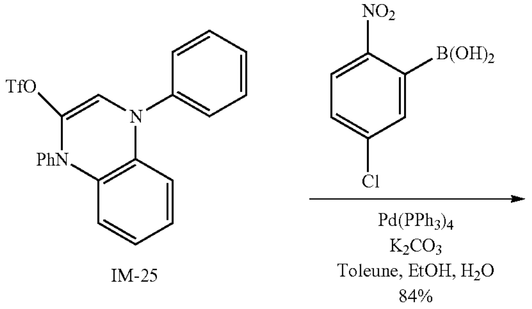

IM-25

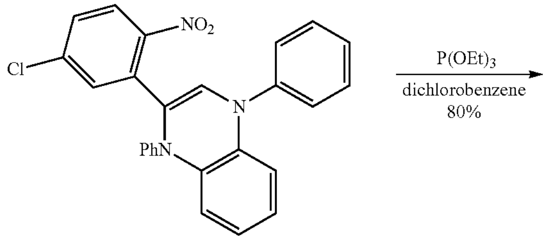

IM-26

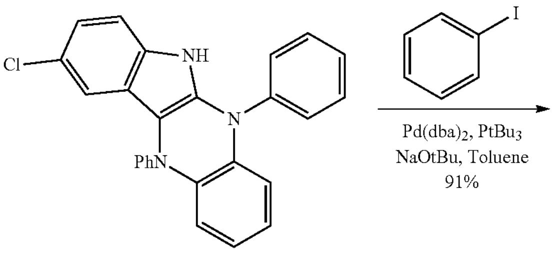

IM-27

-continued

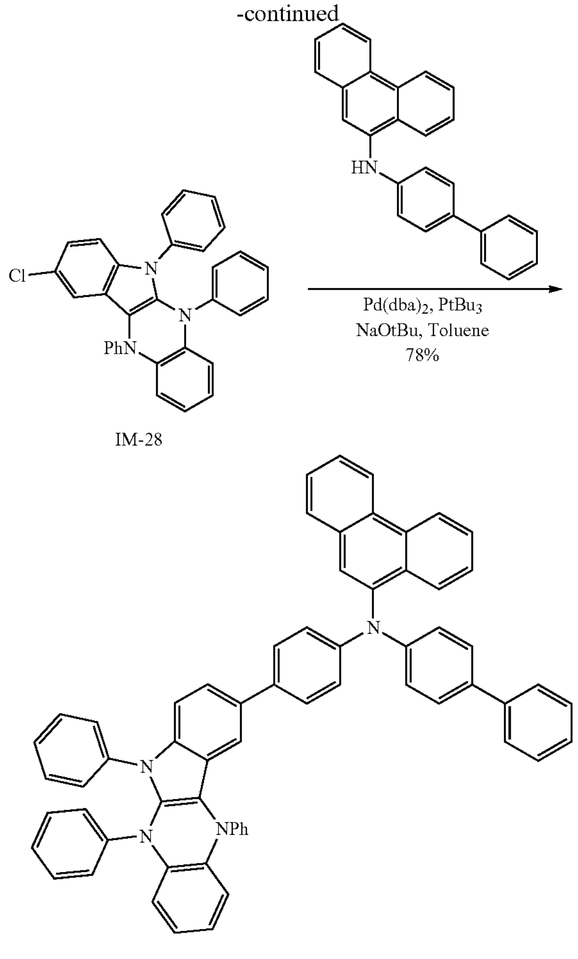

IM-28

D34

Synthesis of Intermediate IM-25

In an Ar atmosphere, 1,4-diphenyl-3,4-dihydroquinoxalin-2(1H)-one (15.00 g, 49.9 mmol) and THF (166 mL, 0.3 M) were added to a 500 mL three neck flask. While stirring the resulting mixture at about −78° C., KHMDS/THF solution (54.9 mL, 1.1 equiv, 1.0 mol) was added dropwise thereto, followed by stirring at the same temperature for about 1 hour. N,N'-bis(trifluoromethanesulfonyl)aniline (21.41 g, 1.2 equiv, 59.9 mmol) and THF solution (15.0 mL, 1 mol/L) were added dropwise thereto, followed by stirring at the same temperature for about 30 minutes. The temperature was elevated to room temperature and the stirring was conducted for about 2 hours. 10% NaOH aqueous solution was added thereto, and then the reaction solution was extracted with AcOEt. After removing the aqueous layer, an organic layer was washed with sodium bicarbonate aqueous solution and saturated saline in order, and then dried over $MgSO_4$. $MgSO_4$ was filtered out and organic layers were concentrated. The crude product IM-25 (17.49 g, yield 81%) thus obtained was used in the next step without purification.

Intermediate IM-25 was identified by measuring FAB-MS in which a molecular ion peak was observed at mass m/z=432.

Synthesis of Intermediate IM-26

In an Ar atmosphere, (2-bromophenyl)(2-bromo-4-chlorophenyl) ether (10.00 g, 27.6 mmol) and THF (92 mL, 0.3M) were added to a 500 mL three neck flask. While stirring the resulting mixture at about −78° C., nBuLi/n-hexane solution (37.9 mL, 2.2 equiv, 1.6 mol) was added dropwise thereto, followed by stirring at the same temperature for about 1 hour. IM-12 (8.11 g, 1.1 equiv, 30.3 mmol) in THF solution (8 mL, 1 mol/L) was added dropwise thereto, followed by stirring at the same temperature for about 30 minutes. The temperature was elevated to room temperature and the stirring was conducted for about 8 hours. The reaction solution was quenched with a saturated aqueous ammonium chloride solution, and then extracted with toluene. After removing aqueous layer, an organic layer was washed with sodium bicarbonate aqueous solution and saturated saline sequentially, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-26 (5.50 g, yield 50%).

Intermediate IM-26 was identified by measuring FAB-MS in which a molecular ion peak was observed at mass m/z=398.

Synthesis of Intermediate IM-27

In an Ar atmosphere, IM-26 (12.00 g, 27.3 mmol), o-dichlorobenzene (55 mL) and $P(OEt)_3$ (18.13 g, 4 equiv, 109.1 mmol) were added sequentially into a 300 mL three neck flask, and the mixture was stirred and heated at about 160° C. for about 24 hours. After cooling in the air to room temperature, the reaction solution was evaporated. The crude product thus obtained was purified by silica gel column chromatography (using a mixture of hexane and toluene as developing solvent) to obtain Intermediate IM-27 (8.90 g, yield 80%).

Intermediate IM-27 was identified by measuring FAB-MS in which a molecular ion peak was observed at mass m/z=407.

Synthesis of Intermediate IM-28

In an Ar atmosphere, IM-27 (7.00 g, 17.2 mmol), $Pd(dba)_2$ (0.30 g, 0.03 equiv, 0.5 mmol), NaOtBu (3.30 g, 2.0 equiv, 34.3 mmol), toluene (86 mL), iodobenzene (3.85 g, 1.1 equiv, 18.9 mmol) and $tBu_3P$ (0.35 g, 0.1 equiv, 1.7 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-28 (7.56 g, yield 91%).

Intermediate IM-28 was identified by measuring FAB-MS in which a molecular ion peak was observed at mass m/z=484.

Synthesis of Compound D34

In an Ar atmosphere, IM-28 (5.00 g, 10.3 mmol), $Pd(dba)_2$ (0.18 g, 0.03 equiv, 0.3 mmol), NaOtBu (1.99 g, 2.0 equiv, 20.3 mmol), toluene (52 mL), N-[(1,1'-biphenyl)-4-yl]phenanthren-9-amine (3.93 g, 1.1 equiv, 11.4 mmol)

and $tBu_3P$ (0.21 g, 0.1 equiv, 1.0 mmol) were added sequentially into a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound D34 (7.00 g, yield 78%) as a solid.

Compound D34 was identified by measuring FAB-MS in which a molecular ion peak was observed at mass m/z=869.

11. Synthesis of Compound A17

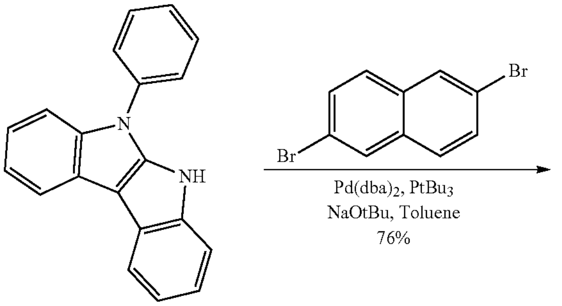

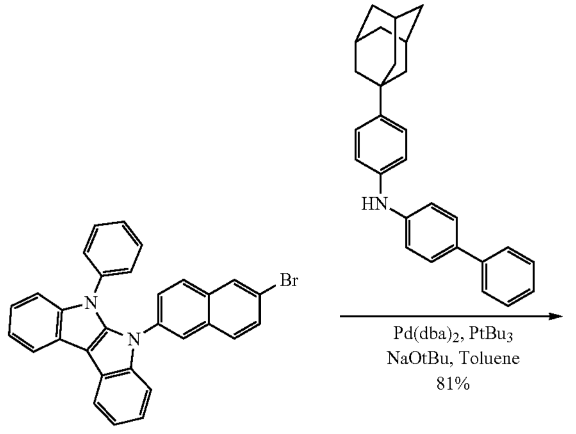

IM-29

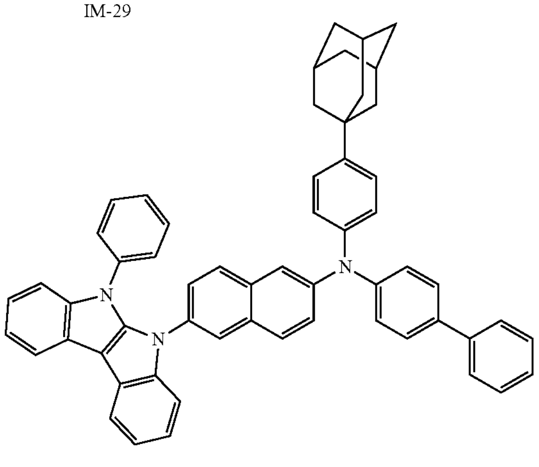

A17

Synthesis of Intermediate IM-29

In an Ar atmosphere, 5-phenyl-5,6-dihydroindolo[2,3-b]indole (5.00 g, 17.7 mmol), $Pd(dba)_2$ (0.31 g, 0.03 equiv, 0.5 mmol), NaOtBu (11.65 g, 1.0 equiv, 1.70 mmol), toluene (88 mL), 2,6-dibromonaphthalene (5.57 g, 1.1 equiv, 19.5 mmol) and $tBu_3P$ (0.36 g, 0.1 equiv, 1.8 mmol) were added sequentially into a 300 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Intermediate IM-29 (6.56 g, yield 76%).

Intermediate IM-29 was identified by measuring FAB-MS in which a molecular ion peak was observed at mass m/z=487.

Synthesis of Compound A17

In an Ar atmosphere, IM-29 (5.00 g, 11.4 mmol), $Pd(dba)_2$ (0.20 g, 0.03 equiv, 0.3 mmol), NaOtBu (2.20 g, 2.0 equiv, 22.8 mmol), toluene (57 mL), N-{4-[(3r,5r,7r)-adamantan-1-yl]phenyl}-(1,1'-biphenyl)-4-amine (4.28 g, 1.1 equiv, 12.6 mmol) and $tBu_3P$ (0.23 g, 0.1 equiv, 1.1 mmol) were added sequentially into a 200 mL three neck flask, and the mixture was stirred and heated to reflux for about 6 hours. After cooling in the air to room temperature, water was added to the reactant and an organic layer was separated and taken. Toluene was added to the remaining aqueous layer, followed by extraction of the aqueous layer. Organic layers were combined and washed with saline, and then dried over $MgSO_4$. $MgSO_4$ was filtered out and organic layers were concentrated. The crude product thus obtained was purified by silica gel column chromatography (using a mixture of hexane and toluene as developing solvent) to obtain Compound A17 (6.53 g, yield 81%) as a solid.

Compound A17 was identified by measuring FAB-MS in which a molecular ion peak was observed at mass m/z=786.

The above-described synthesis examples illustrate exemplary embodiments, and the reaction condition may be changed, if necessary. In addition, the compound according to an embodiment of the inventive concept may be synthesized to have a variety of substituents by using known methods and materials in the art. The compound according to an embodiment of the inventive concept may have a characteristic suitable for an organic electroluminescence device by introducing a variety of substituents to the core structure represented by Formula 1.

(Device Manufacturing Example)

Organic electroluminescence devices of Examples 1 to 11 were manufactured by using Example Compounds A2, A13, A22, A35, A42, B6, B13, B23, C66, D34 and A17 as a material for a hole transport layer.

Example Compounds
A2
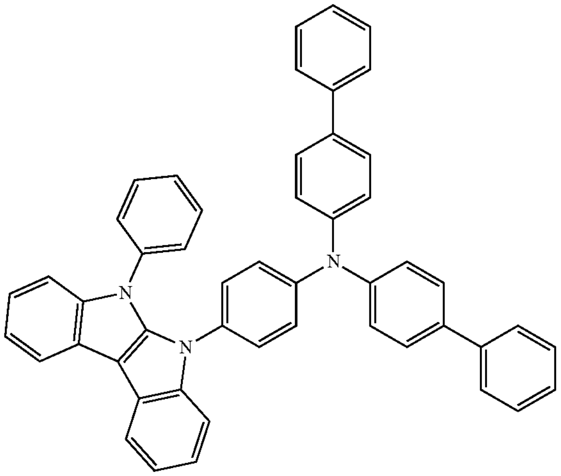
A13
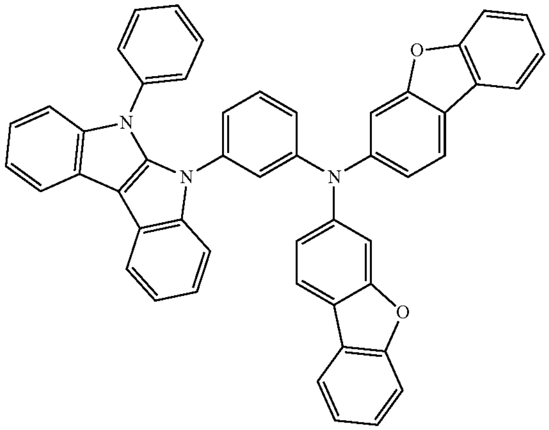
A22
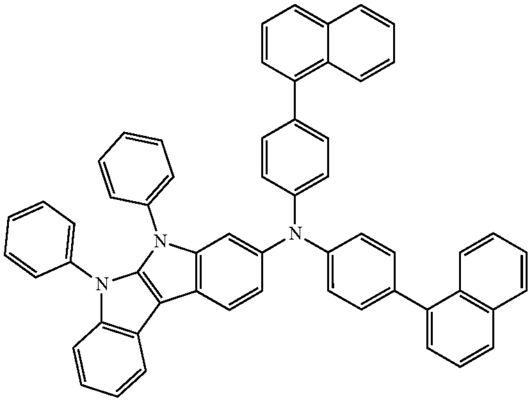
-continued
A35
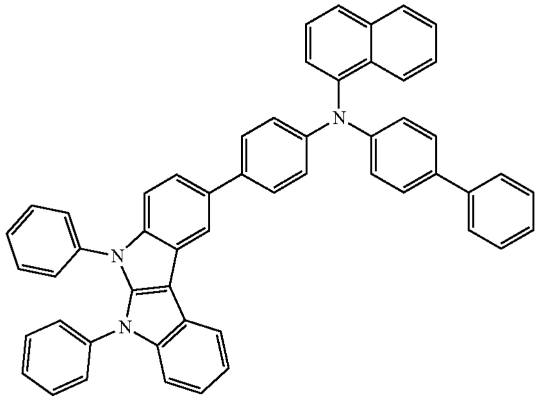
A42
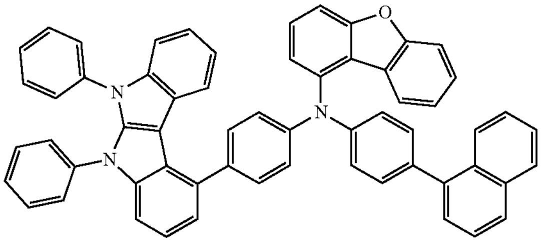
B6
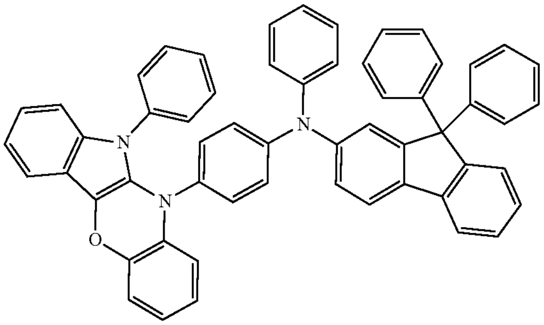
B13
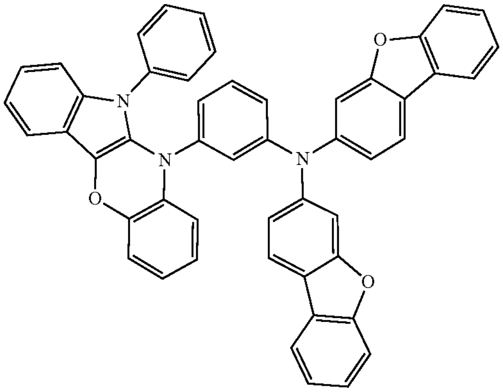

-continued
B23
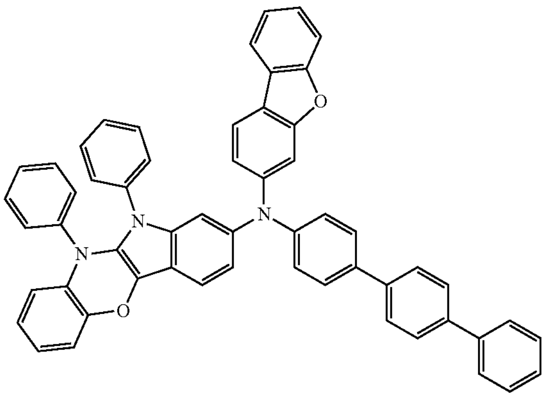
C66
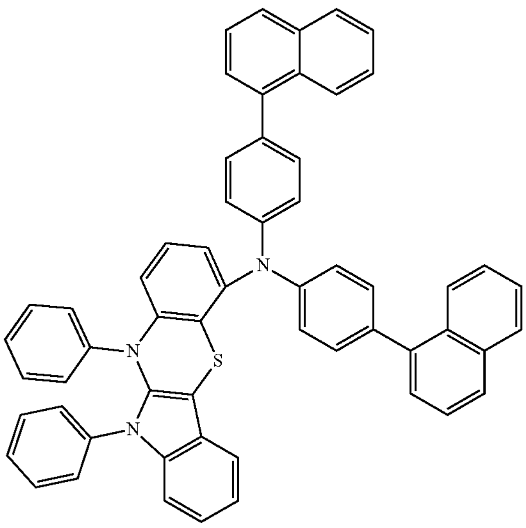
D34
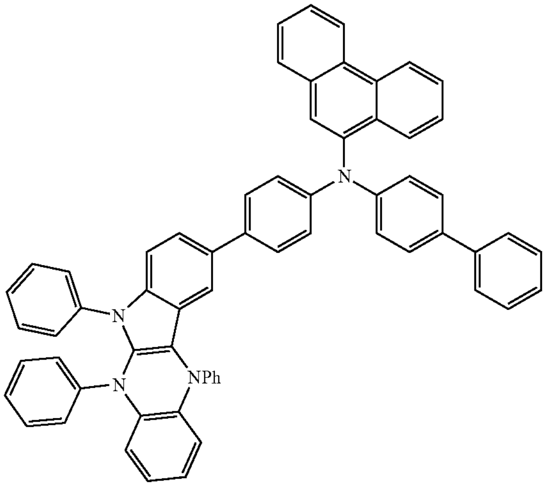
-continued
A17
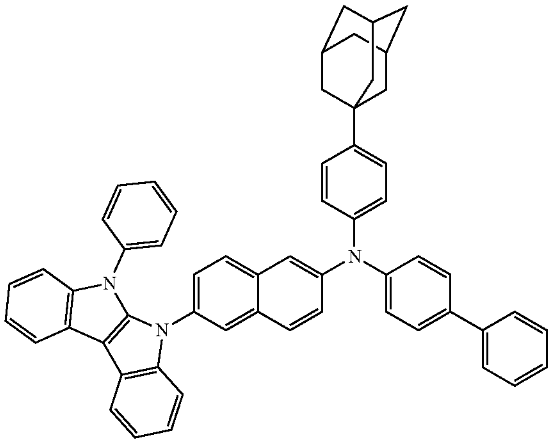
Organic electroluminescence devices of Comparative Examples 1 to 10 were manufactured by using the following known compounds as a material for a hole transport layer. [Comparative Compounds]
R1
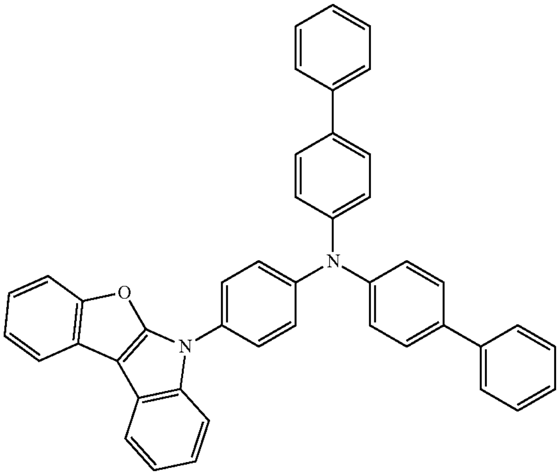
R2
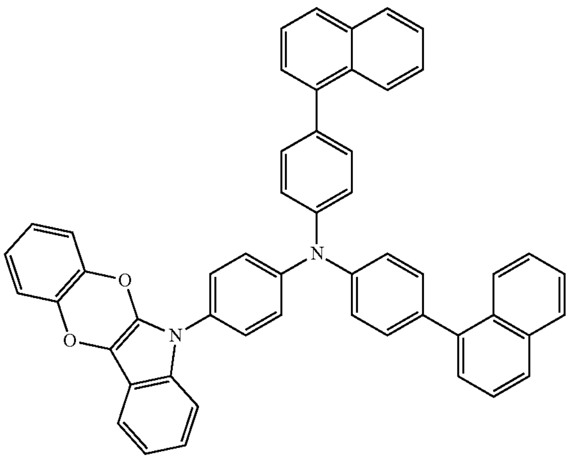

-continued
R3
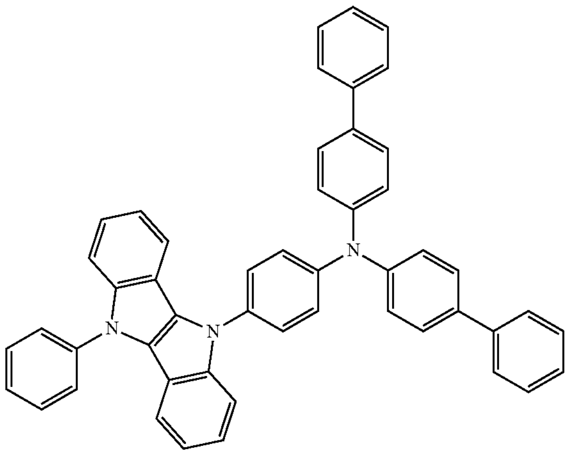
R4
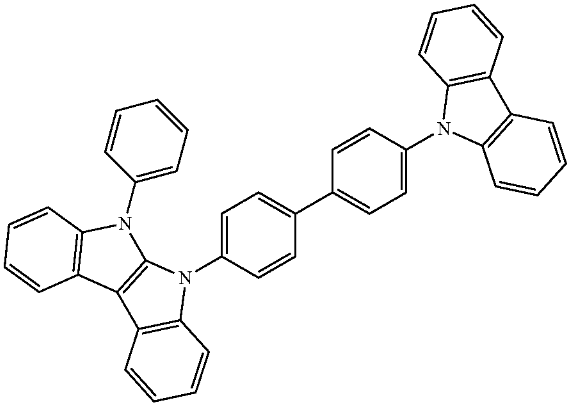
R5
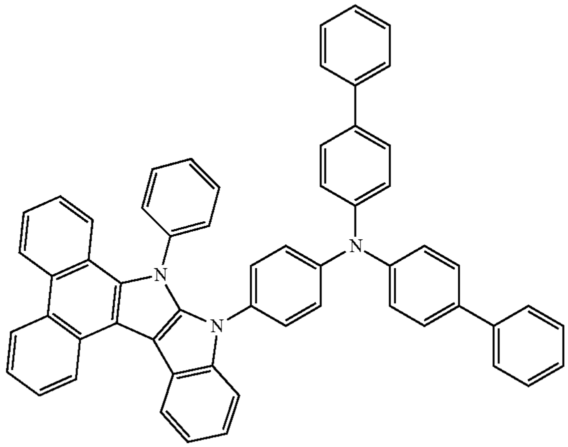
-continued
R6
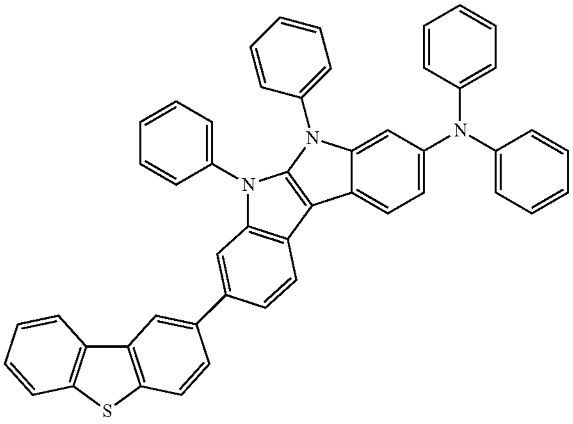
R7
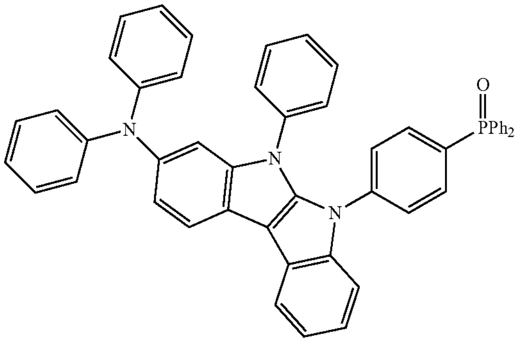
R8
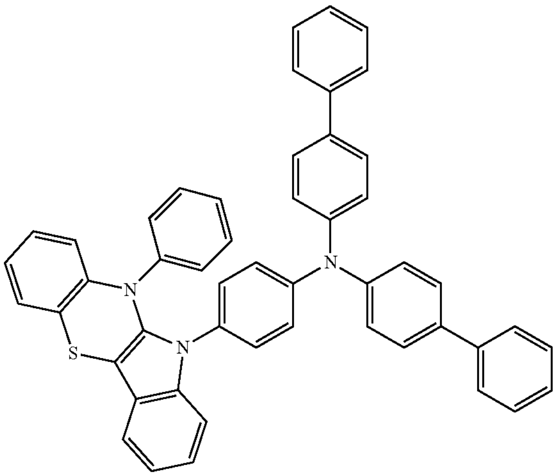

-continued

R9

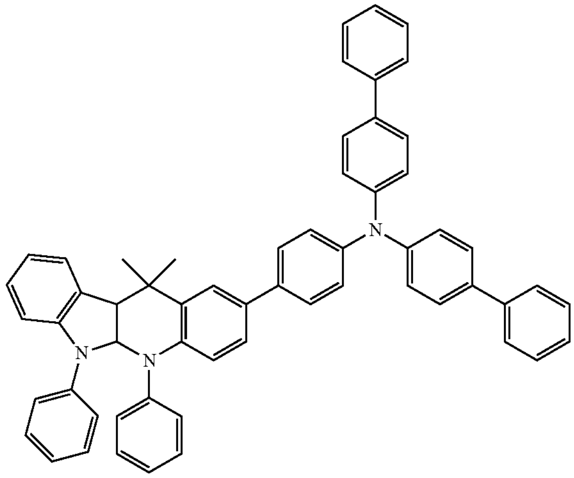

R10

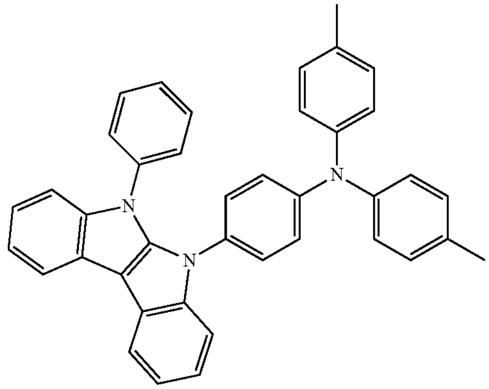

Organic electroluminescence devices of Examples 1 to 11 and Comparative Examples 1 to 10 were manufactured by the following method.

ITO glass substrate (Corning Incorporated) with ITO layer of a thickness of about 1,500 Å was cut into a size of 50 mm×50 mm×0.7 mm, followed by performing ultrasonic cleaning with isopropyl alcohol and pure water for about 5 minutes each. After performing UV irradiation and ozone treatment for about 30 minutes, the ITO glass substrate was set in a vacuum deposition apparatus.

On the substrate, a hole injection layer was formed by vacuum deposition of a known compound 1-TNATA to a thickness of about 600 Å, and a hole transport layer was formed by vacuum deposition of Example Compounds or Comparative Compounds to a thickness of about 300 Å.

On the hole transport layer, an emission layer was formed by co-deposition of 9,10-di-naphthalen-2-yl-anthracene (ADN) as a known blue fluorescence host and 2,5,8,11-tetra-t-butylperylene (TBP) as a known blue fluorescence dopant at a weight ratio of 97:3 to a thickness of about 250 Å.

Next, an electron transport layer was formed by depositing $Alq_3$ to a thickness of about 250 Å on the emission layer, and then an electron injection layer was formed by depositing LiF to a thickness of about 10 Å on the electron transport layer. LiF/A1 electrode was formed by vacuum deposition of A1 to a thickness of about 1,000 Å (a second electrode) to manufacture an organic electroluminescence device.

The driving voltage, efficiency and half-life of the organic electroluminescence devices manufactured in Examples 1 to 11 and Comparative Examples 1 to 10 were measured and shown in Table 1 below.

TABLE 1

| Device manufacturing example | Hole transport layer | Voltage (V) | Efficiency (cd/A) | Life LT50 (h) |
|---|---|---|---|---|
| Example 1 | Example Compound A2 | 5.4 | 7.7 | 2000 |
| Example 2 | Example Compound A13 | 5.5 | 7.8 | 1950 |
| Example 3 | Example Compound A22 | 5.6 | 7.6 | 2100 |
| Example 4 | Example Compound A35 | 5.7 | 7.5 | 2050 |
| Example 5 | Example Compound A42 | 5.6 | 7.8 | 1900 |
| Example 6 | Example Compound B6 | 5.6 | 7.8 | 2050 |
| Example 7 | Example Compound B13 | 5.6 | 7.9 | 2000 |
| Example 8 | Example Compound B23 | 5.6 | 7.7 | 2100 |
| Example 9 | Example Compound C66 | 5.6 | 7.7 | 1900 |
| Example 10 | Example Compound D34 | 5.6 | 7.6 | 2000 |
| Example 11 | Example Compound A17 | 5.7 | 7.9 | 2000 |
| Comparative Example 1 | Comparative Compound R1 | 6.4 | 6.0 | 1650 |
| Comparative Example 2 | Comparative Compound R2 | 6.5 | 6.1 | 1600 |
| Comparative Example 3 | Comparative Compound R3 | 6.3 | 6.0 | 1550 |
| Comparative Example 4 | Comparative Compound R4 | 6.4 | 5.8 | 1550 |
| Comparative Example 5 | Comparative Compound R5 | 6.1 | 5.7 | 1600 |
| Comparative Example 6 | Comparative Compound R6 | 5.9 | 5.8 | 1600 |
| Comparative Example 7 | Comparative Compound R7 | 6.0 | 5.4 | 1450 |
| Comparative Example 8 | Comparative Compound R8 | 5.9 | 6.8 | 1680 |
| Comparative Example 9 | Comparative Compound R9 | 6.2 | 5.5 | 1500 |
| Comparative Example 10 | Comparative Compound R10 | 5.9 | 7.5 | 1800 |

The above results are a measured value at a current density of about 10 $mA/cm^2$, and the half-life means time required for a luminance half-time from an initial luminance of 1,000 $cd/m^2$. Referring to the results in Table 1, it may be found that the organic electroluminescence devices of Examples 1 to 11 attain low driving voltage, long device life and high efficiency when compared with those of Comparative Examples 1 to 10. Amine compounds are known as a hole transport material which has a strong electron resistance and contributes to a long device life. The condensed cyclic compound according to an embodiment of the inventive concept has an indoloindole group with an excellent heat and charge resistance as a core structure, thereby maintaining the property of amine compounds and increasing thermal stability and electron resistance, which results in extended life of the device using the compound.

In addition, it seems that the condensed cyclic compound according to an embodiment of the inventive concept has an indoloindole core structure in which a nitrogen atom enhances hole transport property of the whole molecule, thereby enhancing the probability of recombining holes and electrons in an emission layer, which results in enhanced emission efficiency of the device using the compound.

Furthermore, it seems that the condensed cyclic compound according to an embodiment of the inventive concept is a polycyclic compound with four condensed rings, in which each of two adjacent rings includes a nitrogen atom substituted with an aryl group, thereby maintaining distorted conformation due to electronic repulsion, and the bulky condensed ring inhibits crystallizability and enhances film-forming property, which results in enhanced emission efficiency of the device using the compound.

The organic electroluminescence devices of Examples 1, 2, 6, 7 and 11 have especially enhanced emission efficiency when compared with those of Comparative Examples. The organic electroluminescence devices of Examples 1, 2, 6, 7 and 11 use condensed cyclic compounds, in which the nitrogen atom included in the indoloindole core structure is substituted with an amine group via a linker, and distortion of aryl group of the linker and indoloindole ring decreases planarity of the whole molecule, thereby inhibiting crystallizability and improving hole transport property. Accordingly, it seems that the organic electroluminescence devices of Examples 1, 2, 6, 7 and 11 have increased probability of recombining holes and electrons in an emission layer and enhanced emission efficiency.

The organic electroluminescence devices of Examples 3, 4, 5, 8, 9 and 10 have especially extended device life when compared with those of Comparative Examples. The organic electroluminescence devices of Examples 3, 4, 5, 8, 9 and 10 use condensed cyclic compounds, in which the benzene ring of indoloindole is substituted with an amine group, and HOMO of the substituent including the amine group expands further to indoloindole. Accordingly, it seems that the improved stability in the radical state extends device life.

The organic electroluminescence devices of Comparative Examples 1 and 2 have especially decreased efficiency when compared with those of Examples. The organic electroluminescence devices of Comparative Examples 1 and 2 use Comparative Compounds R1 and R2, in which although the nitrogen atom of the condensed ring is substituted with an amine group via a linker, the condensed ring contains only one nitrogen atom. Accordingly, it seems that enhanced planarity of the whole molecule and strengthened intermolecular interaction decrease hole transport property and emission efficiency of the device.

The organic electroluminescence device of Comparative Example 3 has especially decreased efficiency when compared with those of Examples. The organic electroluminescence device of Comparative Example 3 uses Comparative Compound R3, in which the core structure is different from those of Example Compounds, although an indoloindole ring is included. Accordingly, it seems that electronic repulsion between aryl groups is relieved and planarity is enhanced, thereby decreasing efficiency of the device.

The organic electroluminescence device of Comparative Example 4 has decreased efficiency and device life when compared with those of Examples. The organic electroluminescence device of Comparative Example 4 uses Comparative Compound R4, which includes a carbazole group unlike Example Compounds having a noncyclic tertiary amine group. Accordingly, it seems that insufficient hole transport property of carbazole group decreases emission efficiency and life of the device.

The organic electroluminescence device of Comparative Example 5 has especially decreased efficiency when compared with those of Examples. The organic electroluminescence device of Comparative Example 5 uses Comparative Compound R5, in which two benzene rings are further condensed to the indoloindole core structure, unlike Example Compounds, thereby increasing the electron density of indoloindole ring in HOMO and decreasing the relative contribution of amine group to HOMO, which seems to decrease hole transport property and emission efficiency of the device.

The organic electroluminescence device of Comparative Example 6 has especially decreased efficiency when compared with those of Examples. The organic electroluminescence device of Comparative Example 6 uses Comparative Compound R6, in which the indoloindole core structure is substituted with a heterocyclic ring, thereby increasing the electron density of indoloindole ring in HOMO and decreasing the relative contribution of amine group to HOMO, which seems to decrease hole transport property and emission efficiency of the device.

The organic electroluminescence device of Comparative Example 7 has especially decreased efficiency when compared with those of Examples. The organic electroluminescence device of Comparative Example 7 uses Comparative Compound R7, which includes a phosphoryl group, thereby changing LUMO level and scattering excitation energy in an emission layer, which seems to decrease emission efficiency of the device.

The organic electroluminescence device of Comparative Example 8 has especially decreased device life when compared with those of Examples. The organic electroluminescence device of Comparative Example 8 uses Comparative Compound R8, in which although the core structure is similar to those of Example Compounds, the substitution site of amine group is different from those of Example Compounds. That is, the amine group is substituted not to the ring containing S with a relatively high electron density but to the indole ring with a relatively low electron density. Accordingly, the electrons of amine group are withdrawn into the condensed ring for relieving electronic polarization in the condensed ring, thereby decreasing the electron resistance of amine group, which seems to decrease device life.

The organic electroluminescence device of Comparative Example 9 has decreased efficiency and device life when compared with those of Examples. The organic electroluminescence device of Comparative Example 9 uses Comparative Compound R9, which includes a carbon atom of sp3 hybrid orbital in the condensed ring. Accordingly, it seems that insufficient thermal stability decreases emission efficiency and life of the device.

The organic electroluminescence device of Comparative Example 10 has especially decreased device life when compared with those of Examples. The organic electroluminescence device of Comparative Example 10 uses Comparative Compound R10, which has an amine group including an aryl group substituted with an alkyl group of straight chain as a substituent. Especially, in Comparative Compound R10, carbon atoms forming sp3 hybrid on benzyl group has a straight chain structure, which is different from Example Compound A-17 used in the organic electroluminescence device of Example 11, in which carbon atoms on benzyl group form a cycloalkyl group. Accordingly, Comparative Compound R10 is unstable in the radical state and easily degraded, which seems to decrease device life.

The organic electroluminescence device according to an embodiment of the inventive concept has high efficiency and a long device life. The organic electroluminescence device according to an embodiment of the inventive concept has a low driving voltage. The organic electroluminescence device according to an embodiment of the inventive concept uses a condensed cyclic compound including an indoloindole core structure and a tertiary amine substituent as a material for a hole transport region, thereby enhancing emission efficiency and a device life.

The organic electroluminescence device according to an embodiment of the inventive concept has high efficiency.

The organic electroluminescence device according to an embodiment of the inventive concept has a long device life.

The condensed cyclic compound according to an embodiment of the inventive concept may be applied to an organic electroluminescence device, thereby contributing to high efficiency and a long device life.

Although the exemplary embodiments of the present invention have been described referring to the attached drawings, it is understood that the present invention should not be limited to these exemplary embodiments but various changes and modifications can be made by one ordinary skilled in the art within the spirit and scope of the present invention as hereinafter claimed. It is also understood that the exemplary embodiments described above are merely descriptive, rather than limiting.

What is claimed is:

1. An organic electroluminescence device, comprising:

a first electrode;

a hole transport region disposed on the first electrode;

an emission layer disposed on the hole transport region;

an electron transport region disposed on the emission layer; and a second electrode disposed on the electron transport region, wherein the hole transport region comprises a condensed cyclic compound represented by the following Formula 1:

[Formula 1]

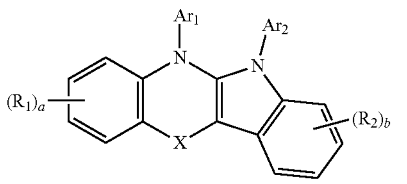

wherein in Formula 1,

X is O, S, $NR_5$, or $SiR_6R_7$, $Ar_1$ is a substituted or unsubstituted aryl group having 6 to 40 carbon atoms for forming a ring, or represented by Formula 2, $Ar_2$ is substituted or unsubstituted aryl group having 6 to 40 carbon atoms for forming a ring, each of R1 and R2 is independently represented by Formula 2, a substituted or unsubstituted aryl group having 6 to 40 carbon atoms for forming a ring, or a substituted or unsubstituted alkyl group having 1 to 20 carbon atoms, each of a and b is independently an integer of 0 to 4, each of R5, R6, and R7 is independently a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring, the substituted alkyl group having 1 to 20 carbon atoms, the substituted aryl group having 6 to 40 carbon atoms for forming a ring, and the substituted heteroaryl group having 2 to 40 carbon atoms for forming a ring are substituted with a hydrogen atom, a deuterium atom, a halogen atom, a cyano group, a substituted or unsubstituted alkyl group having 1 to 40 carbon atoms, a substituted or unsubstituted aryl group having 6 to 40 carbon atoms for forming a ring, or a substituted or unsubstituted heteroaryl group having 2 to 40 carbon atoms for forming a ring, and only one of $R_1$, $R_2$, or $Ar_1$ is represented by following Formula 2:

[Formula 2]

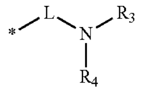

wherein in Formula 2,

L is a direct linkage, or a substituted or unsubstituted arylene group having 6 to 40 carbon atoms for forming a ring, and each of $R_3$ and $R_4$ is independently a substituted or unsubstituted aryl group having 6 to 40 carbon atoms for forming a ring, or a substituted or unsubstituted heteroaryl group having 2 to 40 carbon atoms for forming a ring, and the substituted aryl group having 6 to 40 carbon atoms for forming a ring, and the substituted heteroaryl group having 2 to 40 carbon atoms for forming a ring are substituted with a hydrogen atom, a deuterium atom, a halogen atom, a cyano group, a substituted or unsubstituted cycloalkyl group having 3 to 40 carbon atoms for forming a ring, a substituted or unsubstituted aryl group having 6 to 40 carbon atoms for forming a ring, or a substituted or unsubstituted heteroaryl group having 2 to 40 carbon atoms for forming a ring.

2. The organic electroluminescence device of claim 1, wherein the hole transport region comprises:

a hole injection layer; and a hole transport layer disposed between the hole injection layer and the emission layer, and the hole transport layer comprises the condensed cyclic compound.

3. The organic electroluminescence device of claim 2, wherein the hole transport layer comprises a plurality of organic layers, and an organic layer adjacent to the emission layer among the plurality of organic layers comprises the condensed cyclic compound.

4. The organic electroluminescence device of claim 1, wherein Formula 1 is represented by any one of the following Formulae 1-2 to 1-5:

[Formula 1-2]

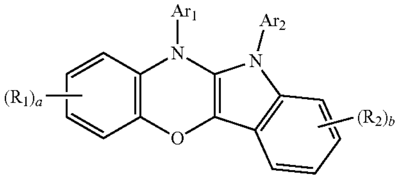

[Formula 1-3]

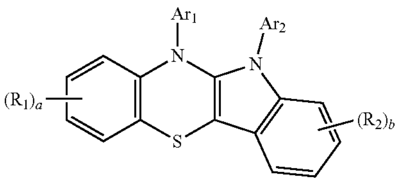

-continued

[Formula 1-4]

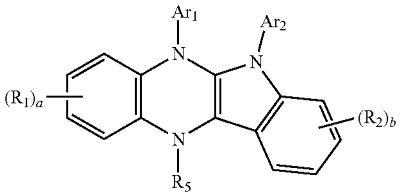

[Formula 1-5]

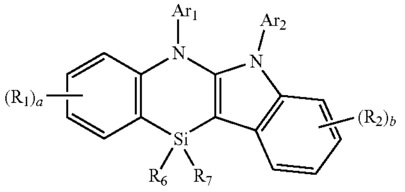

wherein in Formula 1-2 to 1-5, $Ar_1$, $Ar_2$, $R_1$, $R_2$, $R_5$ to $R_7$, a, and b are the same as defined in Formula 1.

5. The organic electroluminescence device of claim 1, wherein Formula 1 is represented by any one of the following Formulae 3-1 to 3-3:

[Formula 3-1]

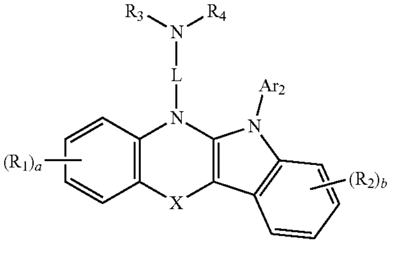

[Formula 3-2]

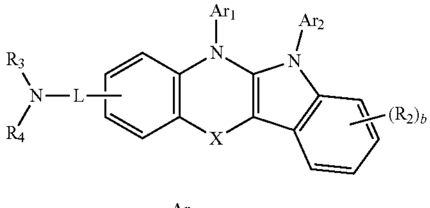

[Formula 3-3]

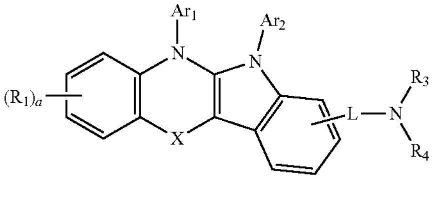

wherein in Formulae 3-1 to 3-3,

X, $Ar_1$, $Ar_2$, $R_1$ to $R_4$, L, a, and b are the same as defined in Formula 1 and 2.

6. The organic electroluminescence device of claim 1, wherein $R_1$ and $R_2$ are each independently a substituted or unsubstituted phenyl group, a substituted or unsubstituted naphthyl group, a substituted or unsubstituted fluorenyl group, a substituted or unsubstituted anthracenyl group, a substituted or unsubstituted phenanthryl group, a substituted or unsubstituted biphenyl group, a substituted or unsubstituted terphenyl group, a substituted or unsubstituted quaterphenyl group, a substituted or unsubstituted quinqphenyl group, a substituted or unsubstituted sexiphenyl group, a substituted or unsubstituted triphenylenyl group, a substituted or unsubstituted pyrenyl group, a substituted or unsubstituted benzofluoranthenyl group, or a substituted or unsubstituted chrysenyl group.

7. The organic electroluminescence device of claim 1, wherein L is a substituted or unsubstituted phenylene group, a substituted or unsubstituted biphenylene group, a substituted or unsubstituted naphthylene group, a substituted or unsubstituted anthracenylene group, a substituted or unsubstituted phenanthrene group, or a substituted or unsubstituted fluorenylene group.

8. The organic electroluminescence device of claim 1, wherein $R_3$ and $R_4$ are each independently a substituted or unsubstituted phenyl group, a substituted or unsubstituted naphthyl group, a substituted or unsubstituted fluorenyl group, a substituted or unsubstituted anthracenyl group, a substituted or unsubstituted phenanthryl group, a substituted or unsubstituted biphenyl group, a substituted or unsubstituted terphenyl group, a substituted or unsubstituted quaterphenyl group, a substituted or unsubstituted thiophene group, a substituted or unsubstituted benzothiophene group, a substituted or unsubstituted dibenzothiophene group, a substituted or unsubstituted furan group, a substituted or unsubstituted benzofuranyl group, a substituted or unsubstituted dibenzofuranyl group, or a substituted or unsubstituted naphthobenzofuranyl group.

9. The organic electroluminescence device of claim 4, wherein Formula 1-2 is represented by any one of the following Formulae 5-1 to 5-3:

[Formula 5-1]

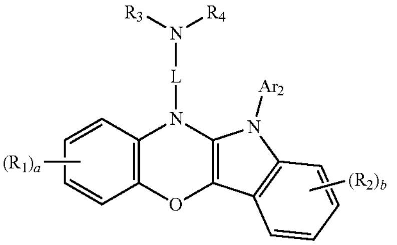

[Formula 5-2]

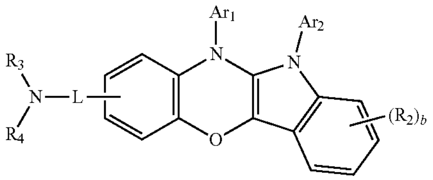

[Formula 5-3]

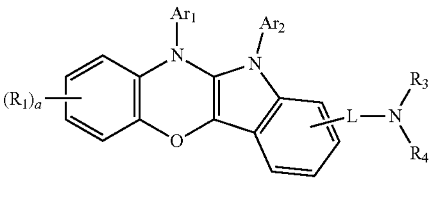

wherein in Formula 5-1 to 5-3, where $Ar_1$, $Ar_2$, $R_1$ to $R_4$, L, a, and b are the same as defined in Formula 1 and 2.

10. The organic electroluminescence device of claim 4, wherein Formula 1-3 is represented by any one of the following Formulae 6-1 to 6-3:

[Formula 6-1]

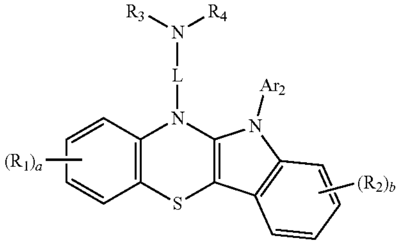

[Formula 6-2]

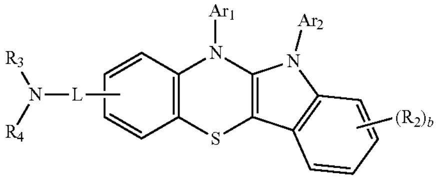

[Formula 6-3]

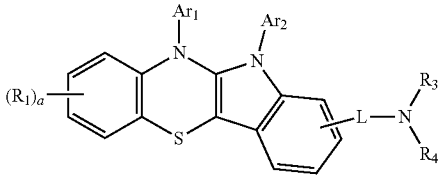

wherein in Formula 6-1 to 6-3, $Ar_1$, $Ar_2$, $R_1$ to $R_4$, L, a, and b are the same as defined in Formula 1 and 2.

11. The organic electroluminescence device of claim 4, wherein Formula 1-4 is represented by any one of the following Formula 7-1 to 7-3:

[Formula 7-1]

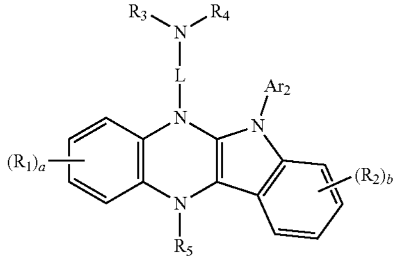

[Formula 7-2]

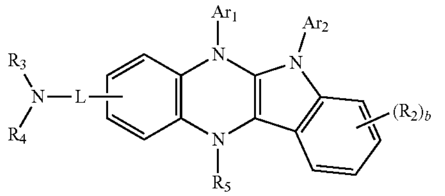

-continued

[Formula 7-3]

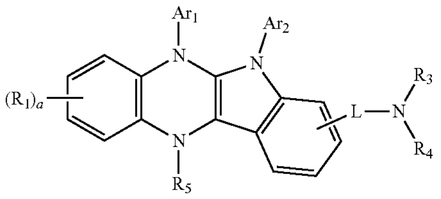

wherein in Formula 7-1 to 7-3, $Ar_1$, $Ar_2$, $R_1$ to $R_5$, L, a, and b are the same as defined in Formulae 1 and 2.

12. The organic electroluminescence device of claim 4, wherein Formula 1-5 is represented by any one of the following Formula 8-1 to 8-3:

[Formula 8-1]

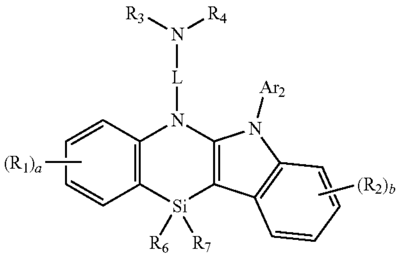

[Formula 8-2]

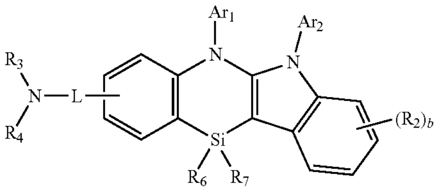

[Formula 8-3]

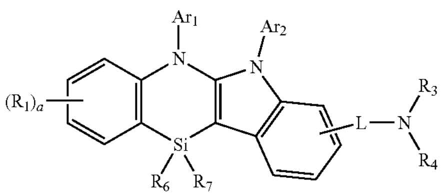

wherein in Formula 8-1 to 8-3, $Ar_1$, $Ar_2$, $R_1$ to $R_4$, $R_6$, $R_7$, L, a, and b are the same as defined in Formula 1 and 2.

13. The organic electroluminescence device of claim 1, wherein the compound represented by Formula 1 is any one selected from the group consisting of compounds represented in the following Compound Groups 2 to 5:

[Compound Group 2]
B1
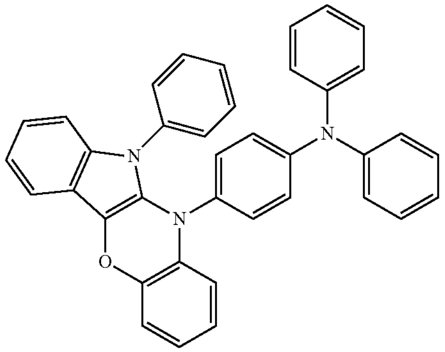
B2
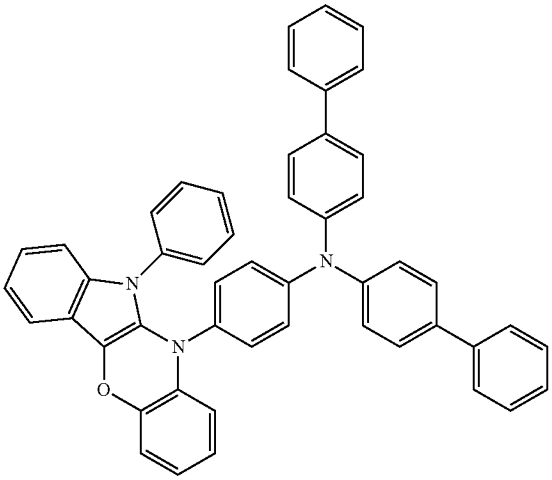
B3
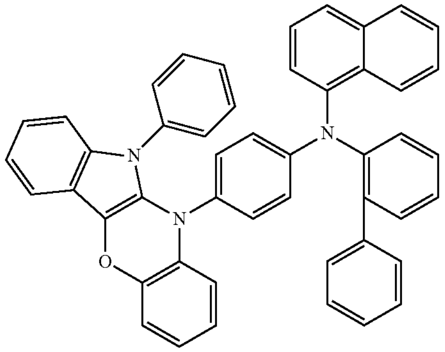
B4
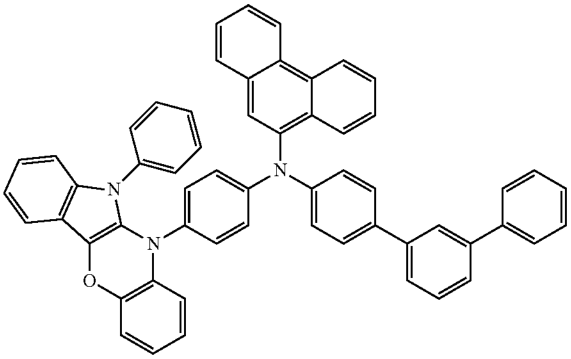
-continued
B5
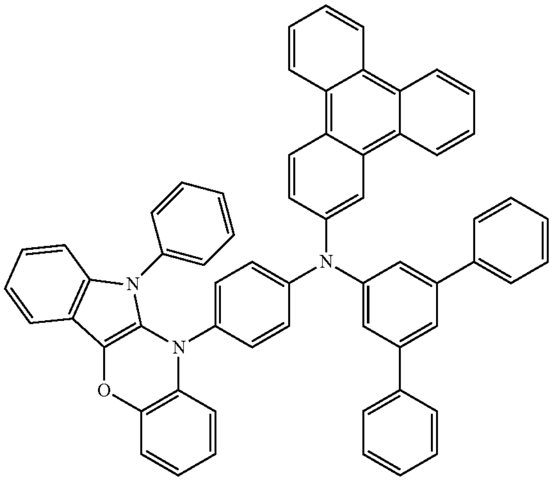
B6
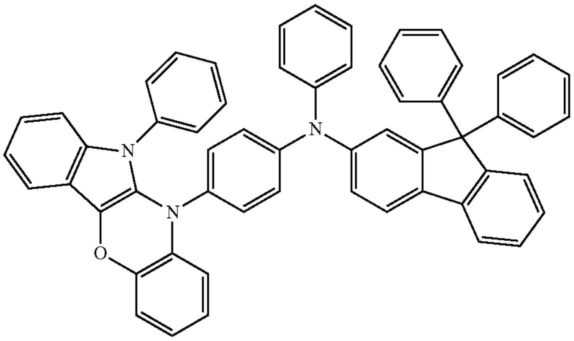
B7
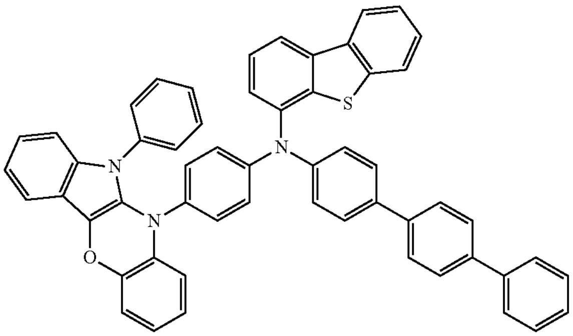

-continued
B8
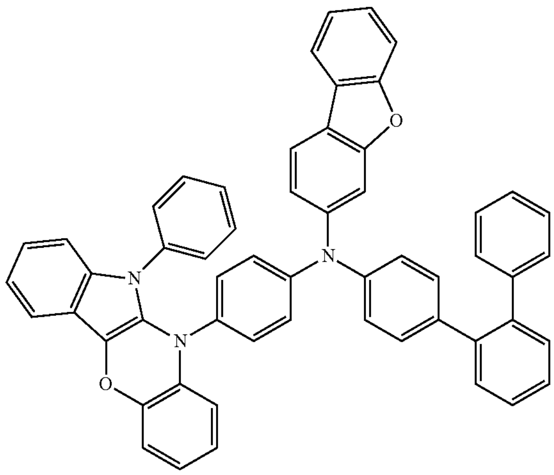
B9
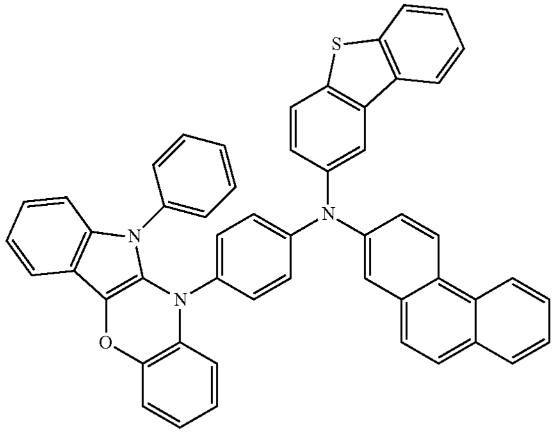
B10
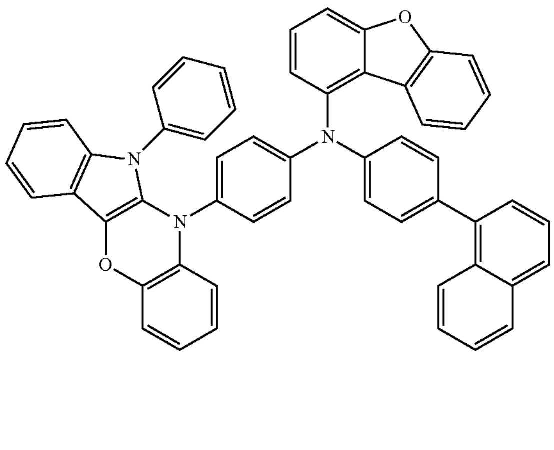
-continued
B11
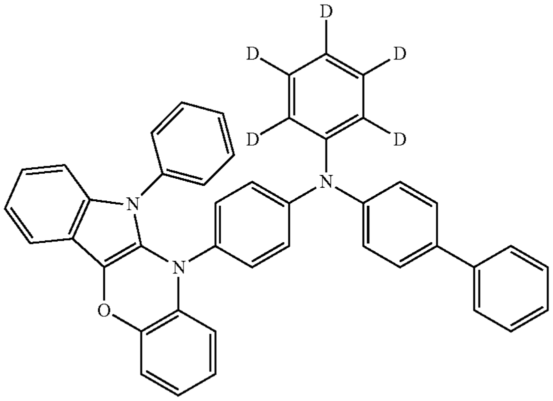
B12
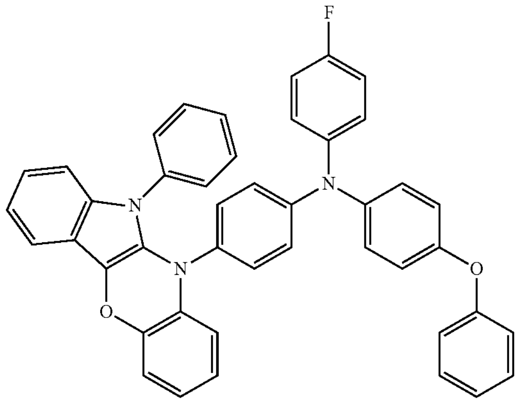
B13
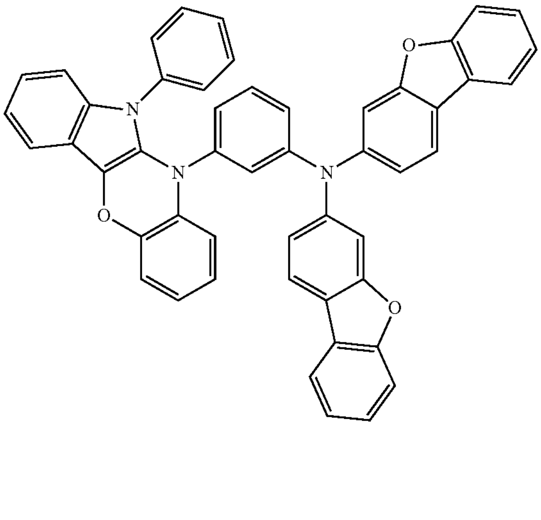

-continued
B14
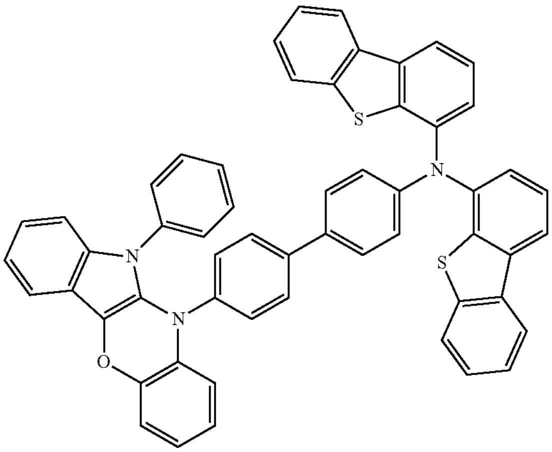
B15
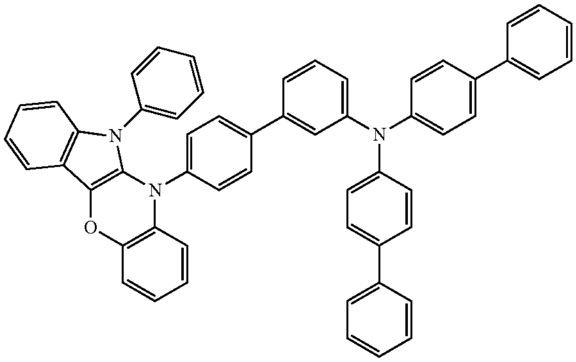
B16
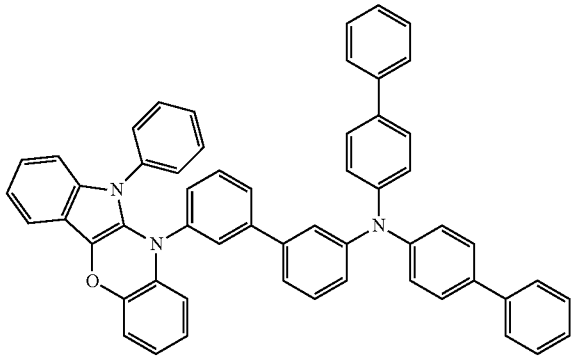
-continued
B17
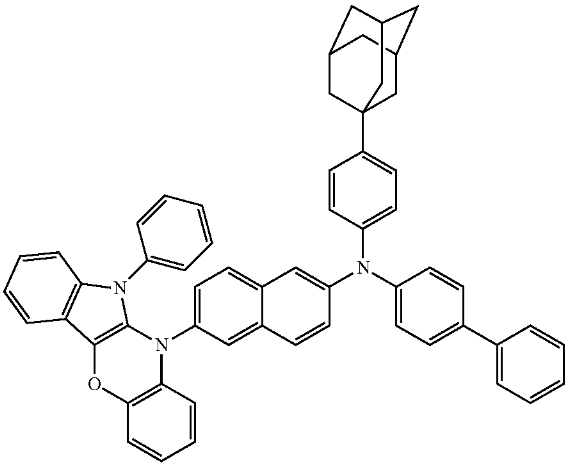
B18
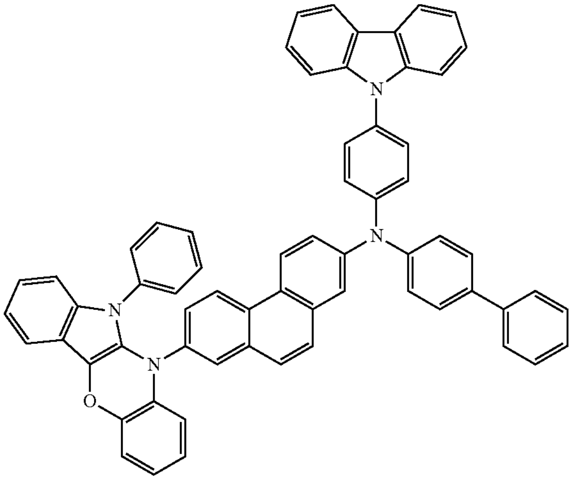
B19
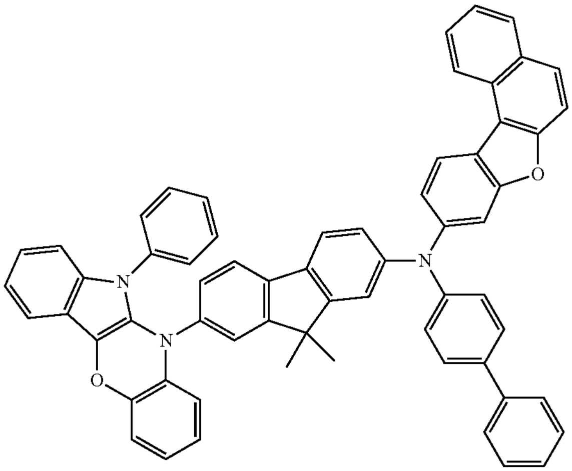

-continued
B20
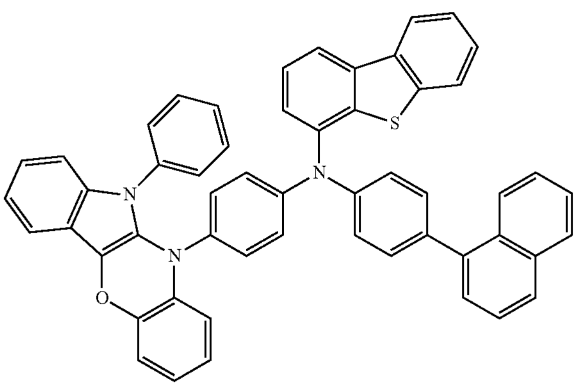
B21
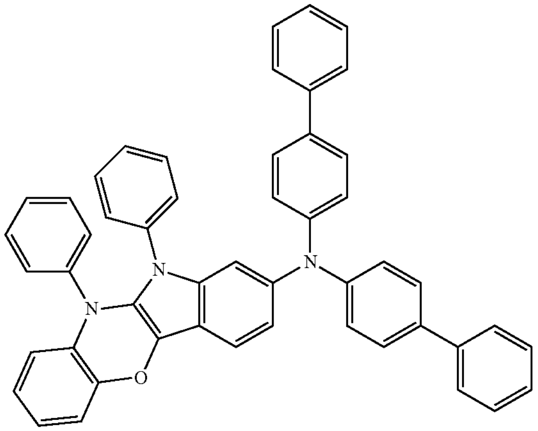
B22
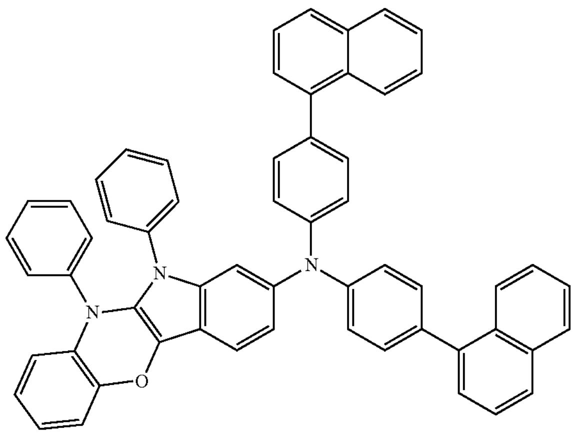
-continued
B23
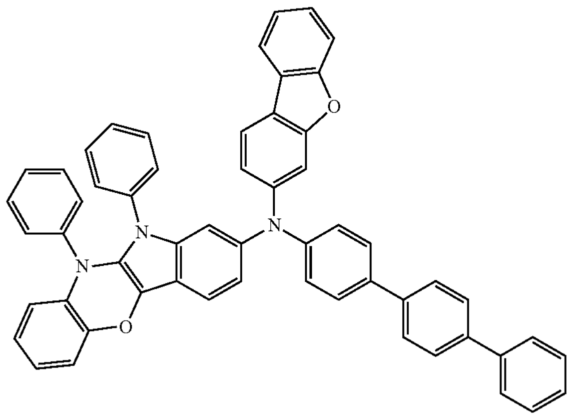
B24
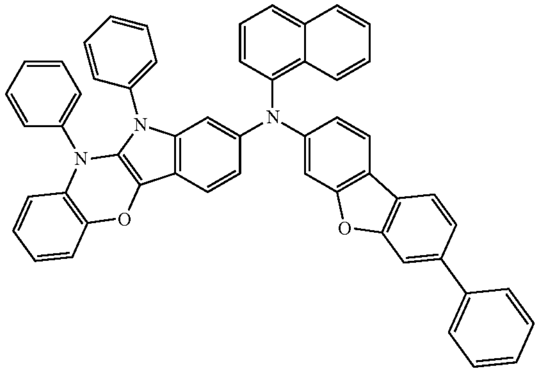
B25
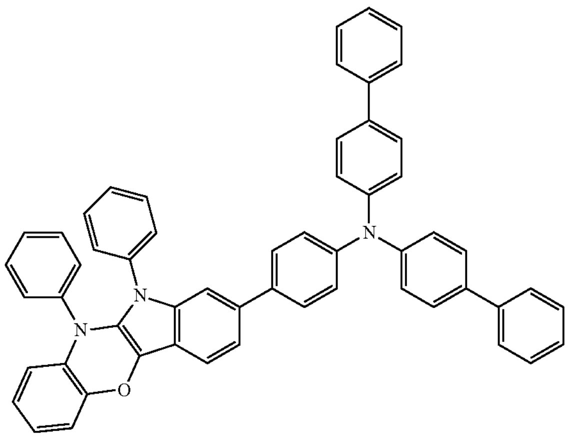

-continued
B26
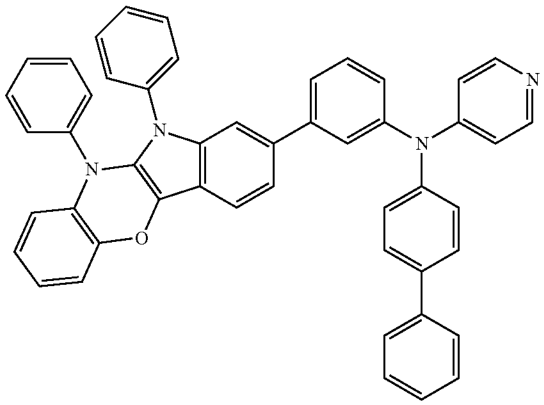
B27
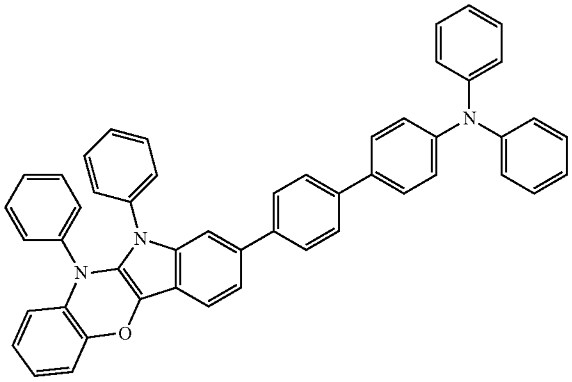
B28
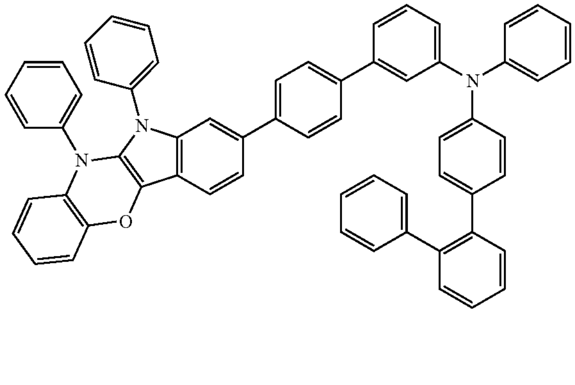
-continued
B29
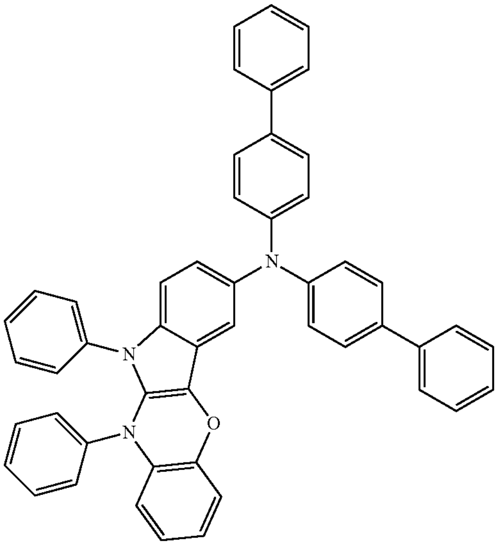
B30
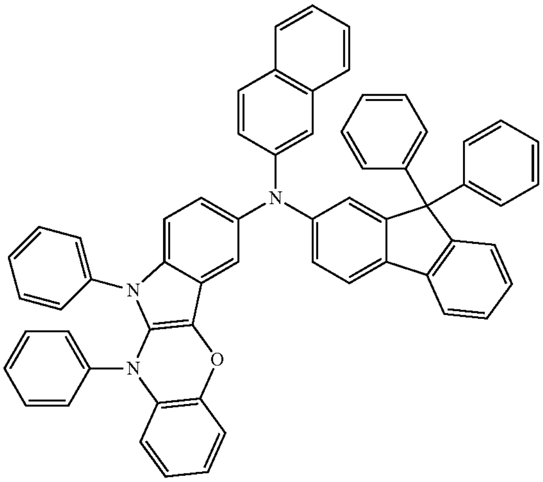
B31
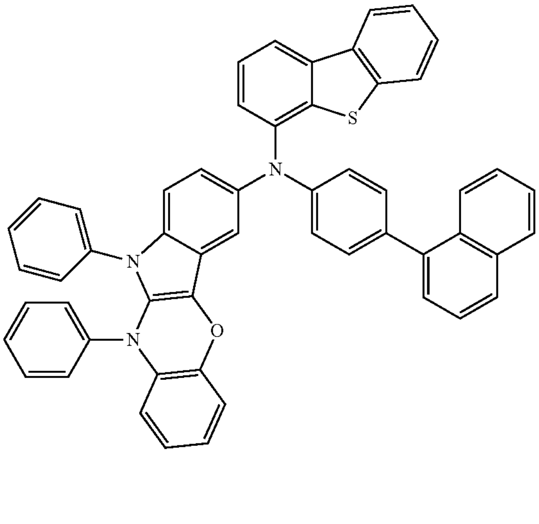

-continued
B32
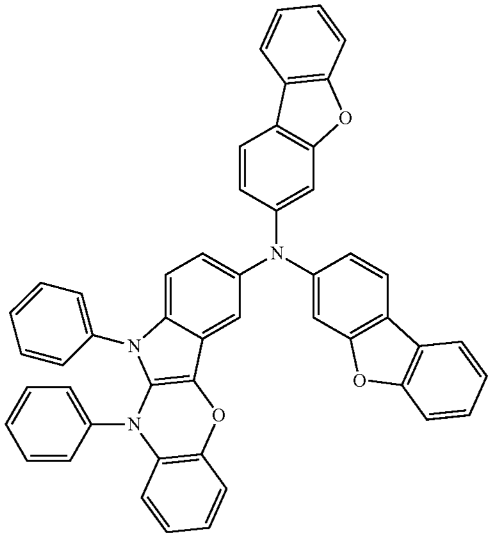
B33
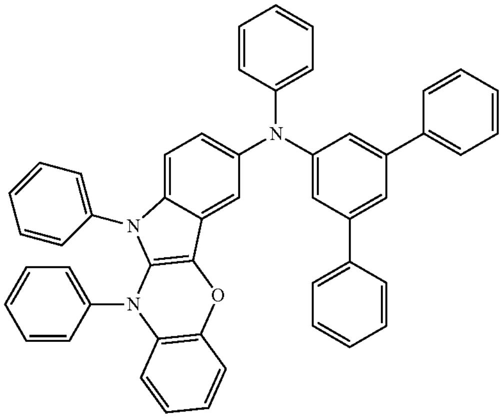
B34
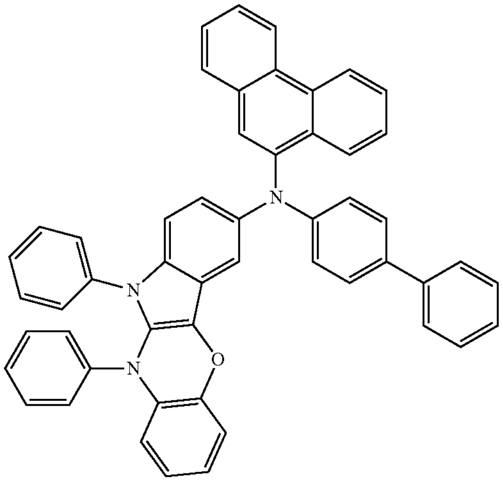
-continued
B35
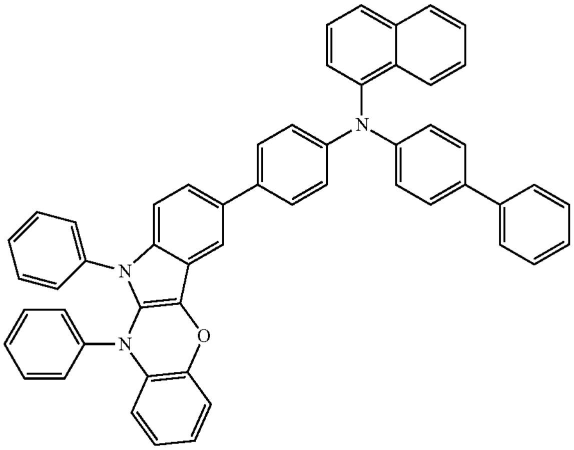
B36
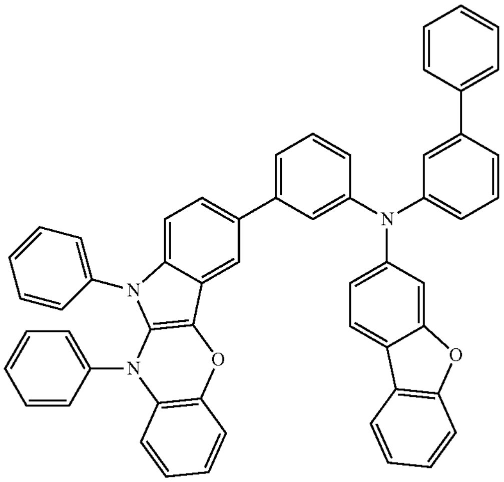
B37
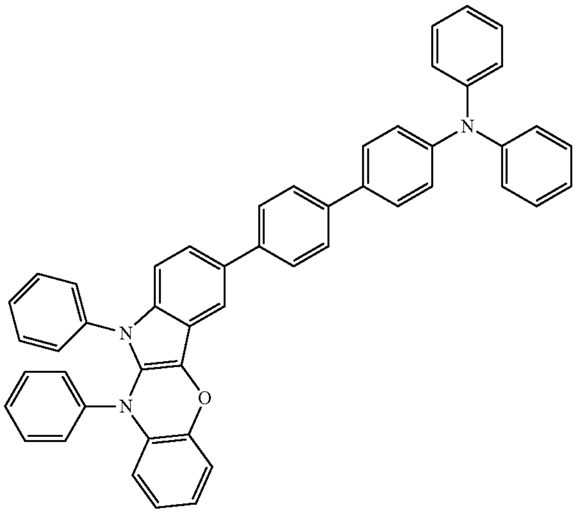

-continued
B38
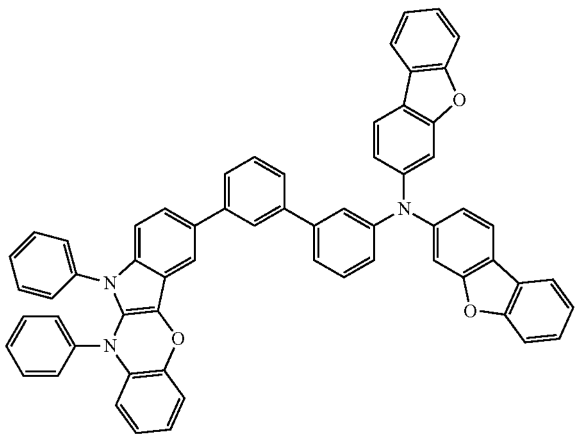
B39
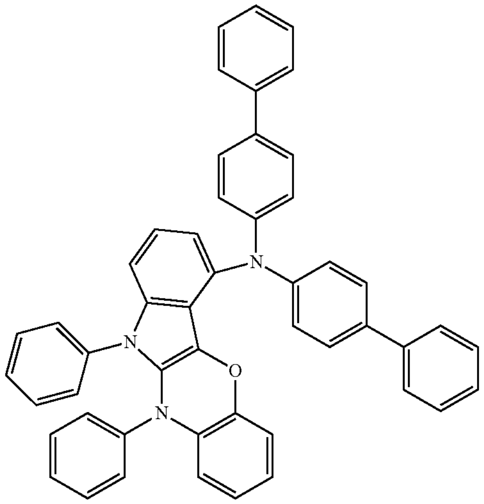
B40
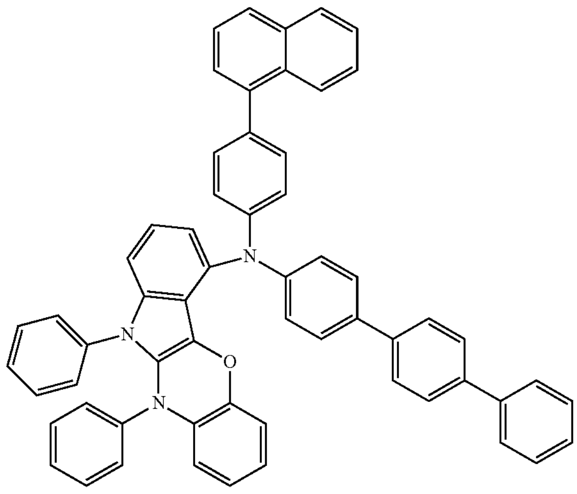
-continued
B41
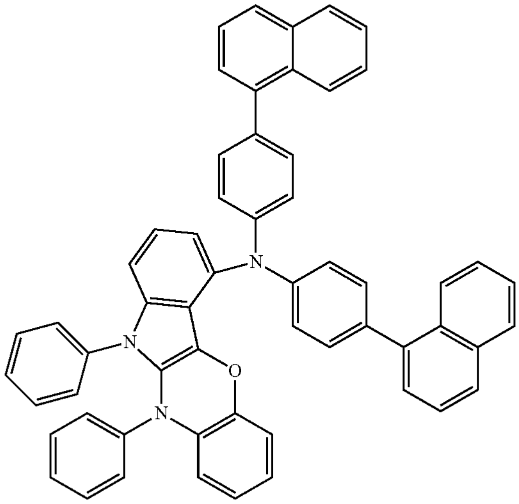
B42
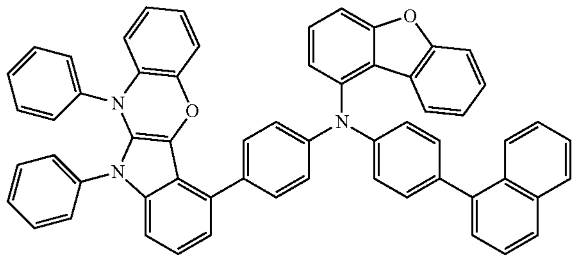
B43
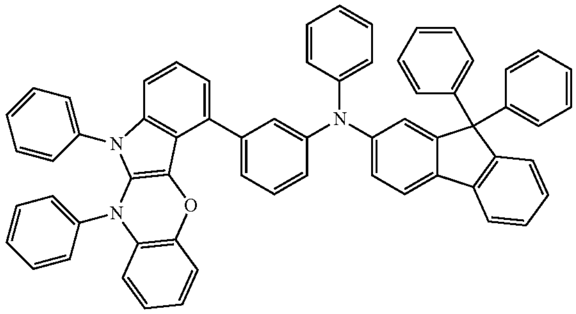
B44
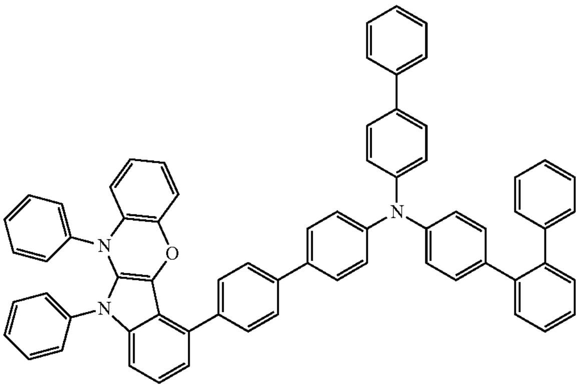

-continued
B45
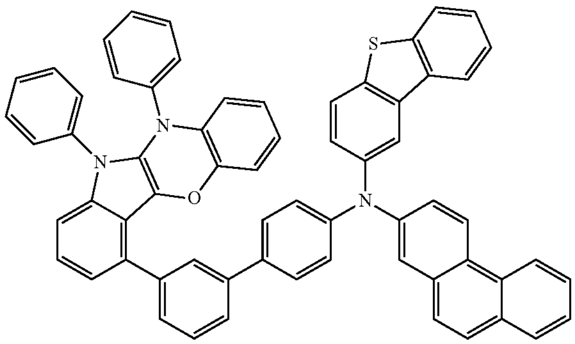
B46
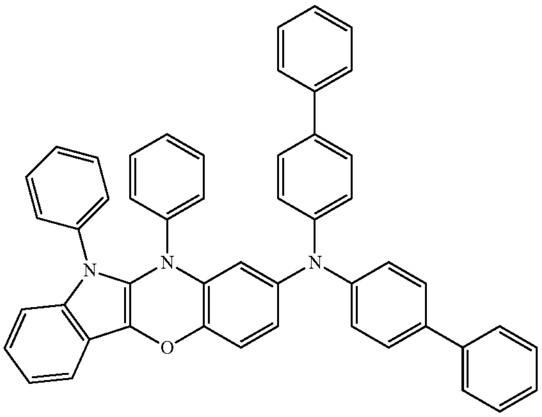
B47
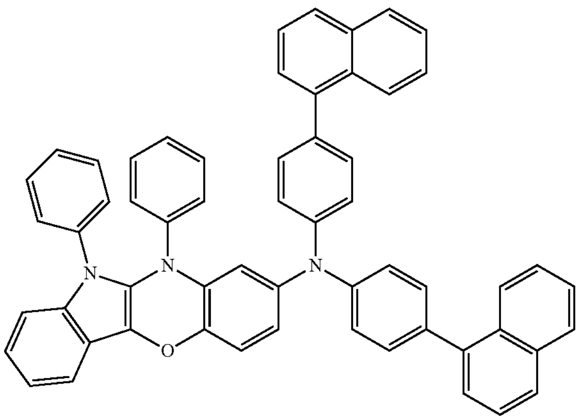
-continued
B48
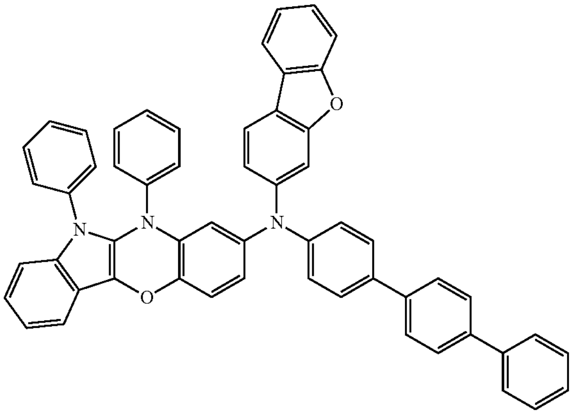
B49
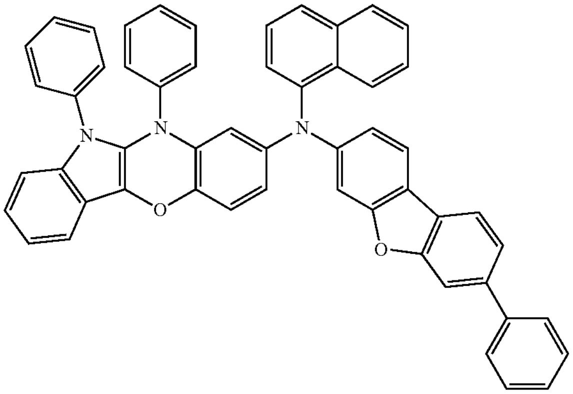
B50
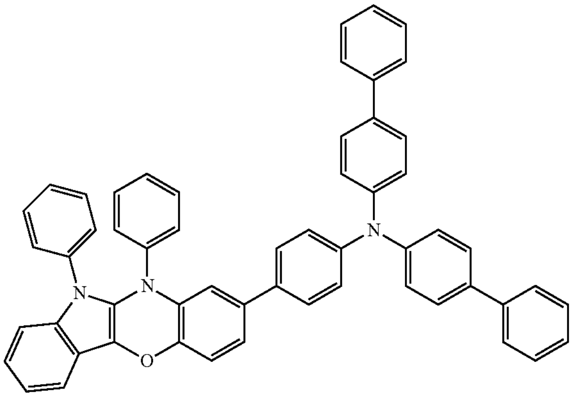

-continued
B51
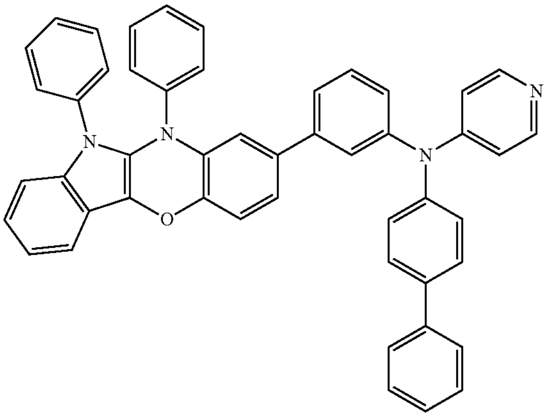
B52
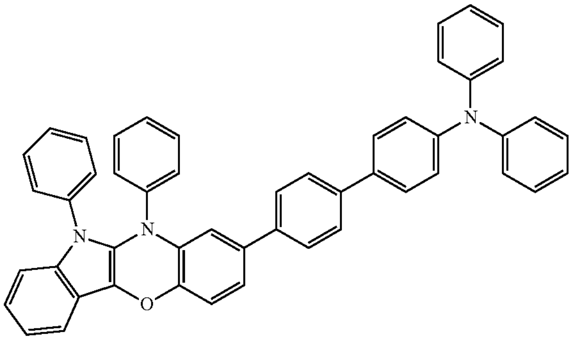
B53
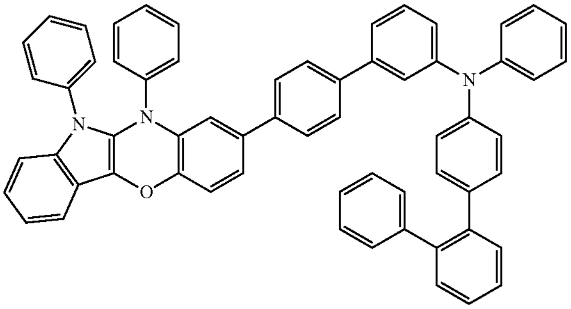
B54
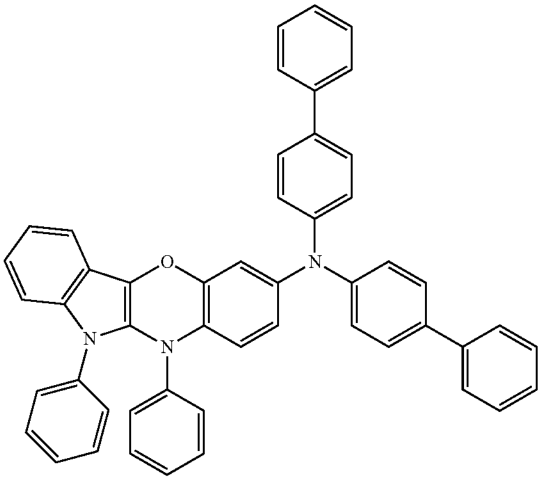
-continued
B55
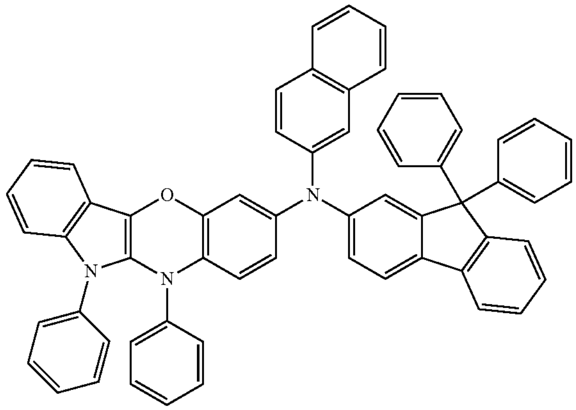
B56
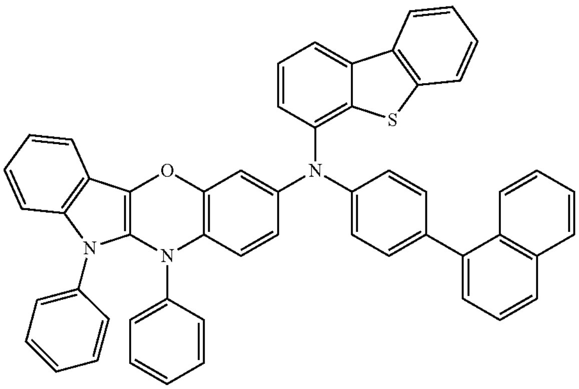
B57
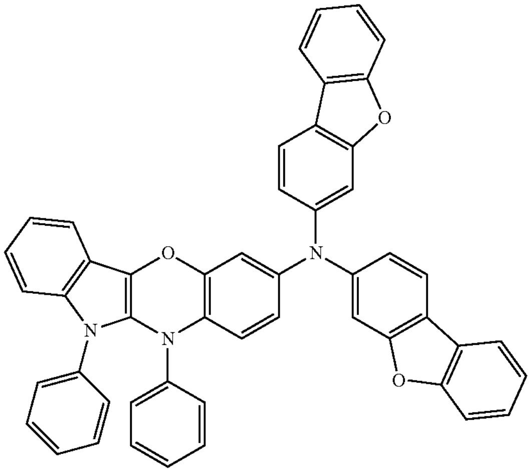

-continued
B58
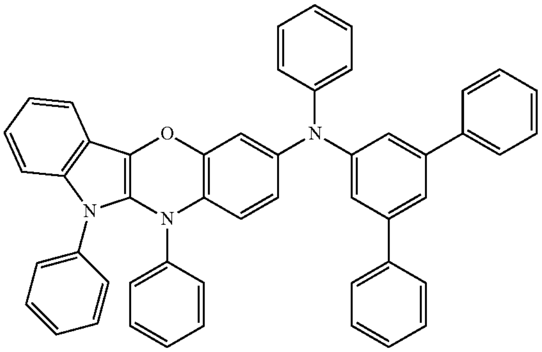
B59
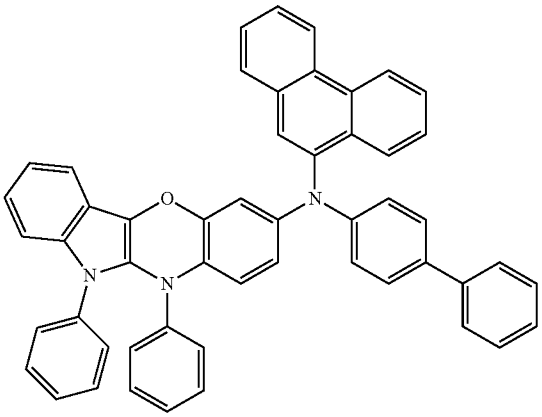
B60
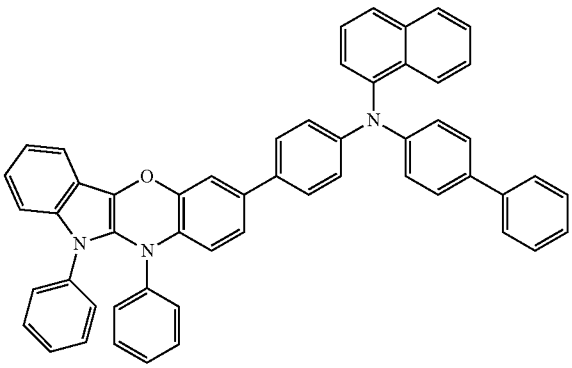
-continued
B61
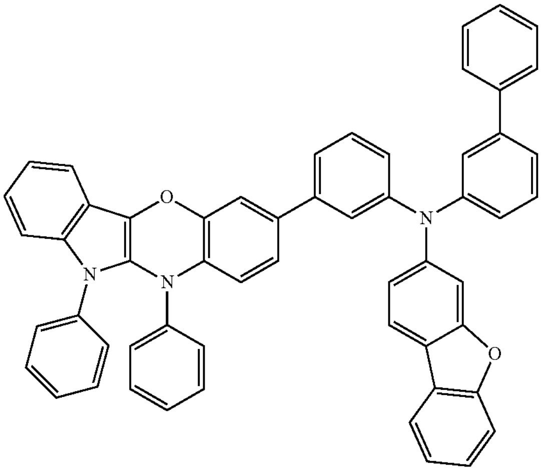
B62
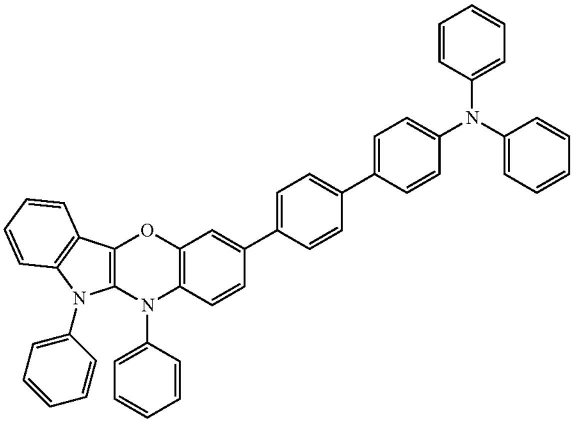
B63
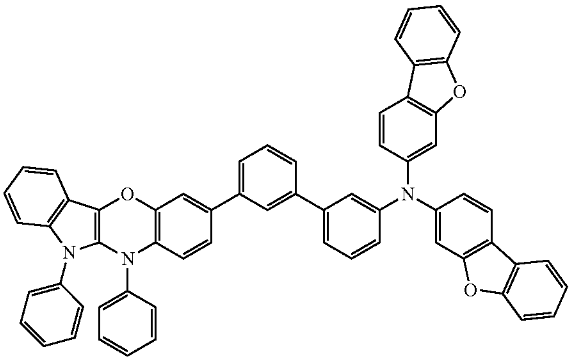

-continued
B64
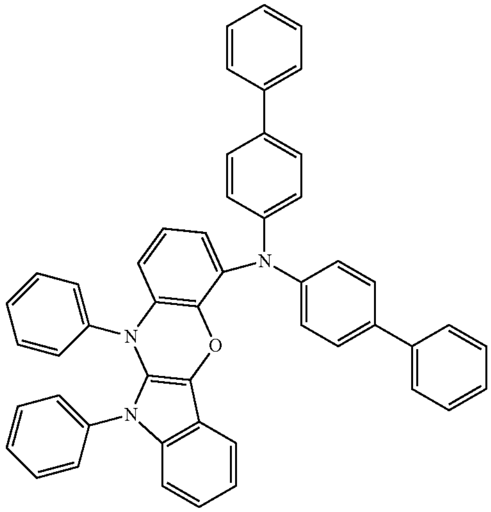
B65
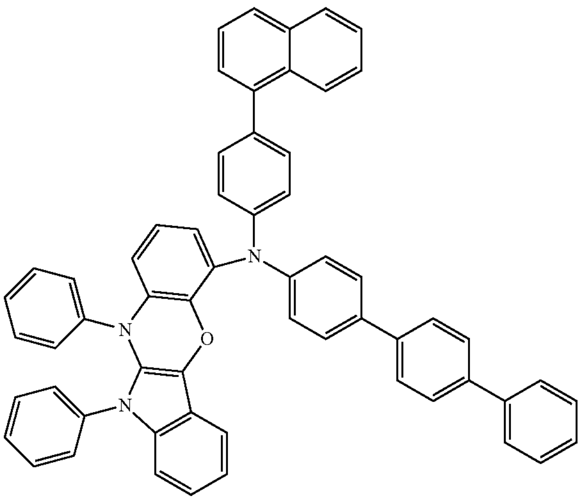
B66
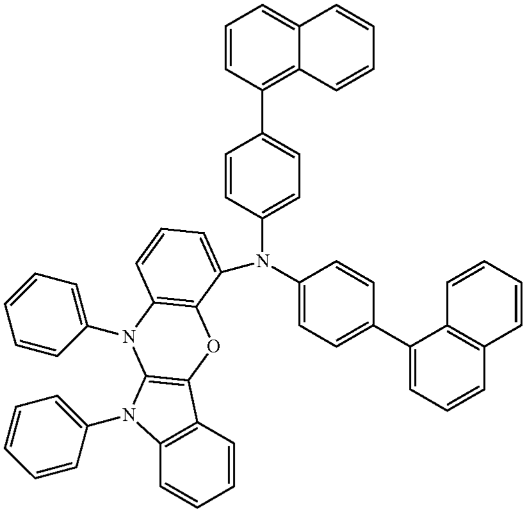
-continued
B67
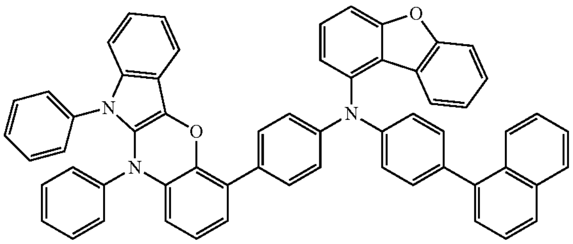
B68
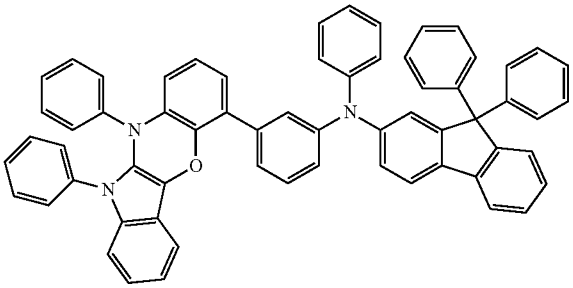
B69
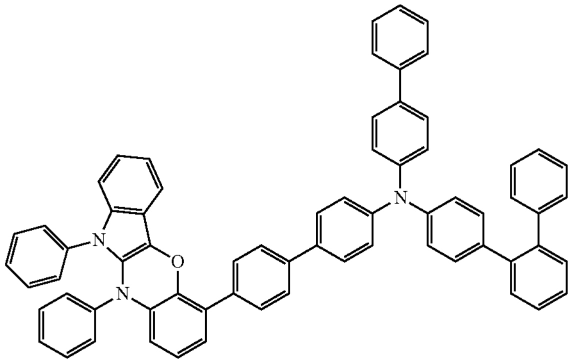
B70
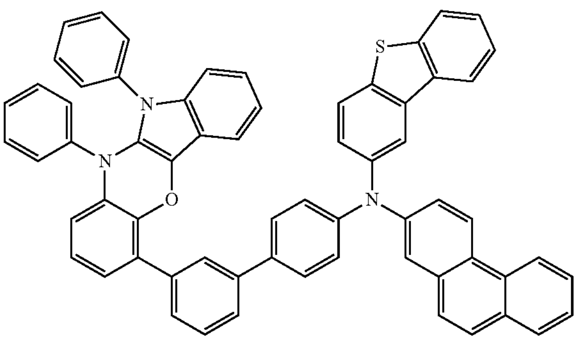

[Compound Group 3]
C1
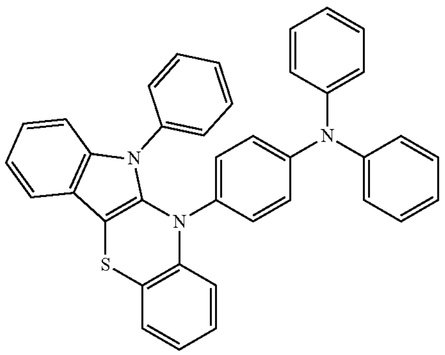
C2
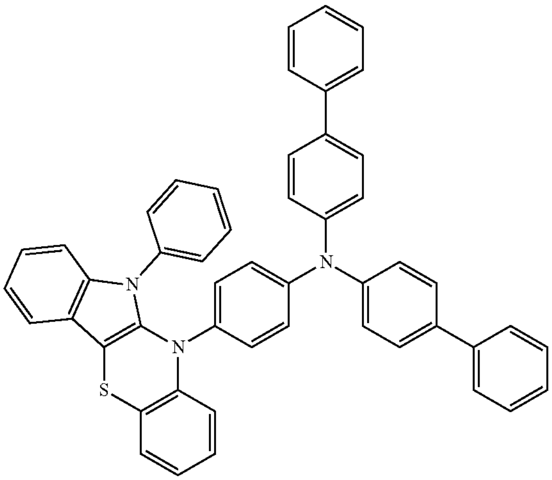
C3
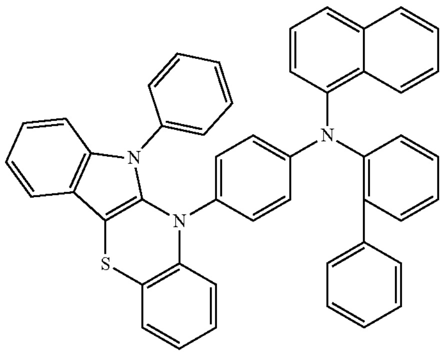
C4
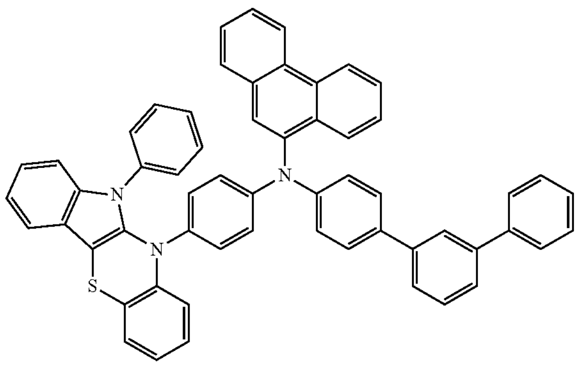
-continued
C5
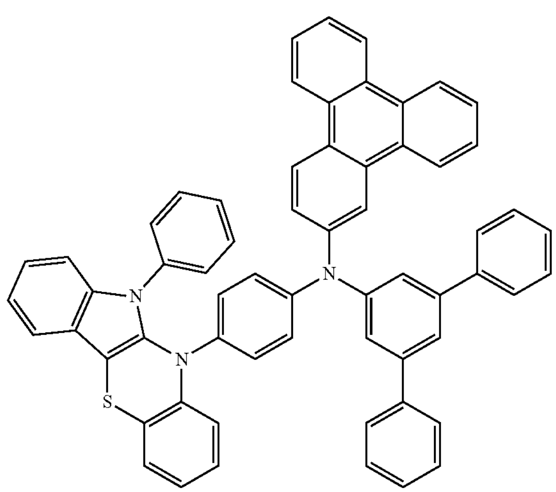
C6
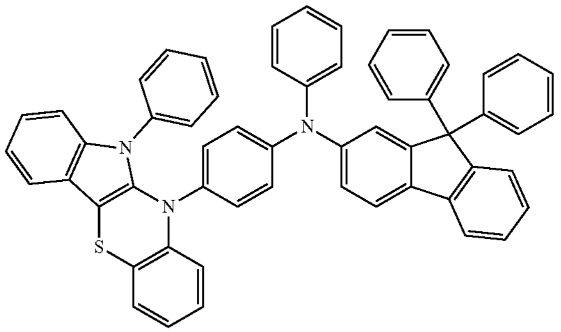
C7
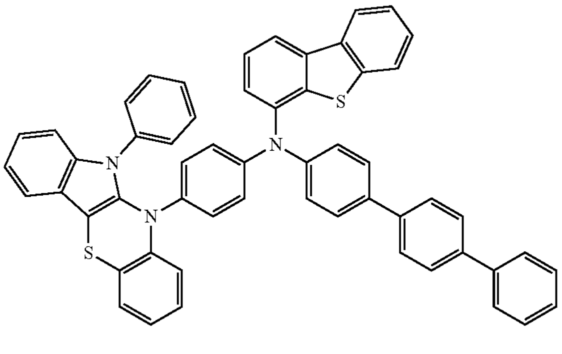

-continued
C8
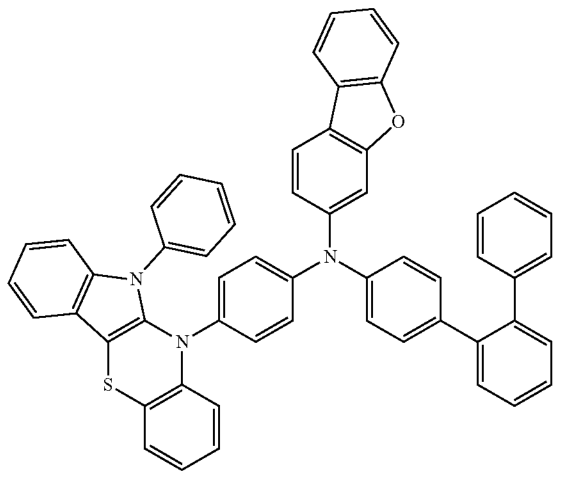
C9
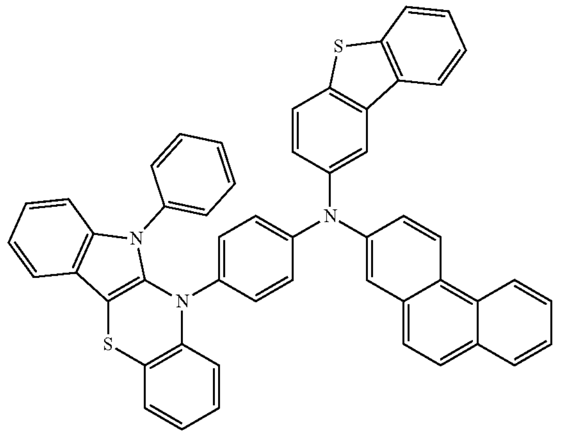
C10
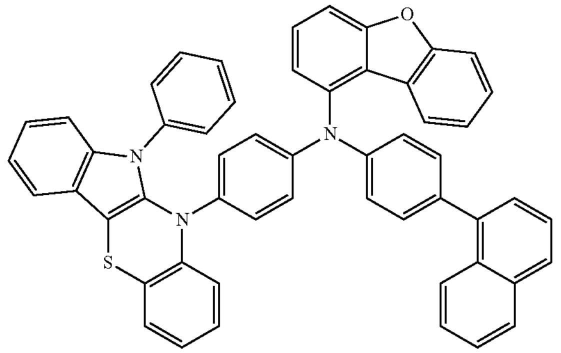
-continued
C11
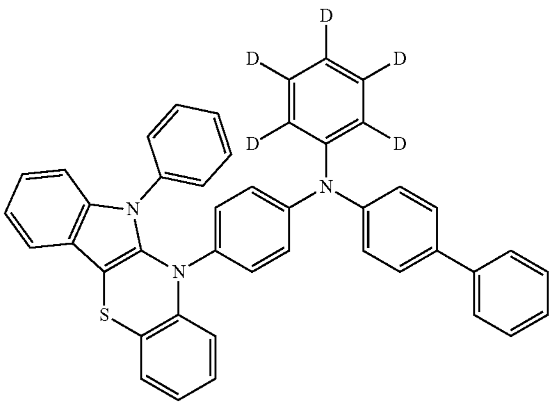
C12
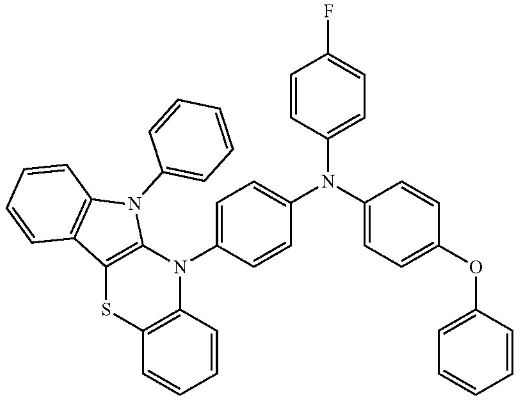
C13
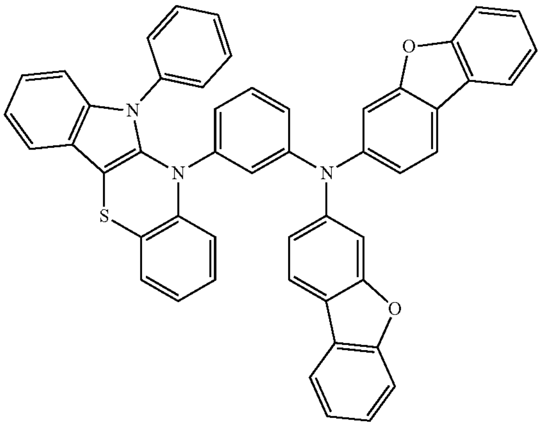

-continued
C14
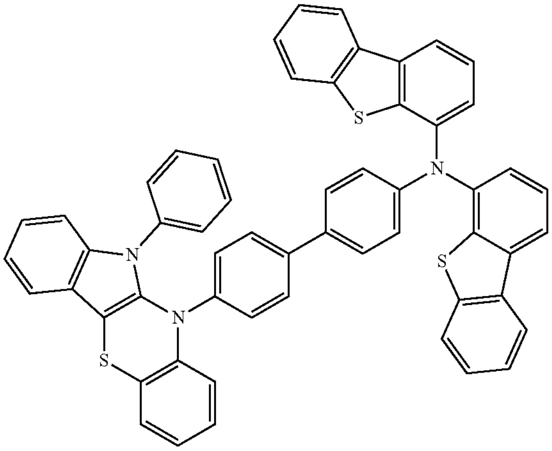
C15
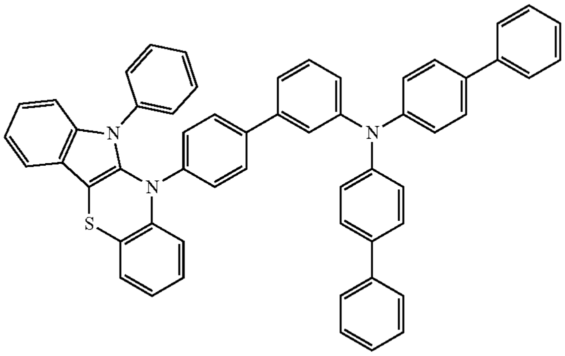
C16
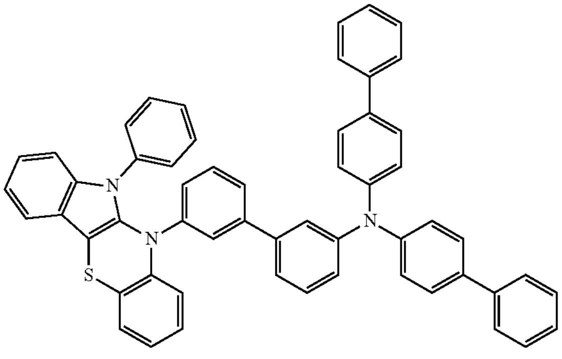
-continued
C17
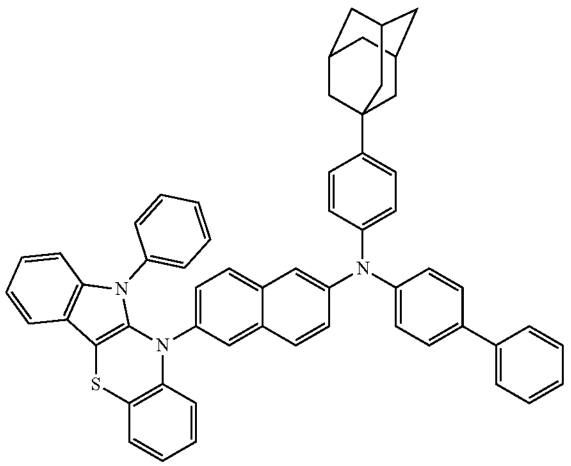
C18
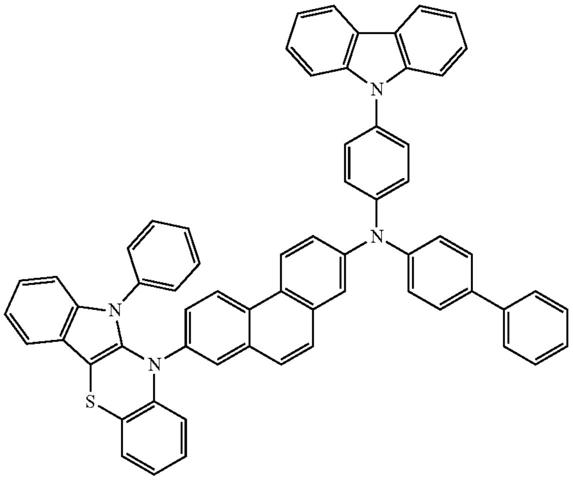
C19
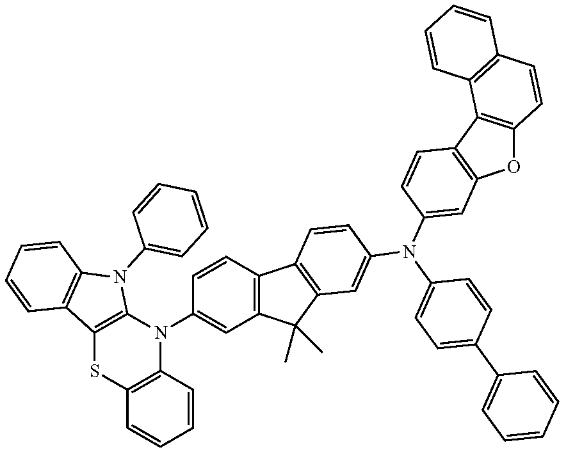

-continued
C20
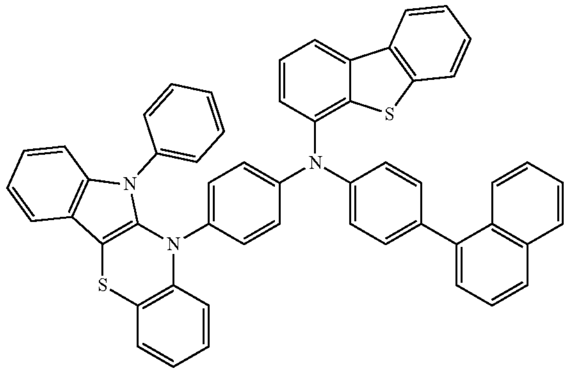
C21
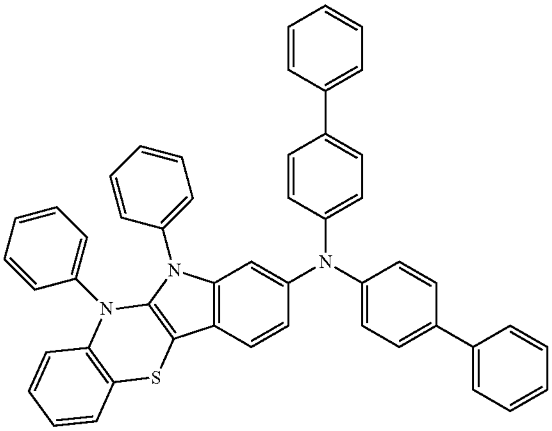
C22
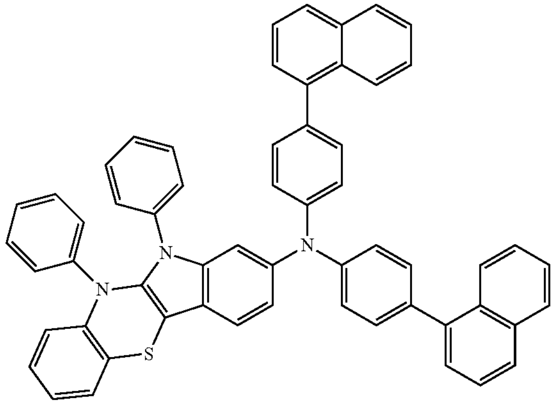
-continued
C23
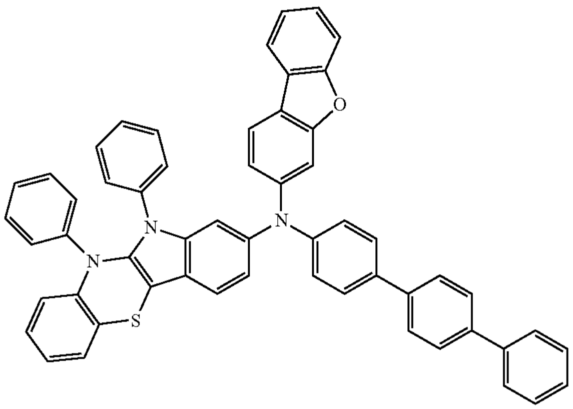
C24
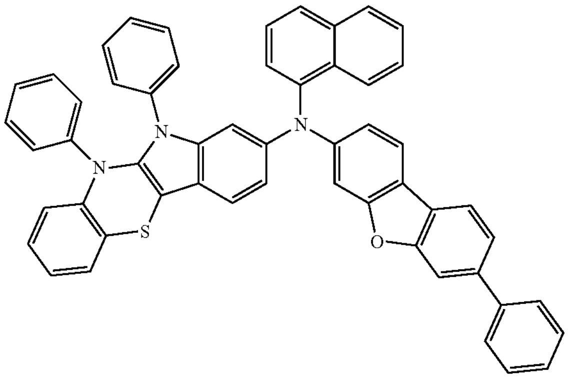
C25
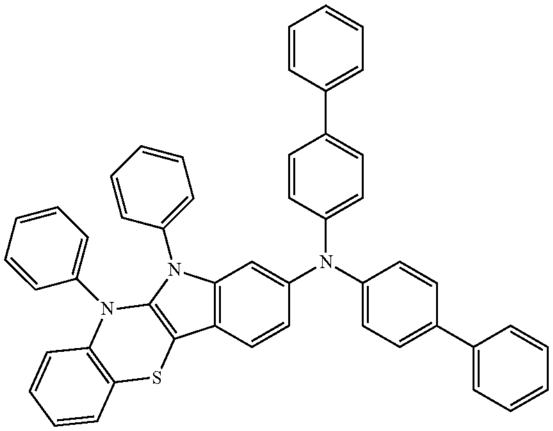

-continued
C26
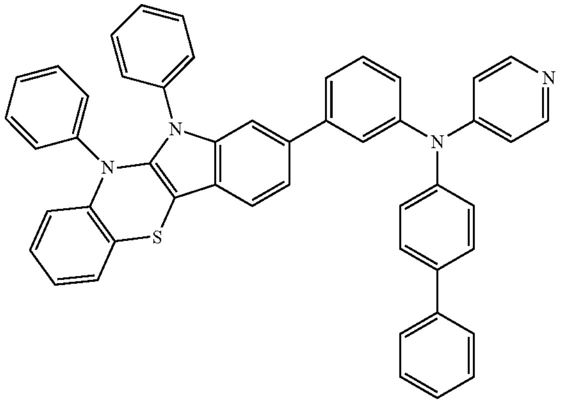
C27
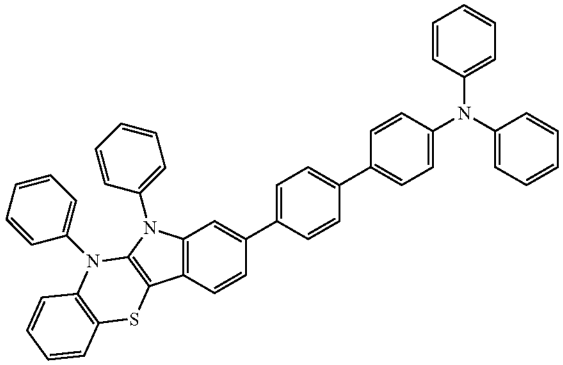
C28
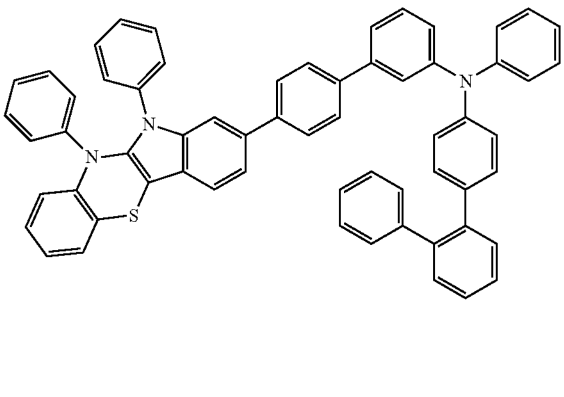
-continued
C29
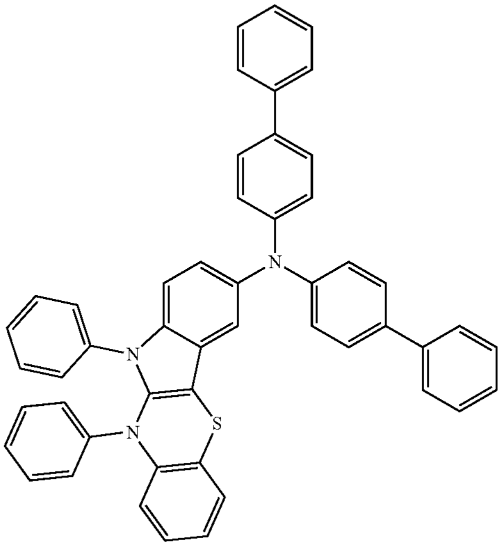
C30
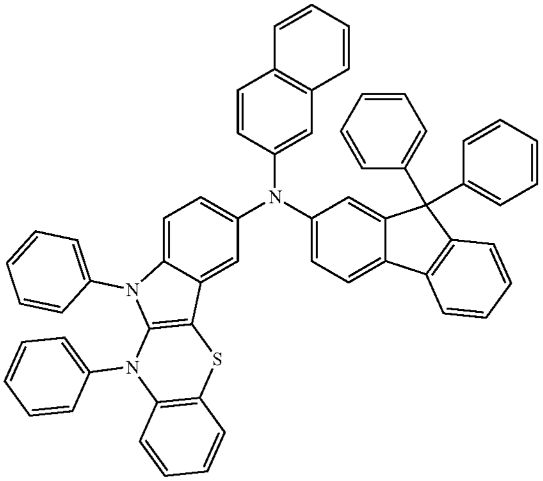
C31
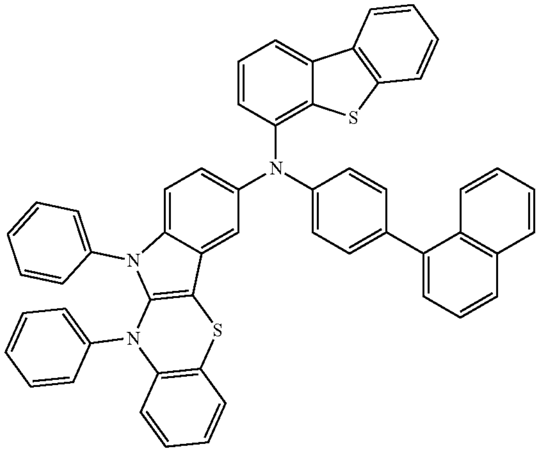

-continued
C32
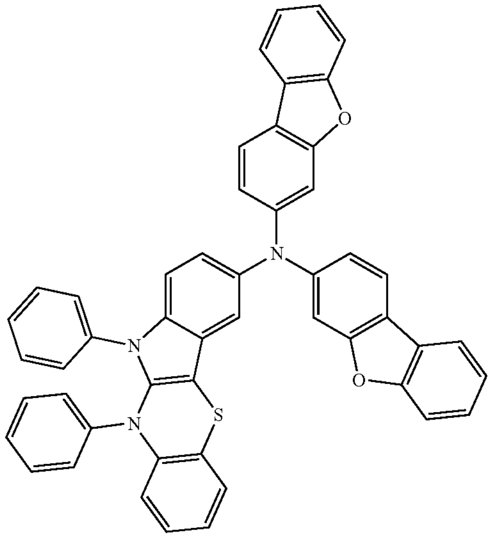
C33
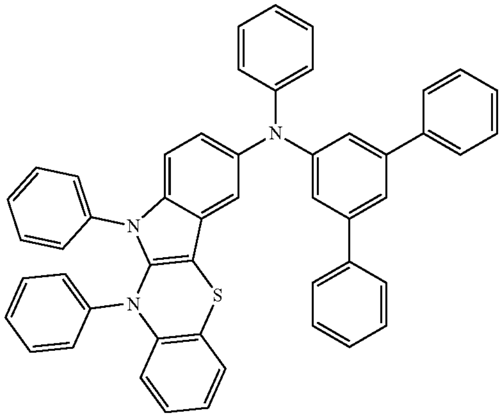
C34
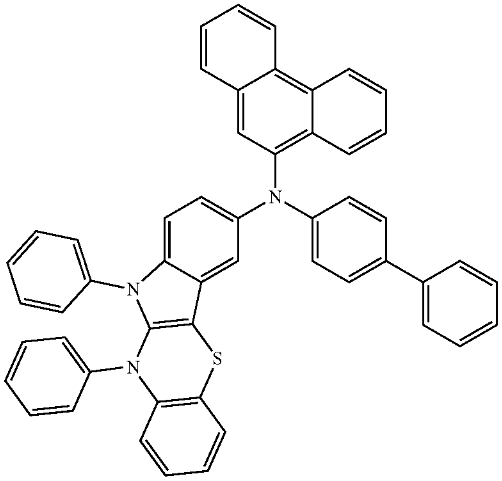
-continued
C35
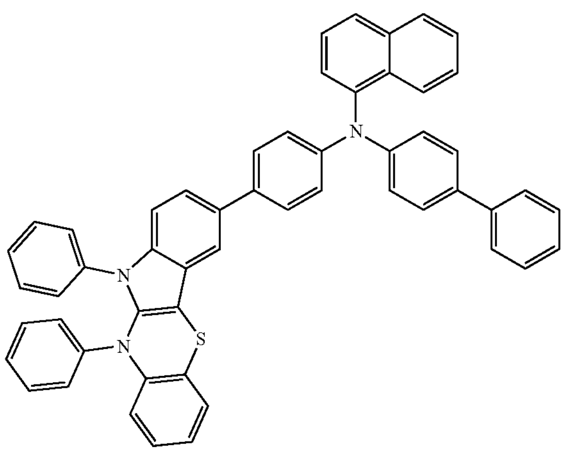
C36
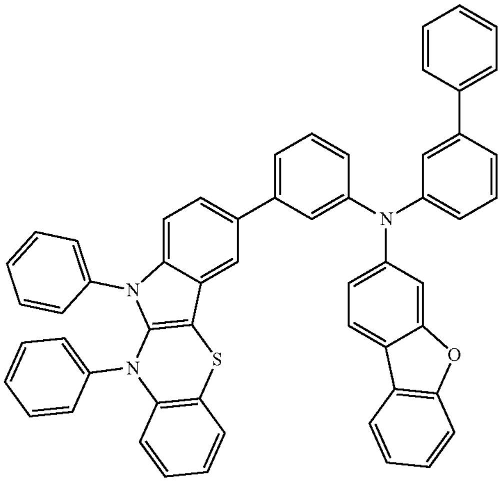
C37
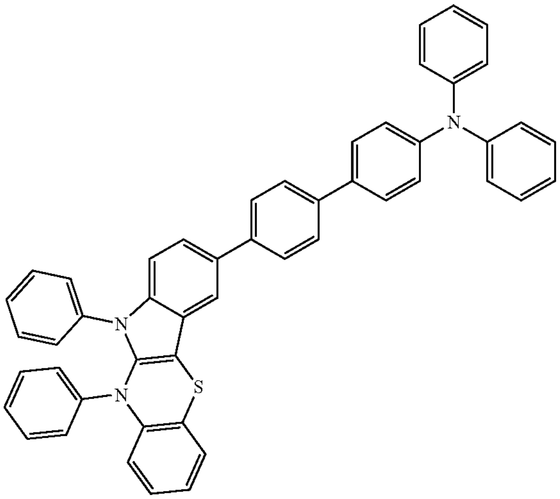

-continued
C38
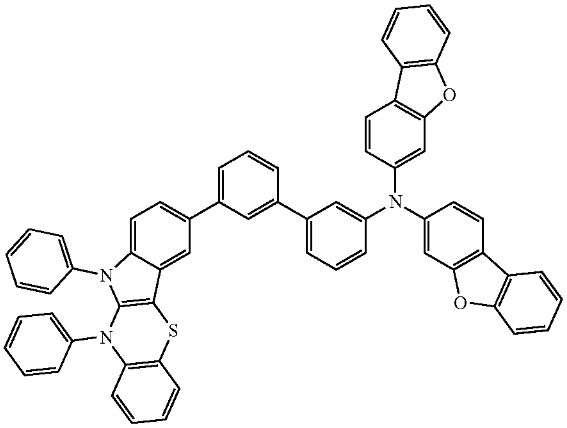
C39
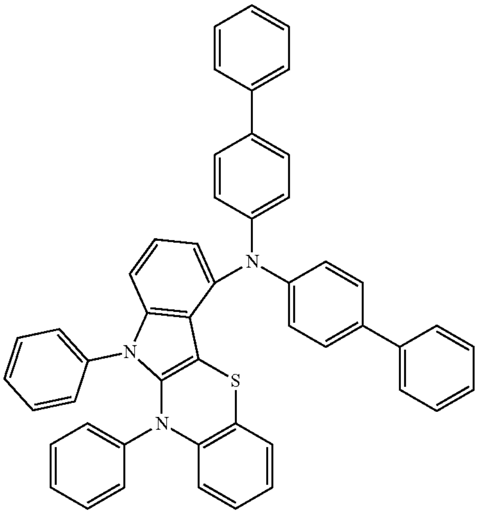
C40
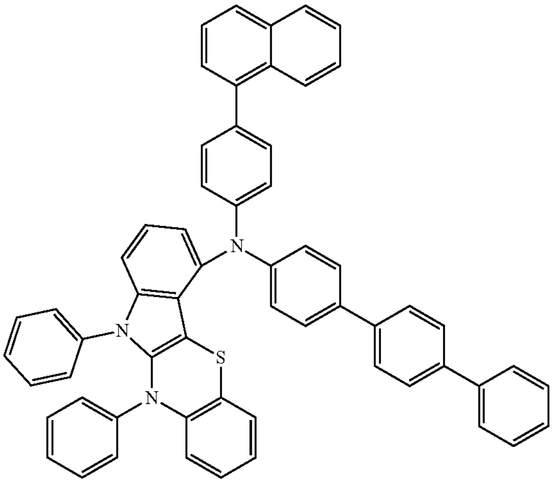
-continued
C41
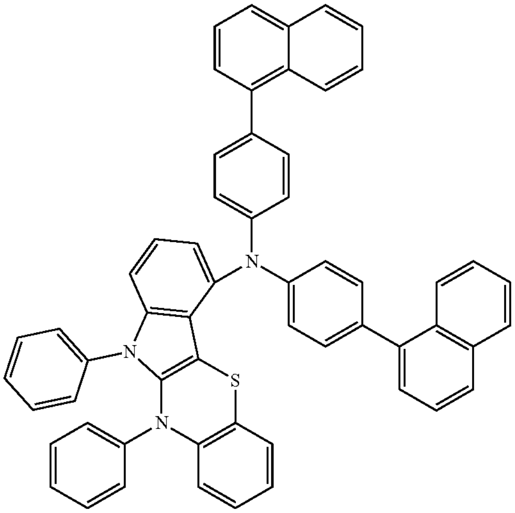
C42
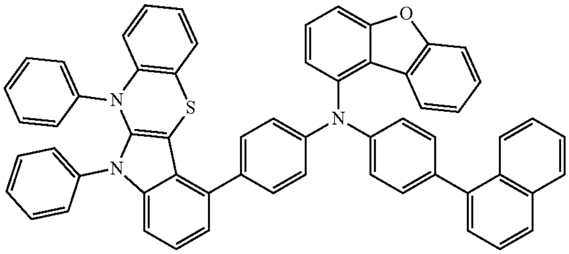
C43
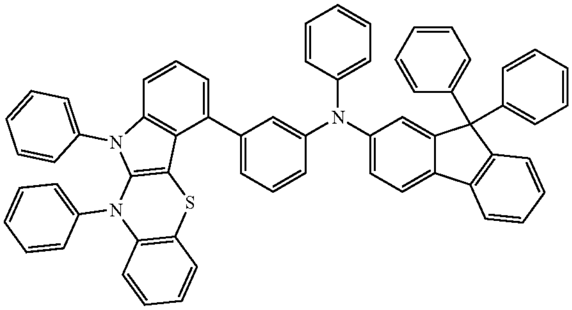
C44
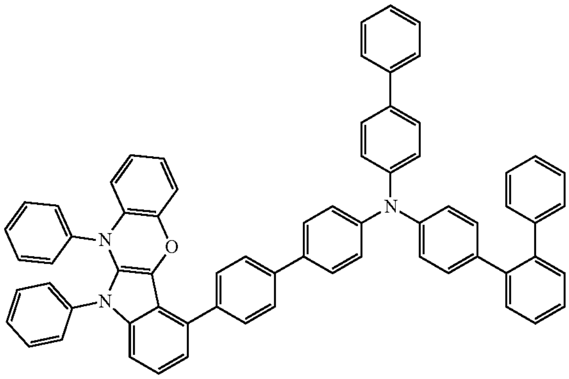

-continued
C45
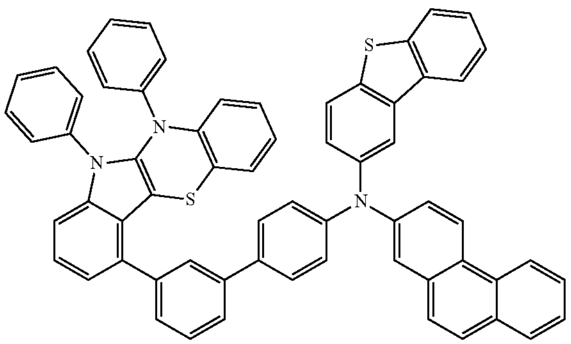
C46
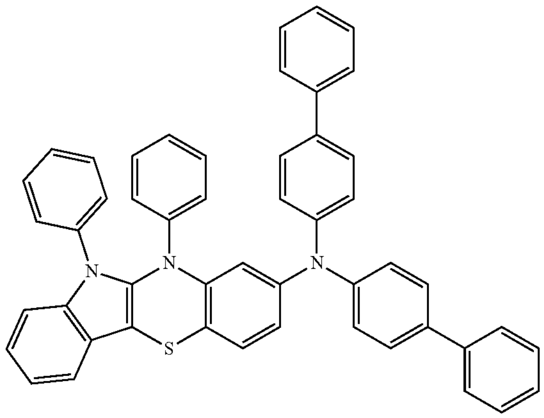
C47
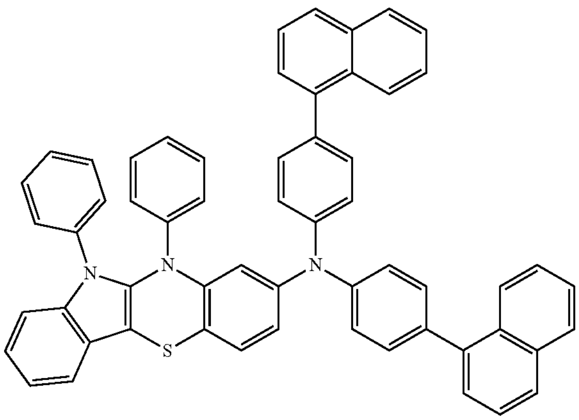
-continued
C48
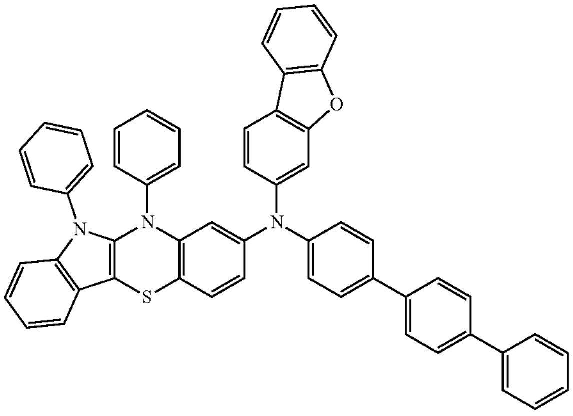
C49
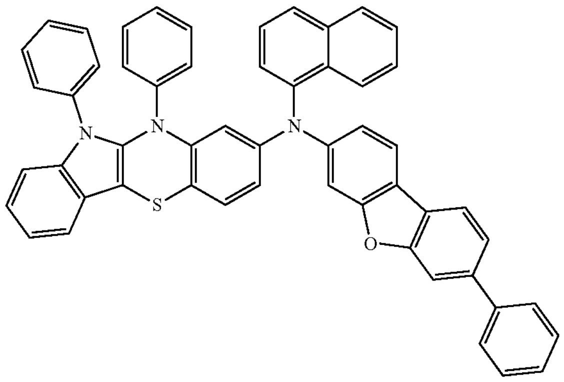
C50
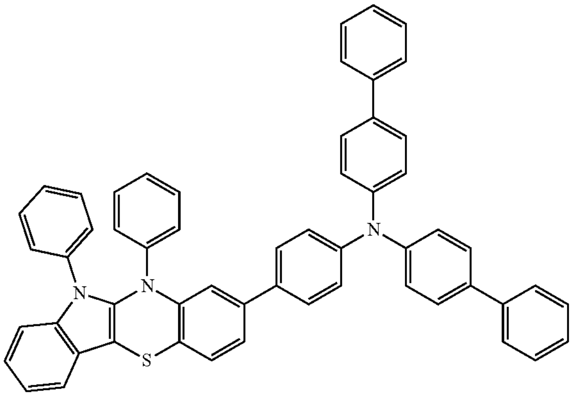

-continued
C51
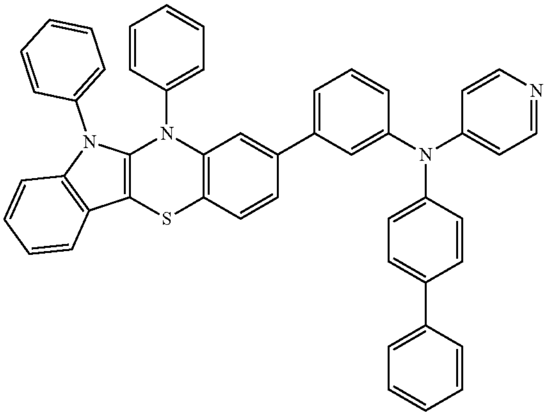
C52
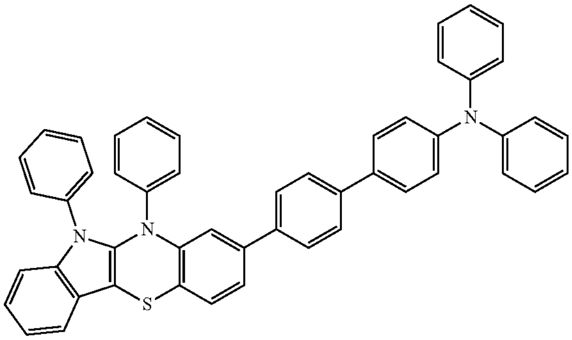
C53
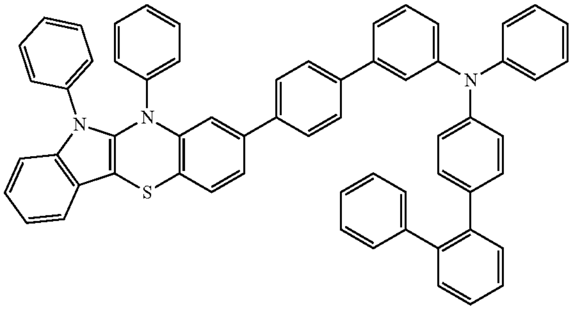
C54
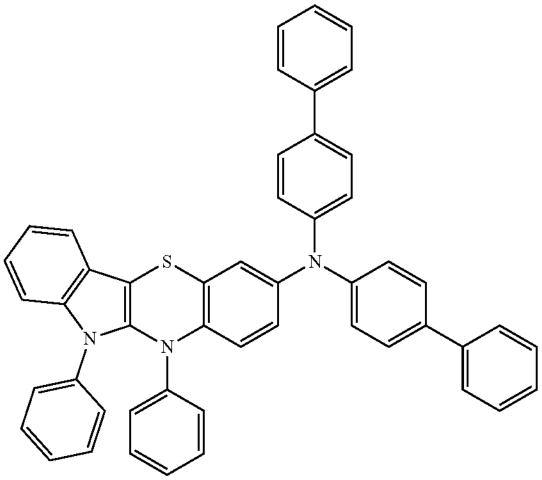
-continued
C55
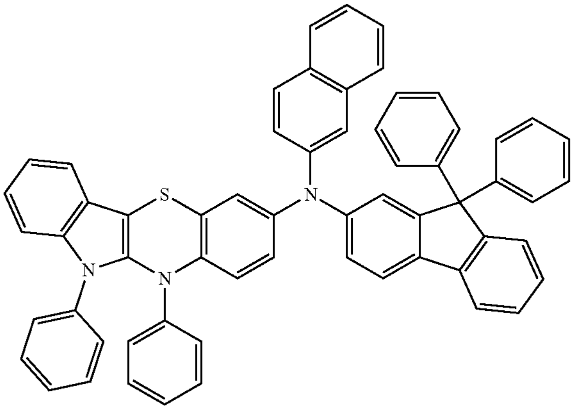
C56
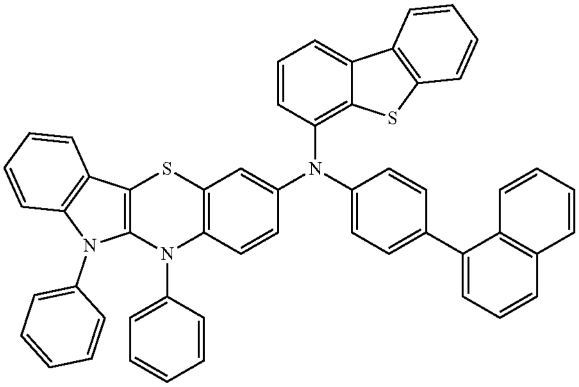
C57
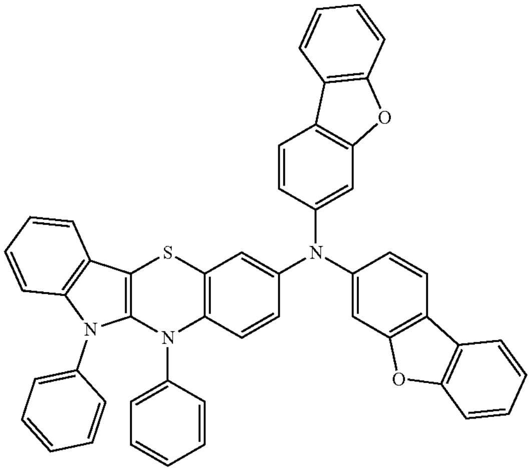

-continued
C58
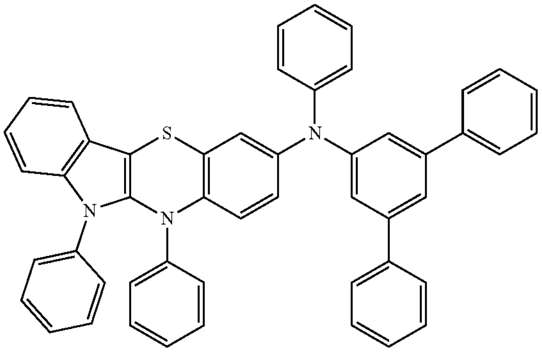
C59
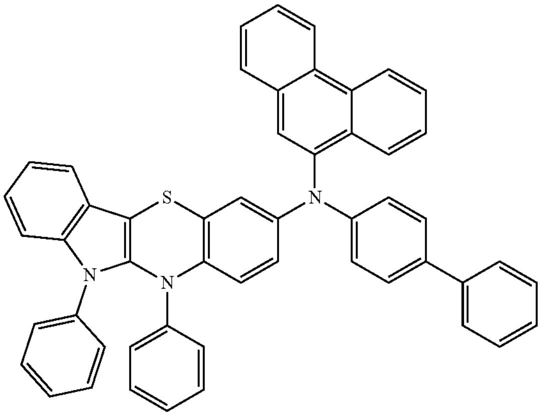
C60
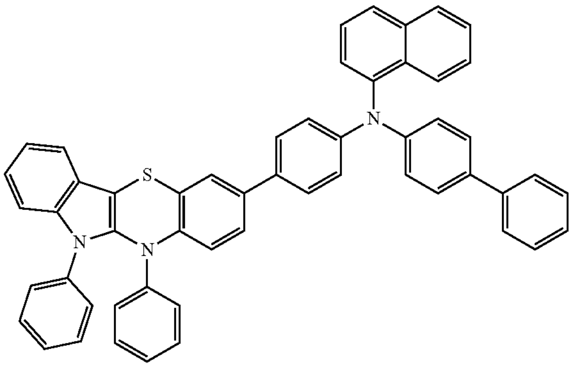
-continued
C61
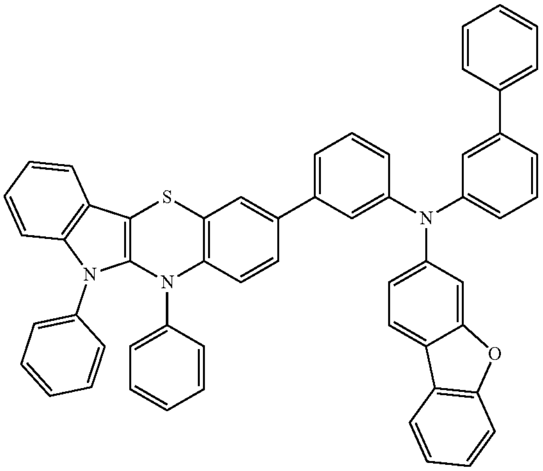
C62
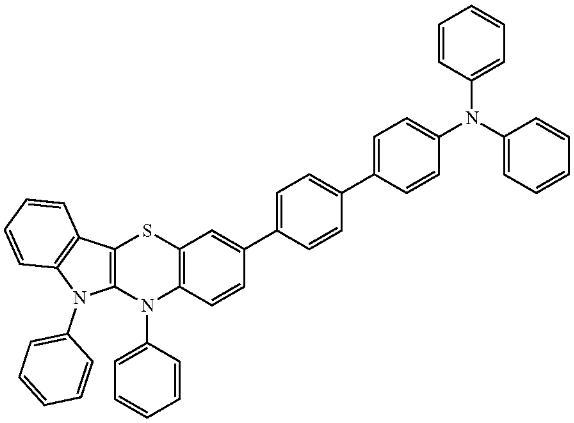
C63
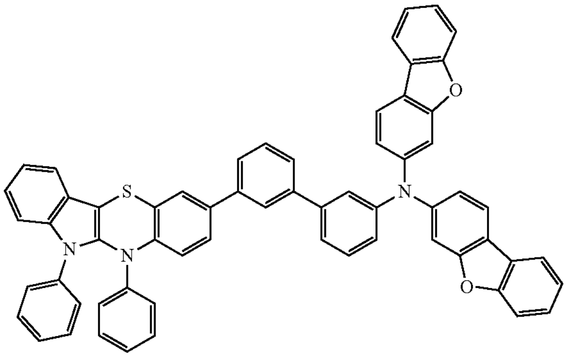

-continued
C64
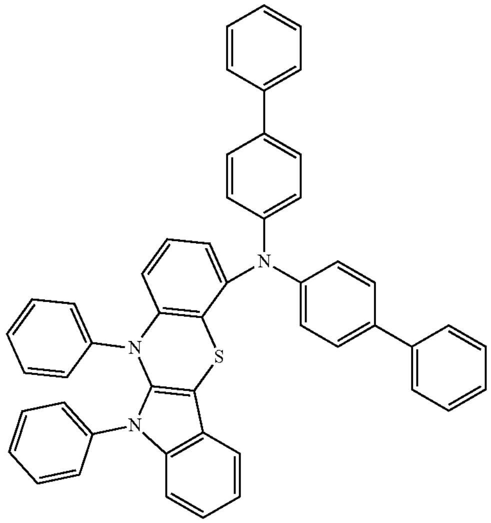
C65
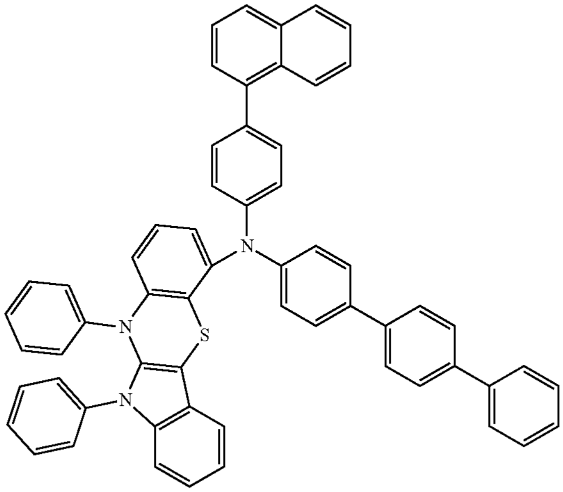
C66
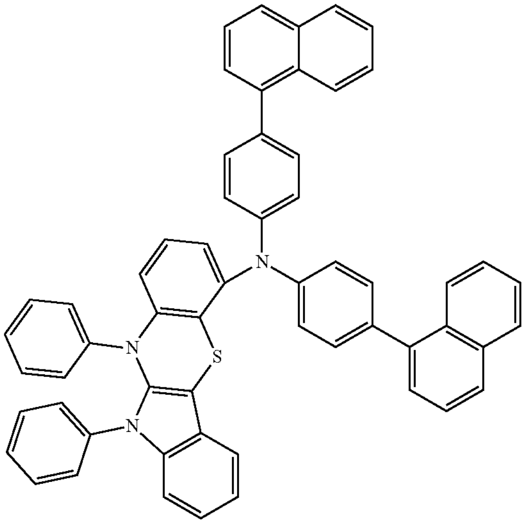
-continued
C67
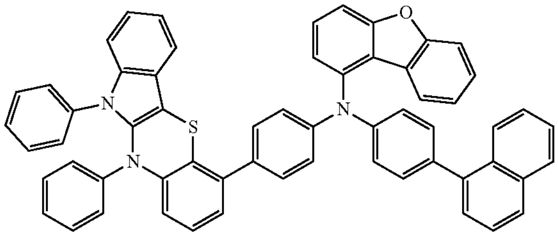
C68
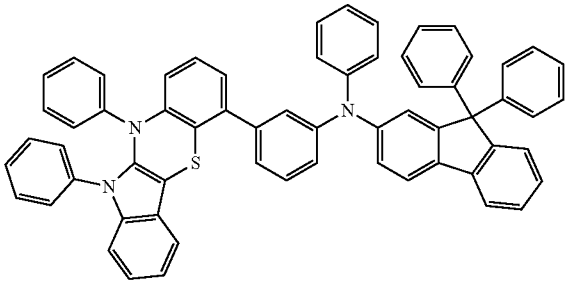
C69
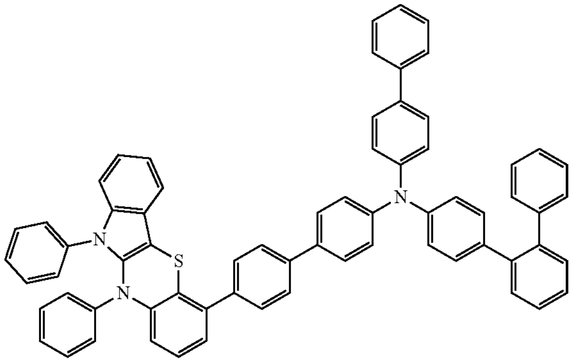
C70
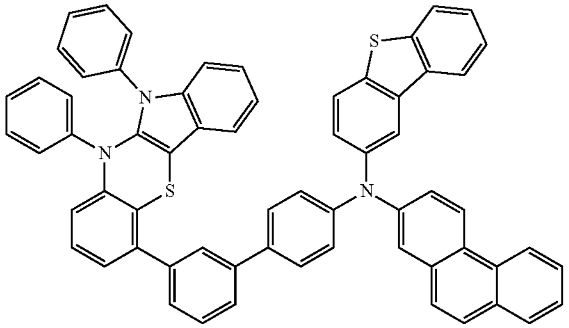

[Compound Group 4]
D1
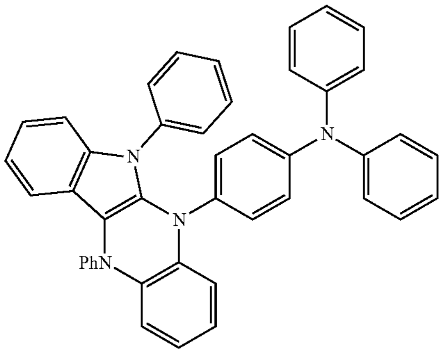
D2
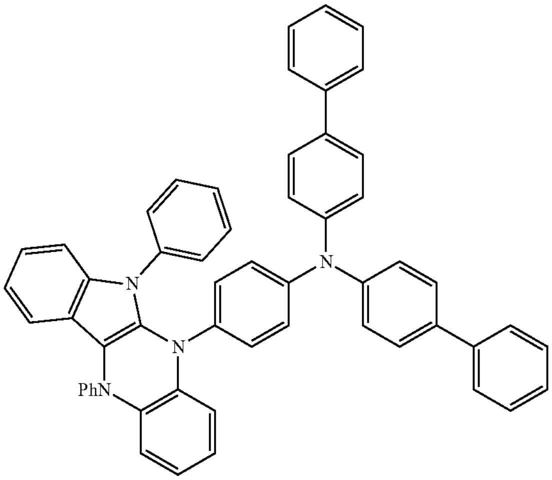
D3
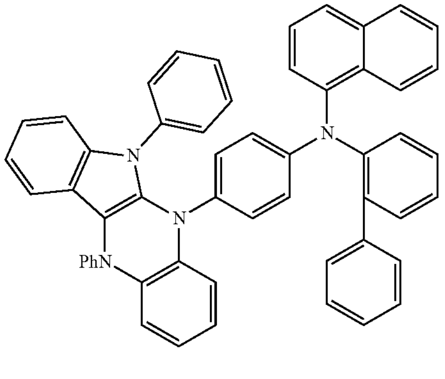
D4
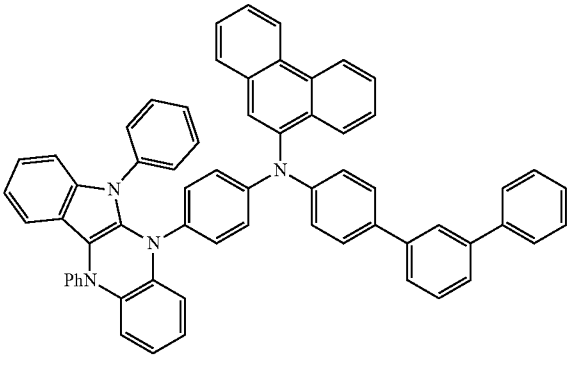
-continued
D5
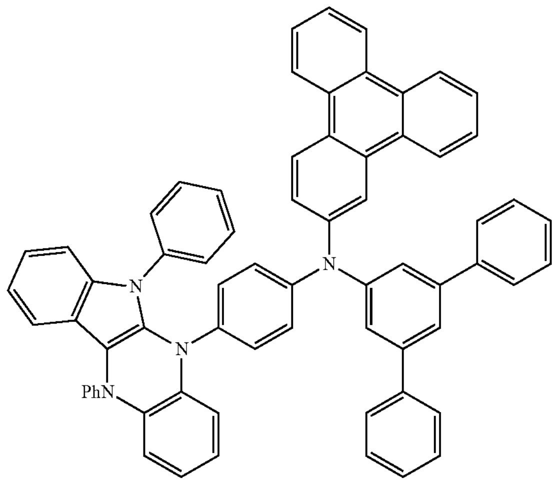
D6
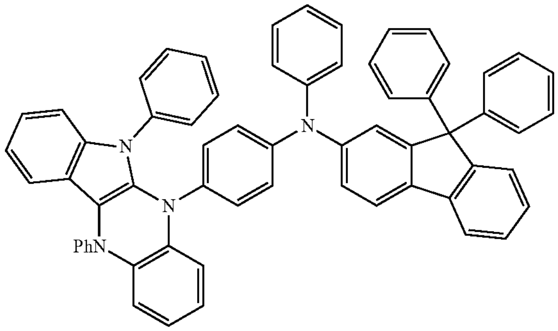
D7
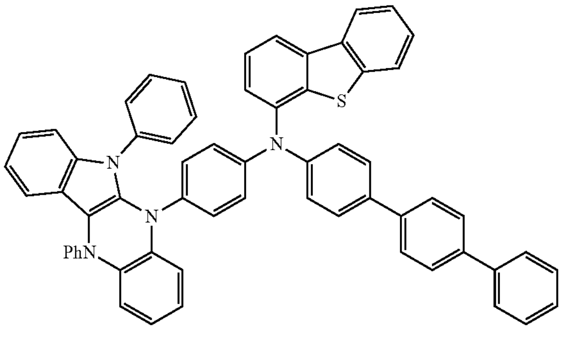

-continued
D8
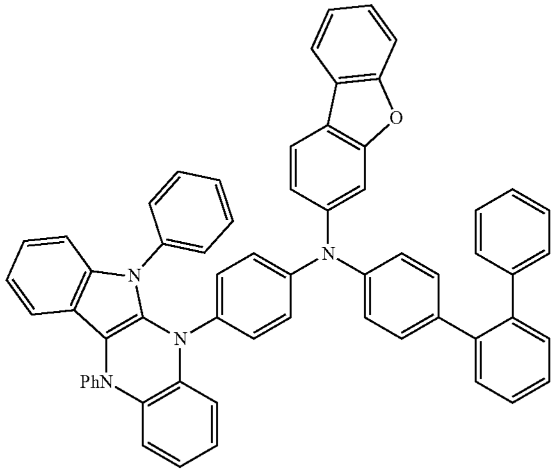
D9
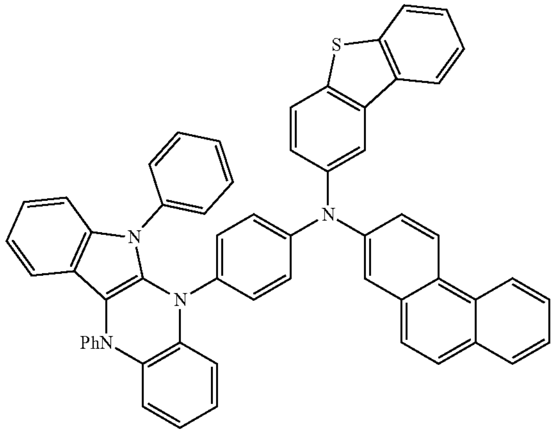
D10
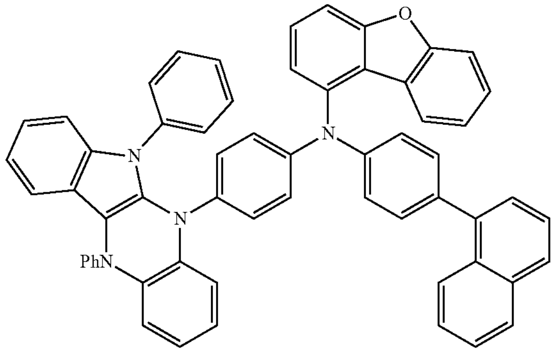
-continued
D11
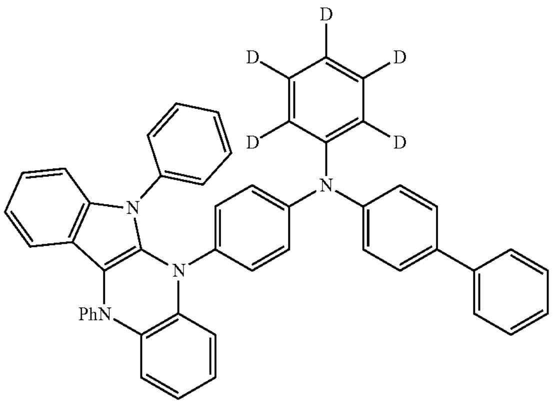
D12
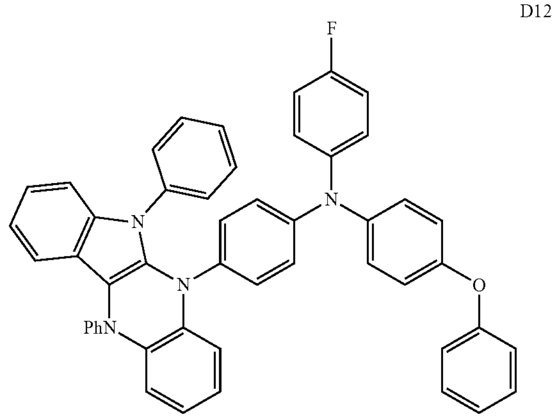
D13
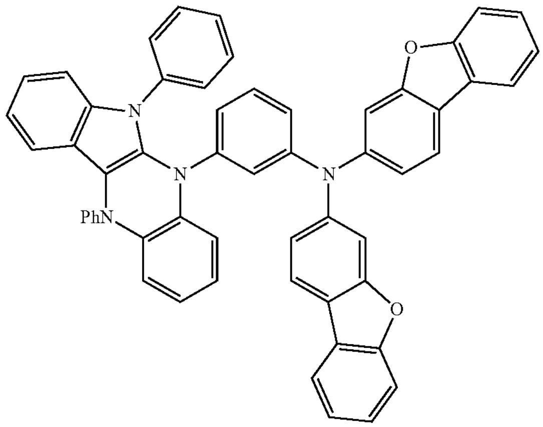

-continued
D14
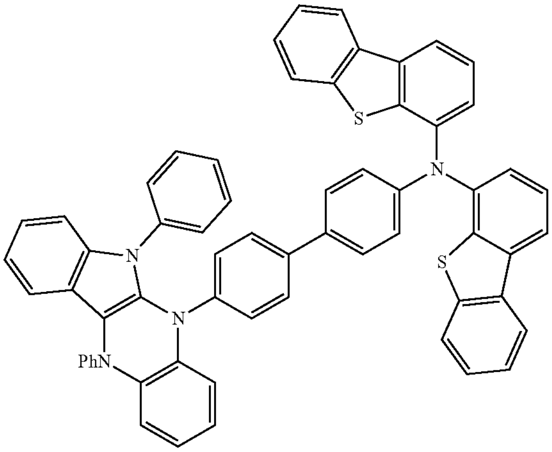
D15
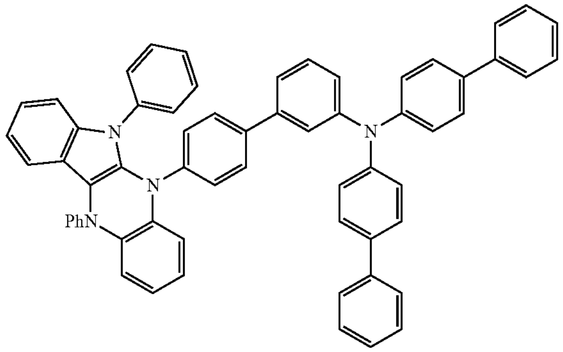
D16
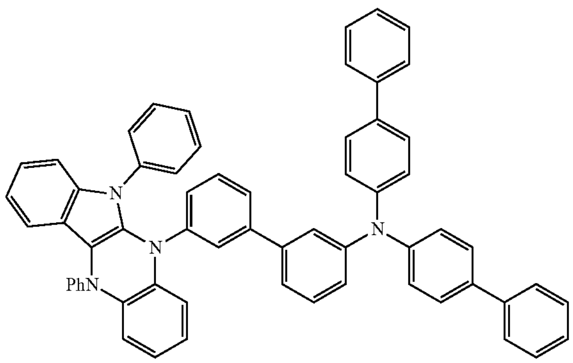
-continued
D17
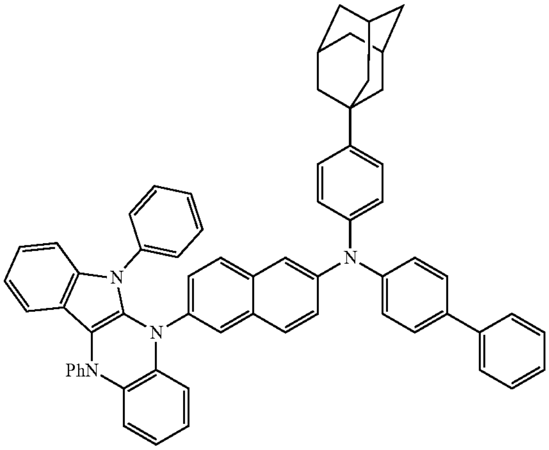
D18
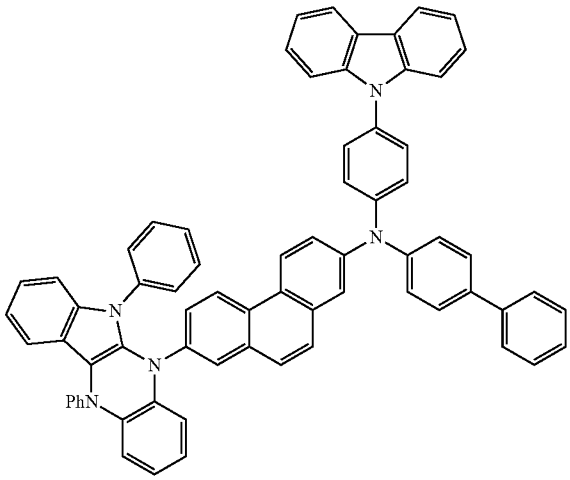
D19
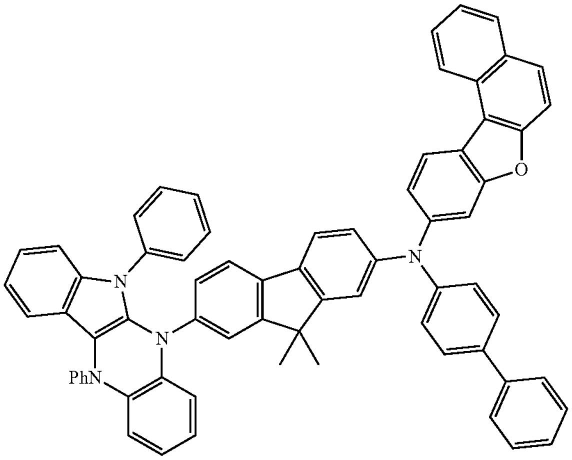

-continued
D20
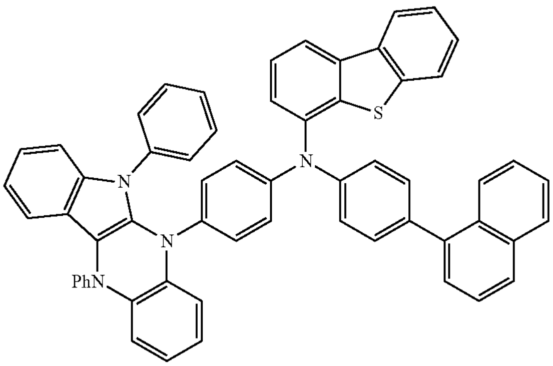
D21
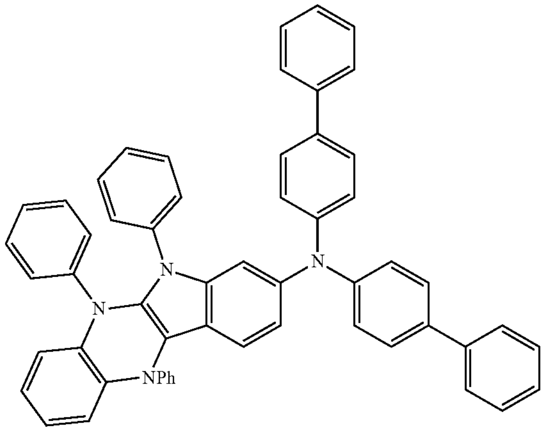
D22
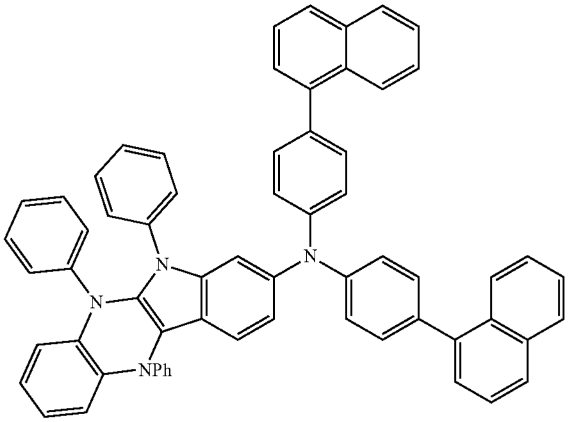
-continued
D23
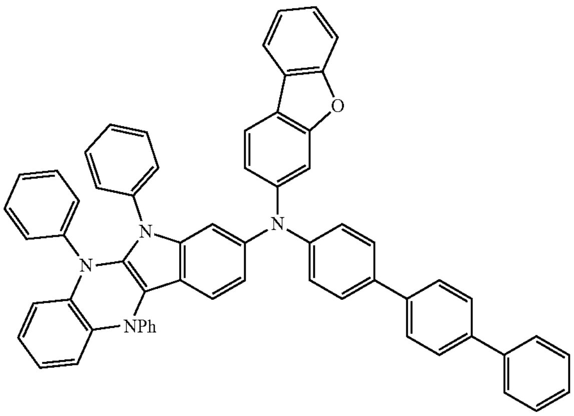
D24
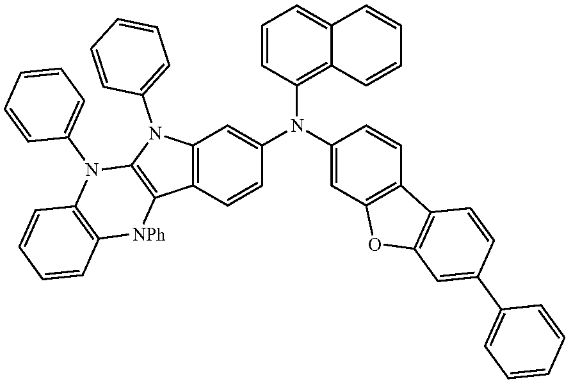
D25
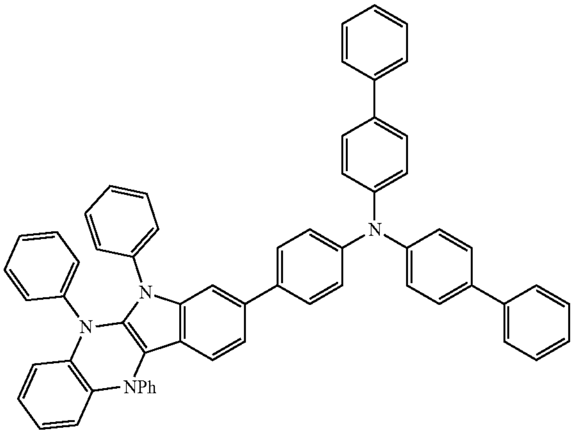

-continued
D26
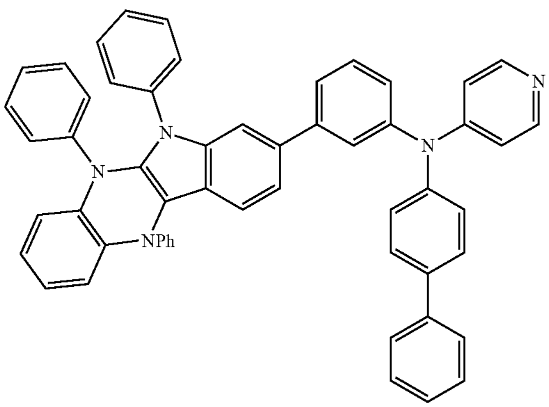
D27
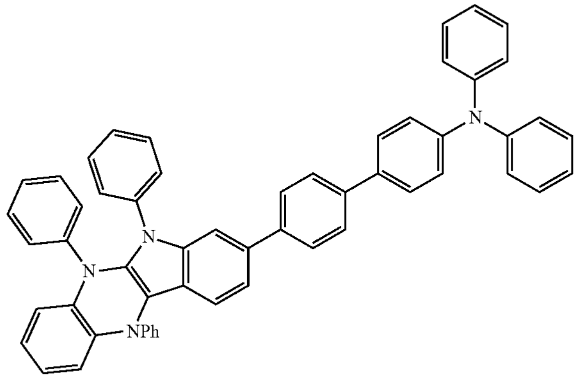
D28
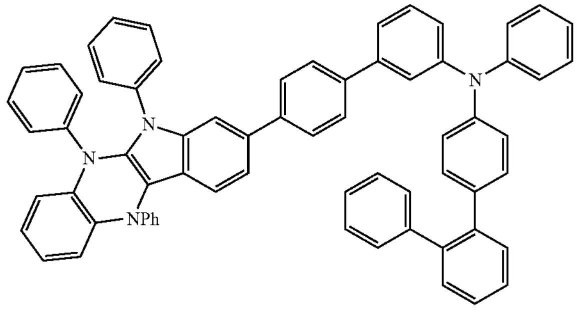
-continued
D29
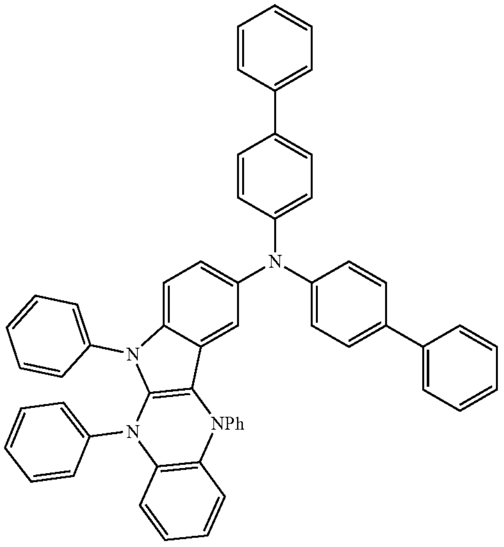
D30
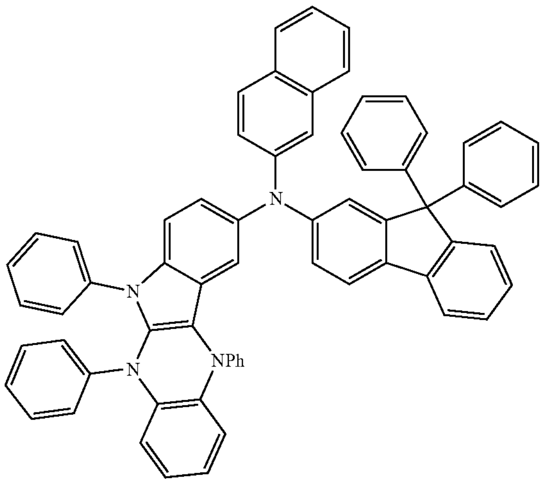
D31
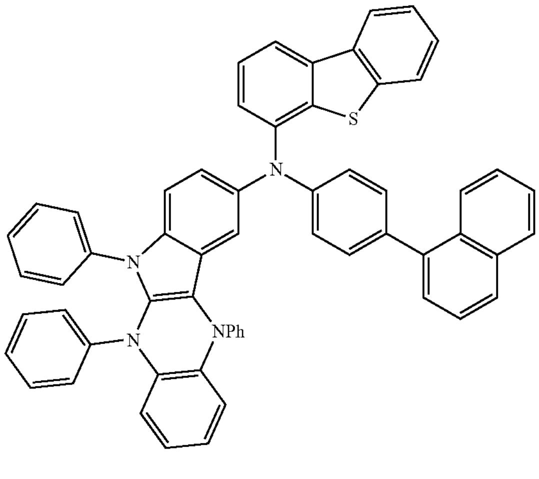

-continued
D32
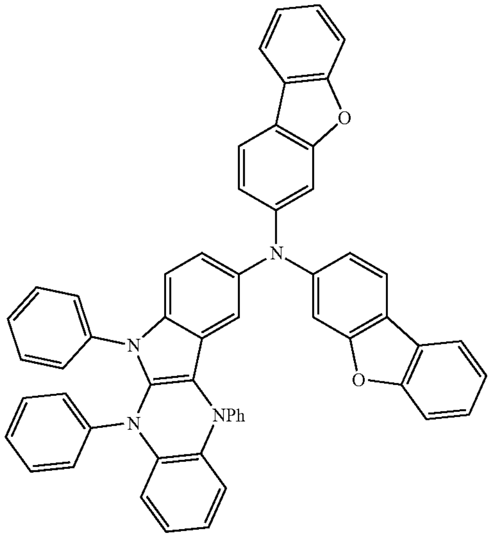
D33
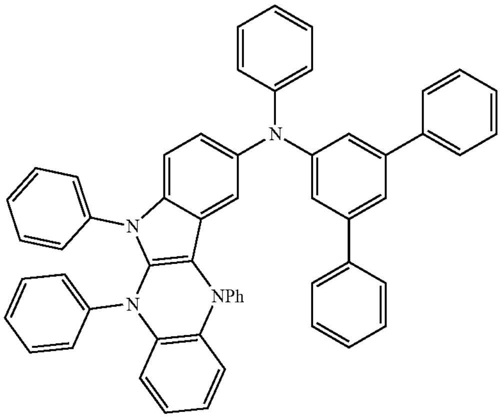
D34
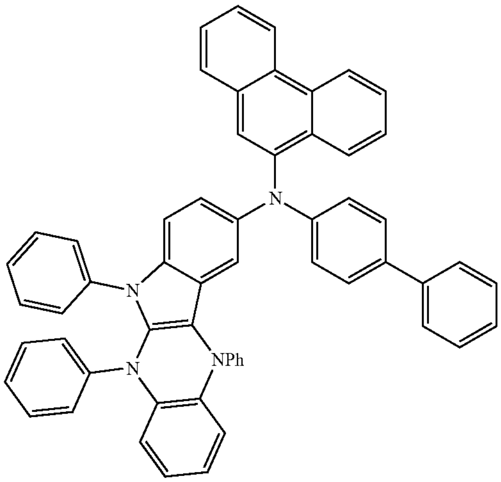
-continued
D35
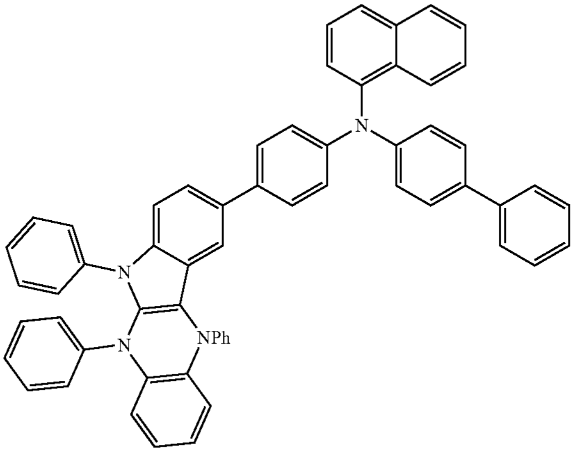
D36
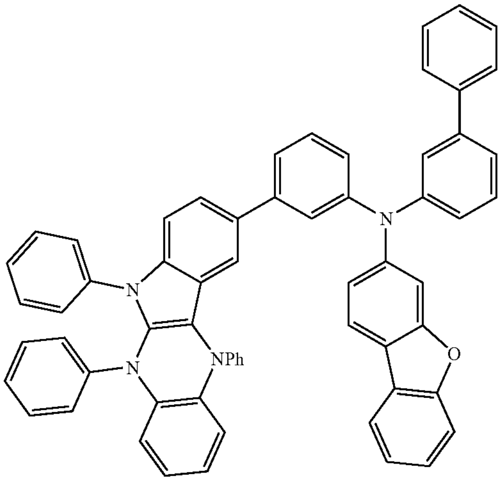
D37
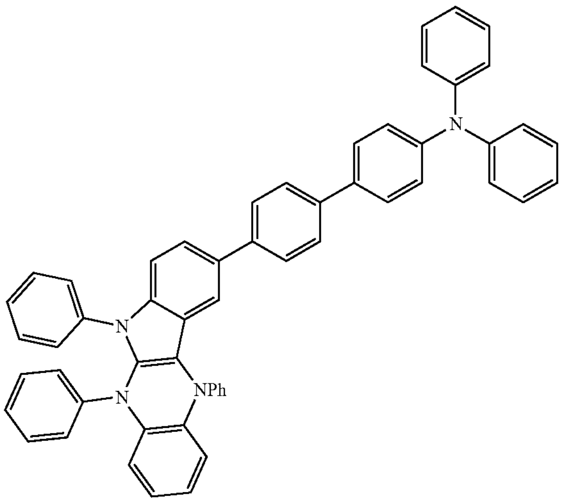

-continued
D38
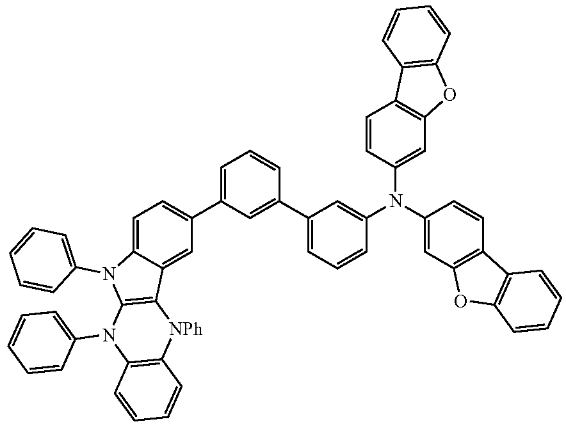
D39
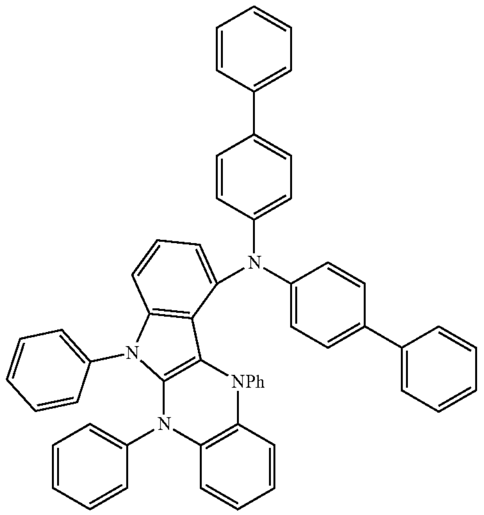
D40
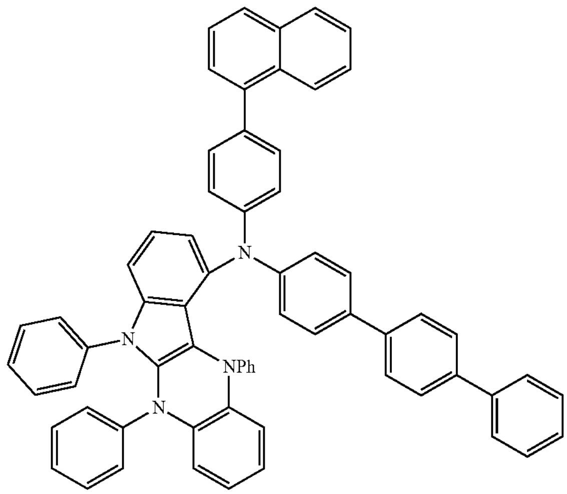
-continued
D41
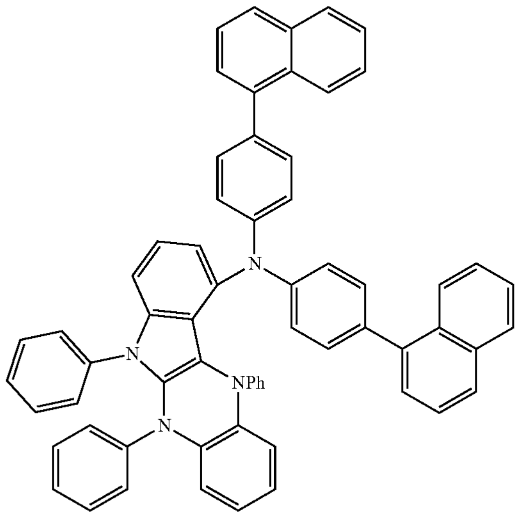
D42
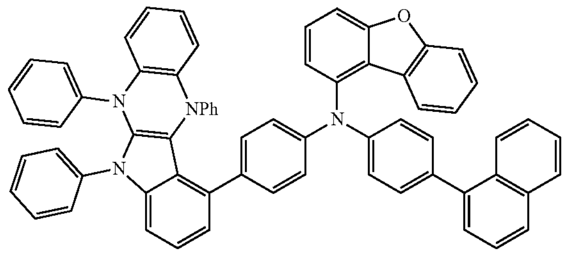
D43
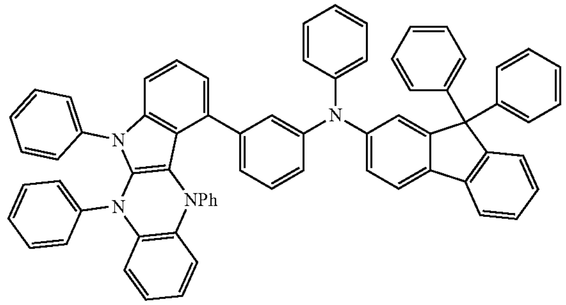
D44
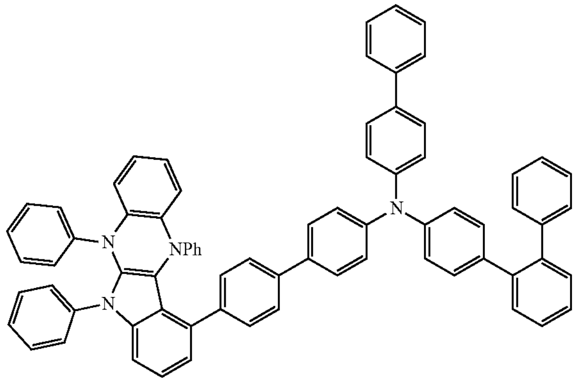

-continued
D45
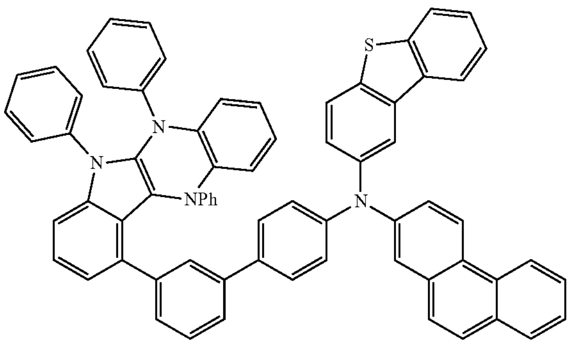
D46
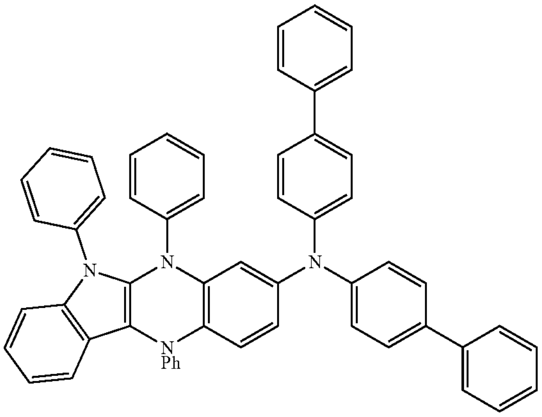
D47
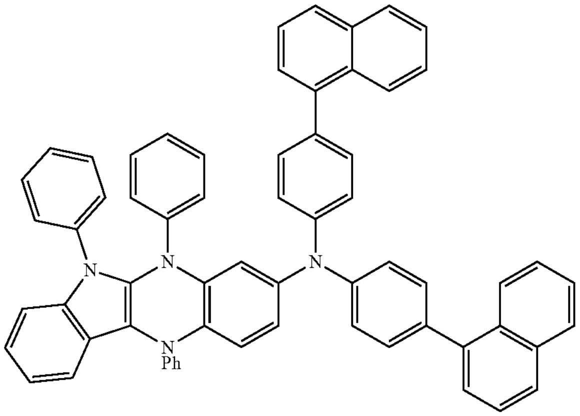
-continued
D48
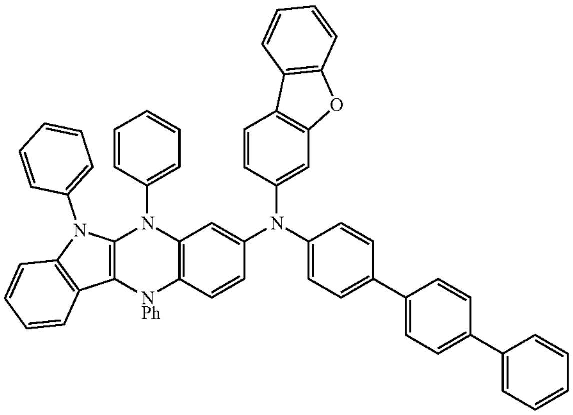
D49
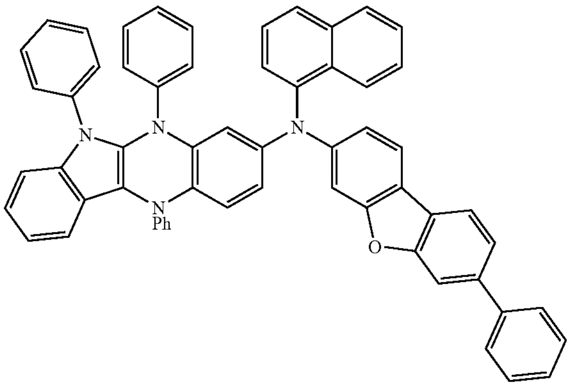
D50
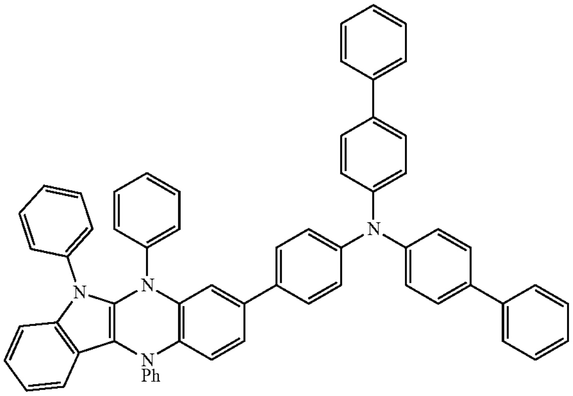

-continued
D51
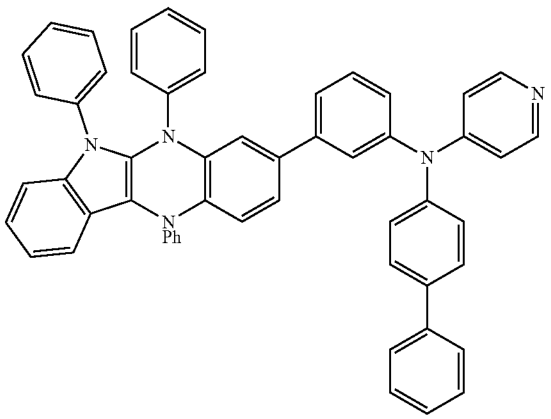
D52
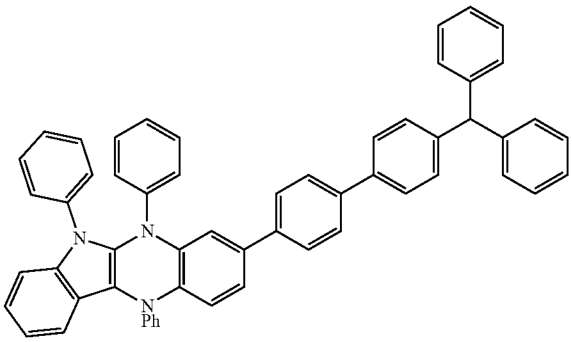
D53
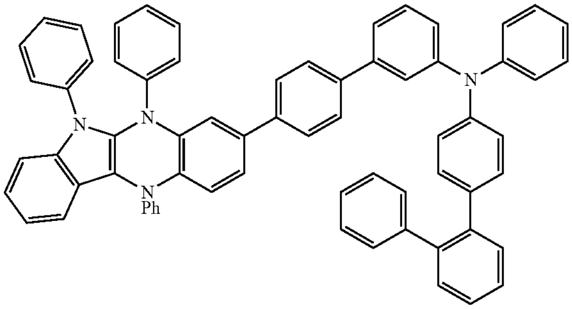
D54
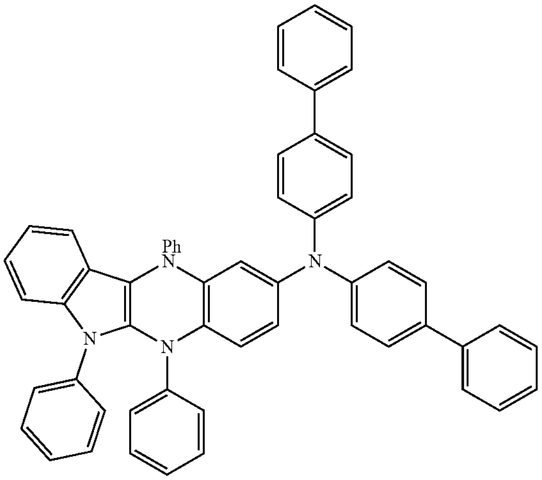
-continued
D55
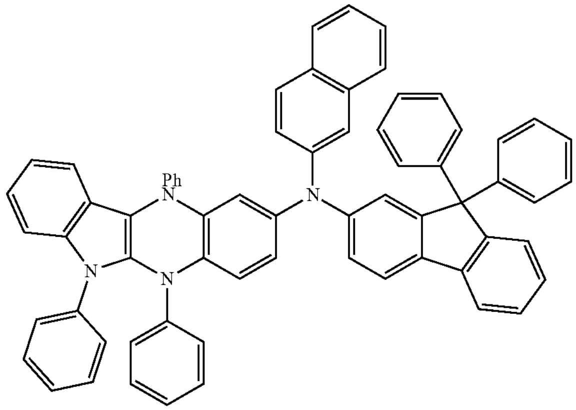
D56
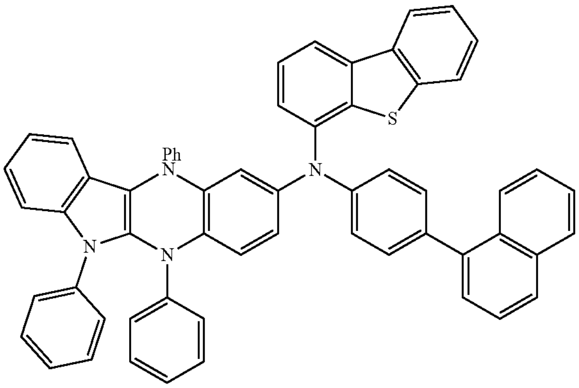
D57
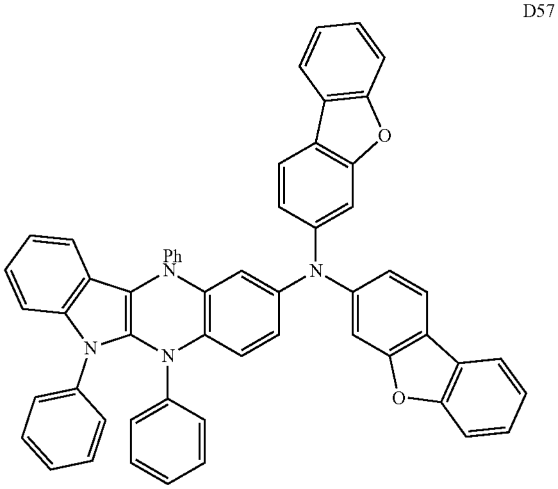

D58
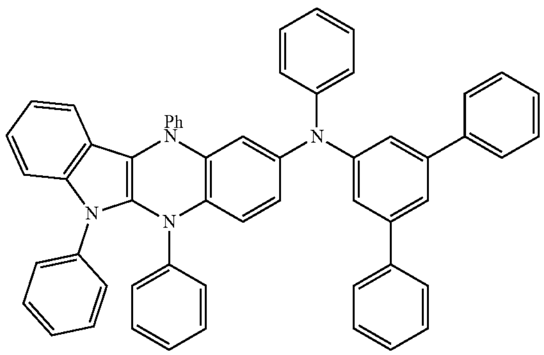
D59
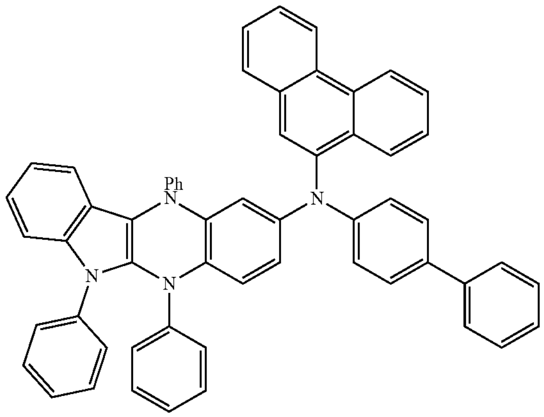
D60
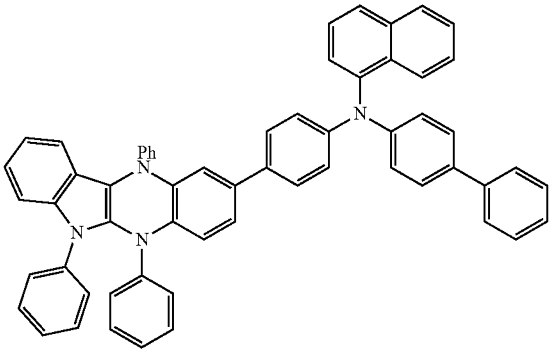
D61
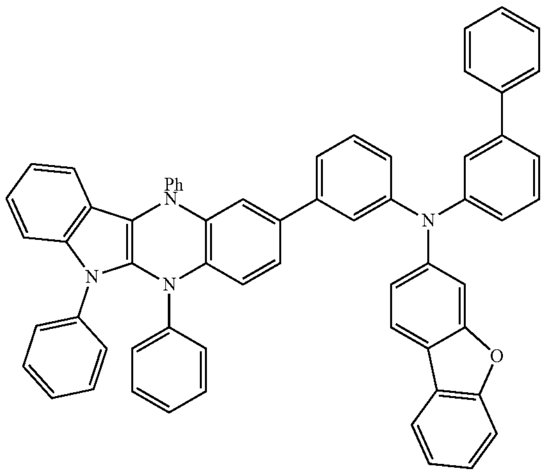
D62
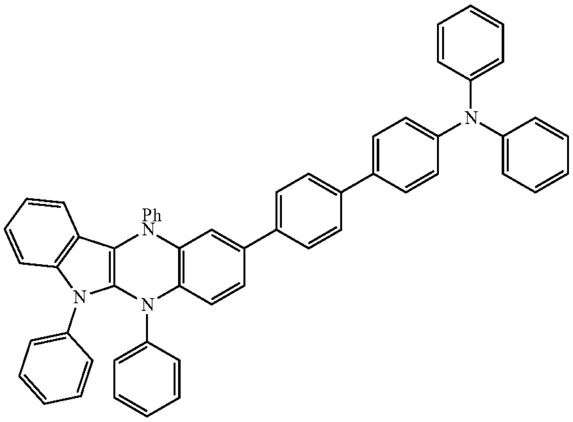
D63
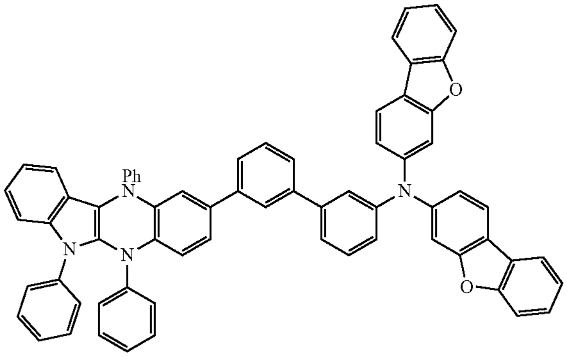

-continued
D64
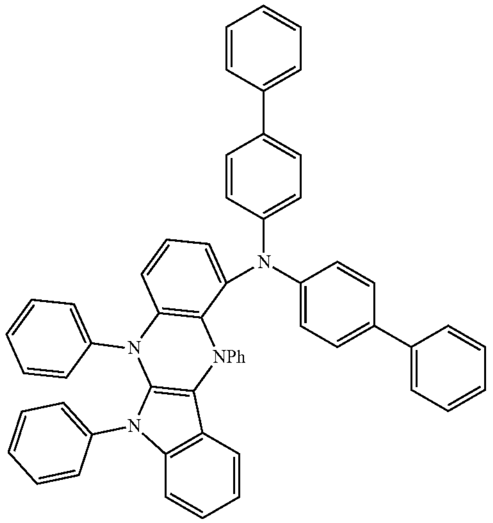
D65
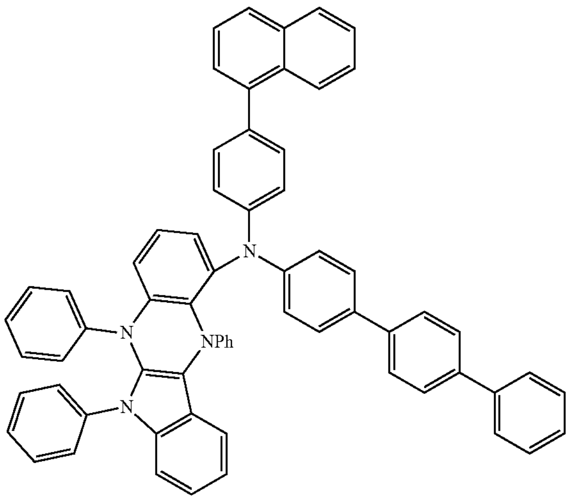
D66
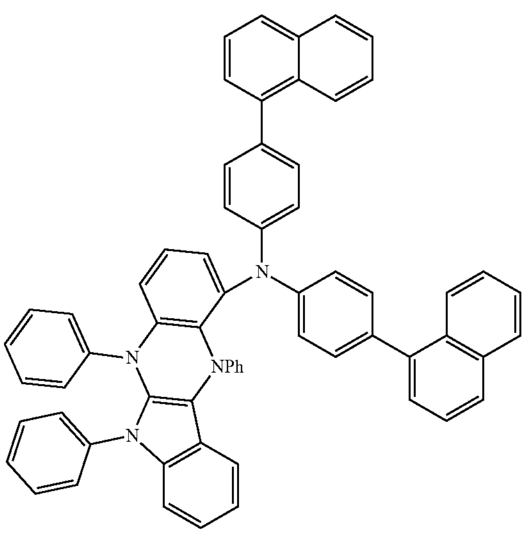
-continued
D67
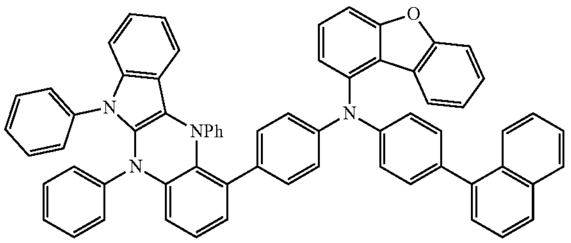
D68
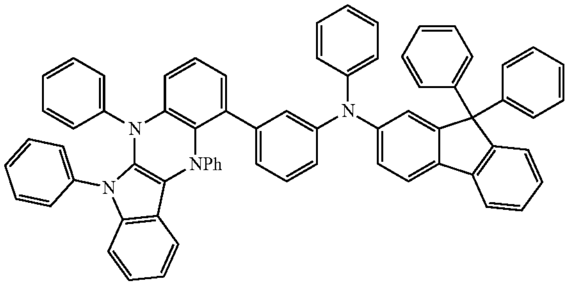
D69
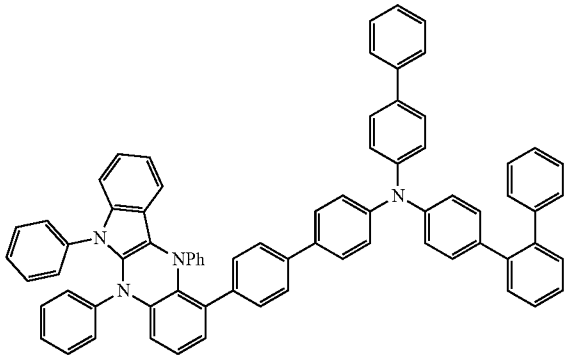
D70
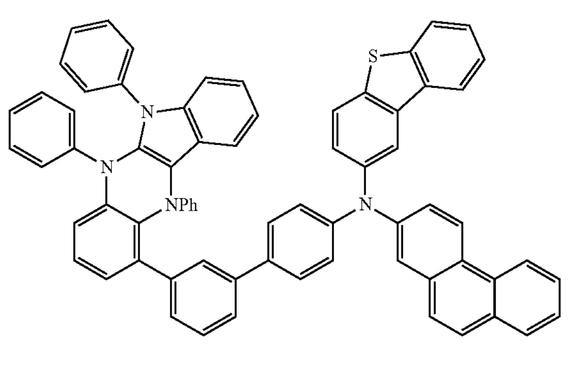

[Compound Group 5]
E1
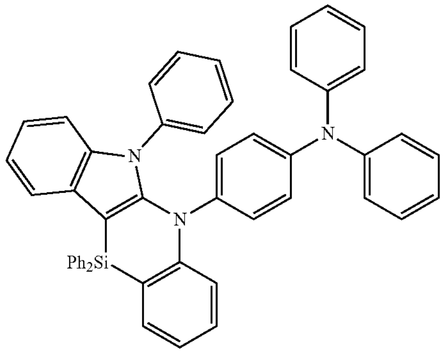
E2
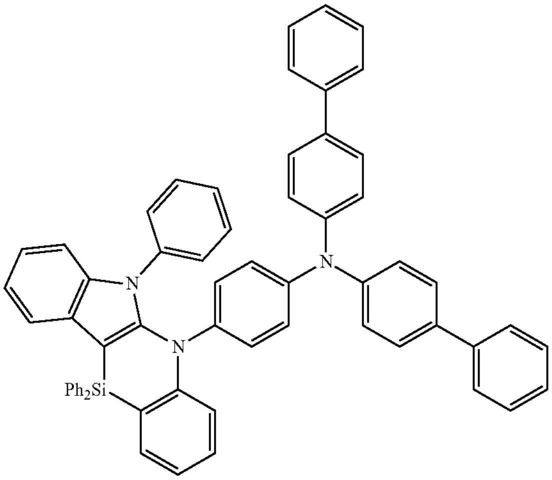
E3
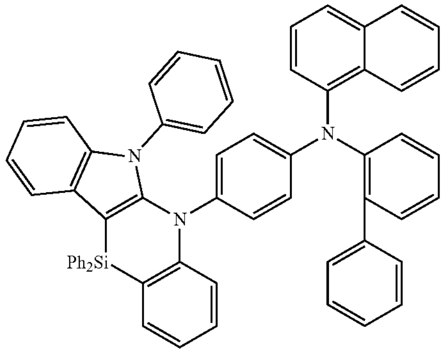
E4
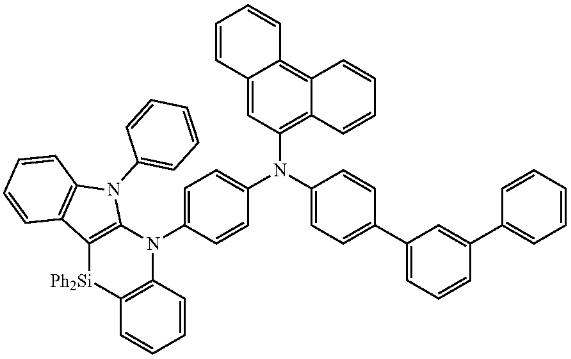
-continued
E5
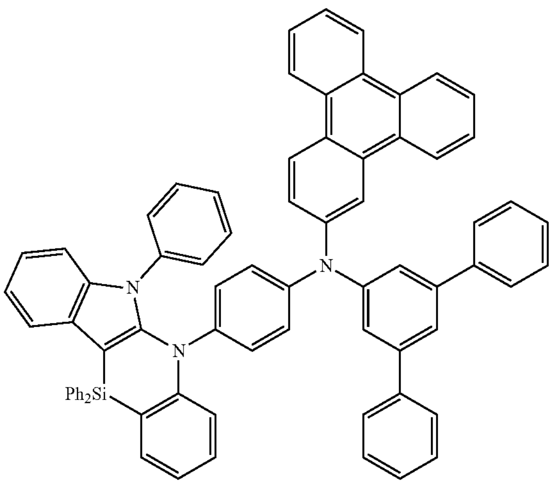
E6
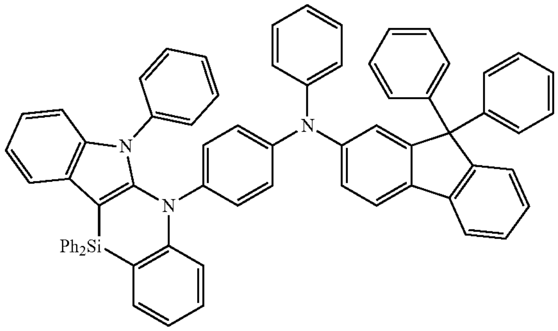
E7
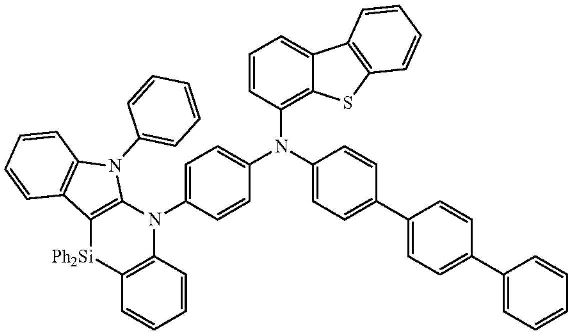

E8
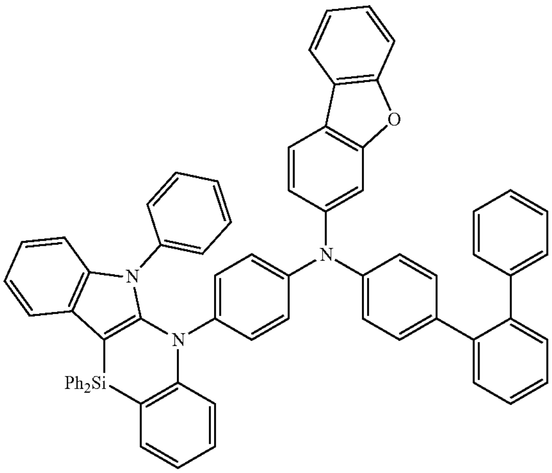
E9
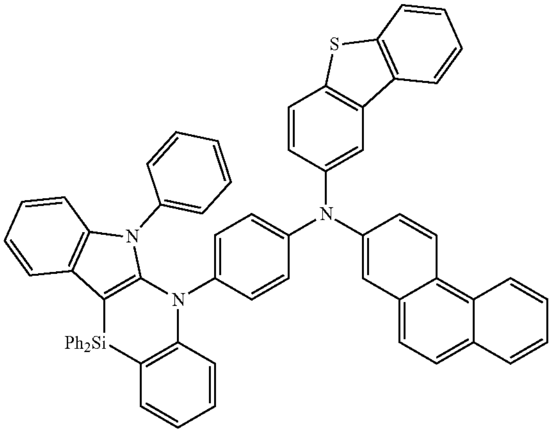
E10
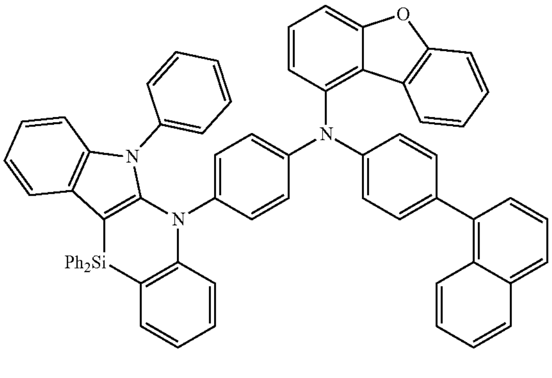
E11
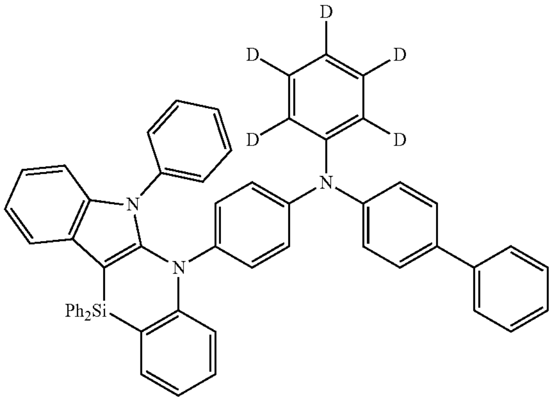
E12
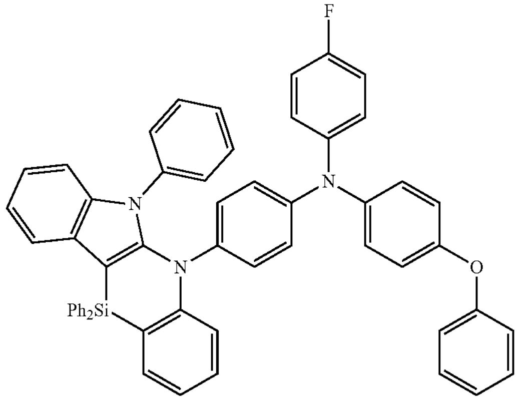
E13
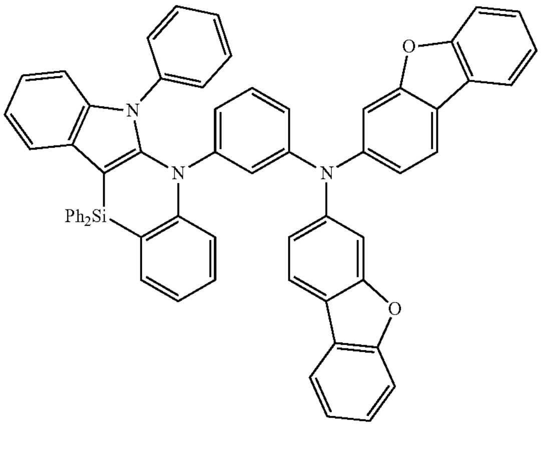

-continued
E14
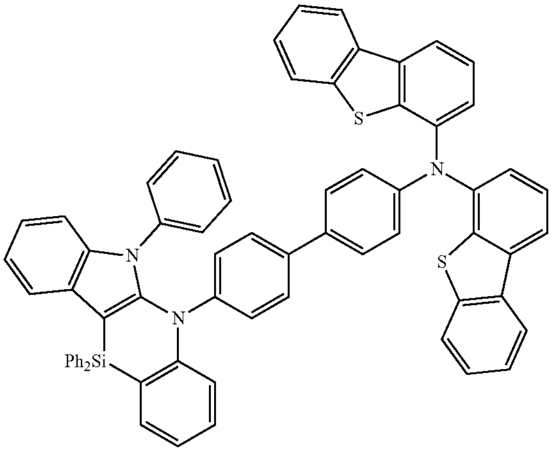
E15
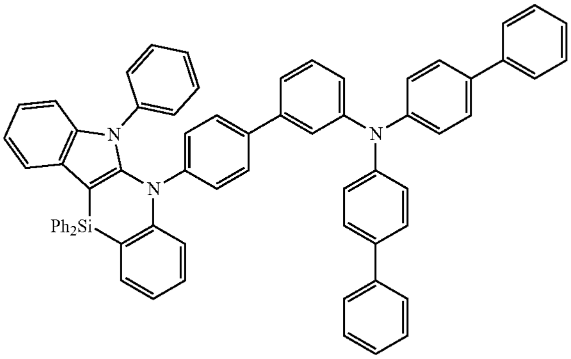
E16
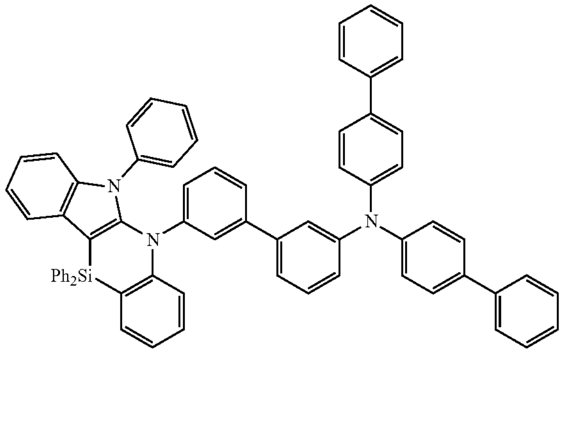
-continued
E17
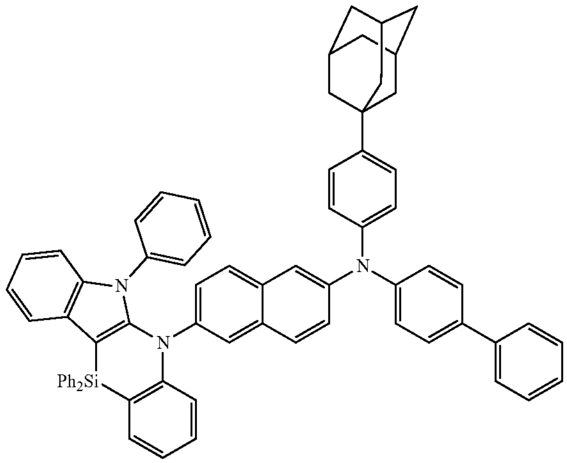
E18
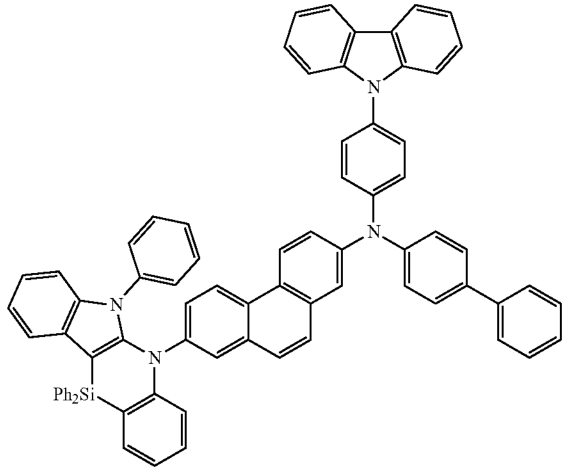
E19
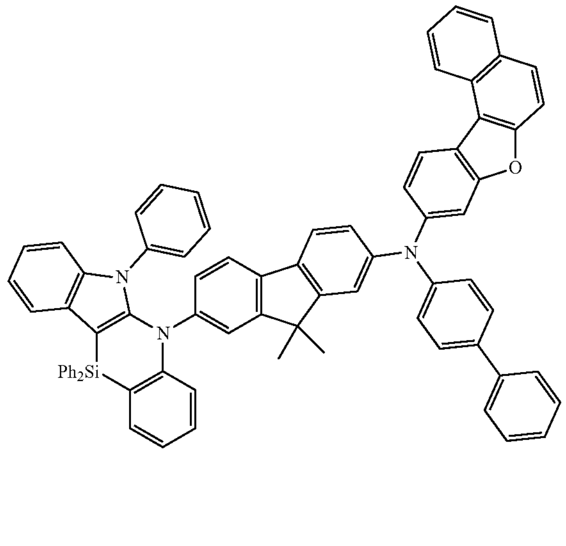

-continued
E20
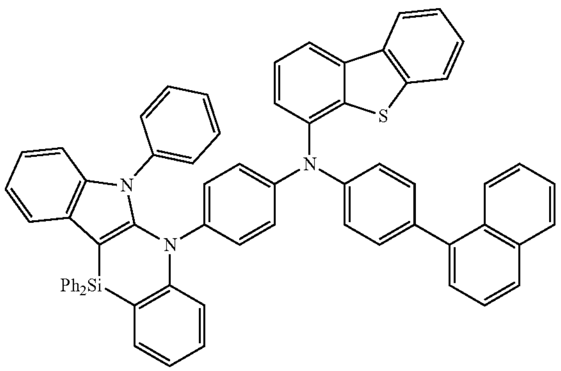
E21
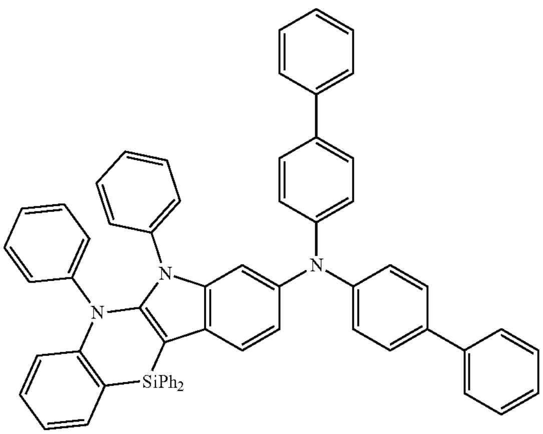
E22
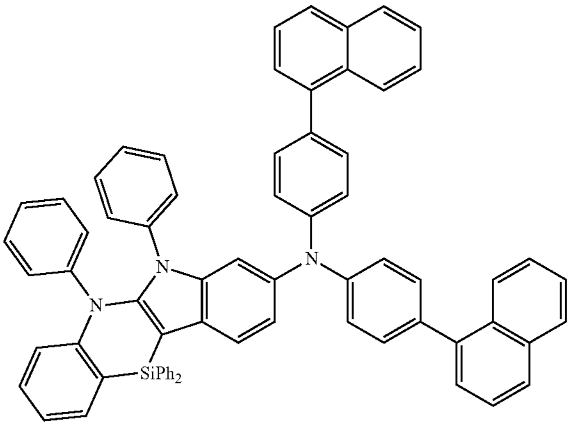
-continued
E23
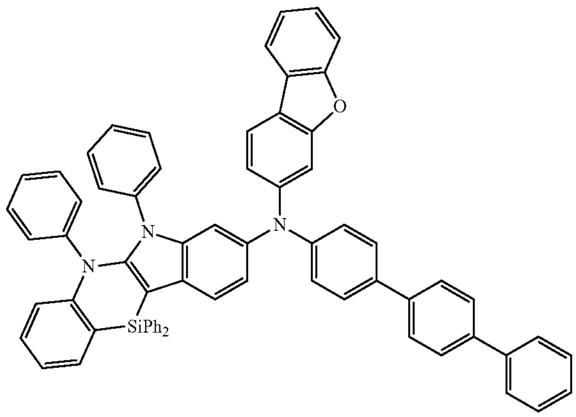
E24
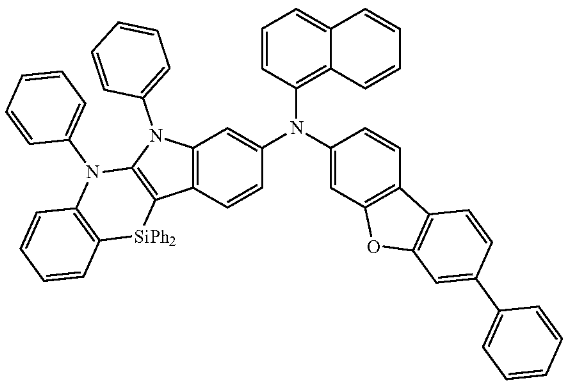
E25
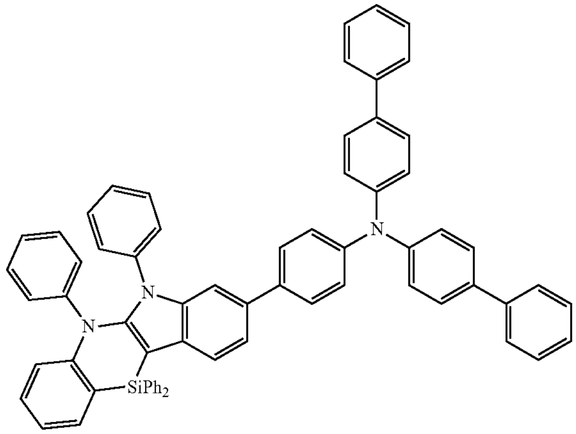

-continued
E26
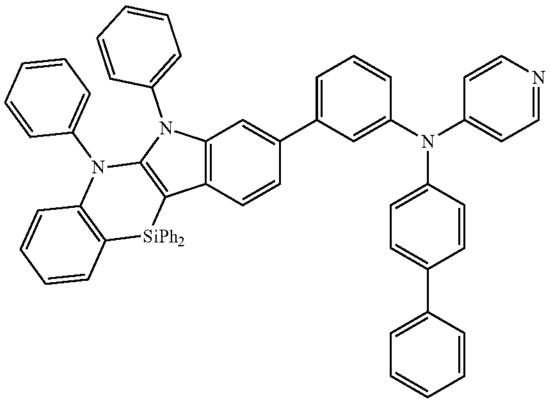
E27
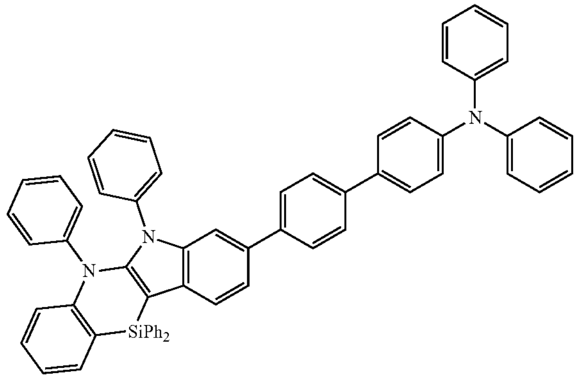
E28
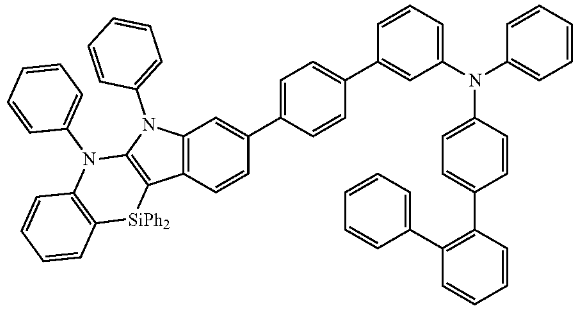
-continued
E29
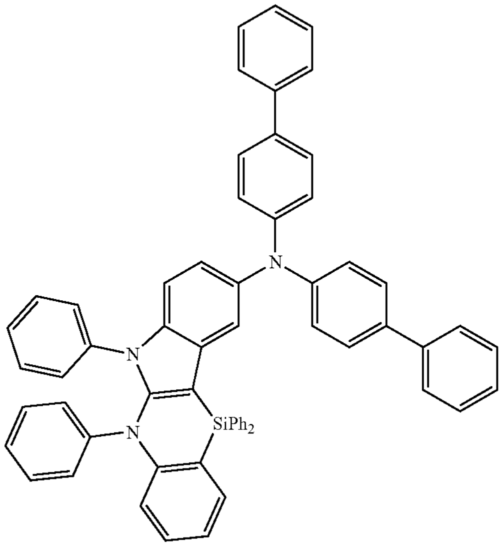
E30
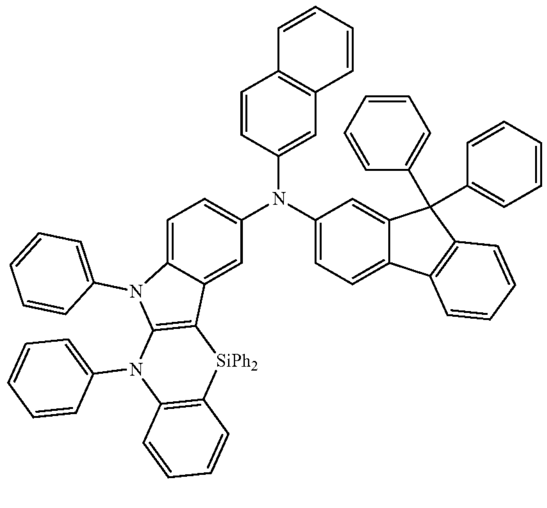
E31
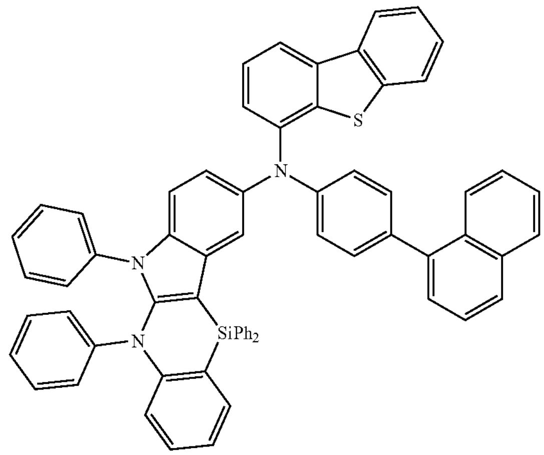

-continued
E32
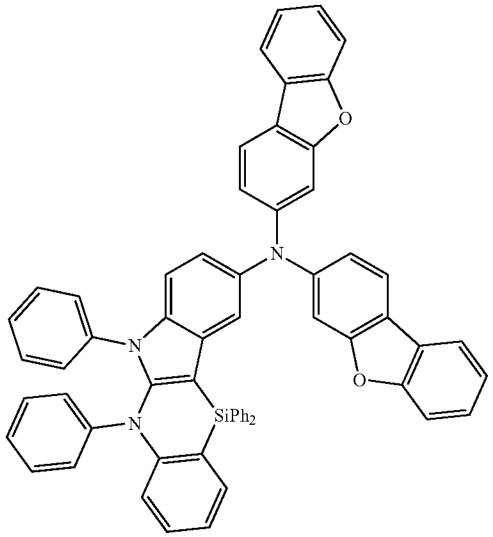
E33
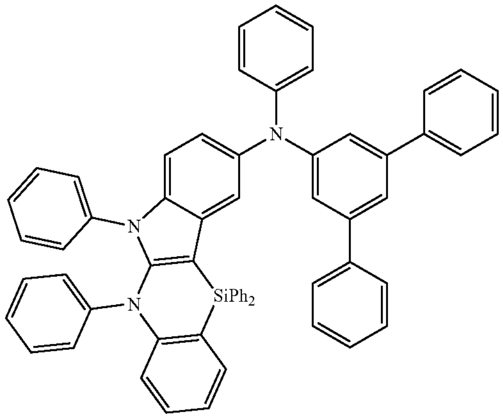
E34
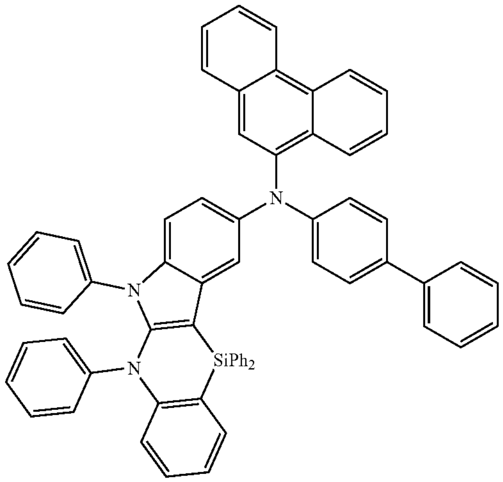
-continued
E35
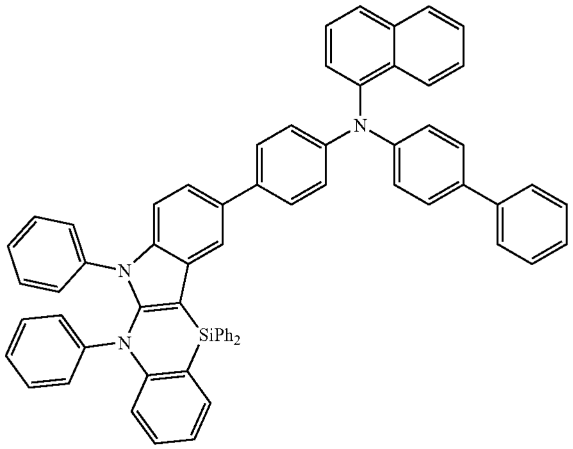
E36
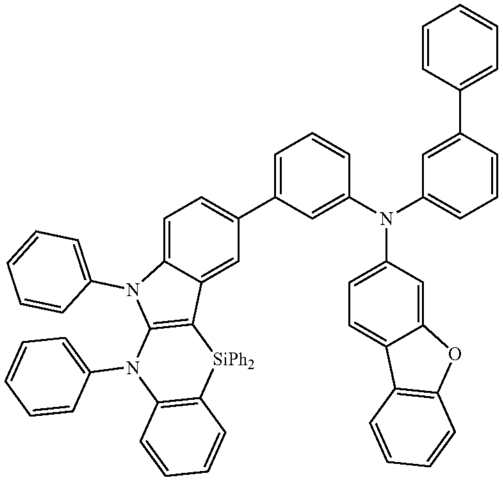
E37
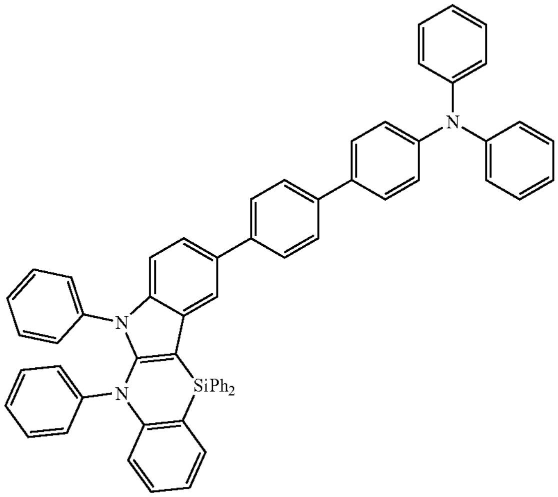

-continued
E38
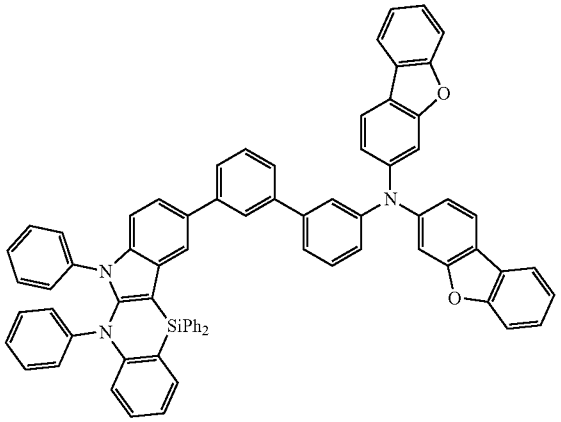
E39
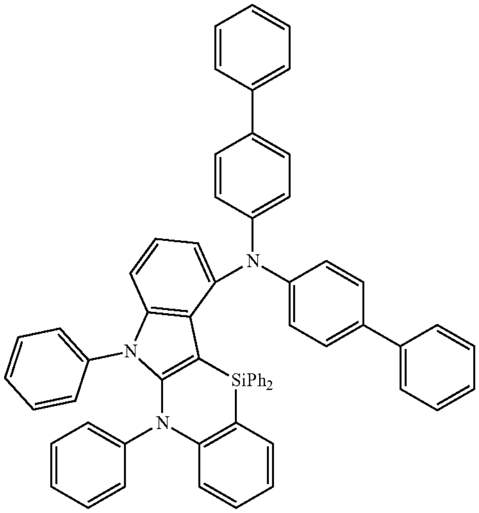
E40
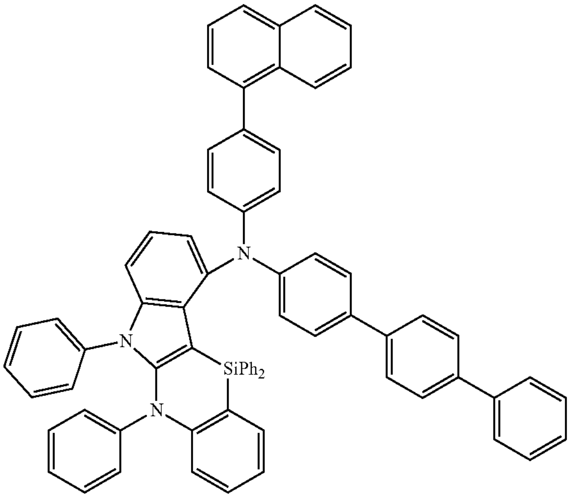
-continued
E41
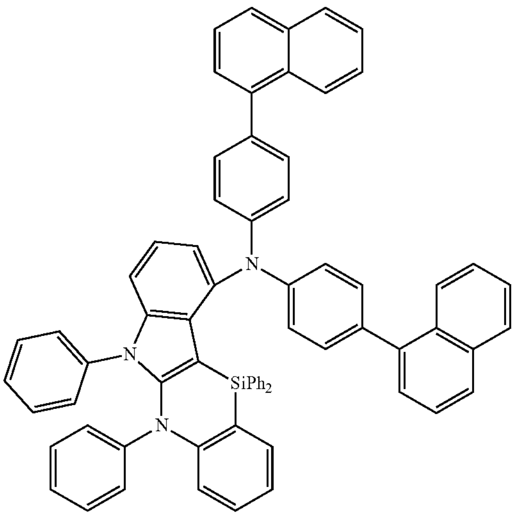
E42
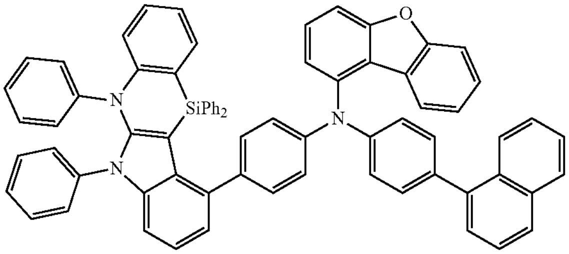
E43
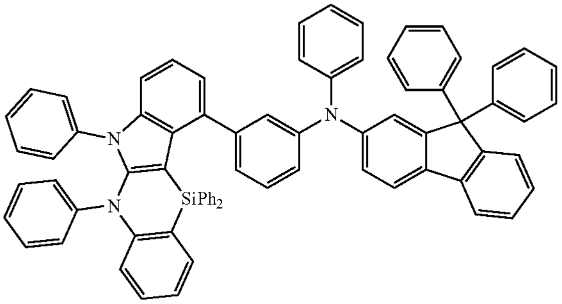
E44
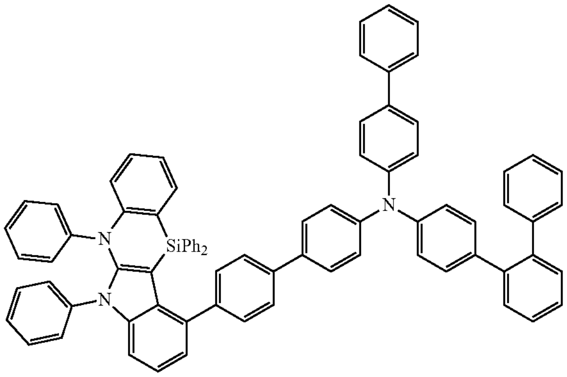

-continued
E45
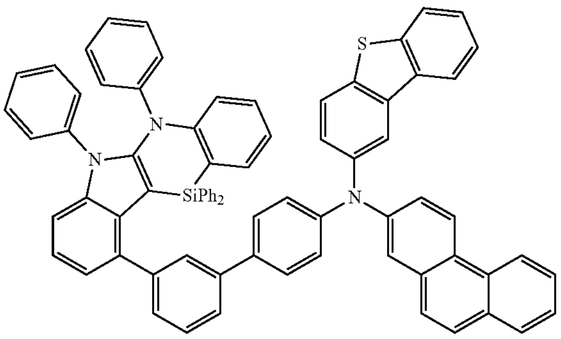
E46
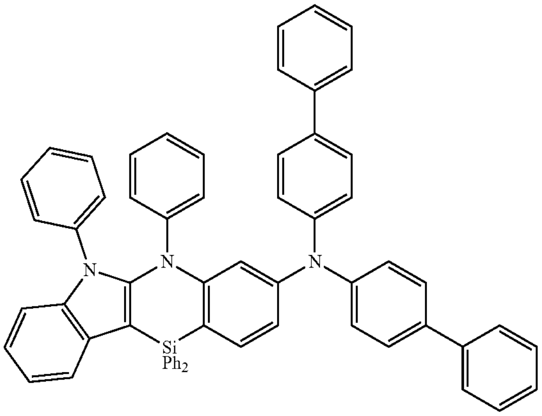
E47
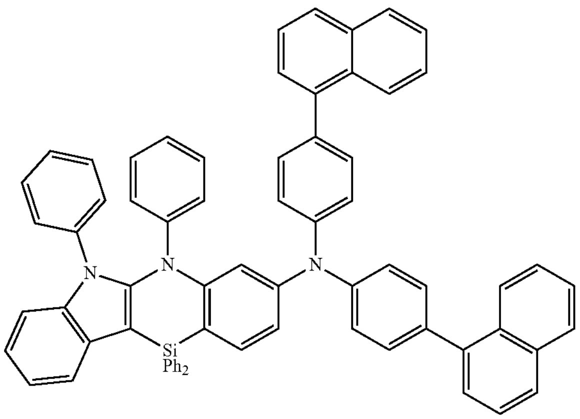
-continued
E48
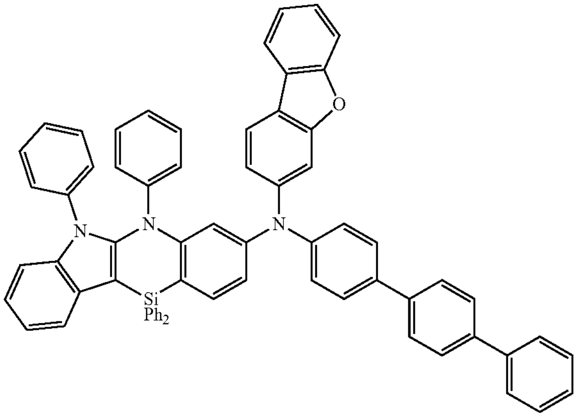
E49
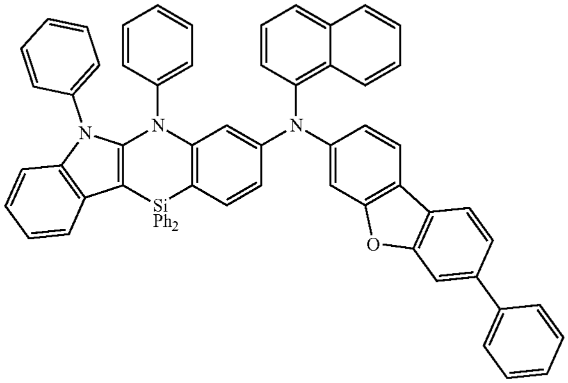
E50
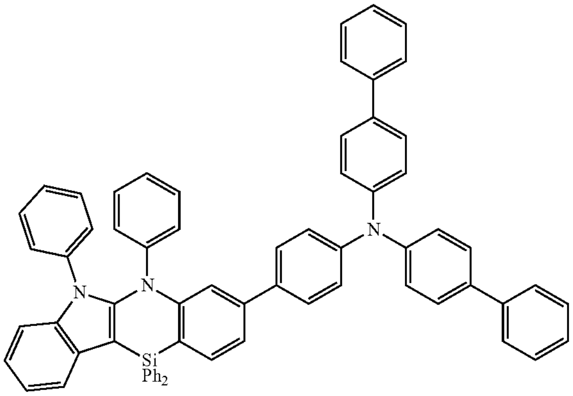

-continued
E51
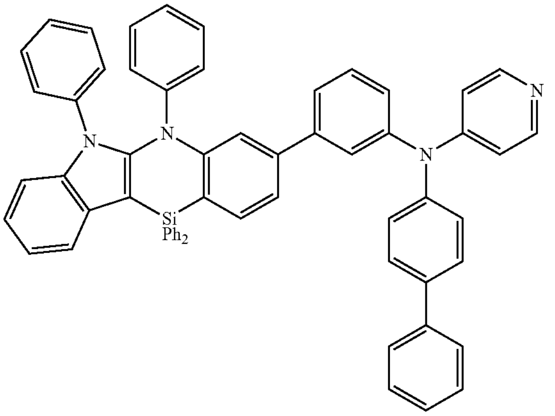
E52
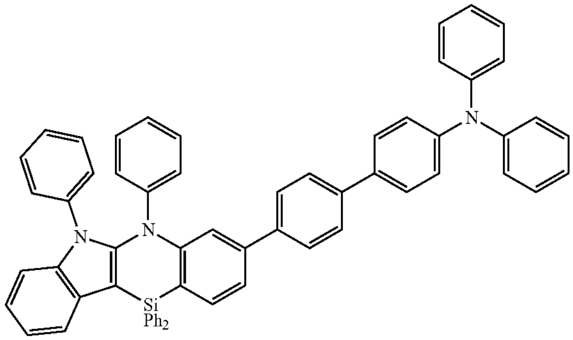
E53
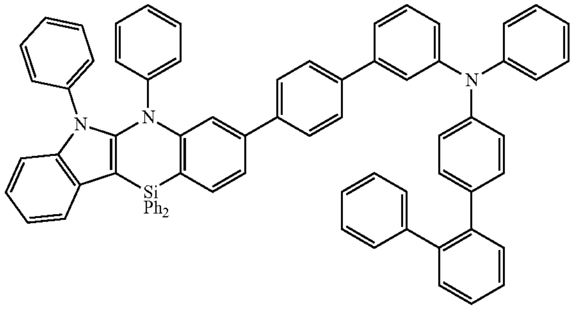
E54
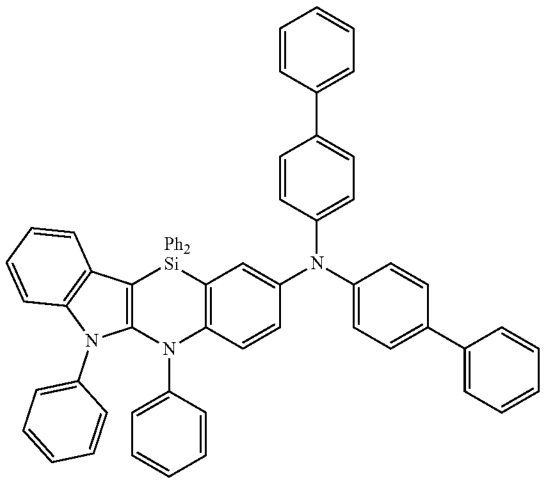
-continued
E55
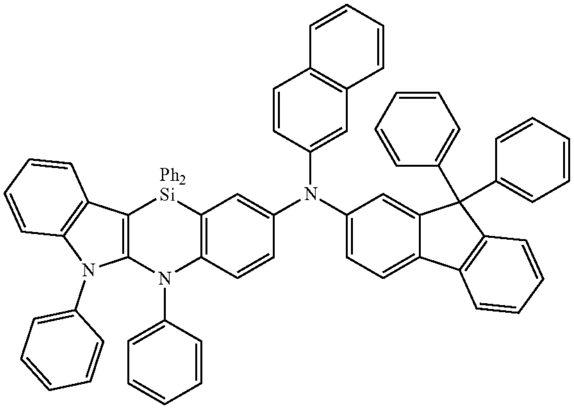
E56
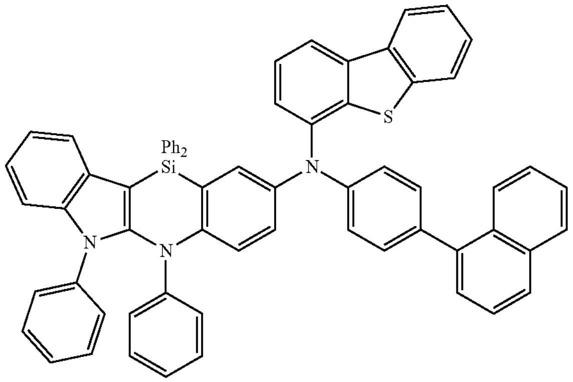
E57
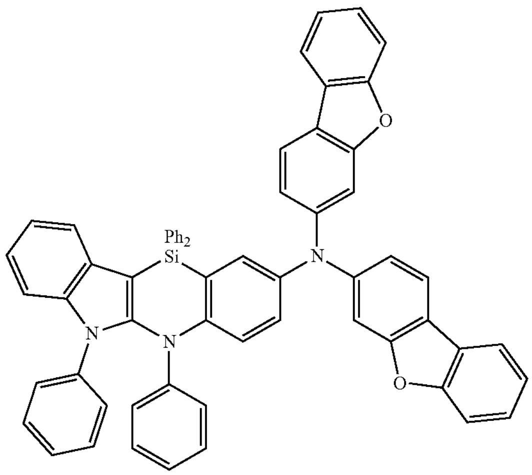

-continued
E58
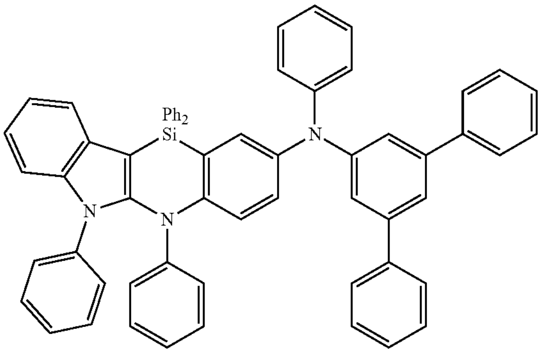
E59
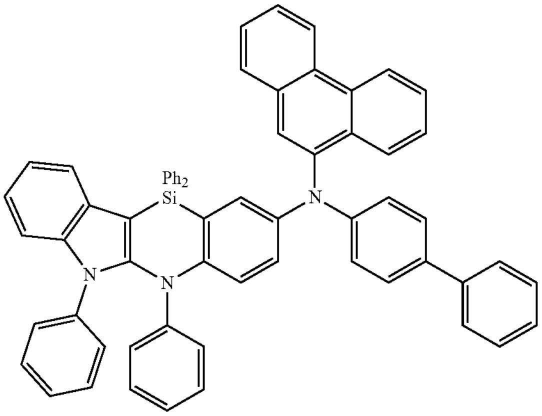
E60
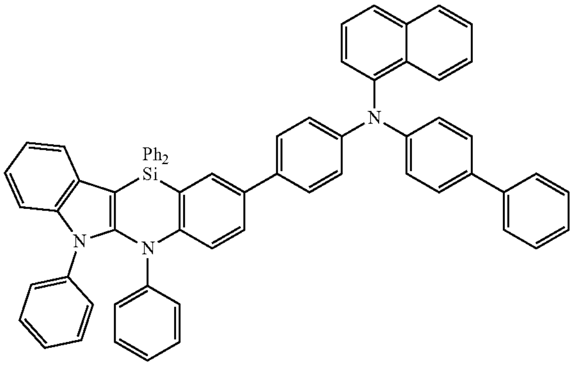
-continued
E61
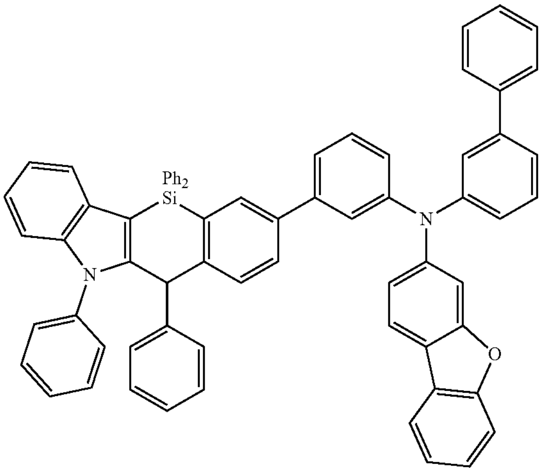
E62
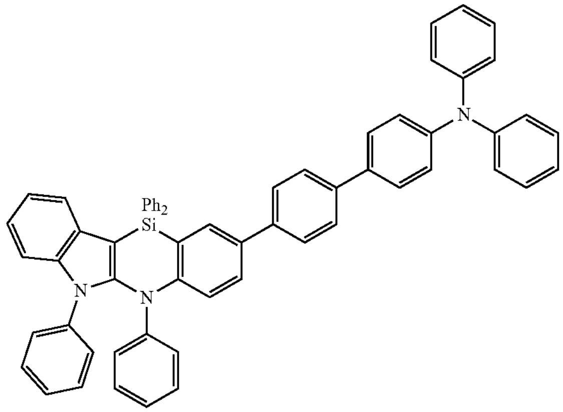
E63
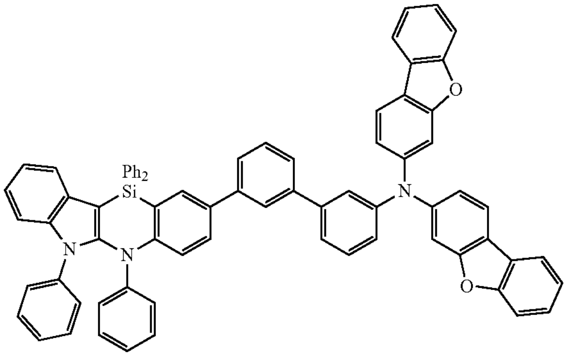

-continued
E64
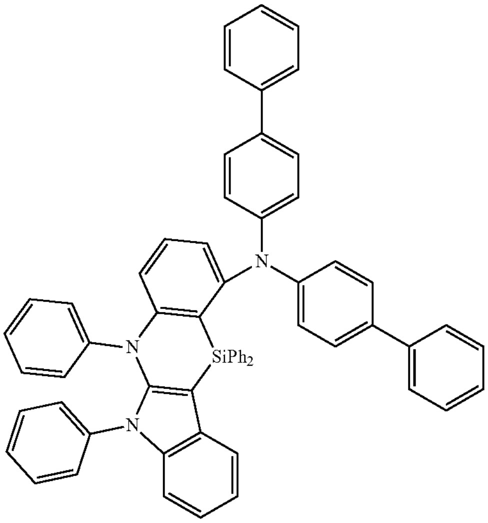
E65
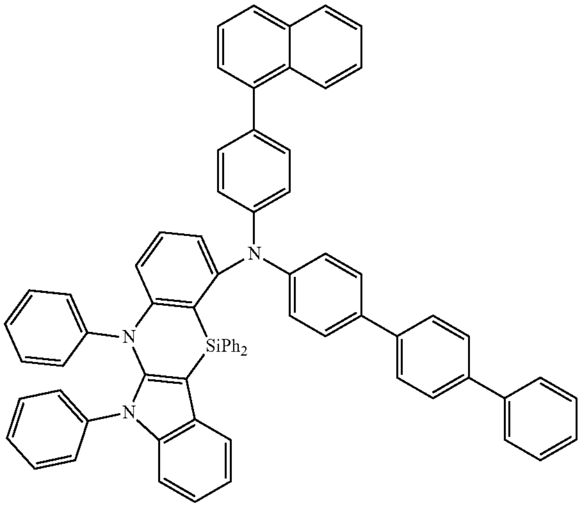
E66
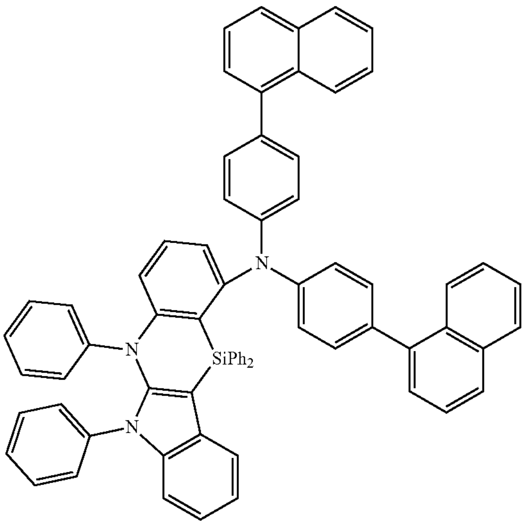
-continued
E67
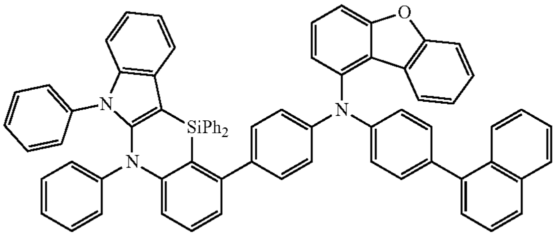
E68
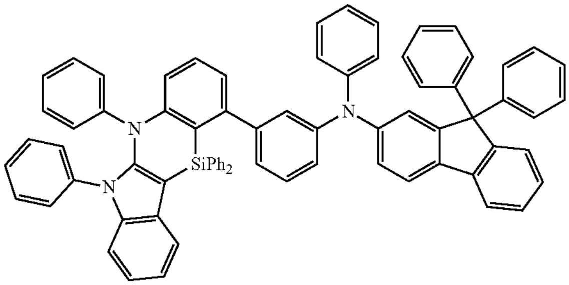
E69
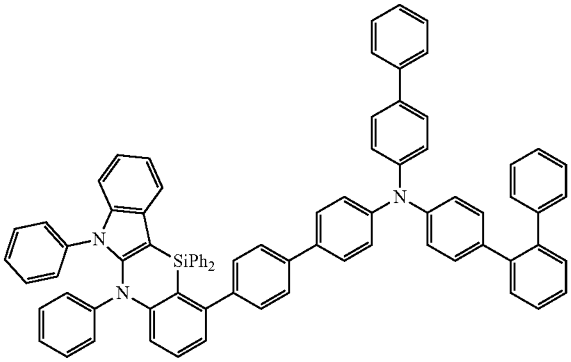
E70
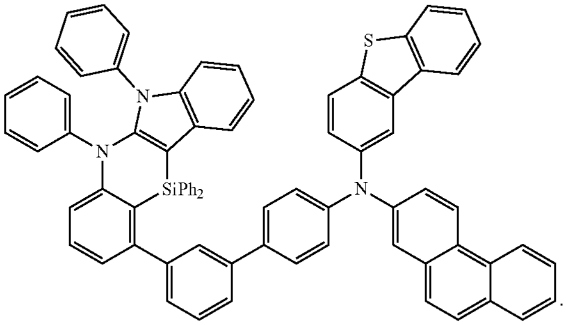
14. A condensed cyclic compound represented by the following Formula 1:
[Formula 1]
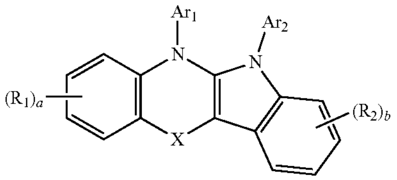

wherein in Formula 1,

X is O, S, $NR_5$, or $SiR_6R_7$, $Ar_1$ is independently a substituted or unsubstituted aryl group having 6 to 40 carbon atoms for forming a ring, or represented by Formula 2, $Ar_2$ is a substituted or unsubstituted aryl group having 6 to 40 carbon atoms for forming a ring, each of $R_1$ and $R_2$ is independently represented by Formula 2, a substituted or unsubstituted aryl group having 6 to 40 carbon atoms for forming a ring, or a substituted or unsubstituted alkyl group having 1 to 20 carbon atoms, each of a and b is independently an integer of 0 to 4, each of $R_5$, $R_6$, and $R_7$ is independently a substituted or unsubstituted alkyl group having 1 to 20 carbon atoms, a substituted or unsubstituted aryl group having 6 to 40 carbon atoms for forming a ring, or a substituted or unsubstituted heteroaryl group having 2 to 40 carbon atoms for forming a ring, the substituted alkyl group having 1 to 20 carbon atoms, the substituted aryl group having 6 to 40 carbon atoms for forming a ring, and the substituted heteroaryl group having 2 to 40 carbon atoms for forming a ring are substituted with a hydrogen atom, a deuterium atom, a halogen atom, a cyano group, a substituted or unsubstituted alkyl group having 1 to 40 carbon atoms, a substituted or unsubstituted aryl group having 6 to 40 carbon atoms for forming a ring, or a substituted or unsubstituted heteroaryl group having 2 to 40 carbon atoms for forming a ring, and only one of $R_1$, $R_2$, or $Ar_1$ is represented by following Formula 2:

[Formula 2]

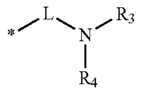

wherein in Formula 2,

L is a direct linkage, or a substituted or unsubstituted arylene group having 6 to 40 carbon atoms for forming a ring, and each of $R_3$ and $R_4$ is independently a substituted or unsubstituted aryl group having 6 to 40 carbon atoms for forming a ring, or a substituted or unsubstituted heteroaryl group having 2 to 40 carbon atoms for forming a ring, and the substituted aryl group having 6 to 40 carbon atoms for forming a ring, and the substituted heteroaryl group having 2 to 40 carbon atoms for forming a ring are substituted with a hydrogen atom, a deuterium atom, a halogen atom, a cyano group, a substituted or unsubstituted cycloalkyl group having 3 to 40 carbon atoms for forming a ring, a substituted or unsubstituted aryl group having 6 to 40 carbon atoms for forming a ring, or a substituted or unsubstituted heteroaryl group having 2 to 40 carbon atoms for forming a ring.

15. The condensed cyclic compound of claim 14, wherein Formula 1 is represented by any one of the following Formulae 1-2 to 1-5:

[Formula 1-2]

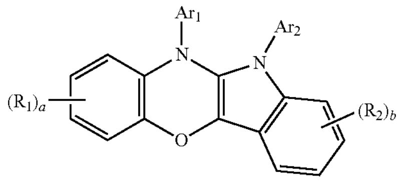

[Formula 1-3]

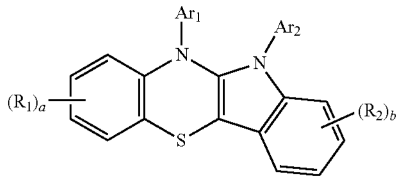

[Formula 1-4]

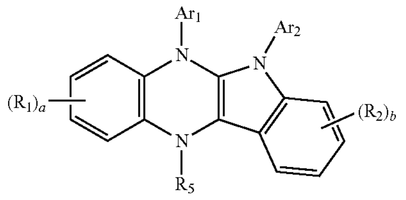

[Formula 1-5]

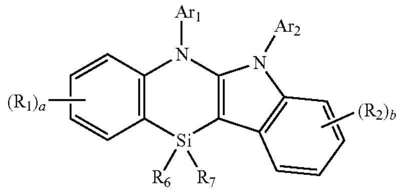

wherein in Formula 1-1 to 1-5, $Ar_1$, $Ar_2$, $R_1$, $R_2$, $R_5$ to $R_7$, a, and b are the same as defined in Formula 1.

16. The condensed cyclic compound of claim 14, wherein Formula 1 is represented by any one of the following Formulae 3-1 to 3-3:

[Formula 3-1]

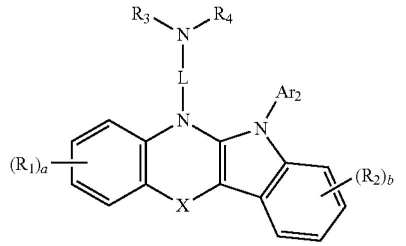

[Formula 3-2]

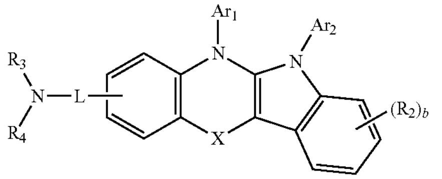

-continued

[Formula 3-3]

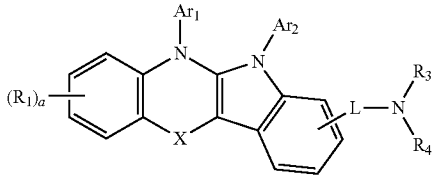

wherein in Formulae 3-2 and 3-1 to 3-3,

X, $Ar_1$, $Ar_2$, $R_1$ to $R_4$, L, a, and b are the same as defined in Formulae 1 and 2.

17. The condensed cyclic compound of claim 14, wherein the compound represented by Formula 1 is a hole transport material.

18. The condensed cyclic compound of claim 15, wherein Formula 1-2 is represented by any one of the following Formulae 5-1 to 5-3:

[Formula 5-1]

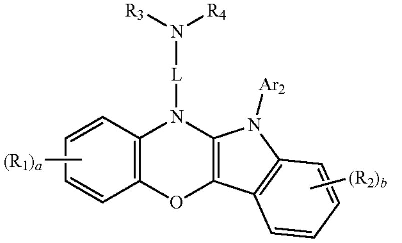

[Formula 5-2]

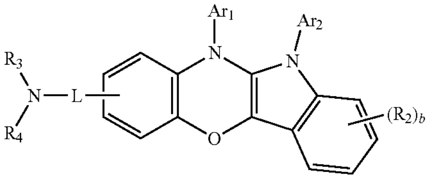

[Formula 5-3]

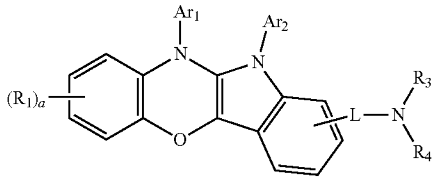

wherein in Formula 5-1 to 5-3, $Ar_1$, $Ar_2$, $R_1$ to $R_4$, L, a, and b are the same as defined in Formulae 1 and 2.

19. The condensed cyclic compound of claim 15, wherein Formula 1-3 is represented by any one of the following Formulae 6-1 to 6-3:

[Formula 6-1]

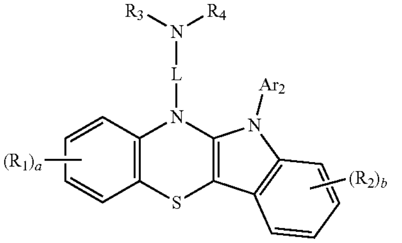

-continued

[Formula 6-2]

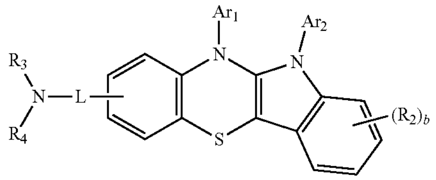

[Formula 6-3]

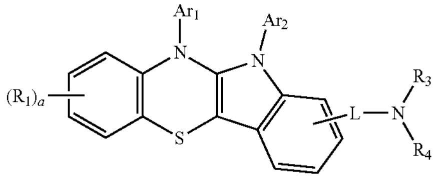

wherein in Formula 6-1 to 6-3, $Ar_1$, $Ar_2$, $R_1$ to $R_4$, L, a, and b are the same as defined in Formulae 1 and 2.

20. The condensed cyclic compound of claim 15, wherein Formula 1-4 is represented by any one of the following Formulae 7-1 to 7-3:

[Formula 7-1]

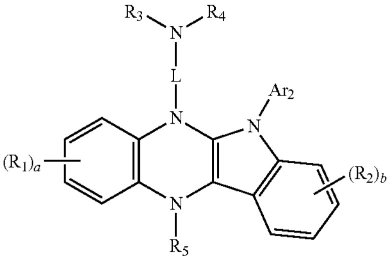

[Formula 7-2]

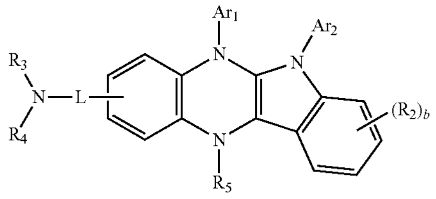

[Formula 7-3]

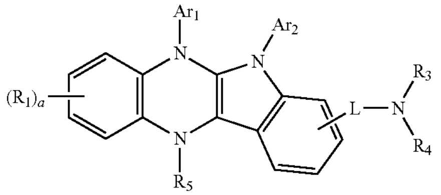

wherein in Formula 7-1 to 7-3, $Ar_1$, $Ar_2$, $R_1$ to $R_5$, L, a, and b are the same as defined in Formulae 1 and 2.

21. The condensed cyclic compound of claim 15, wherein Formula 1-5 is represented by any one of the following Formulae 8-1 to 8-3:

[Formula 8-1]
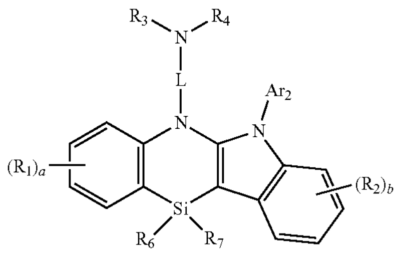
[Formula 8-2]
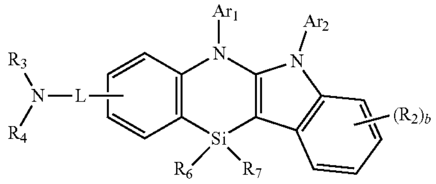
[Formula 8-3]
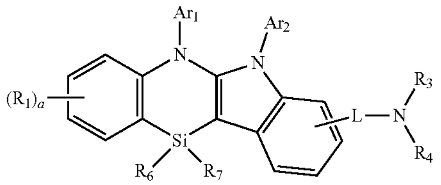
wherein in Formula 8-1 to 8-3,
$Ar_1$, $Ar_2$, $R_1$ to $R_4$, $R_6$, $R_7$, L, a, and b are the same as defined in Formulae 1 and 2.
22. The condensed cyclic compound of claim 14, wherein the compound represented by Formula 1 is any one selected from the group consisting of compounds represented in the following Compound Groups 2 to 5:
[Compound Group 2]
B1
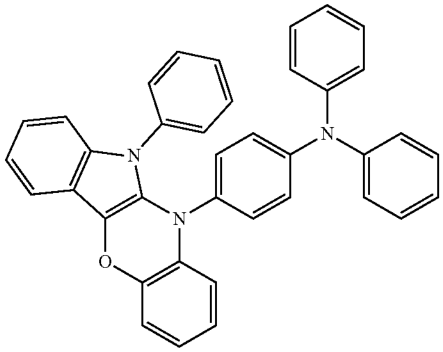
-continued
B2
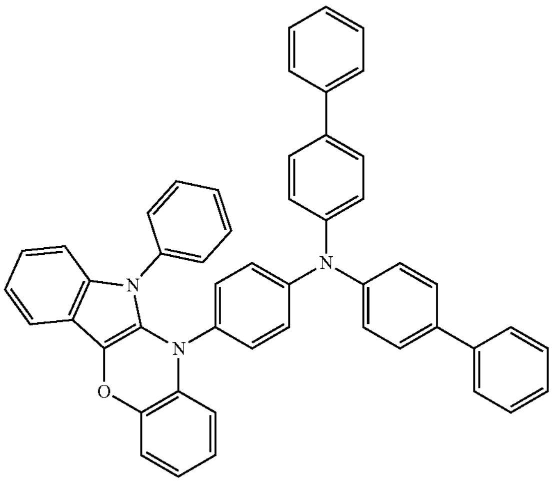
B3
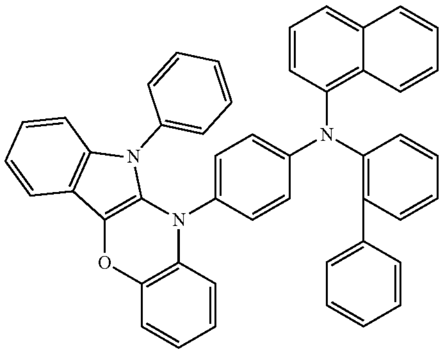
B4
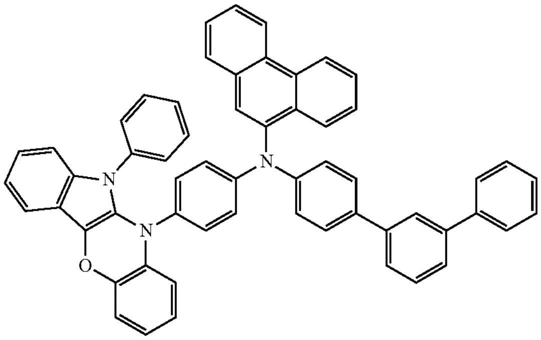

-continued
B5
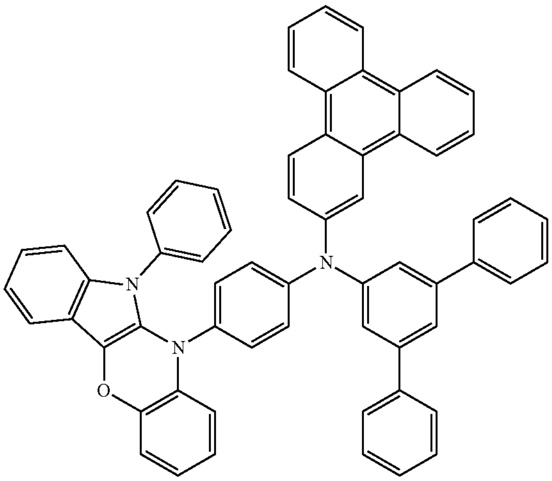
B6
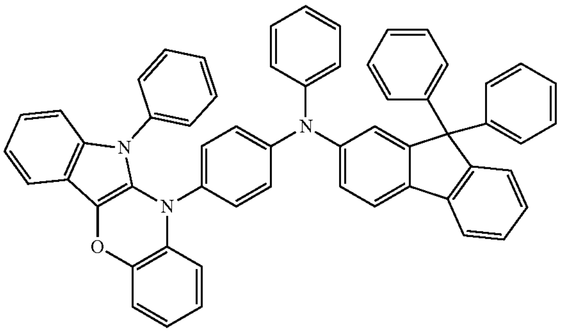
B7
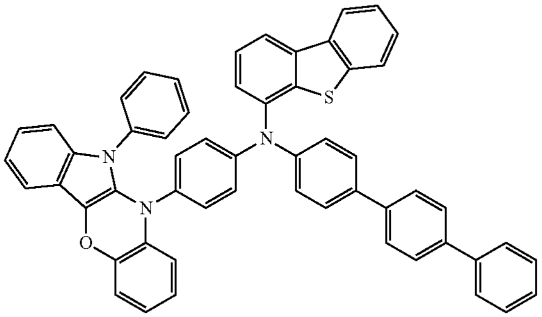
-continued
B8
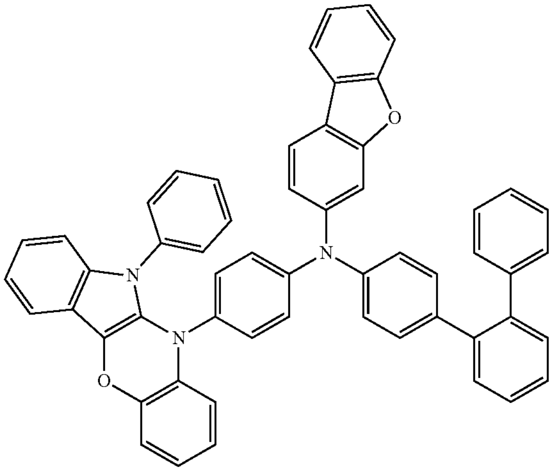
B9
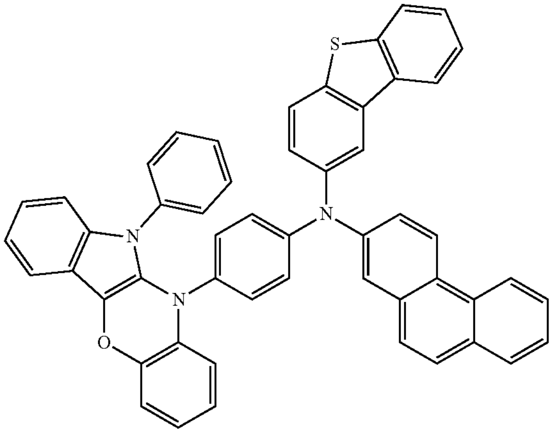
B10
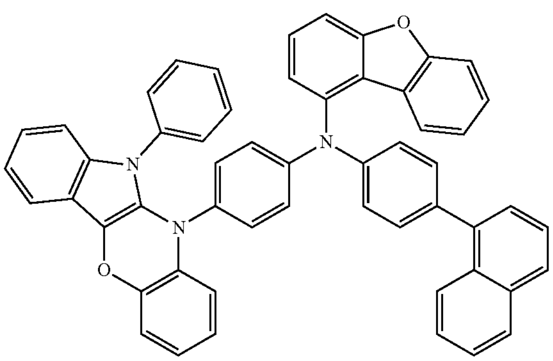

-continued
B11
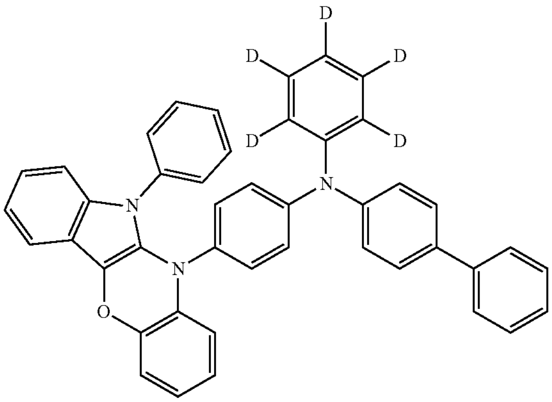
B12
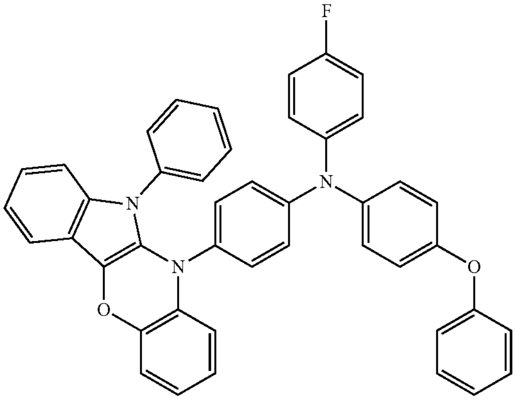
B13
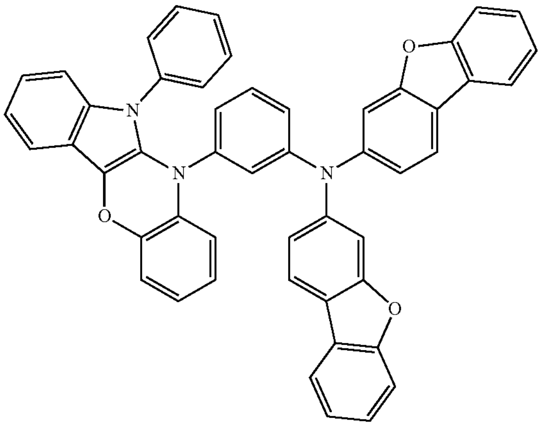
-continued
B14
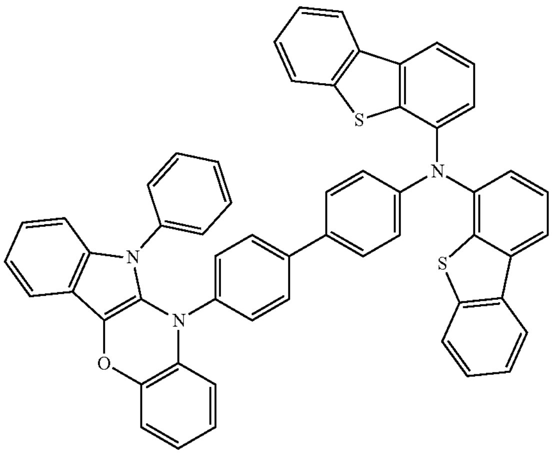
B15
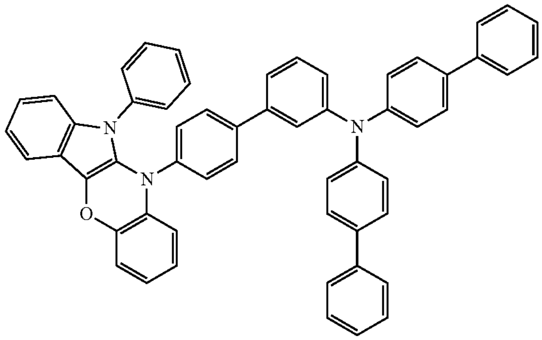
B16
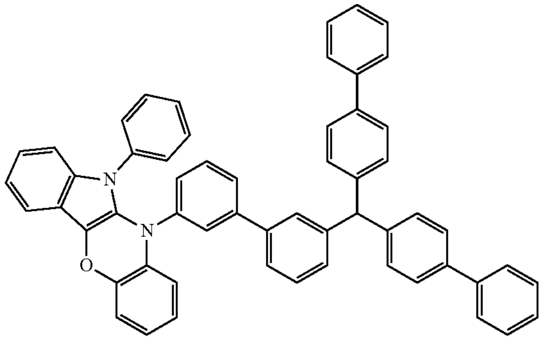
B17
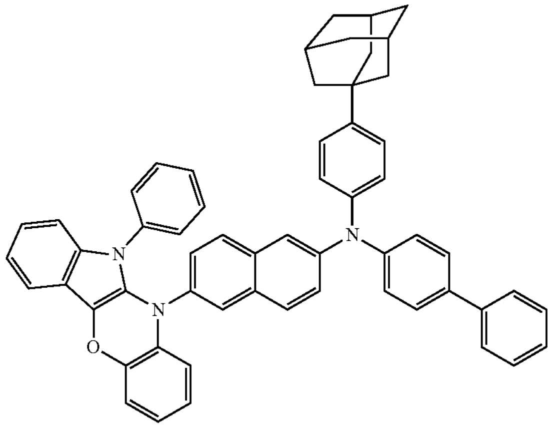

-continued
B18
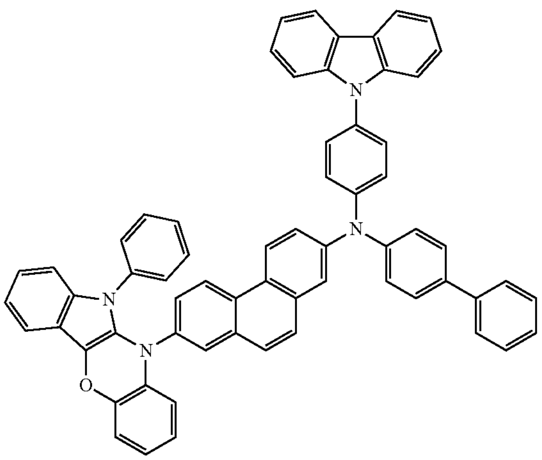
B19
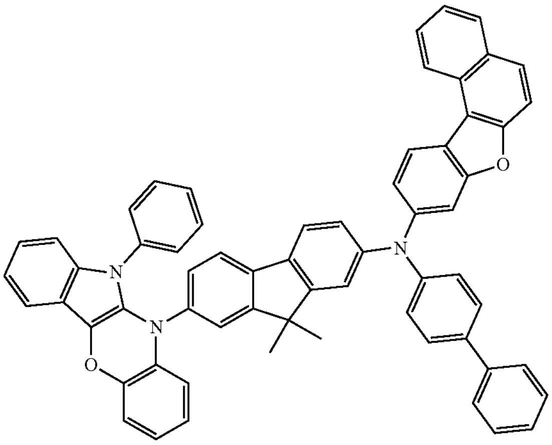
B20
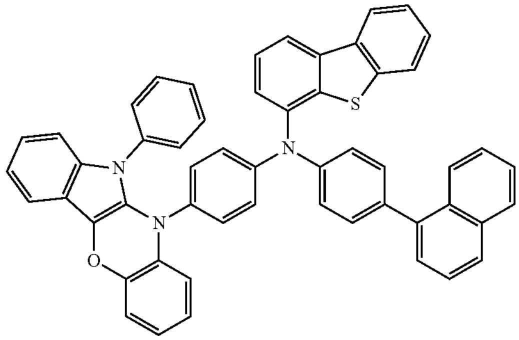
-continued
B21
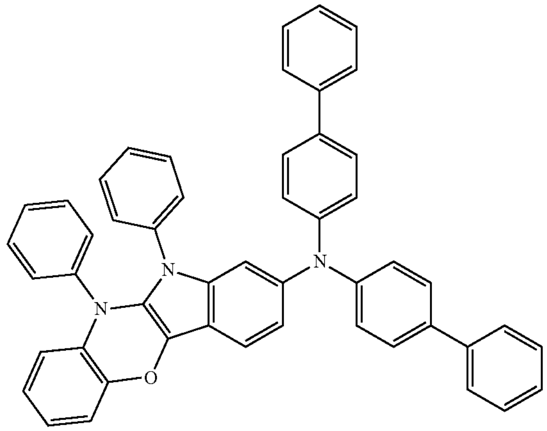
B22
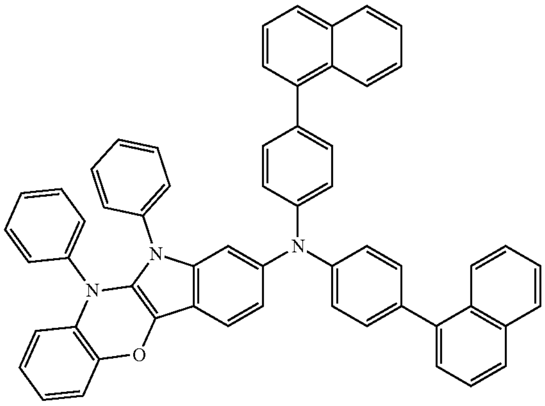
B23
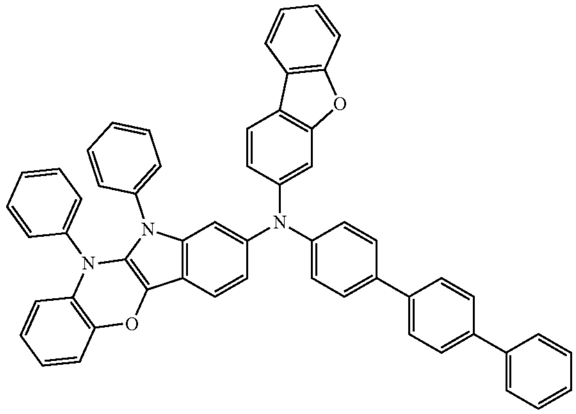

-continued
B24
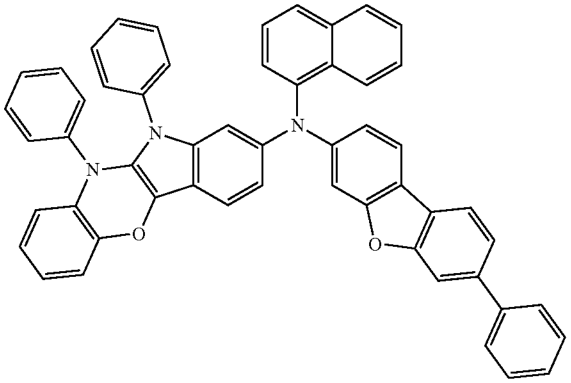
B25
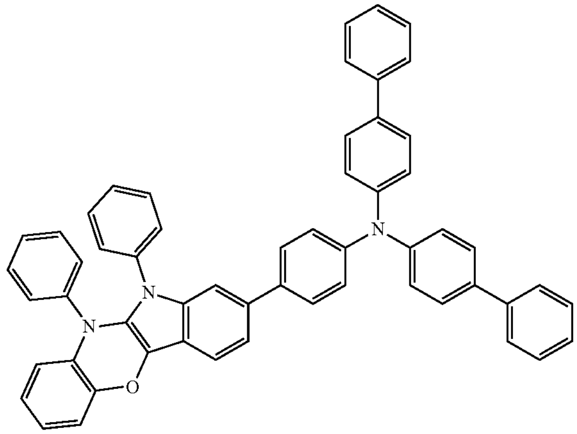
B26
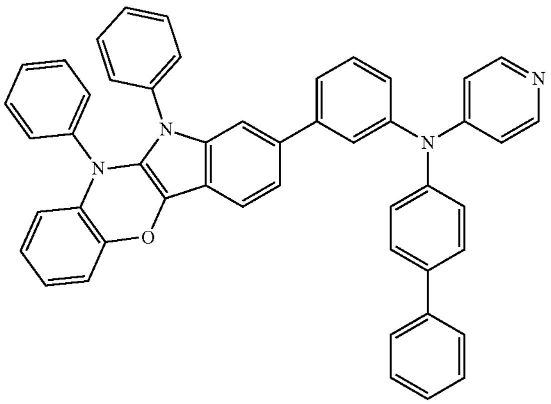
-continued
B27
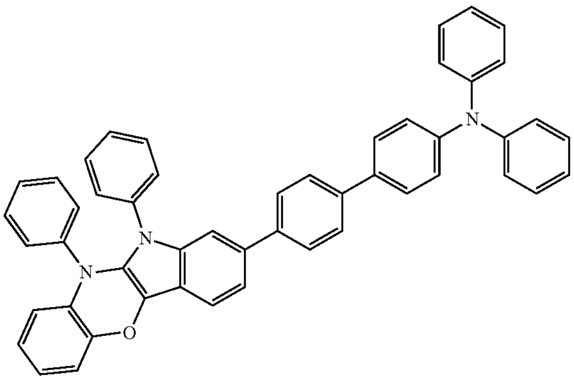
B28
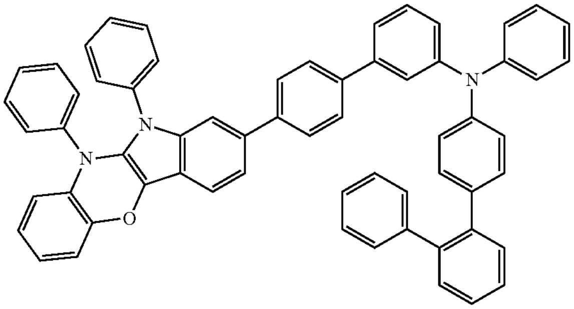
B29
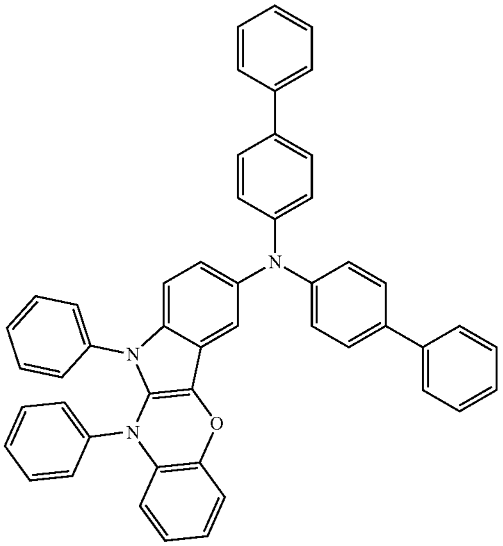

-continued
B30
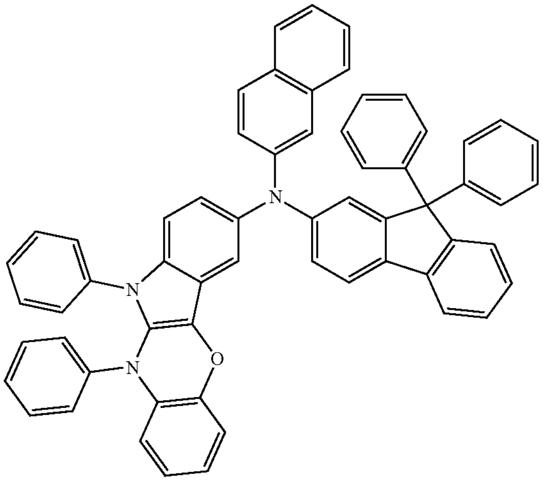
B31
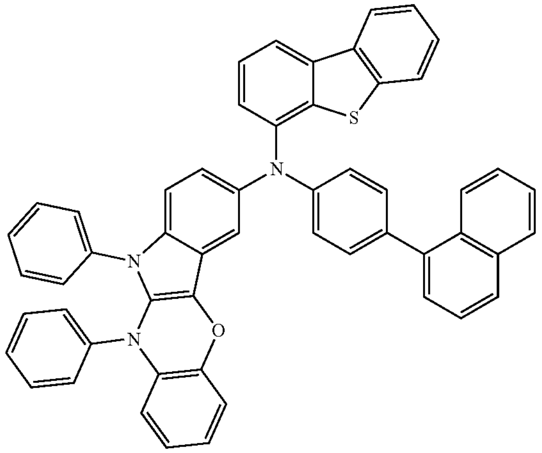
B32
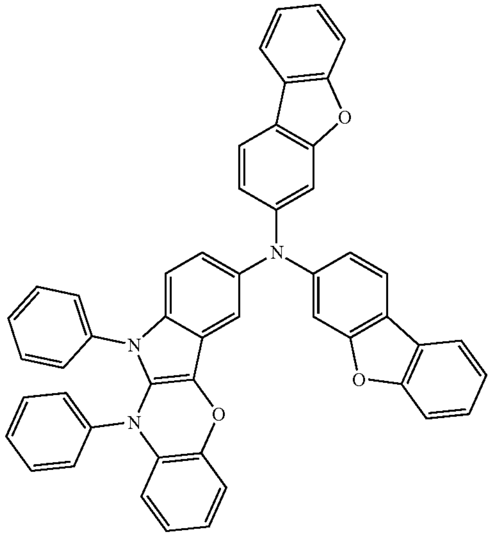
-continued
B33
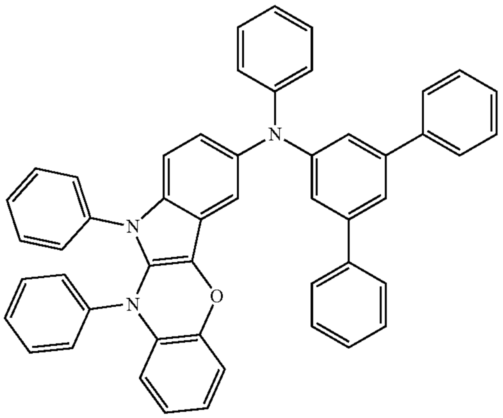
B34
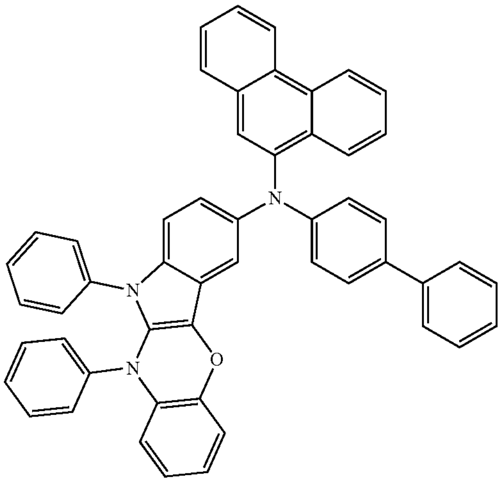
B35
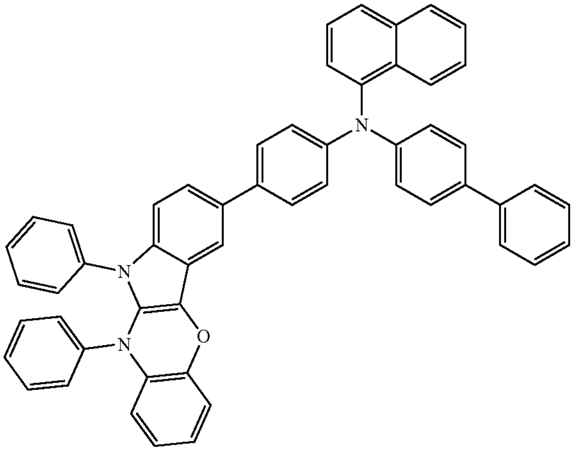

-continued
B36
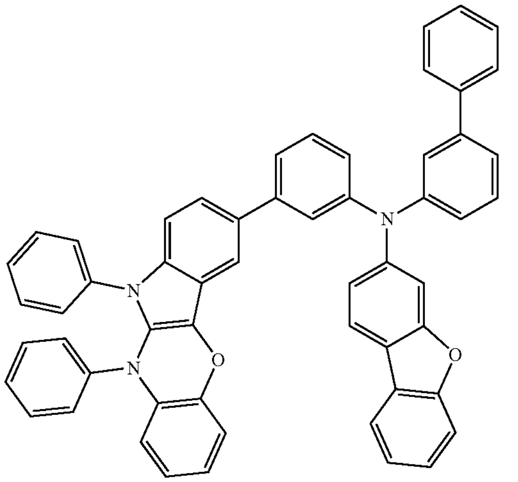
B37
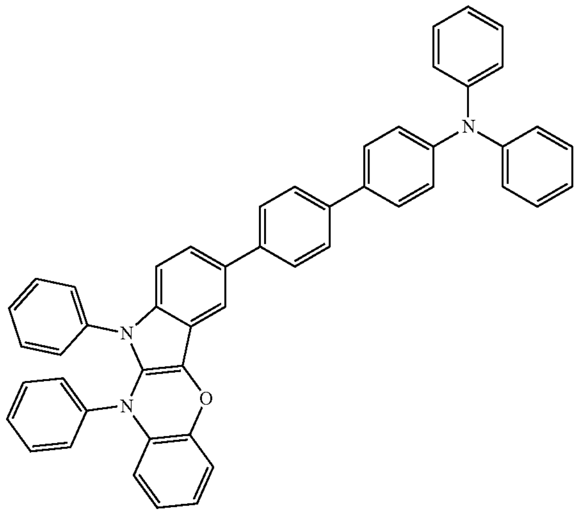
B38
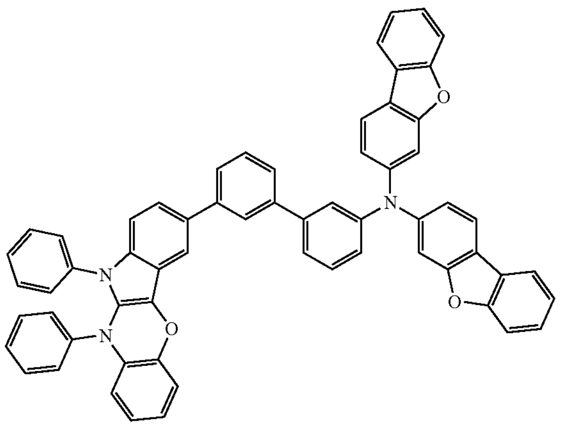
-continued
B39
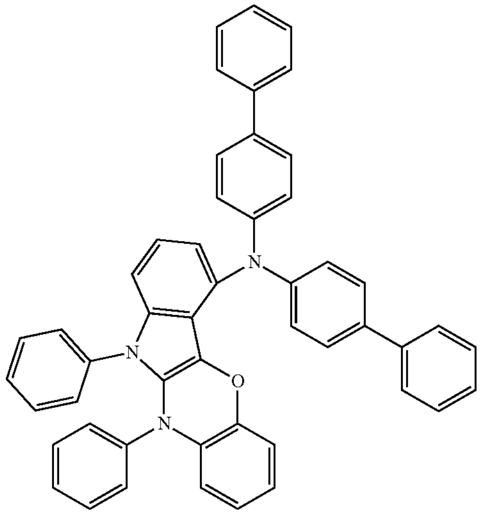
B40
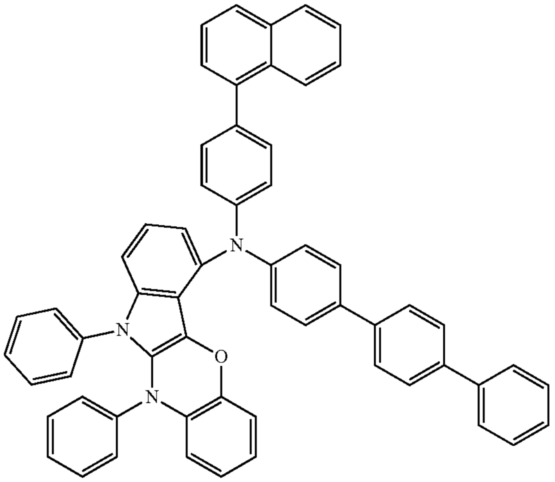
B41
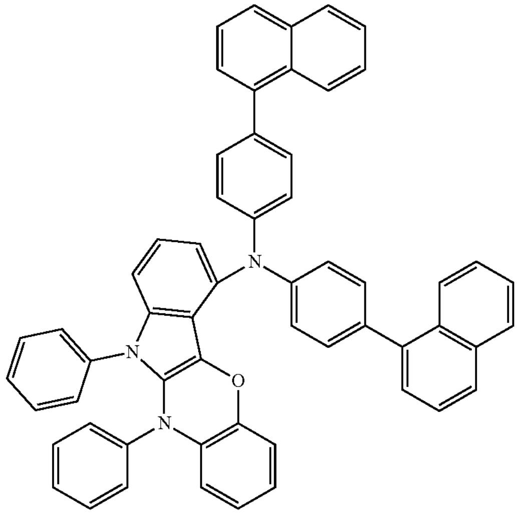

-continued
B42
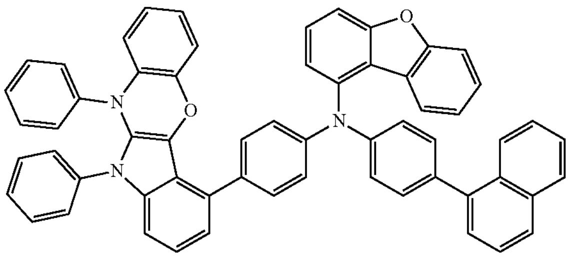
B43
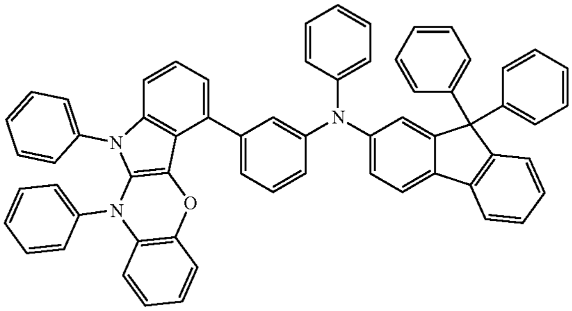
B44
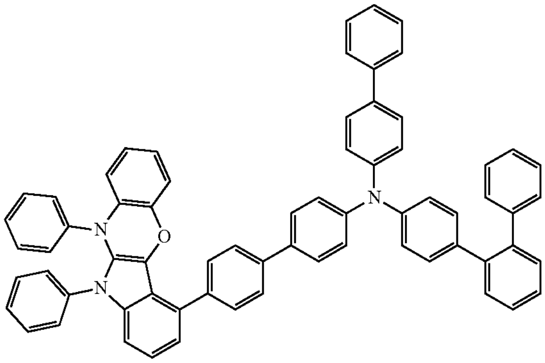
B45
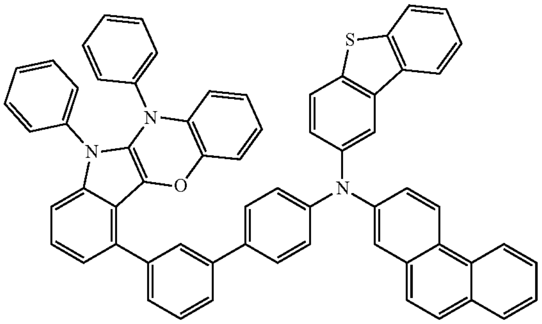
-continued
B46
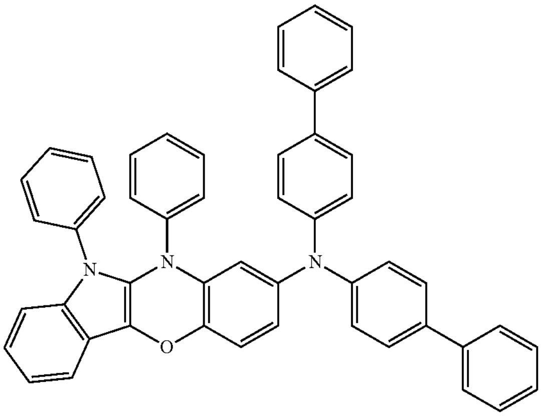
B47
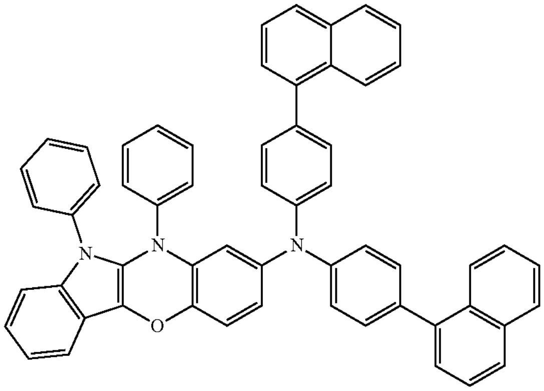
B48
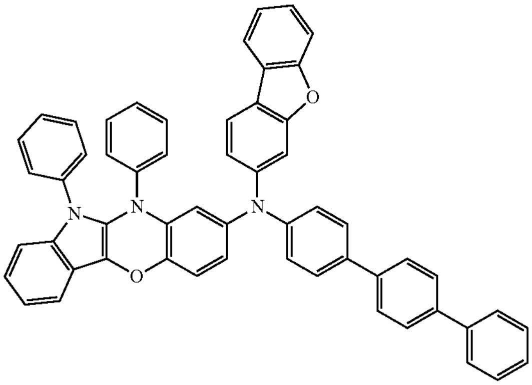

B49
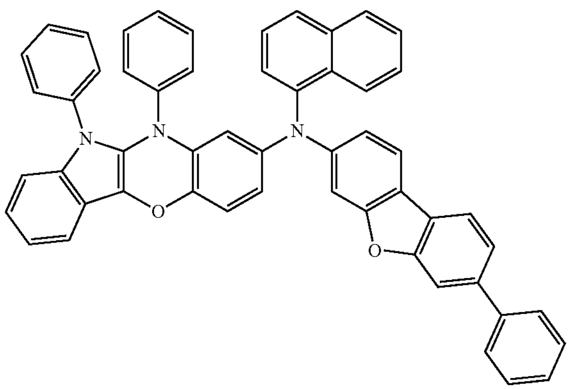
B50
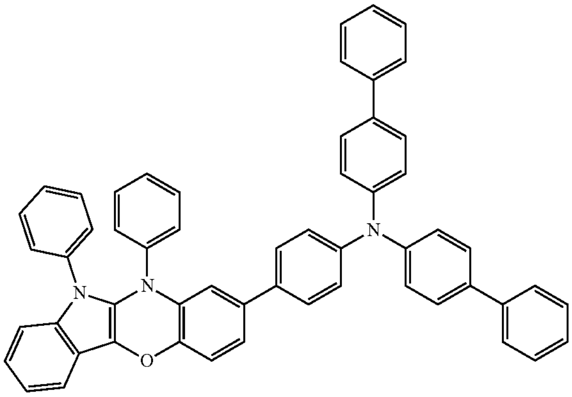
B51
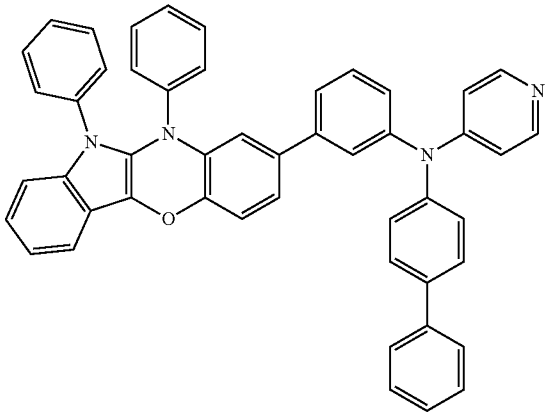
B52
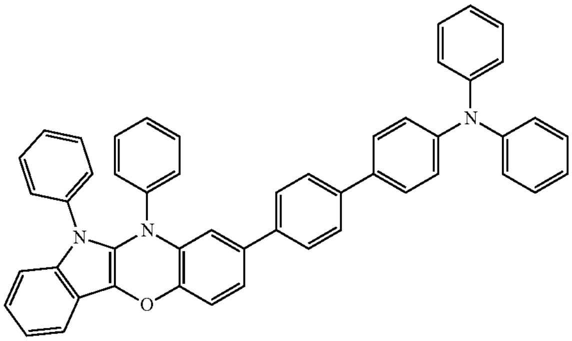
B53
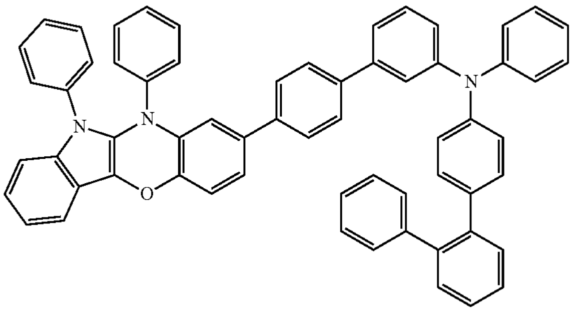
B54
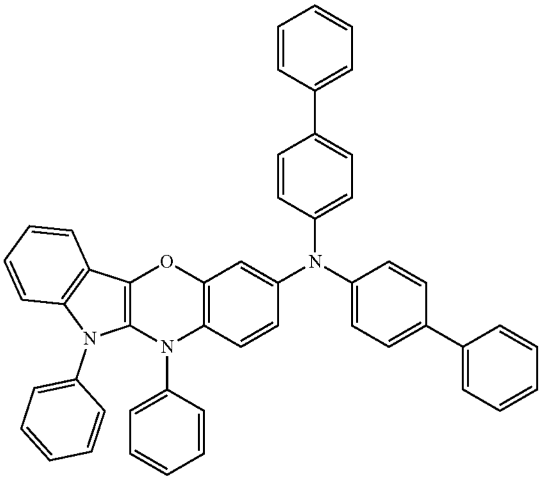
B55
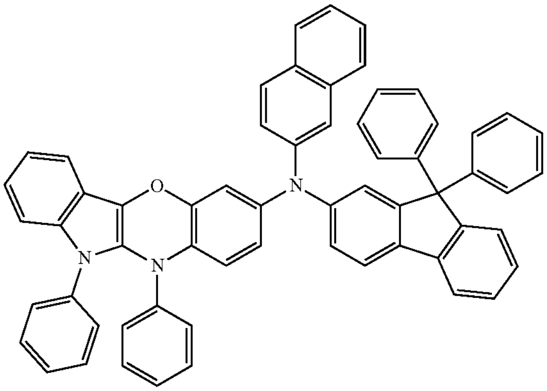
B56
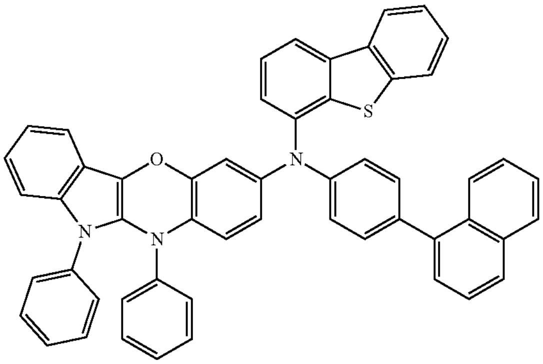

-continued
B57
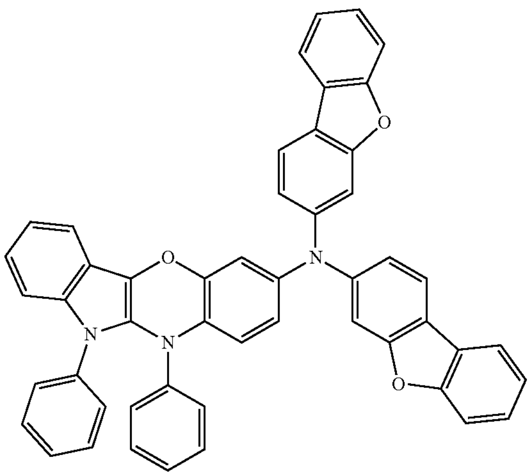
B58
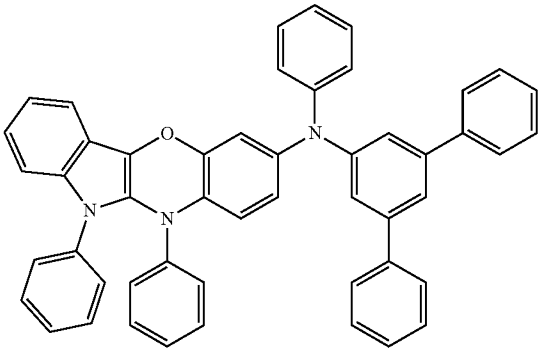
B59
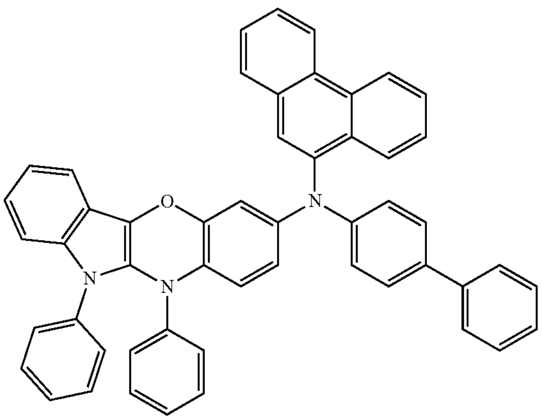
-continued
B60
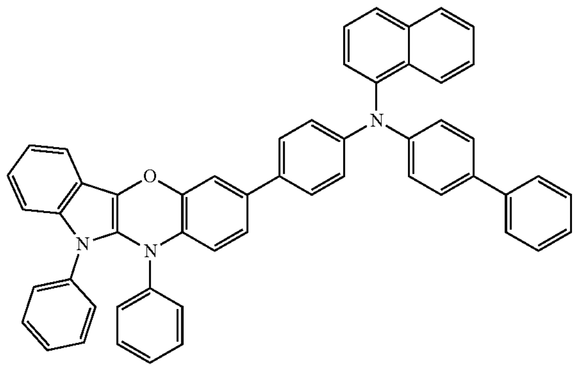
B61
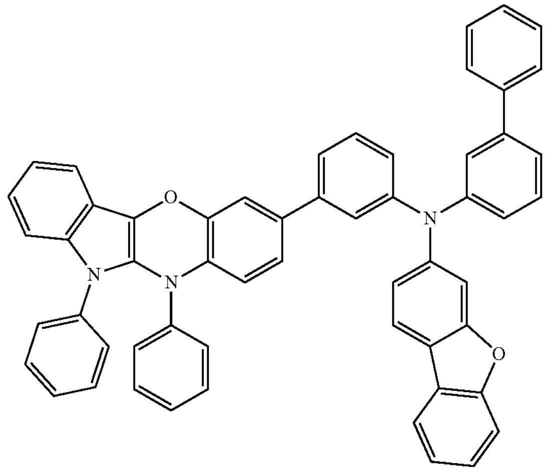
B62
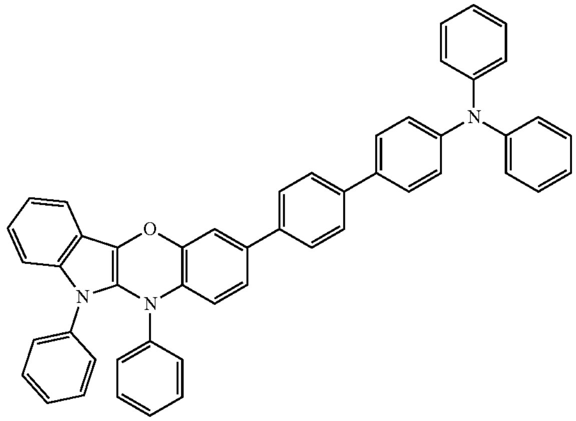

-continued
B63
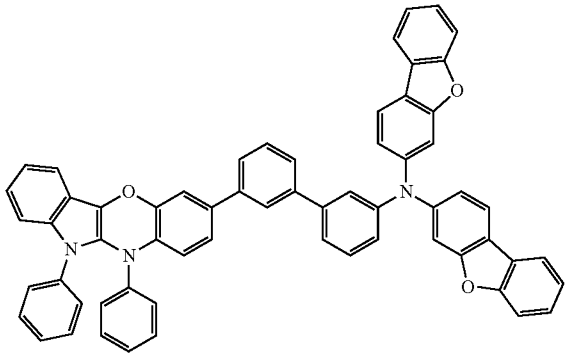
B64
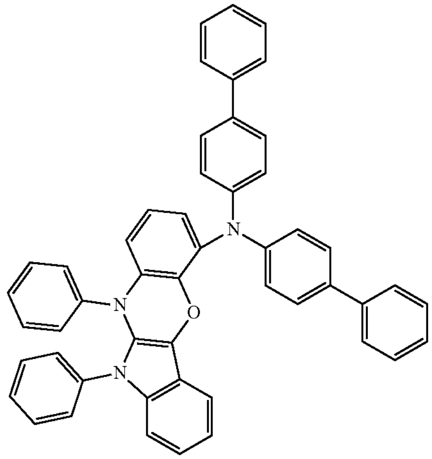
B65
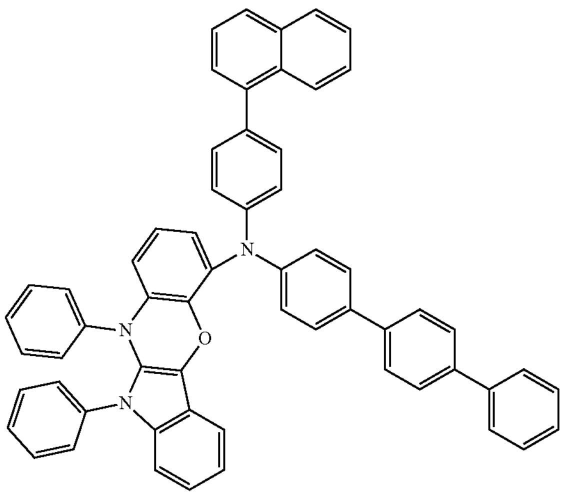
-continued
B66
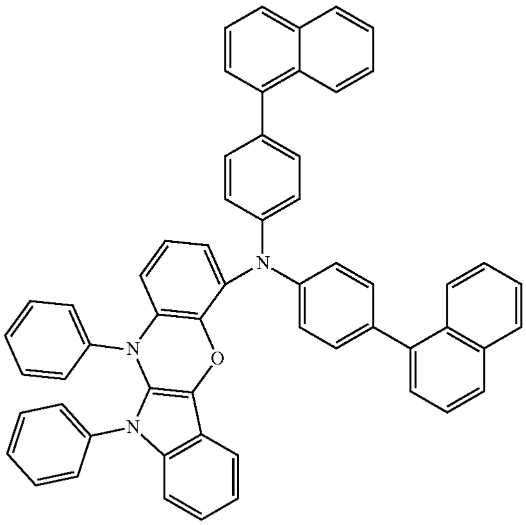
B67
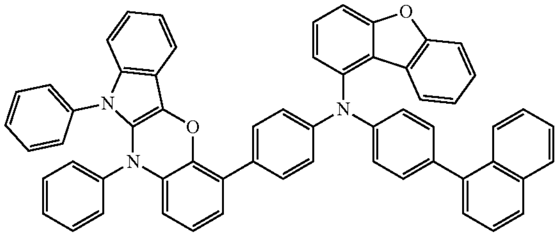
B68
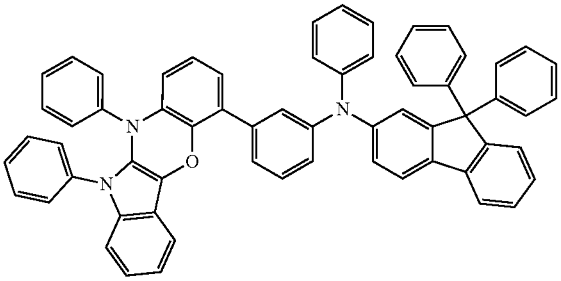
B69
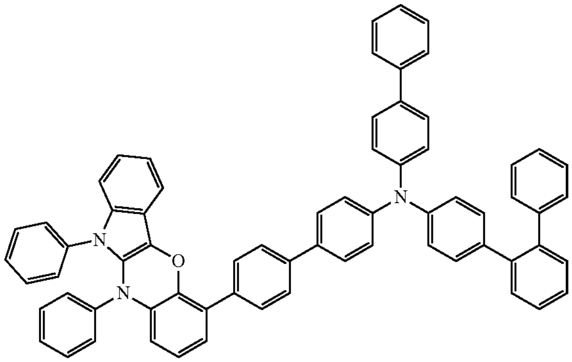

-continued
B70
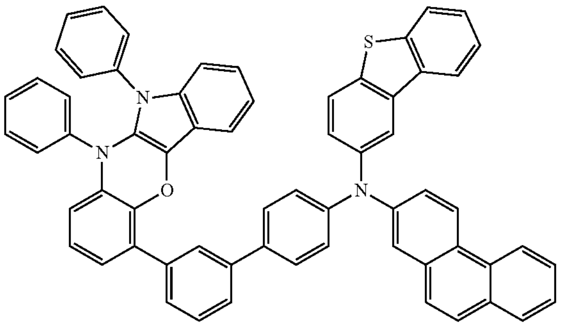
[Compound Group 3]
C1
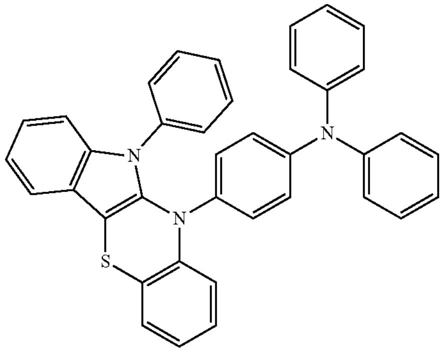
C2
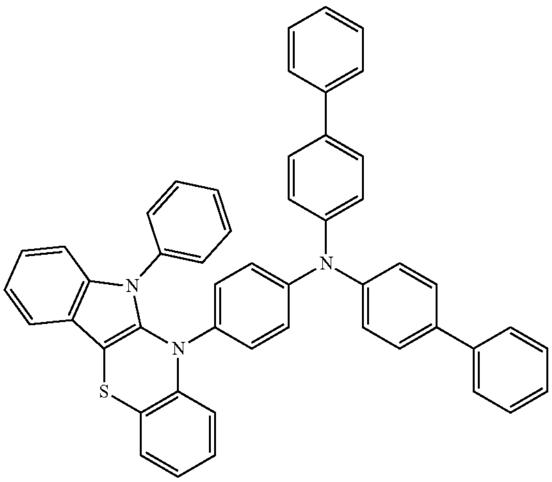
-continued
C3
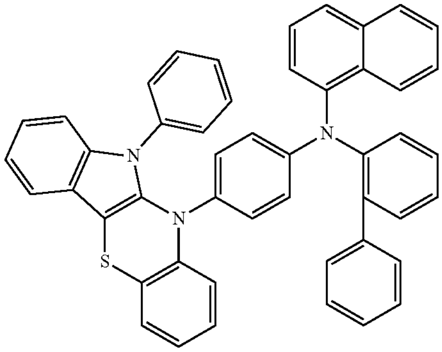
C4
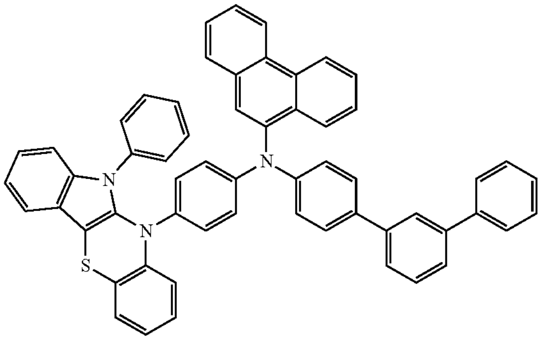
C5
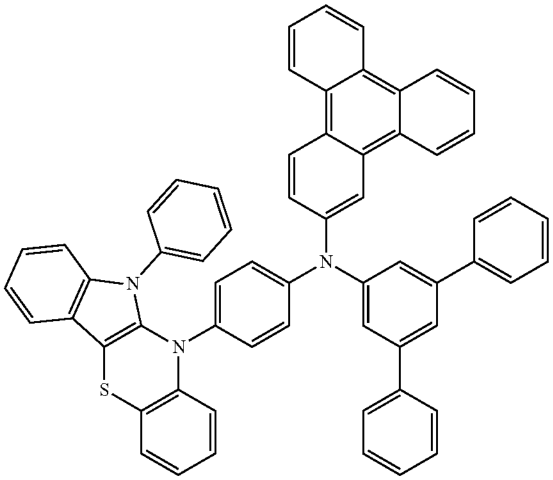
C6
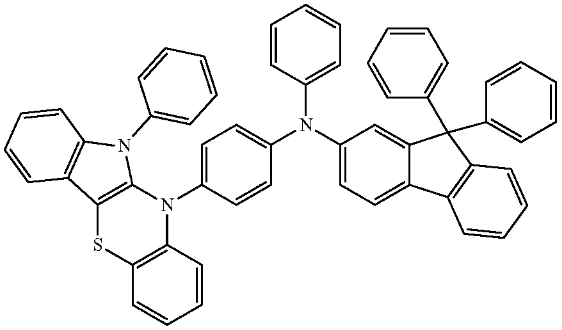

-continued
C7
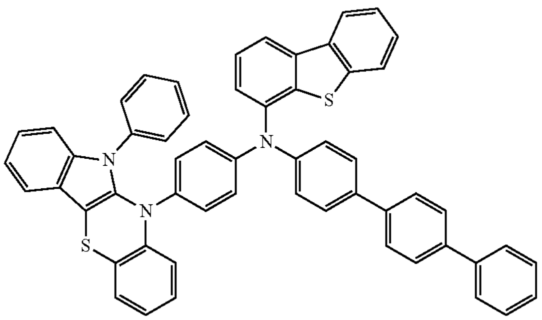
C8
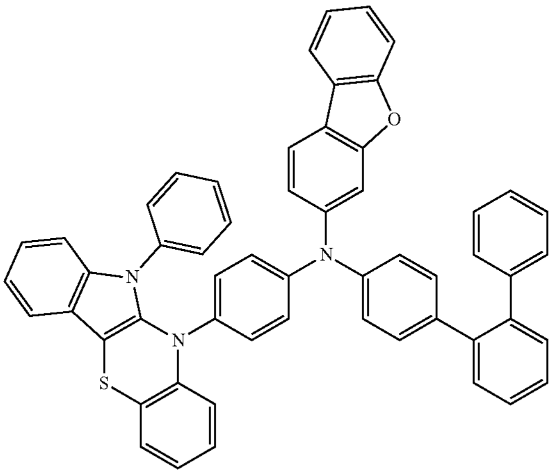
C9
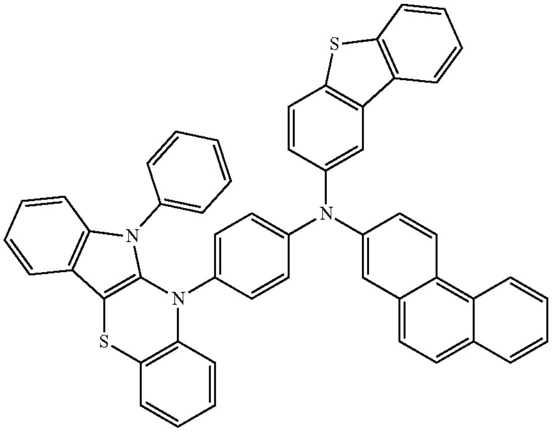
-continued
C10
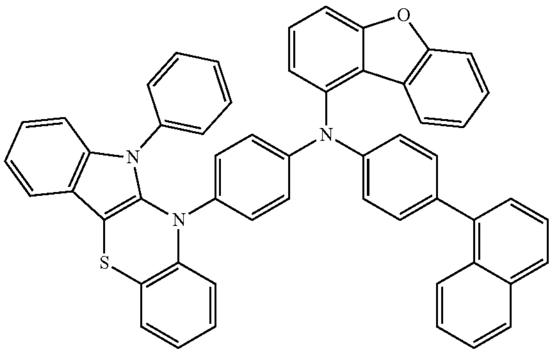
C11
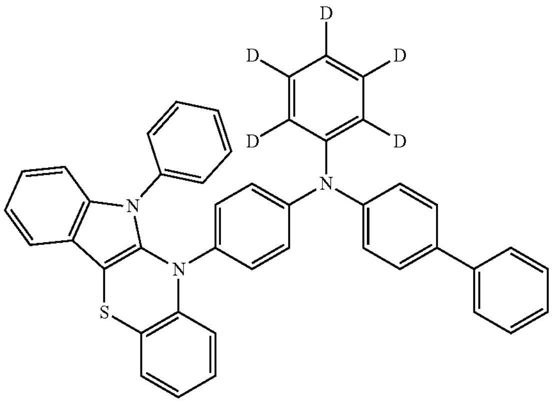
C12
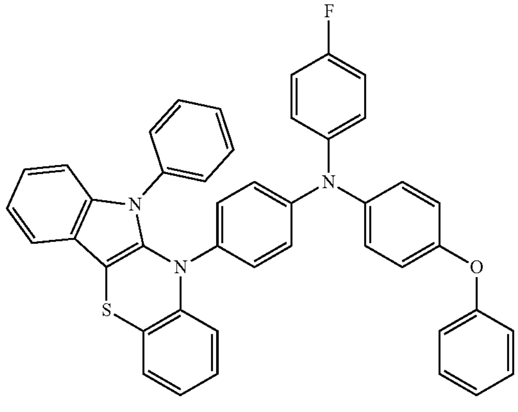

-continued
C13
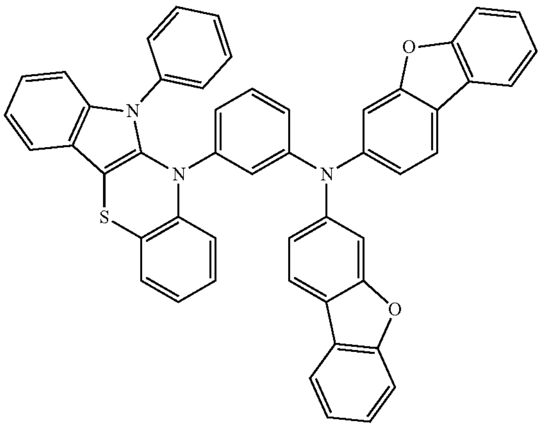
C14
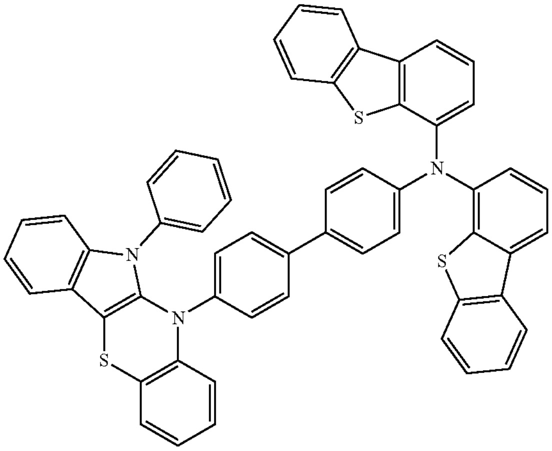
C15
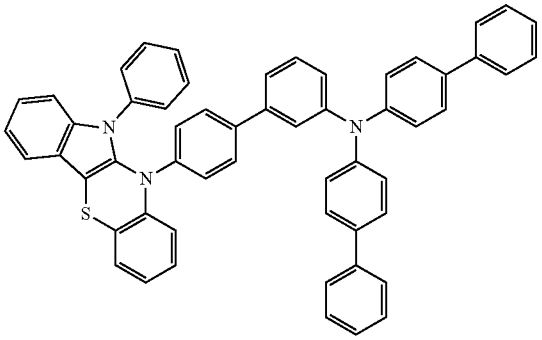
C16
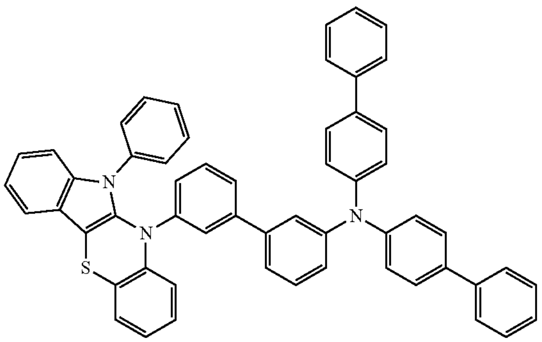
-continued
C17
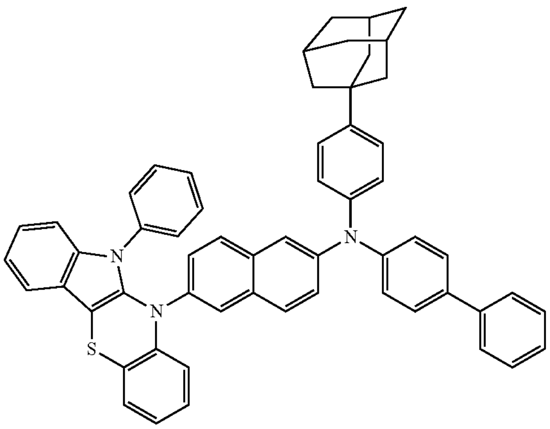
C18
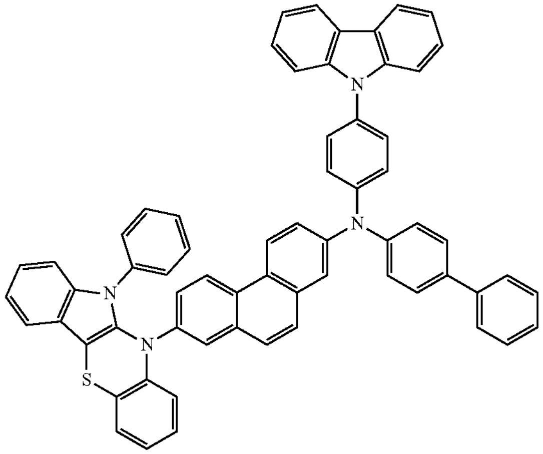
C19
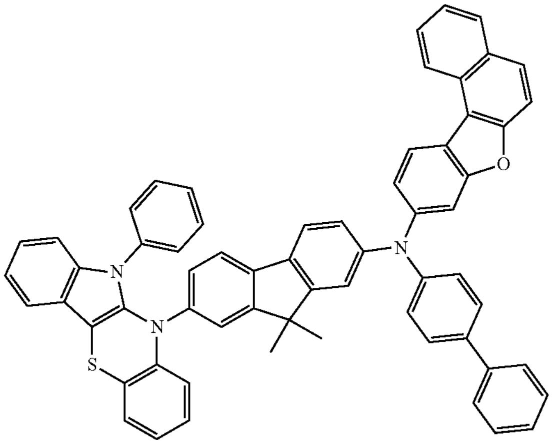

-continued
C20
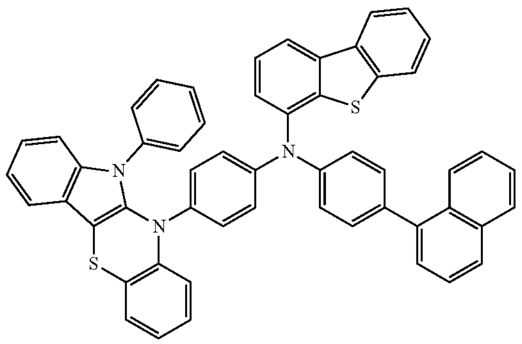
C21
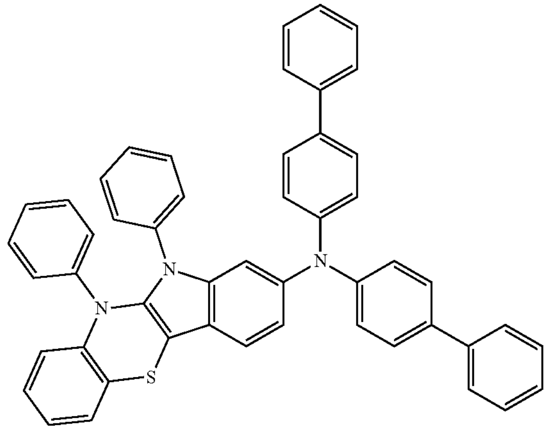
C22
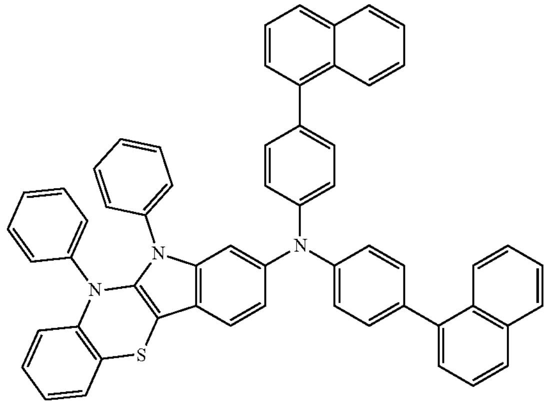
-continued
C23
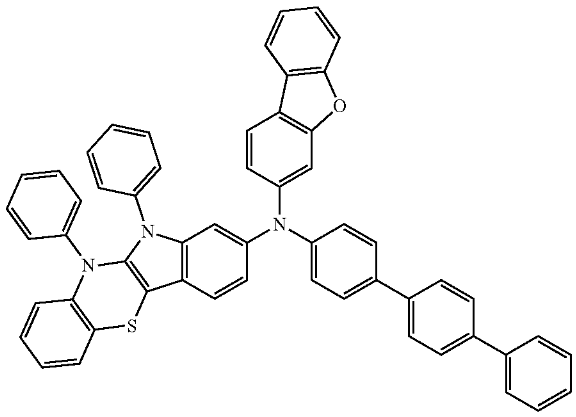
C24
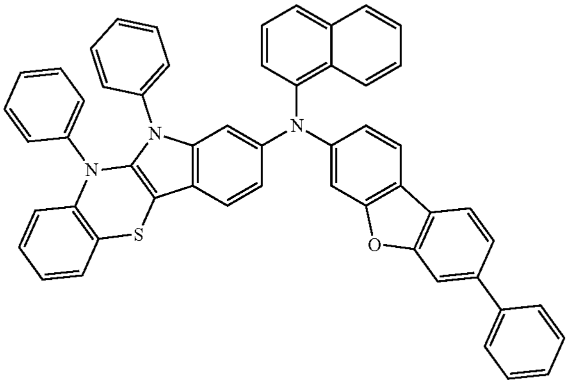
C25
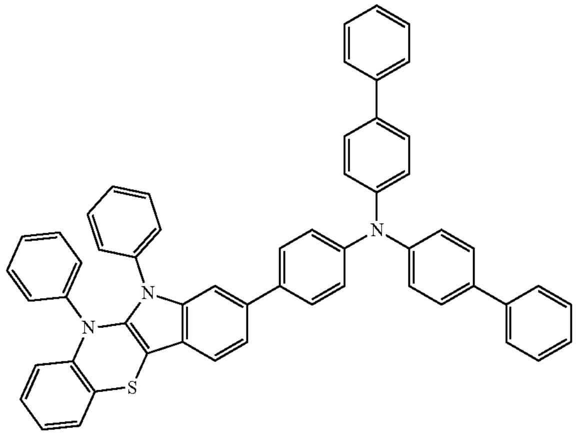

-continued
C26
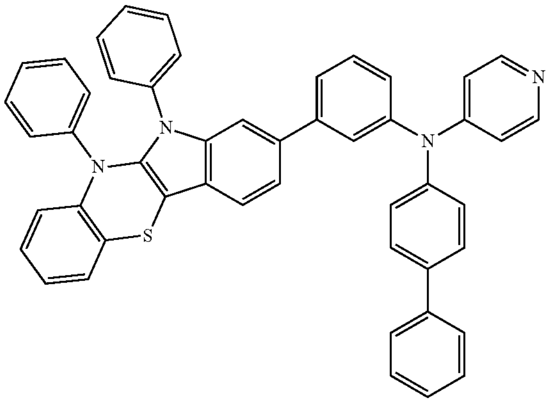
C27
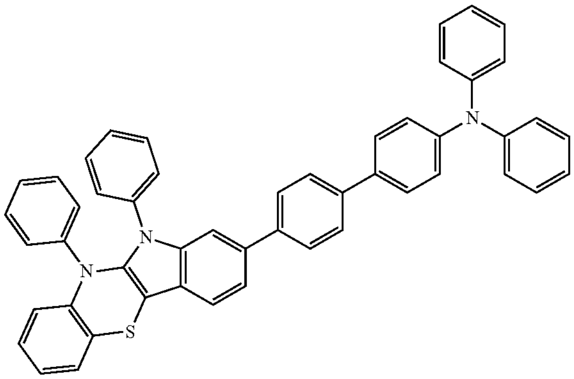
C28
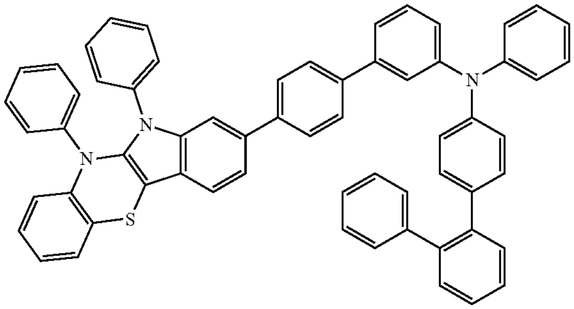
-continued
C29
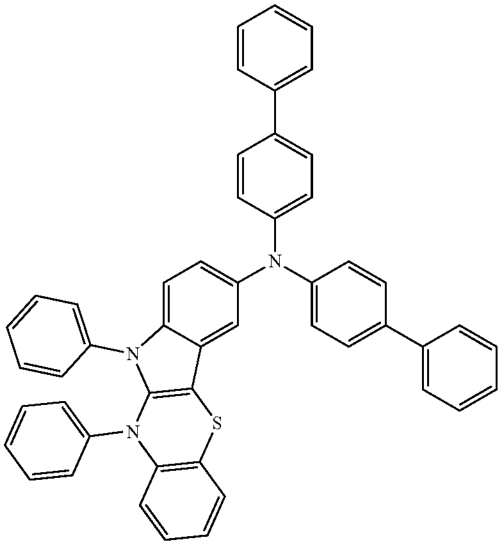
C30
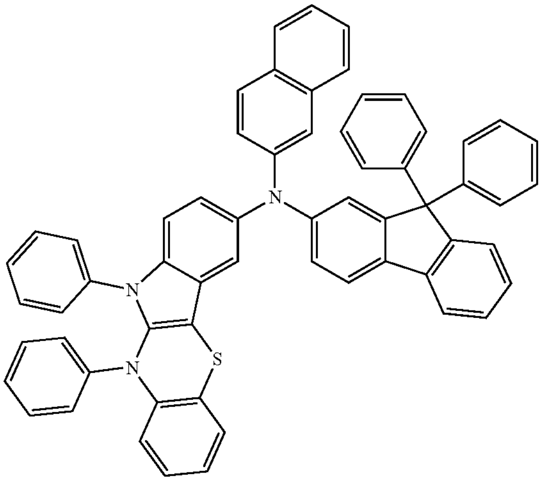
C31
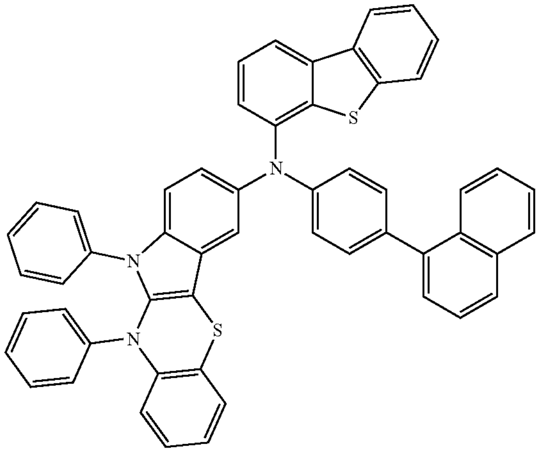

-continued
C32
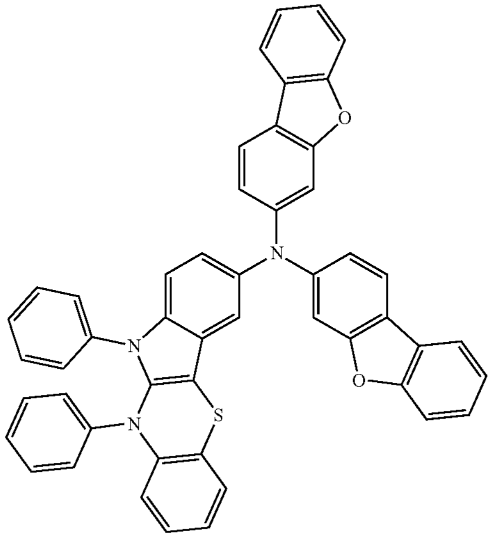
C33
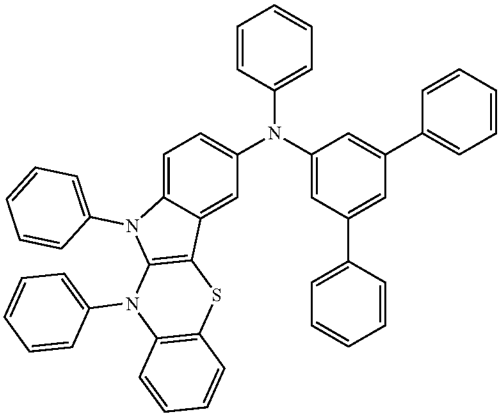
C34
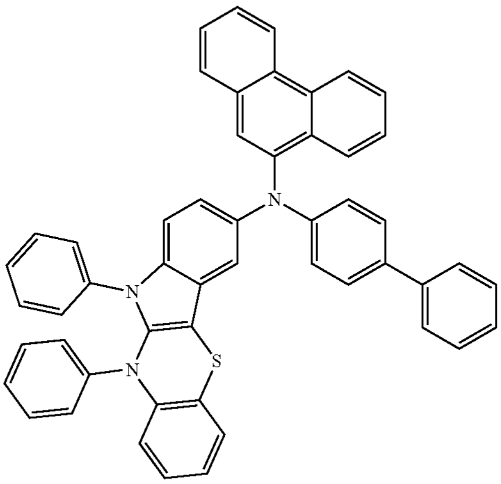
-continued
C35
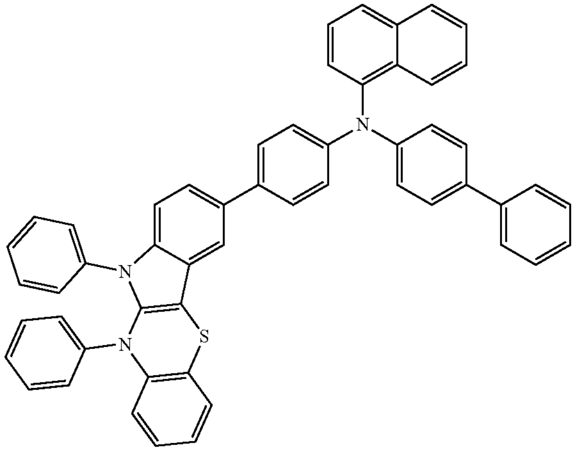
C36
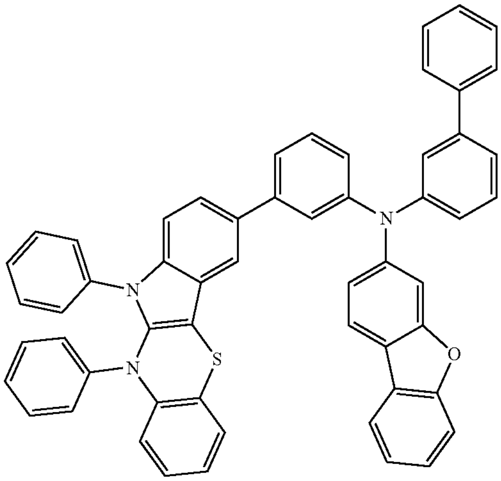
C37
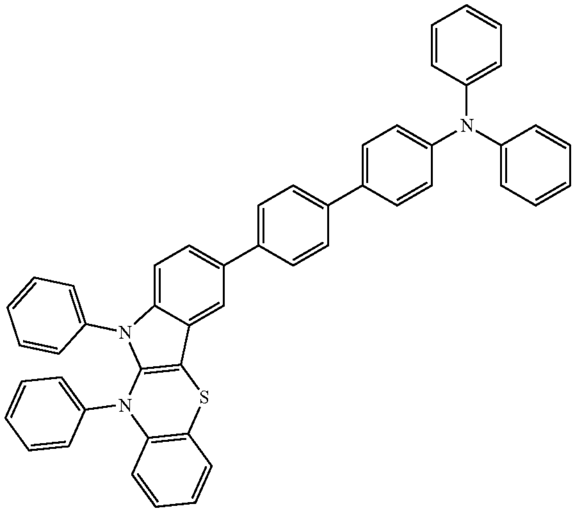

C38
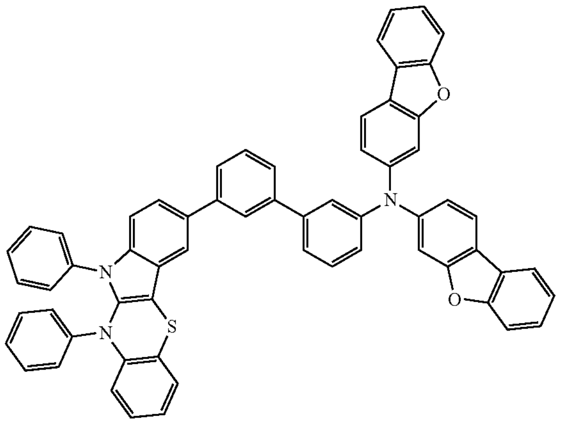
C39
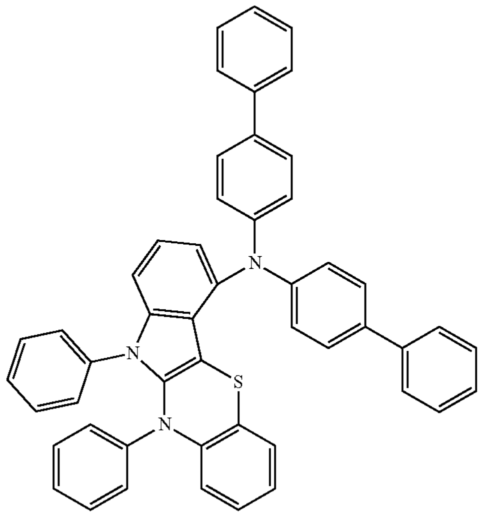
C40
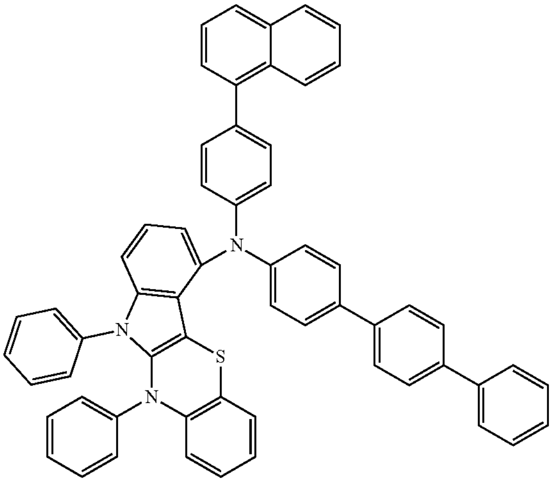
C41
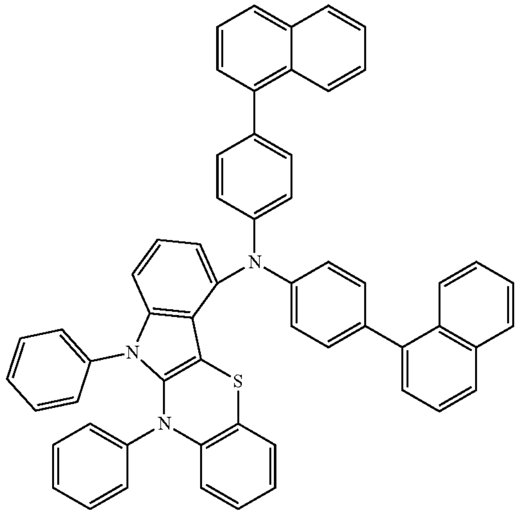
C42
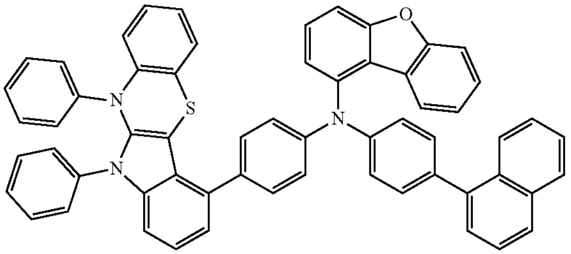
C43
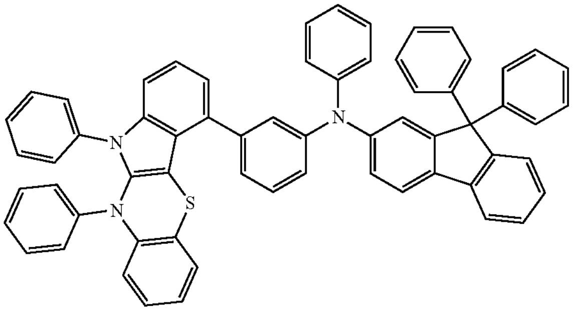
C44
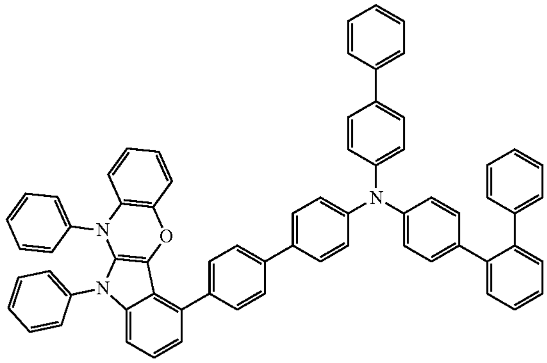

-continued
C45
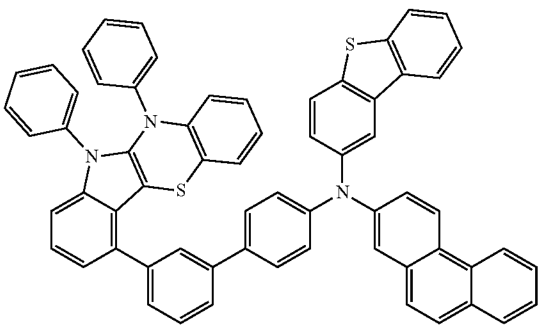
C46
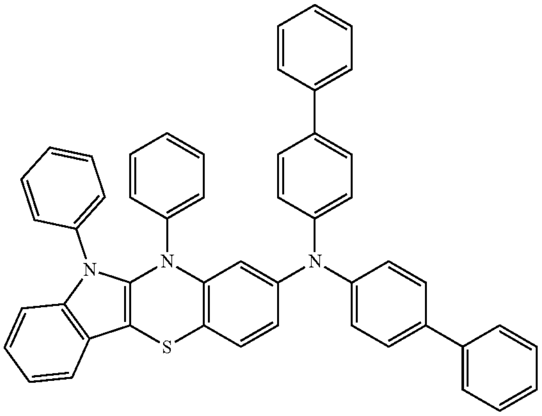
C47
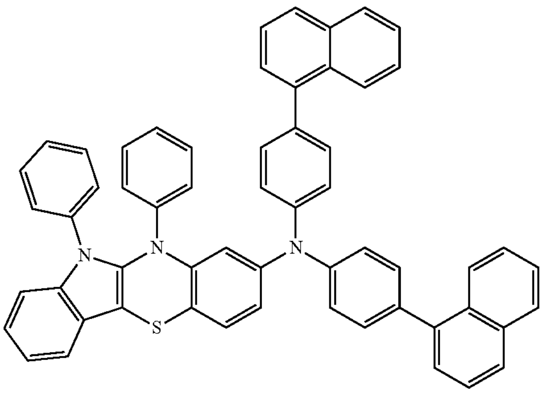
C48
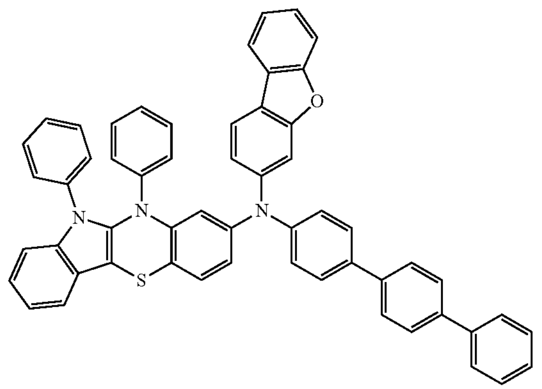
-continued
C49
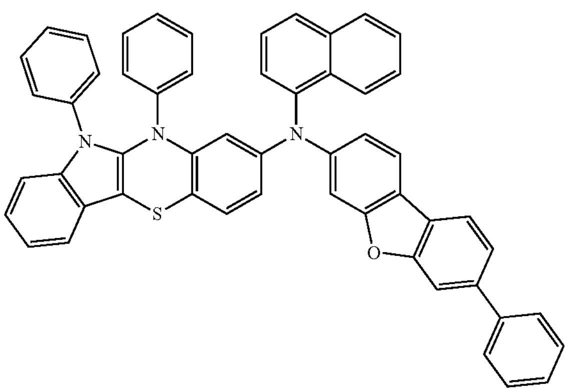
C50
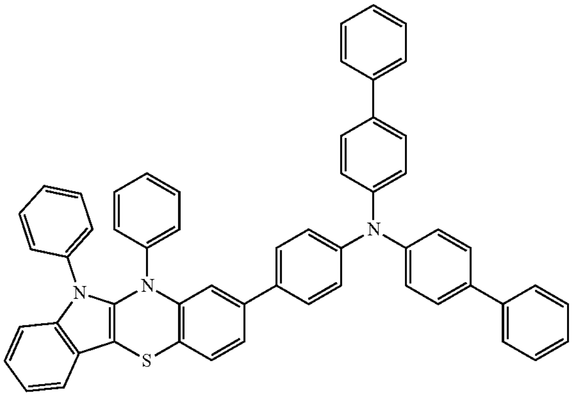
C51
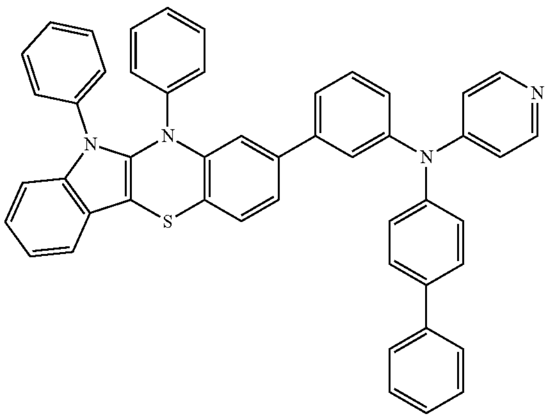
C52
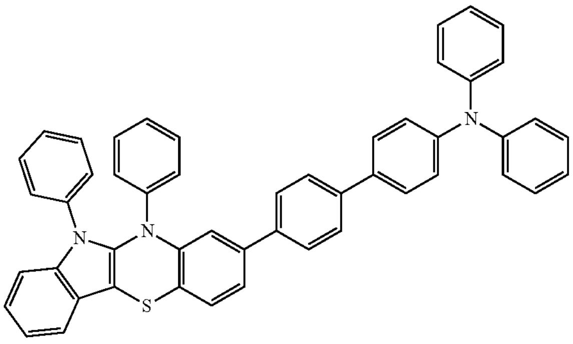

-continued
C53
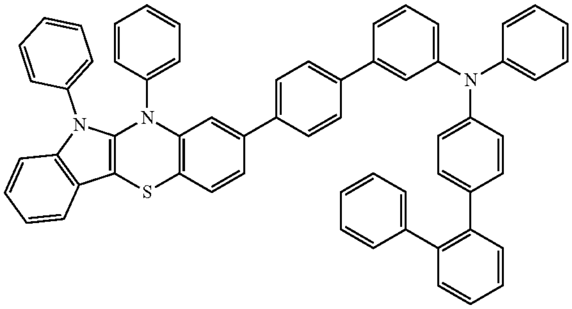
C54
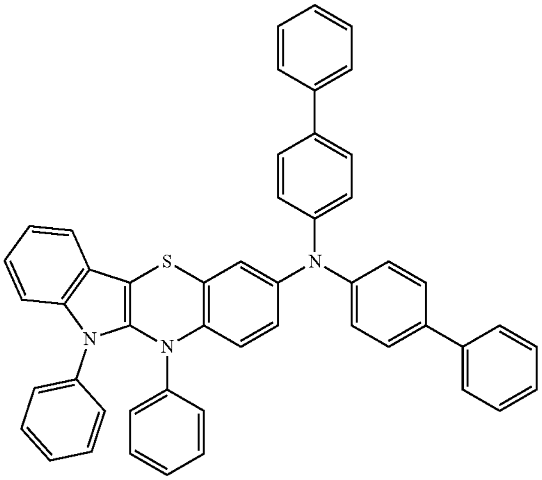
C55
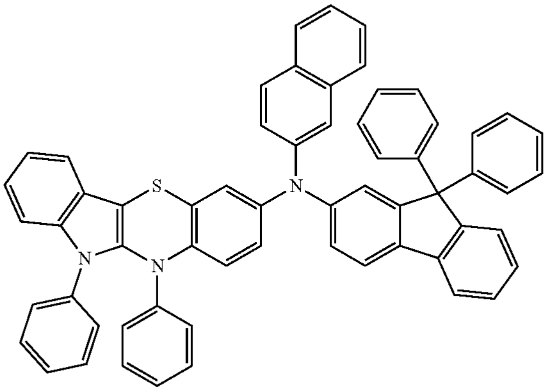
C56
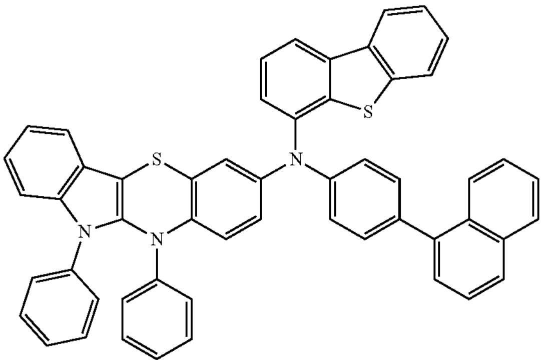
-continued
C57
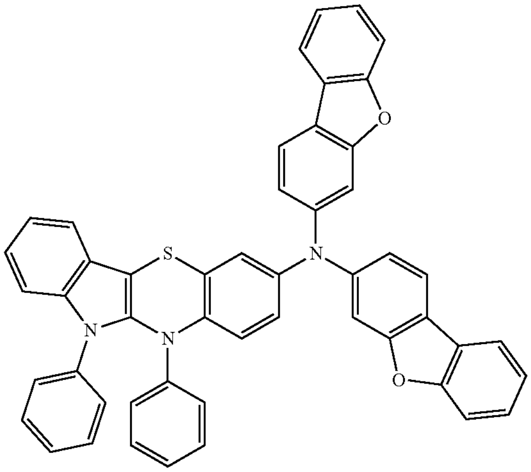
C58
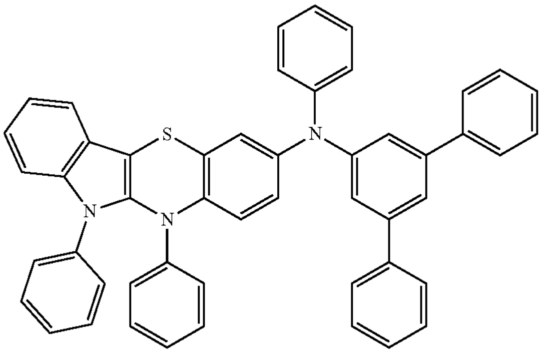
C59
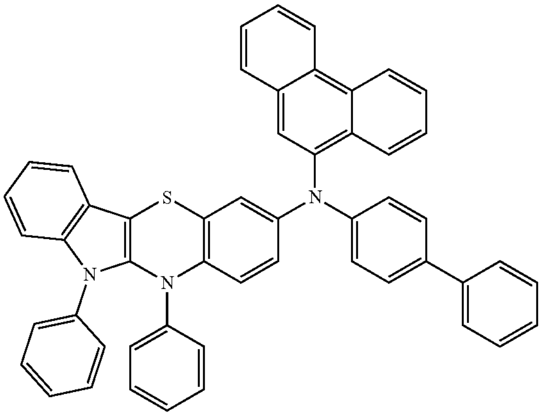

-continued
C60
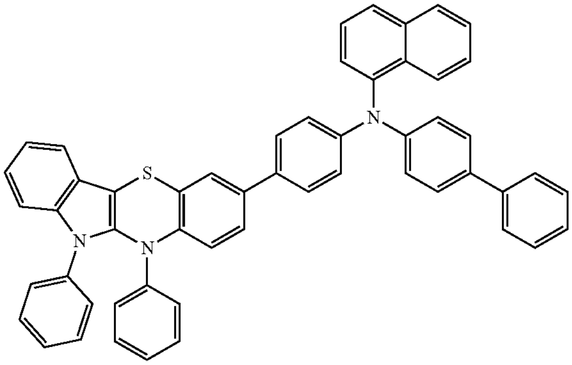
C61
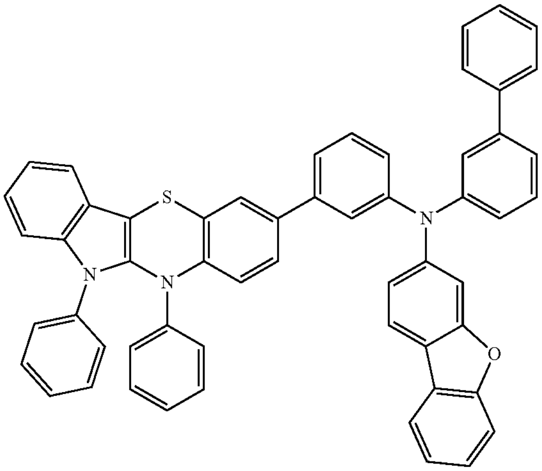
C62
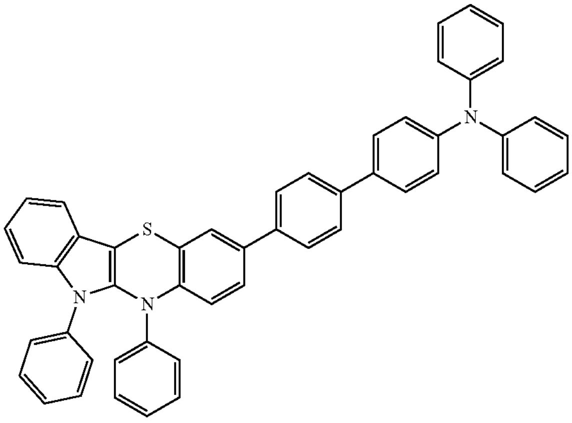
-continued
C63
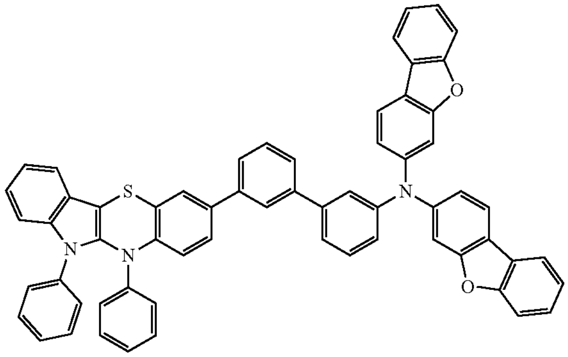
C64
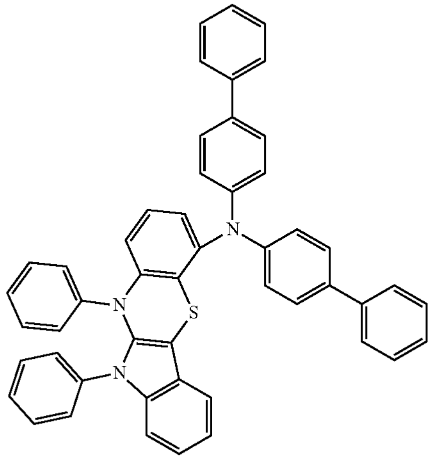
C65
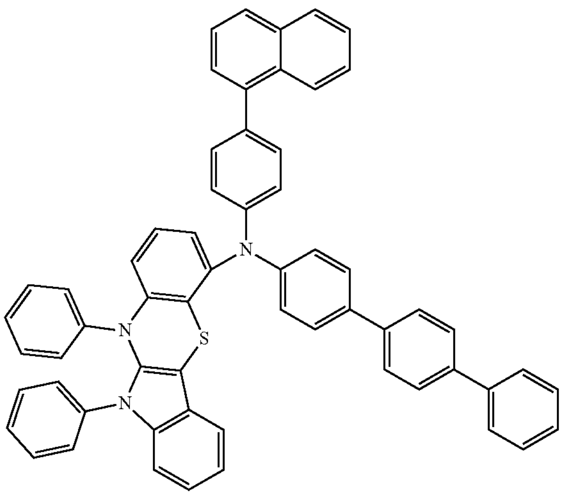

-continued
C66
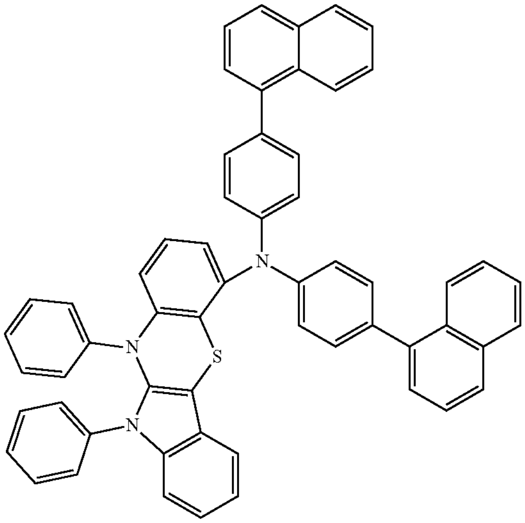
C67
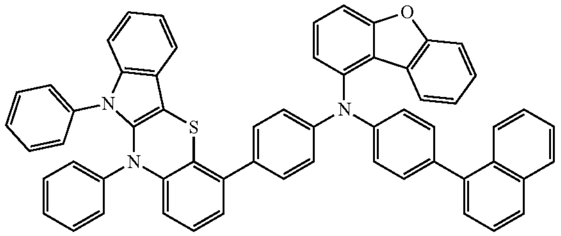
C68
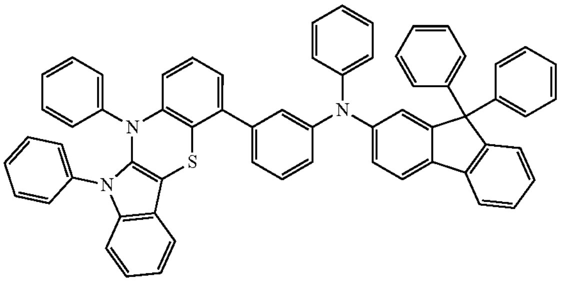
C69
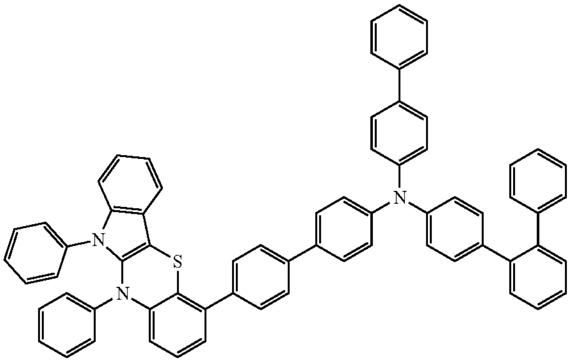
-continued
C70
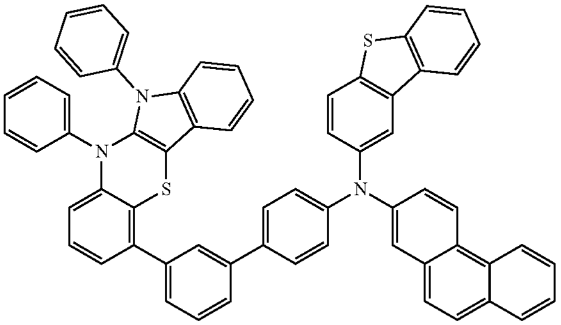
[Compound Group 4]
D1
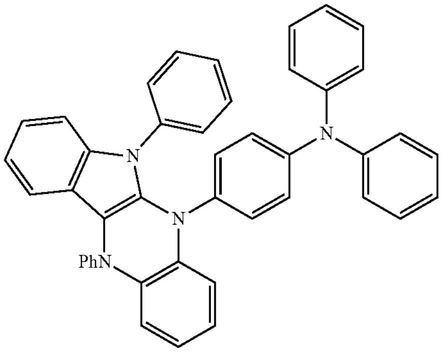
D2
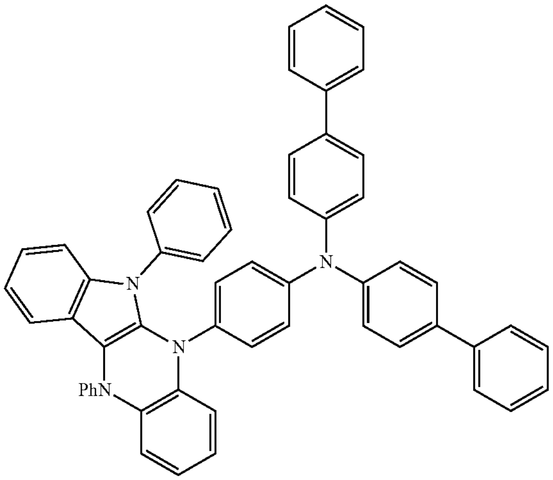

D3
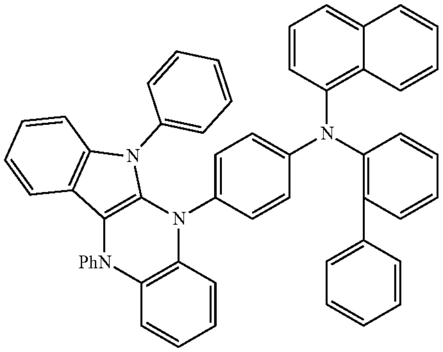
D4
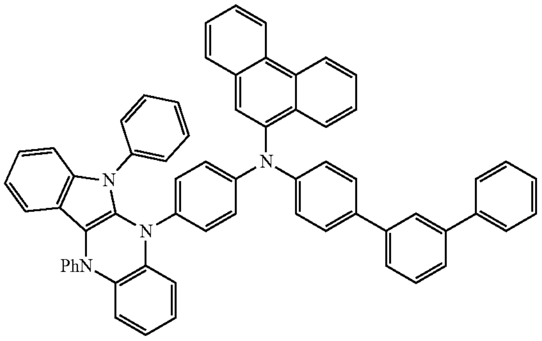
D5
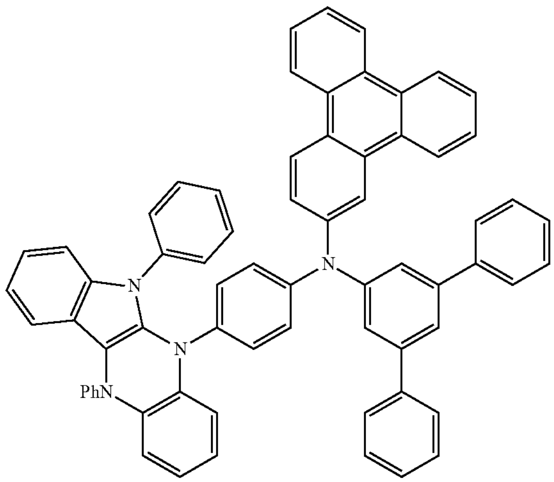
D6
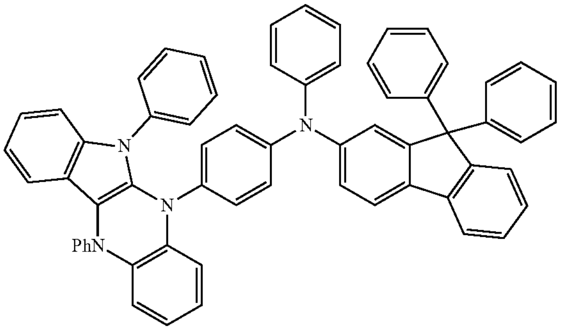
D7
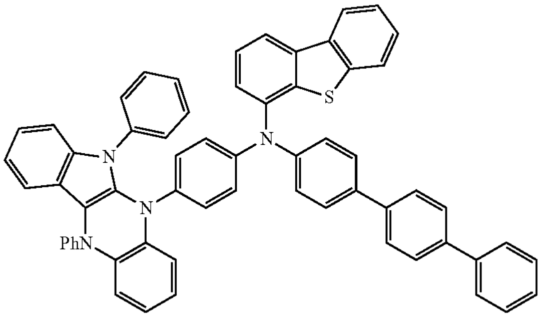
D8
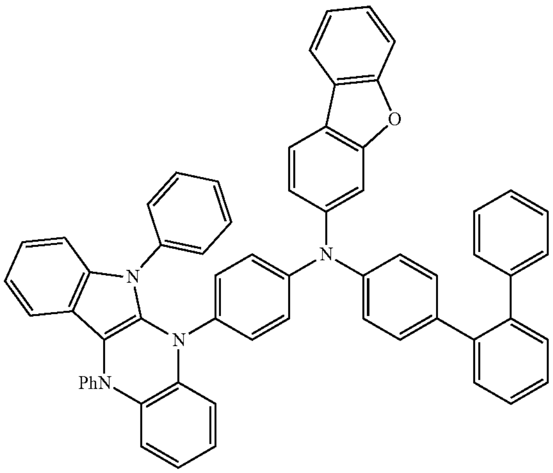
D9
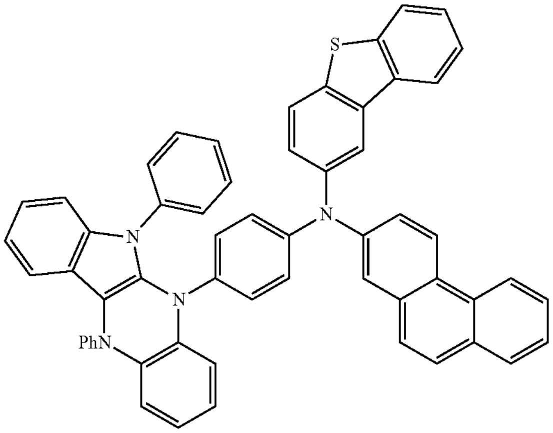

-continued
D10
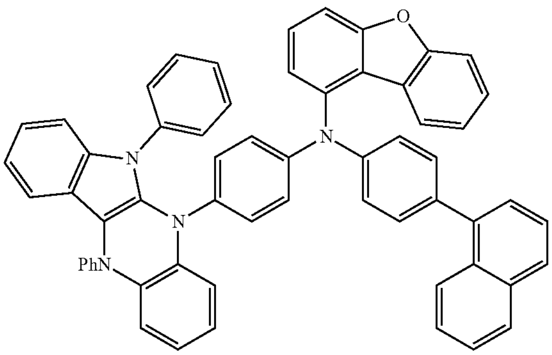
D11
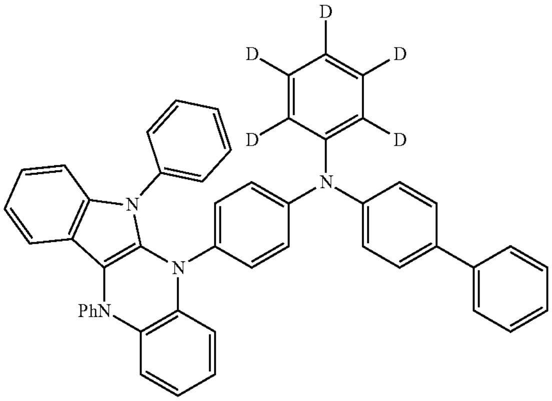
D12
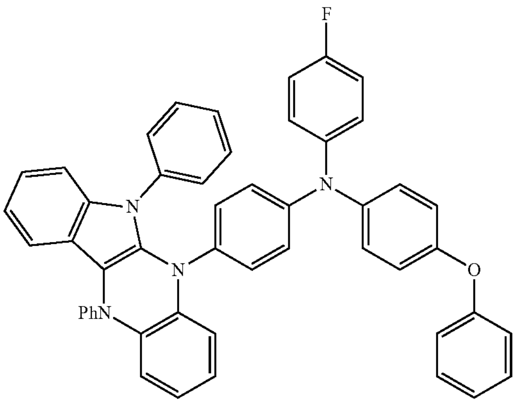
-continued
D13
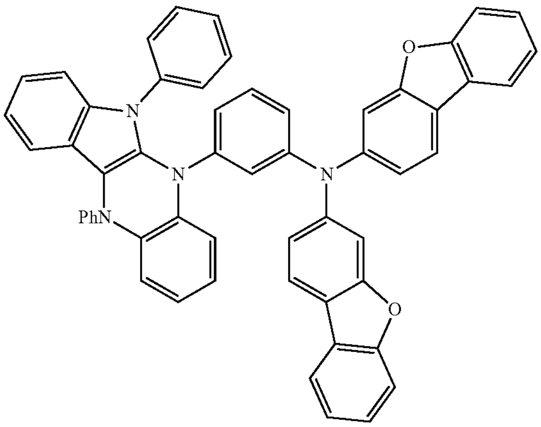
D14
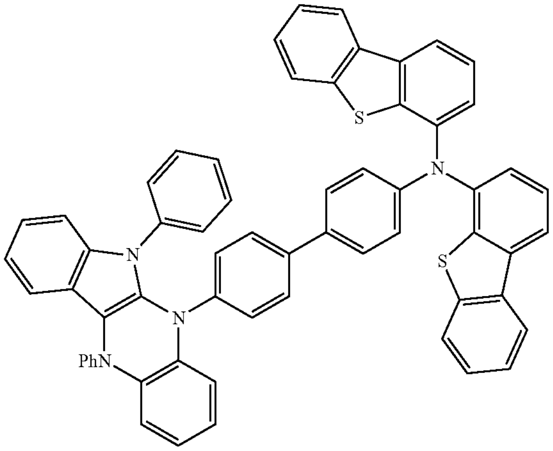
D15
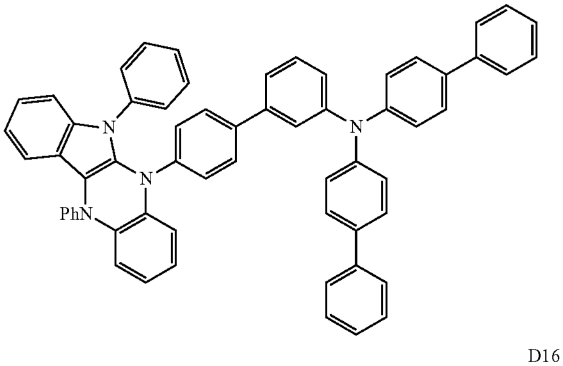
D16
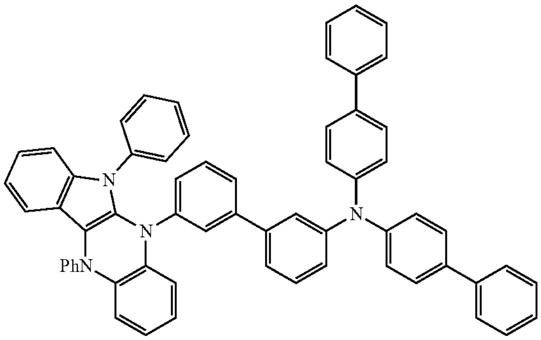

D17
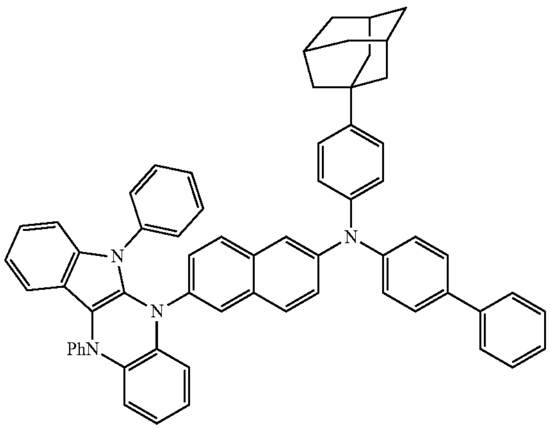
D18
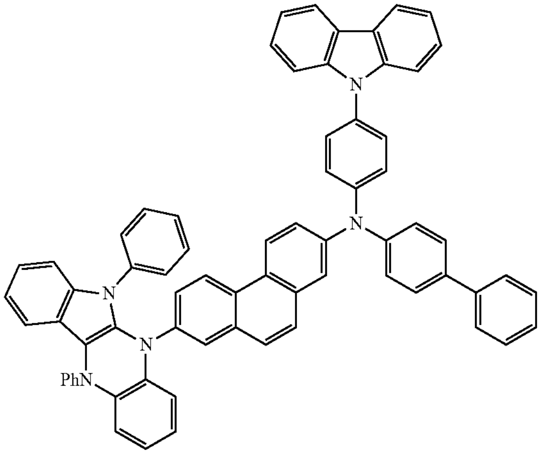
D19
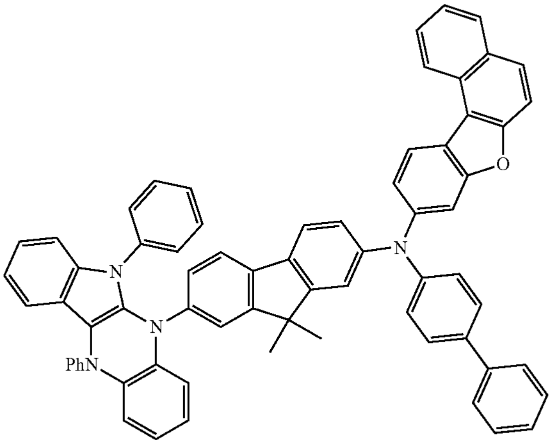
D20
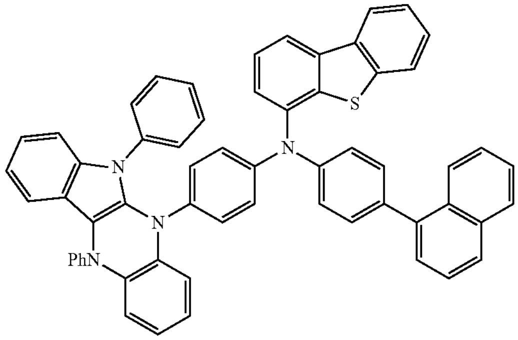
D21
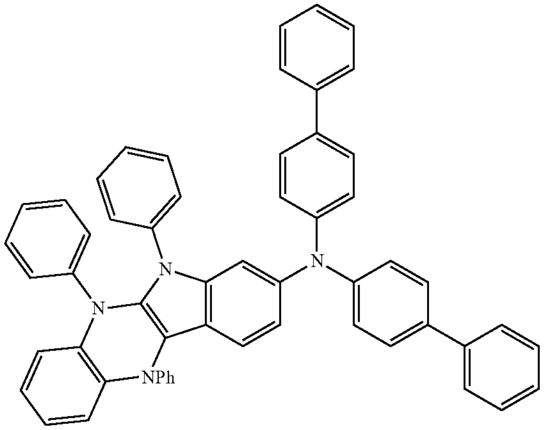
D22
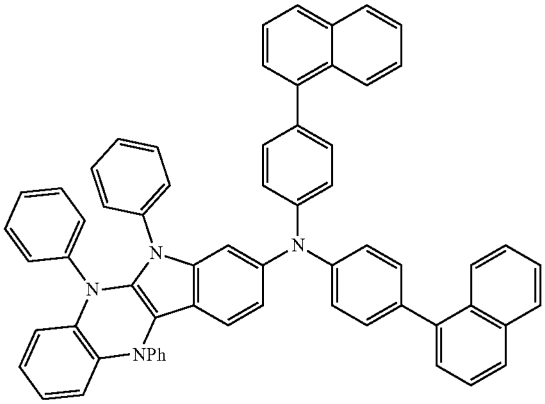

D23
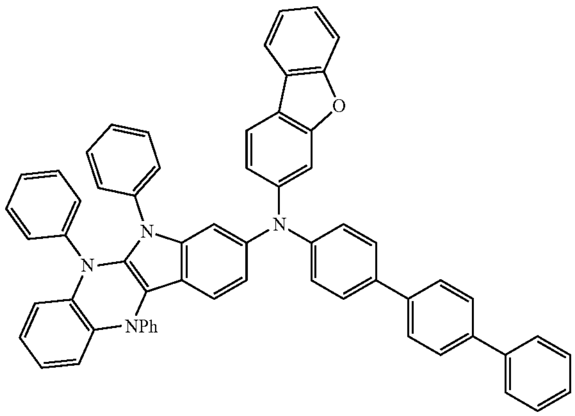
D24
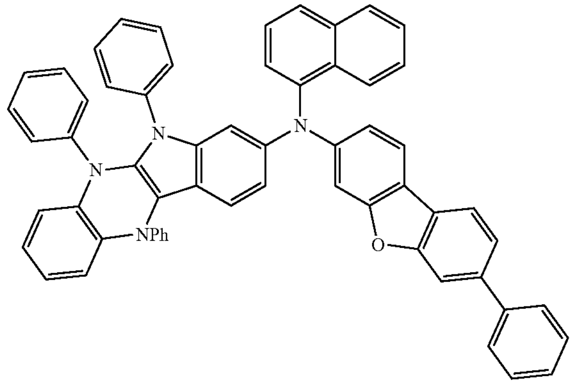
D25
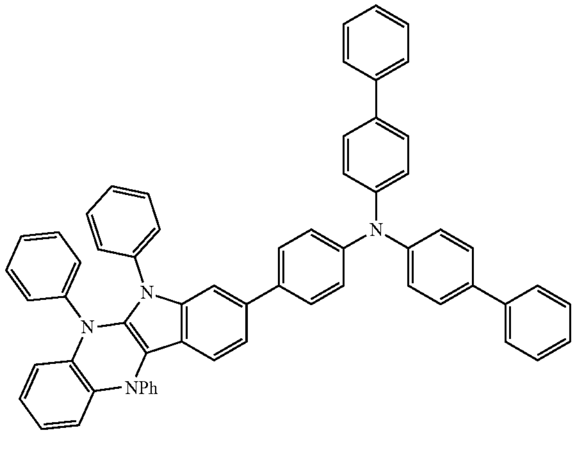
D26
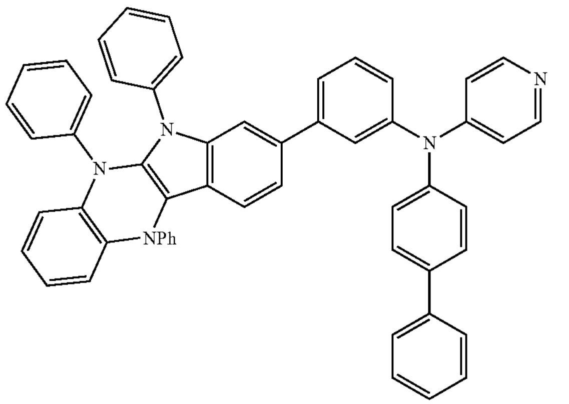
D27
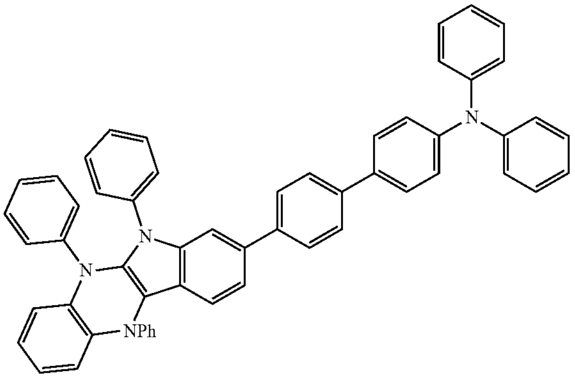
D28
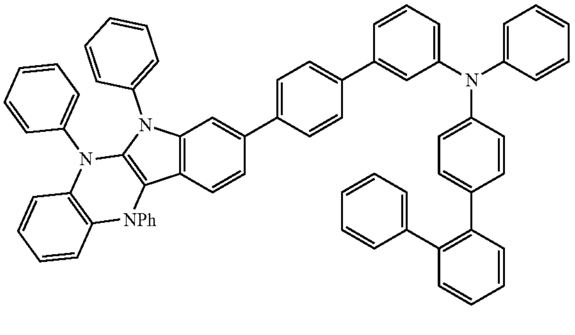

-continued
D29
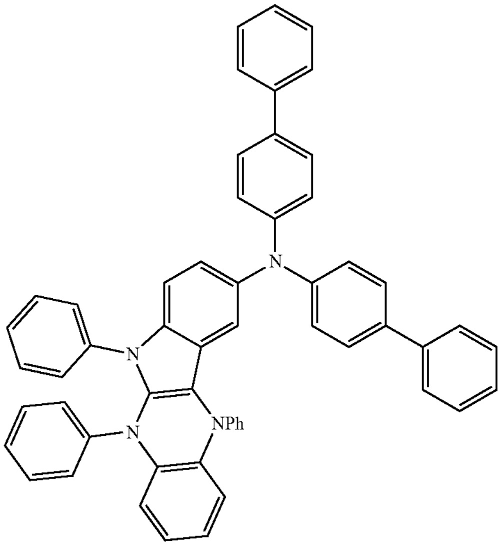
D30
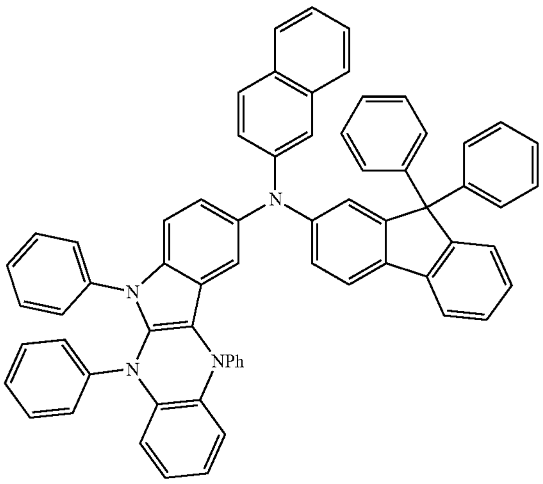
D31
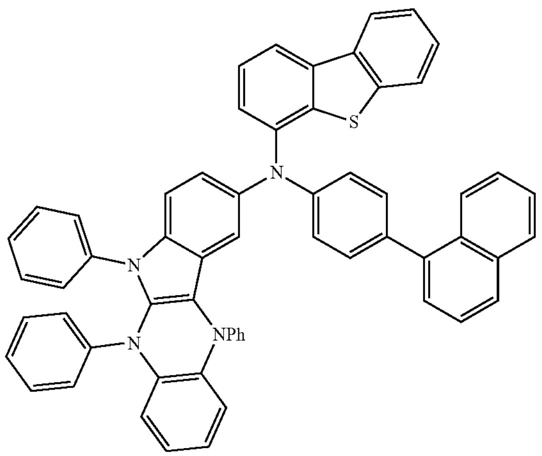
-continued
D32
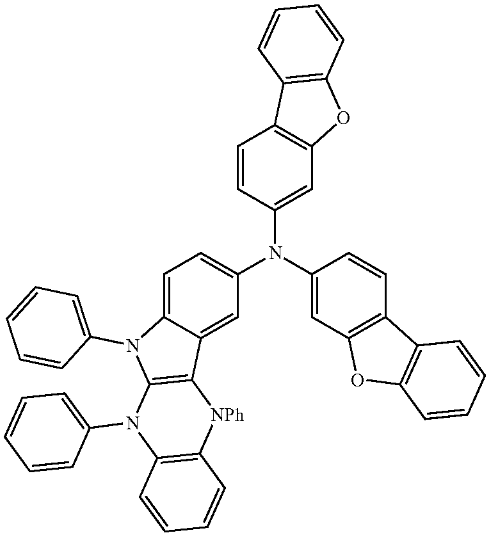
D33
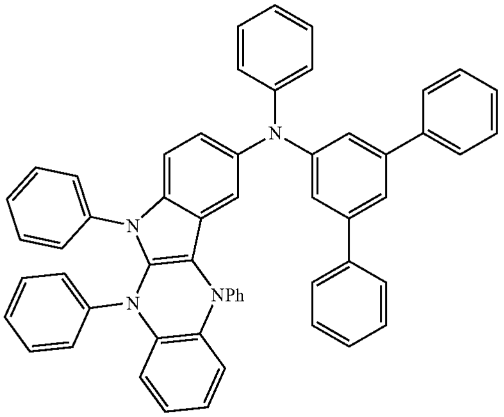
D34
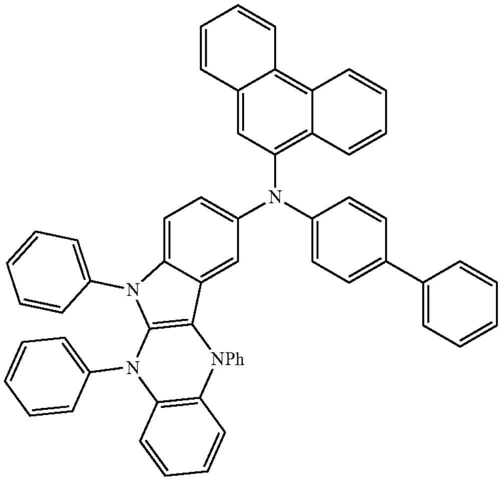

-continued
D35
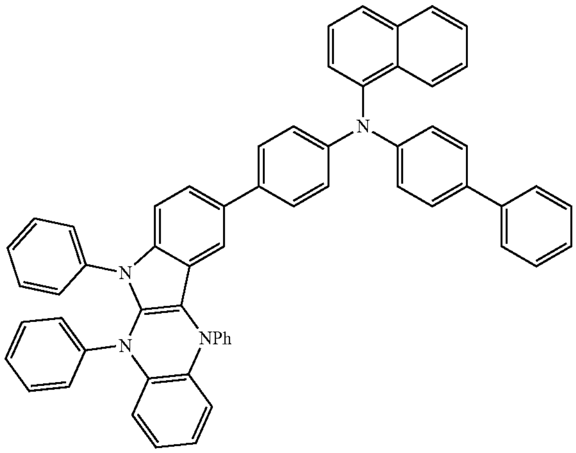
D36
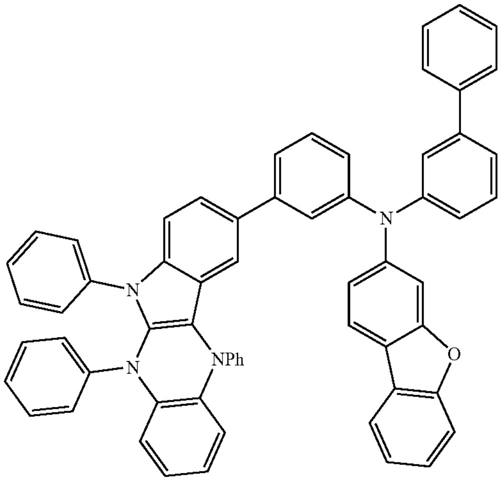
D37
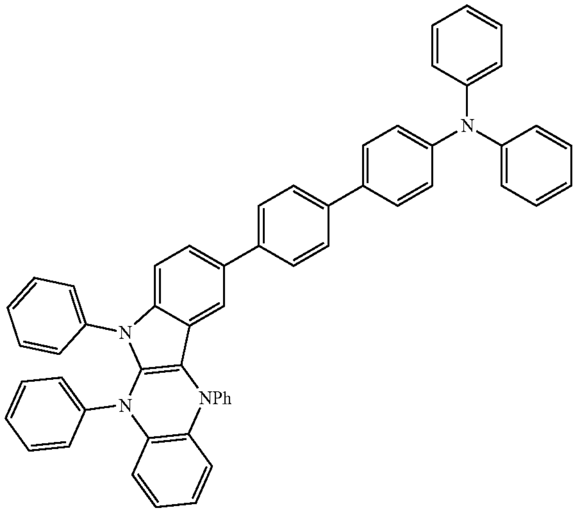
-continued
D38
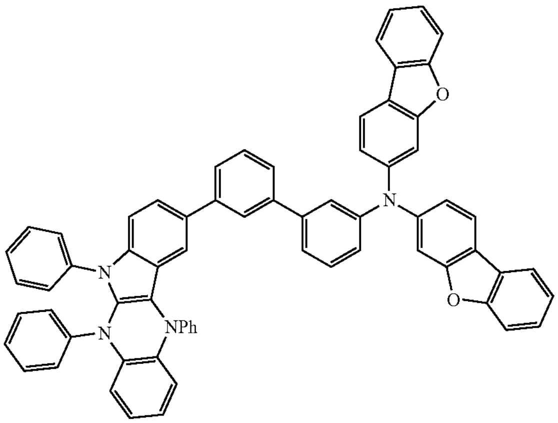
D39
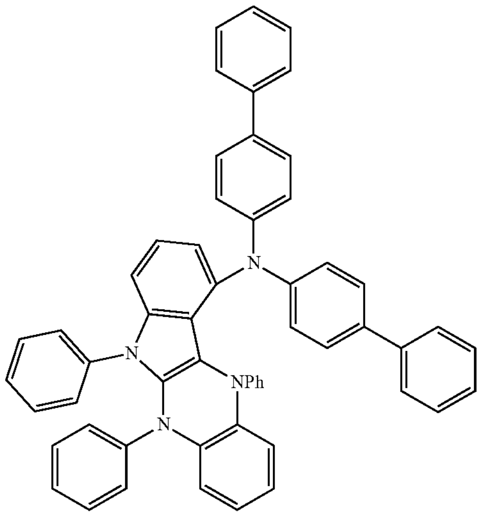
D40
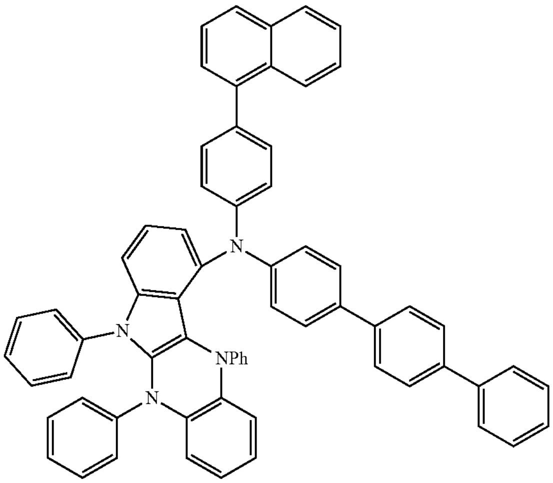

-continued
D41
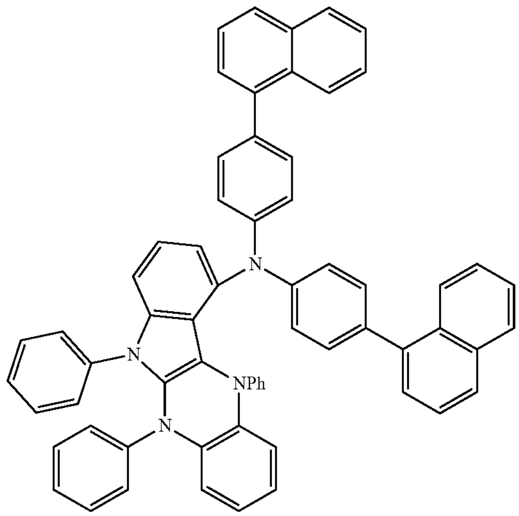
D42
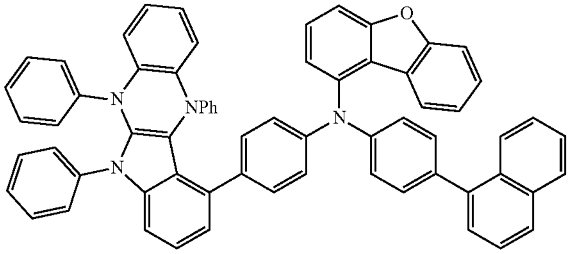
D43
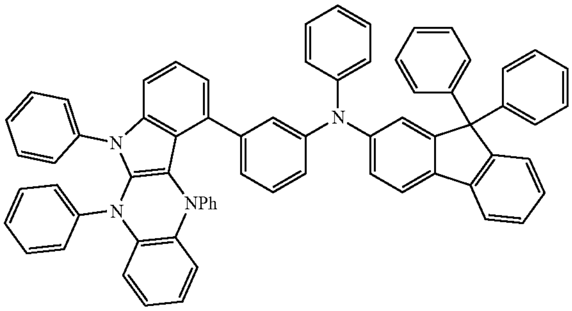
D44
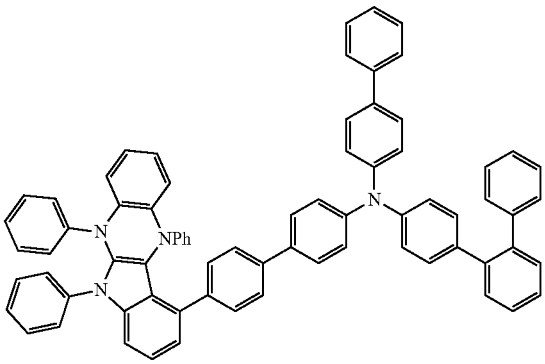
-continued
D45
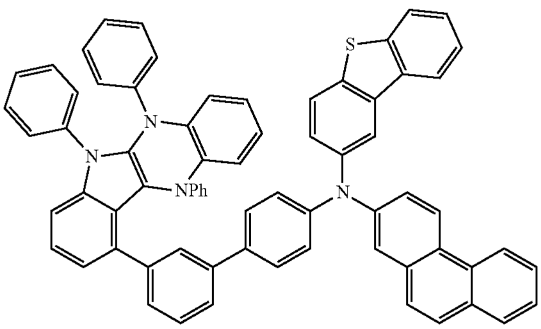
D46
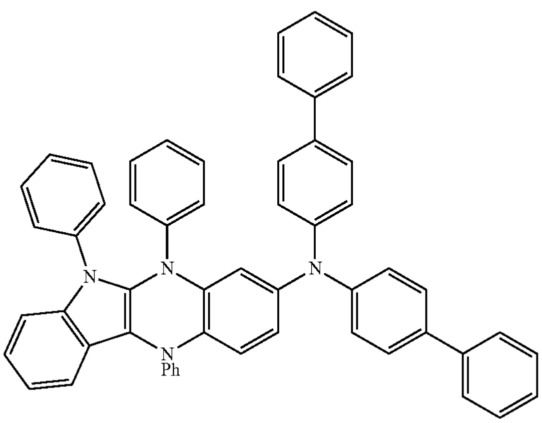
D47
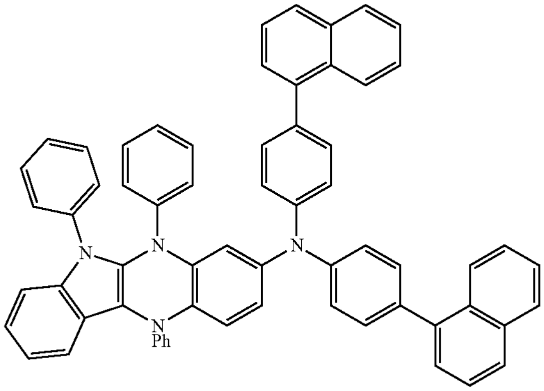
D48
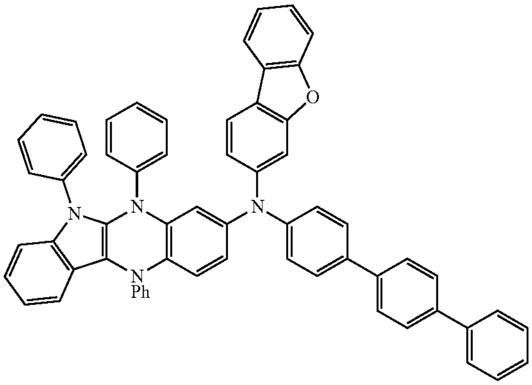

-continued
D49
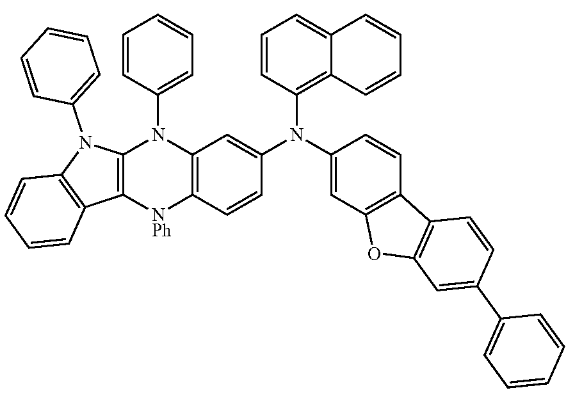
D50
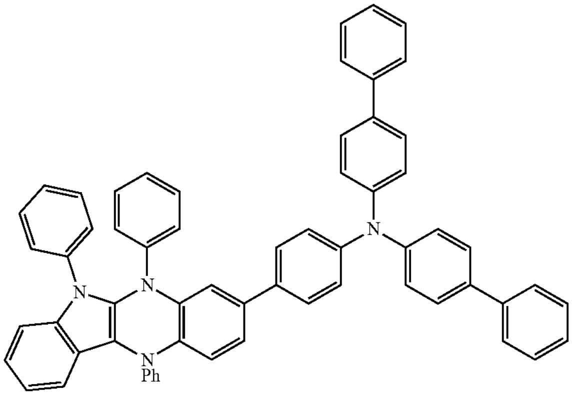
D51
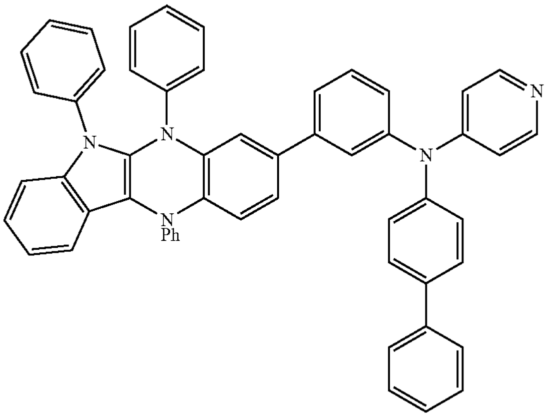
D52
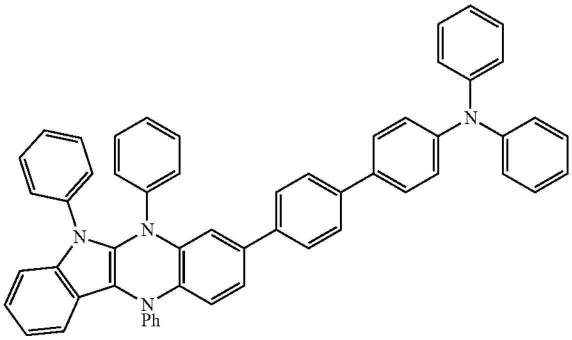
-continued
D53
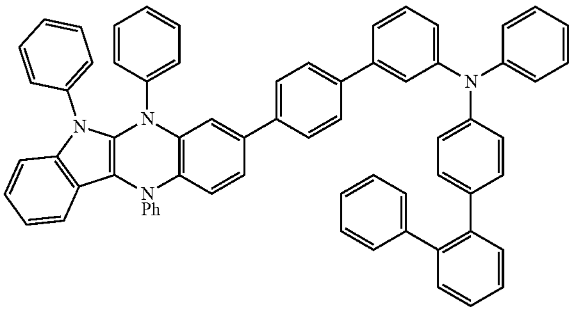
D54
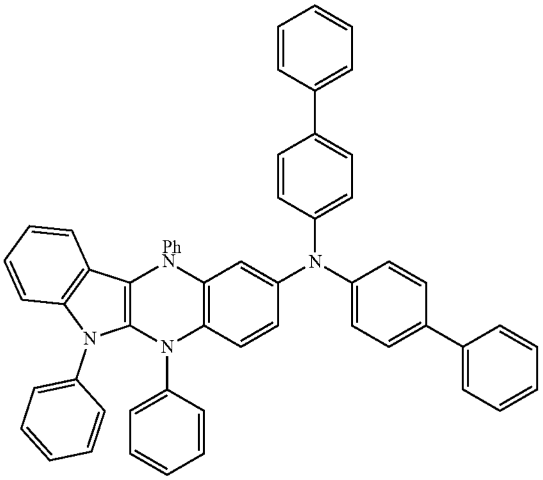
D55
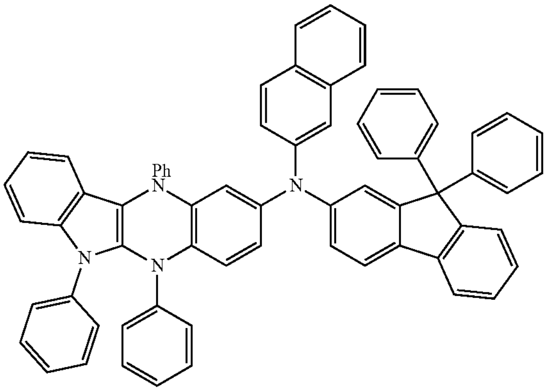
D56
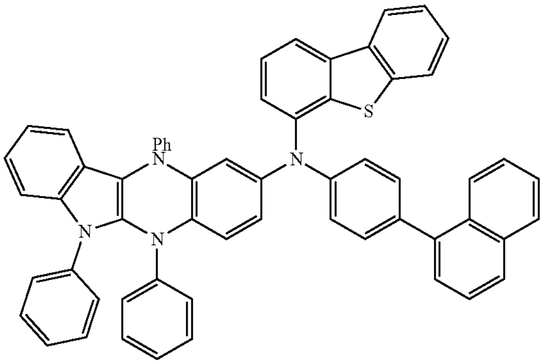

-continued
D57
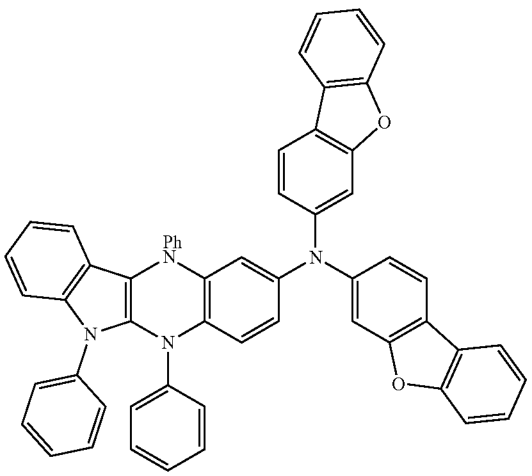
D58
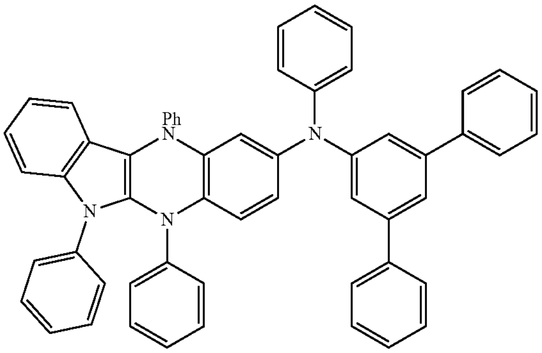
D59
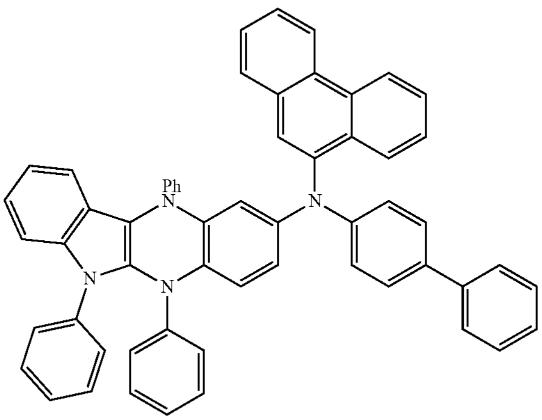
-continued
D60
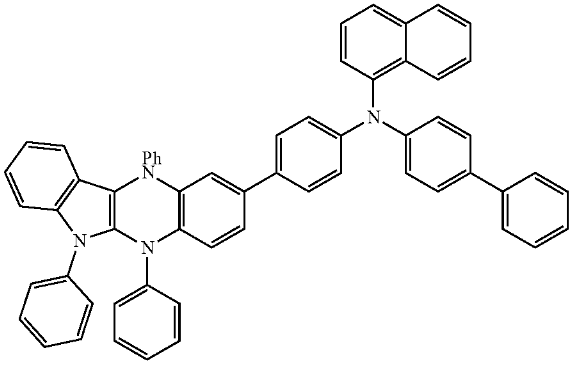
D61
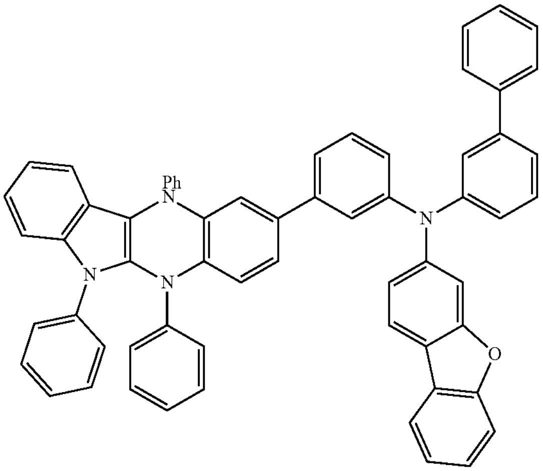
D62
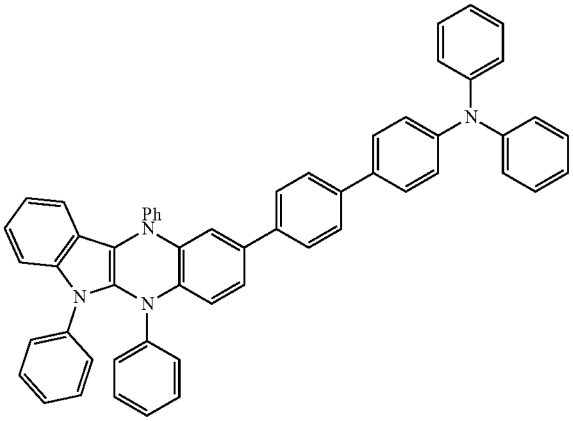

-continued
D63
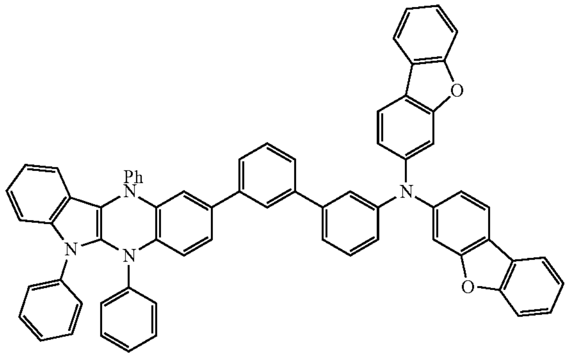
D64
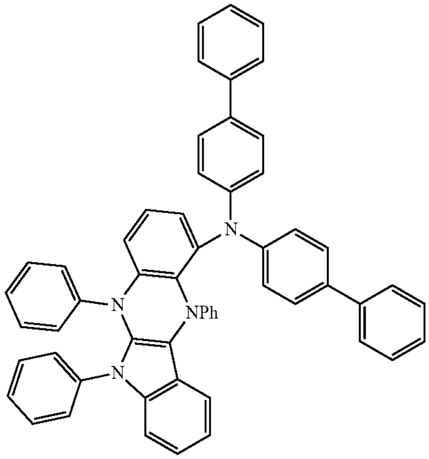
D65
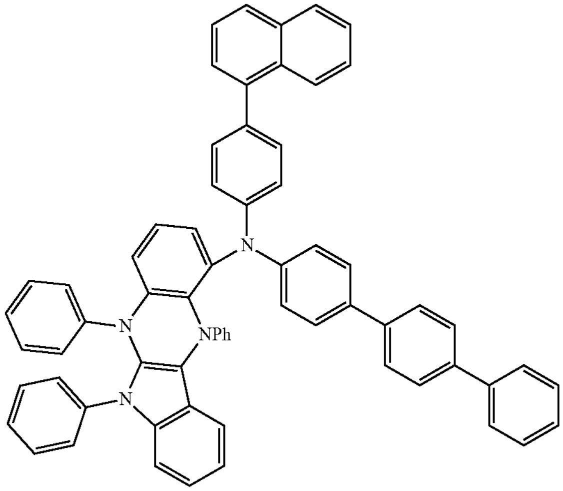
-continued
D66
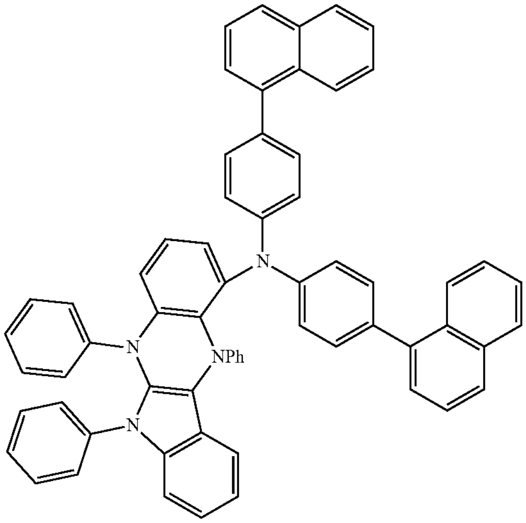
D67
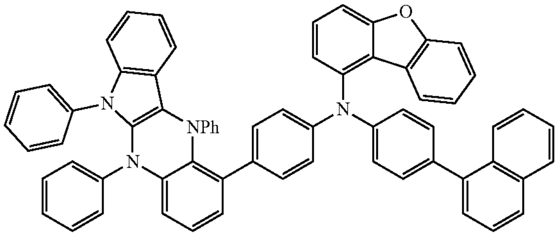
D68
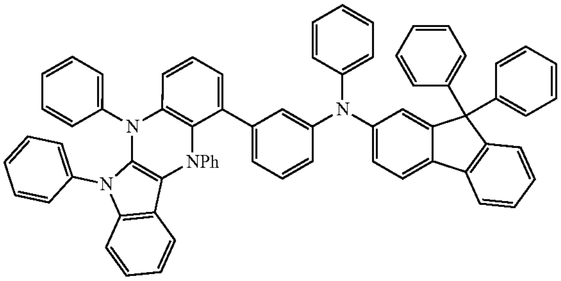
D69
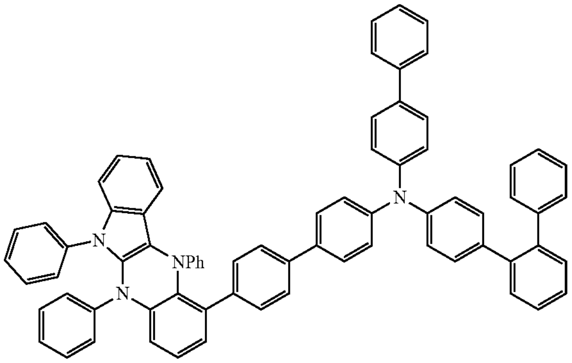

-continued
D70
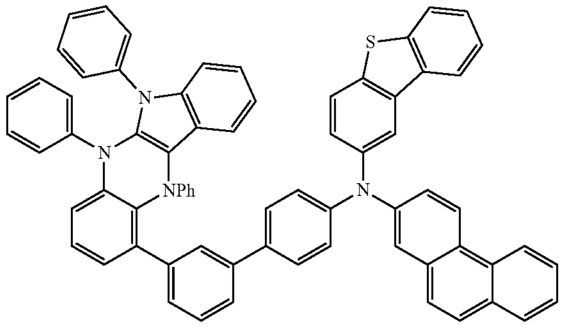
[Compound Group 5]
E1
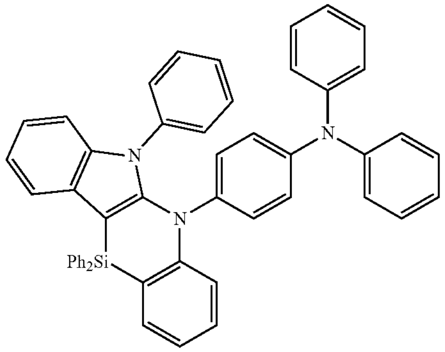
E2
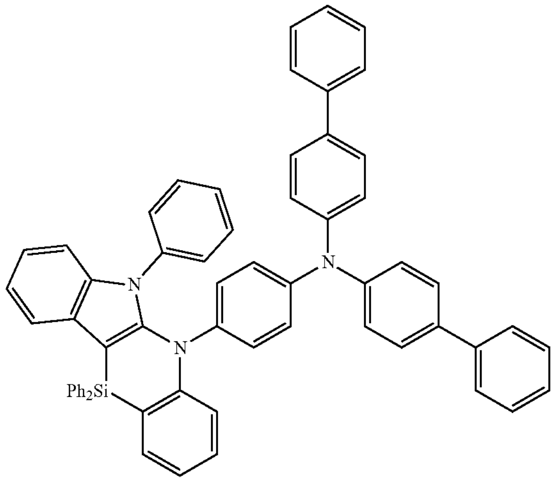
-continued
E3
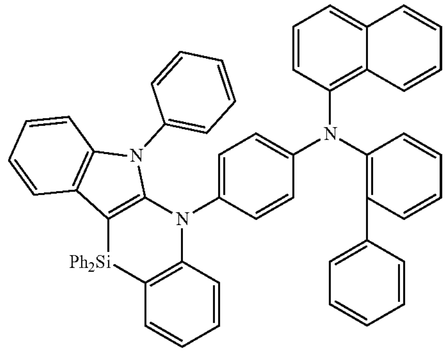
E4
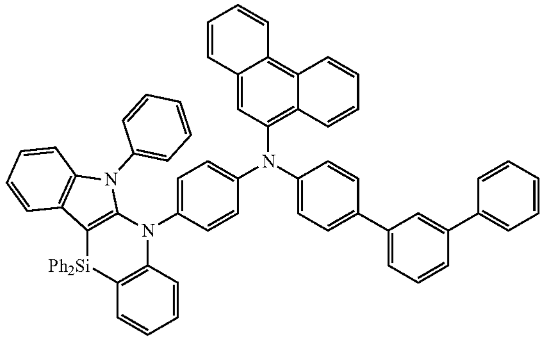
E5
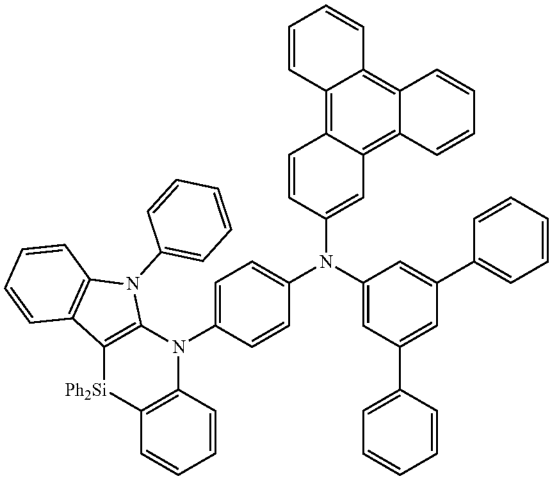
E6
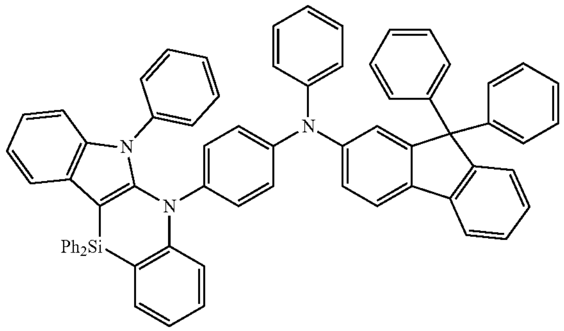

-continued
E7
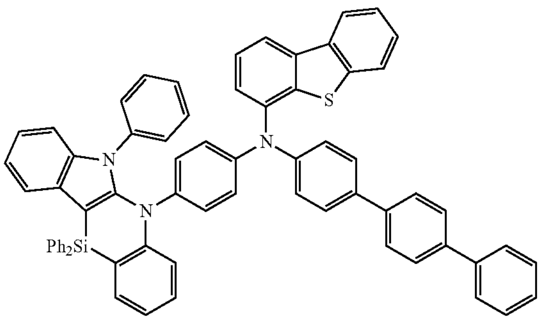
E8
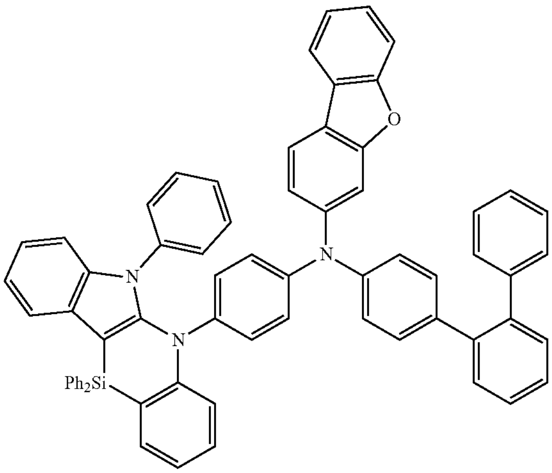
E9
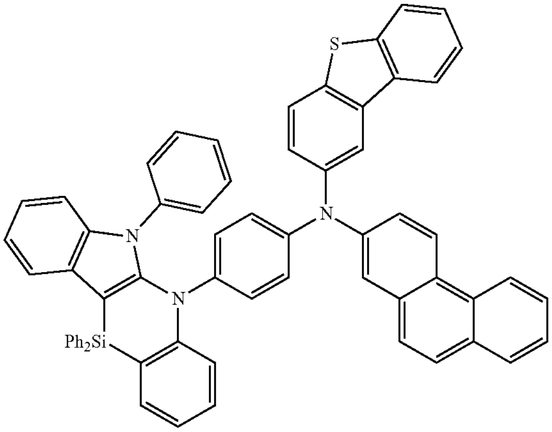
-continued
E10
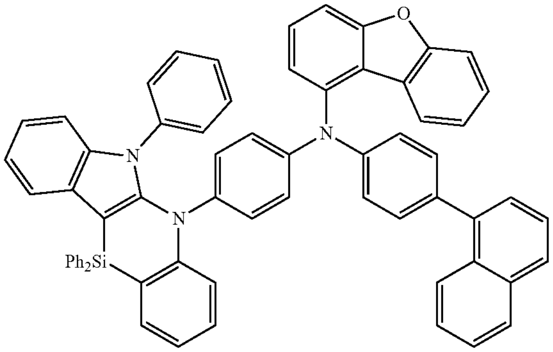
E11
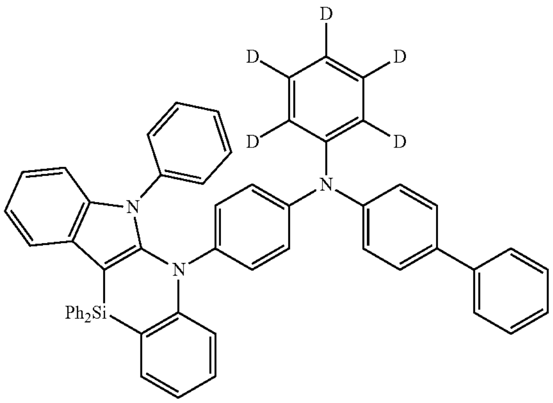
E12
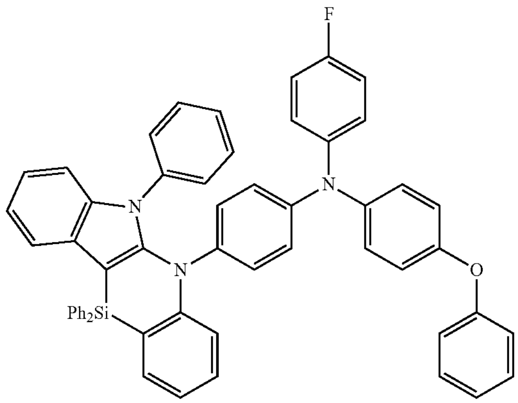

-continued
E13
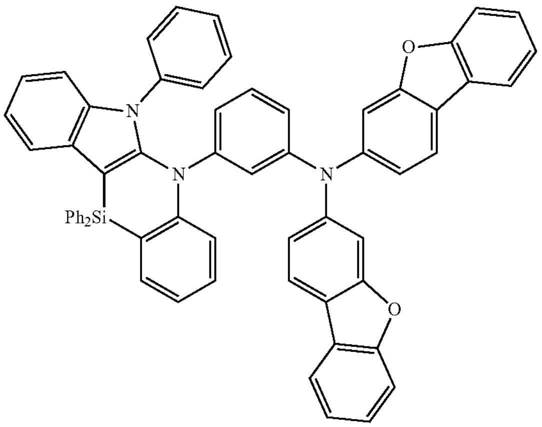
E14
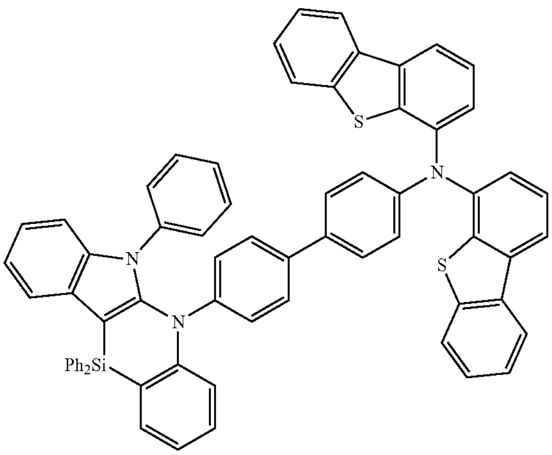
E15
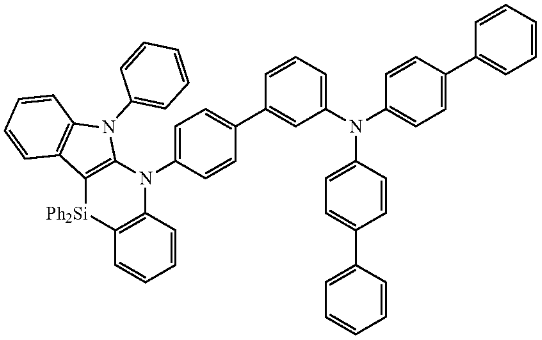
E16
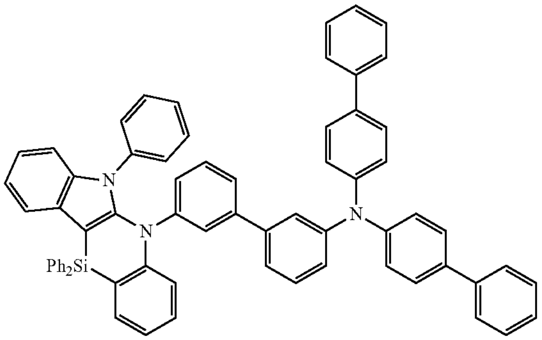
-continued
E17
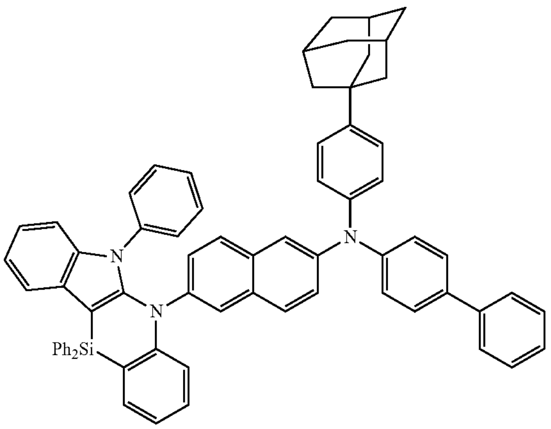
E18
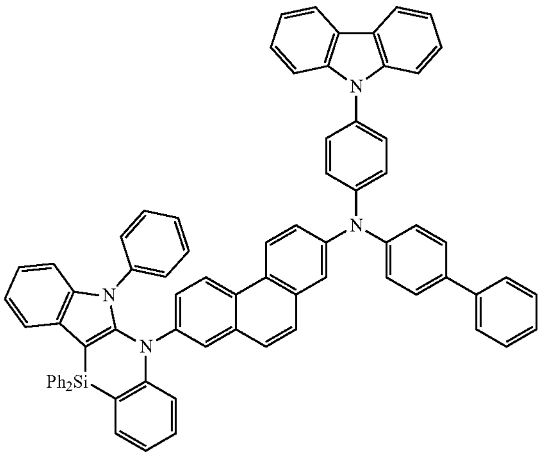
E19
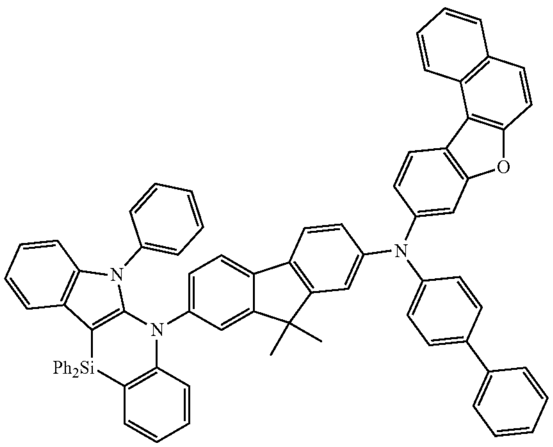

-continued
E20
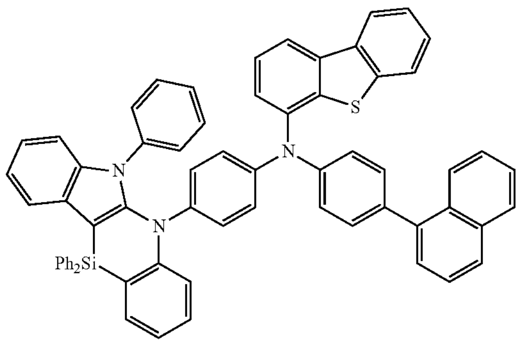
E21
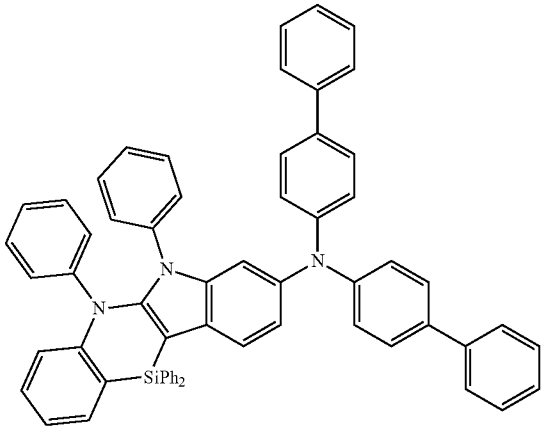
E22
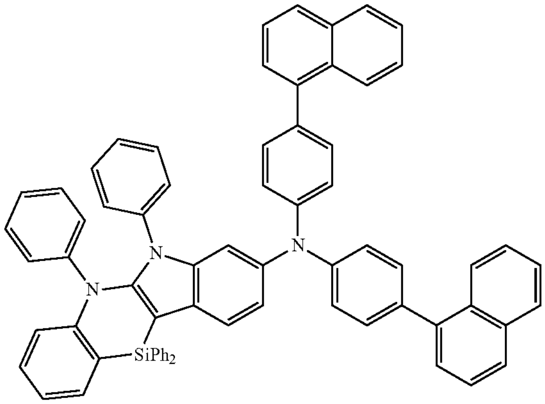
-continued
E23
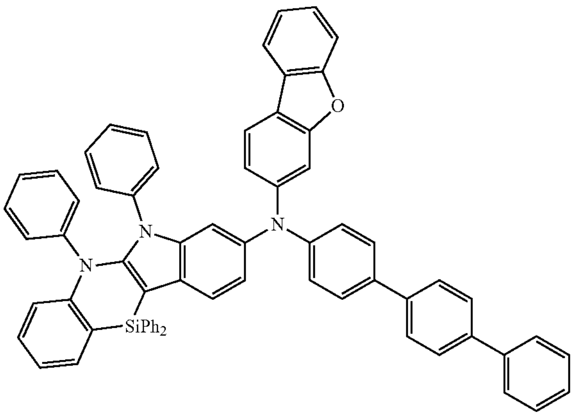
E24
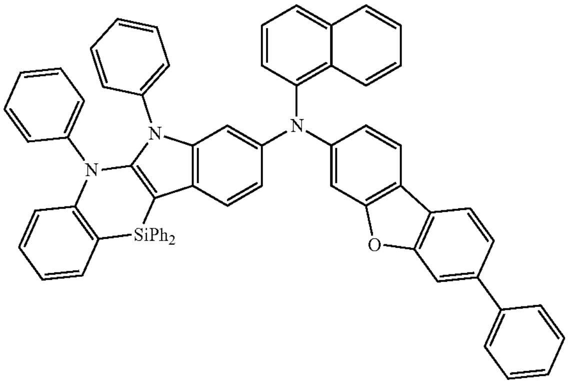
E25
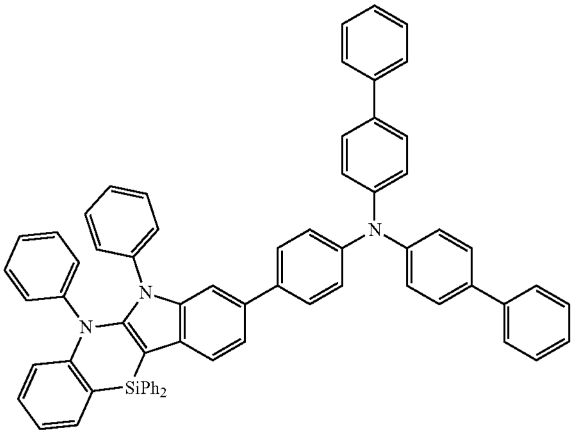

-continued
E26
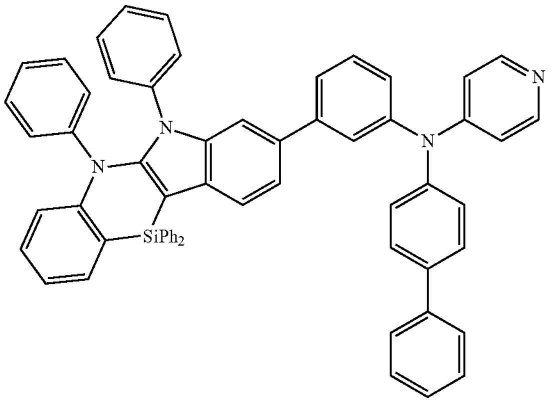
E27
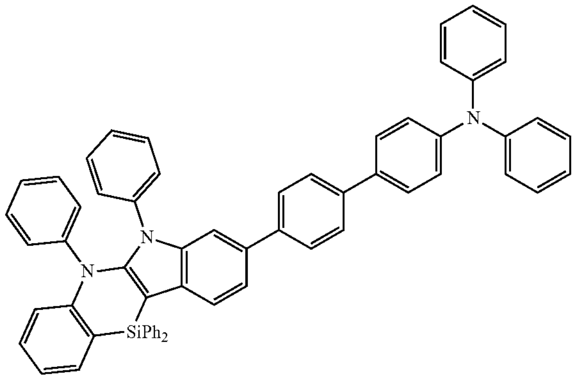
E28
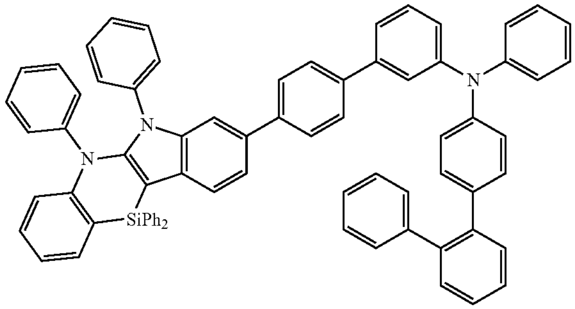
-continued
E29
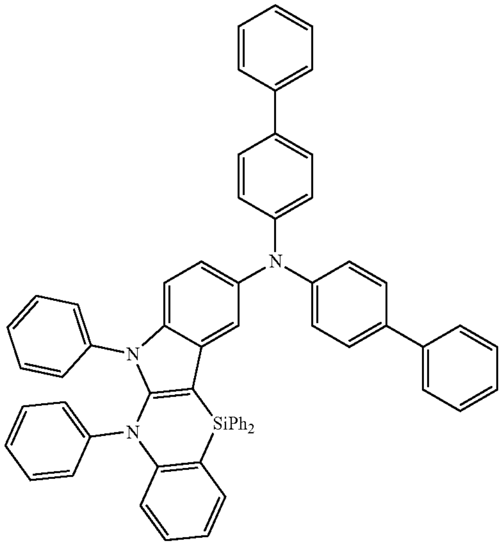
E30
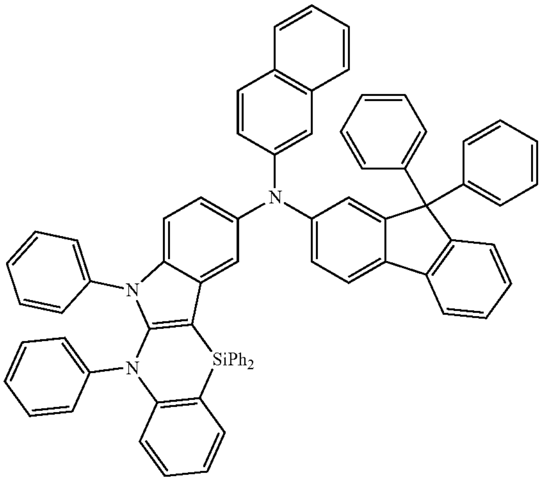
E31
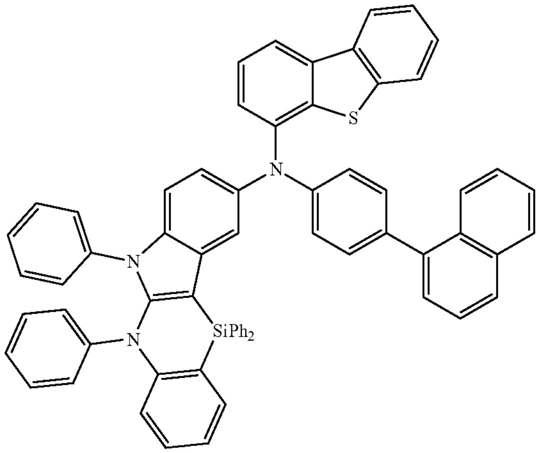

-continued
E32
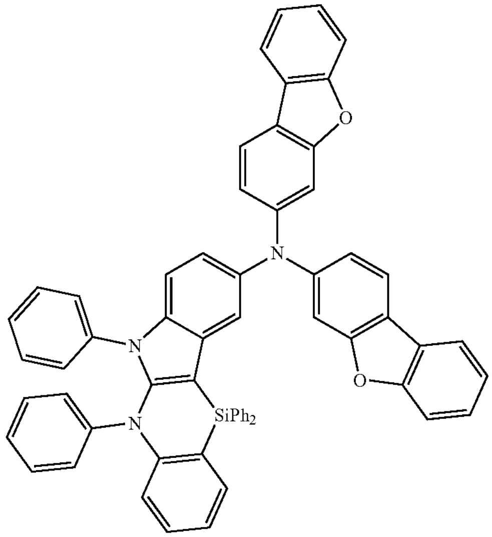
E33
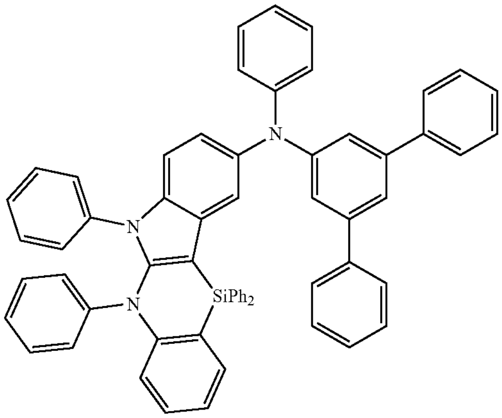
E34
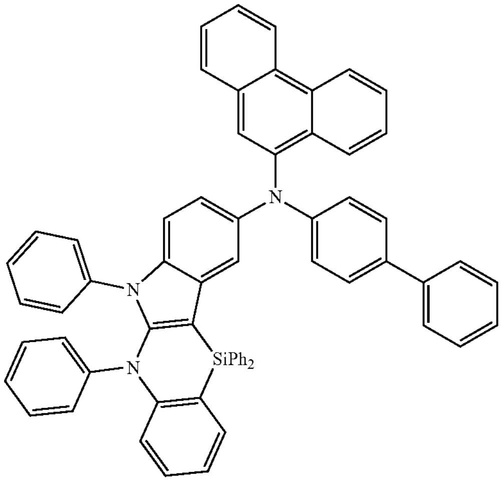
-continued
E35
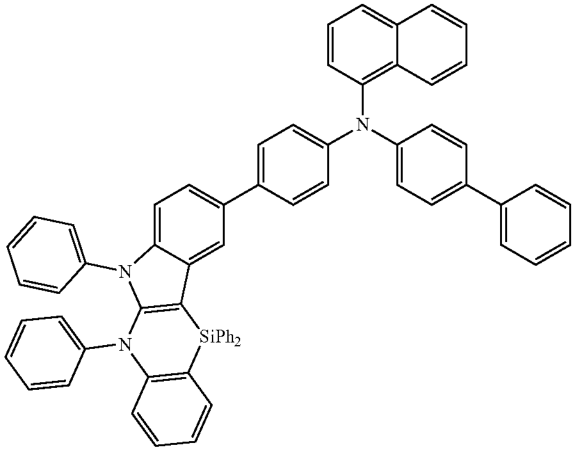
E36
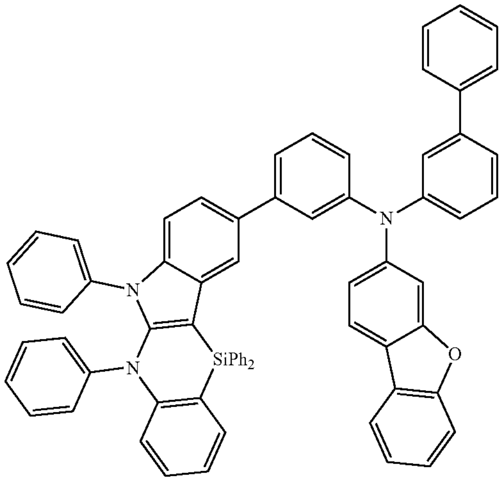
E37
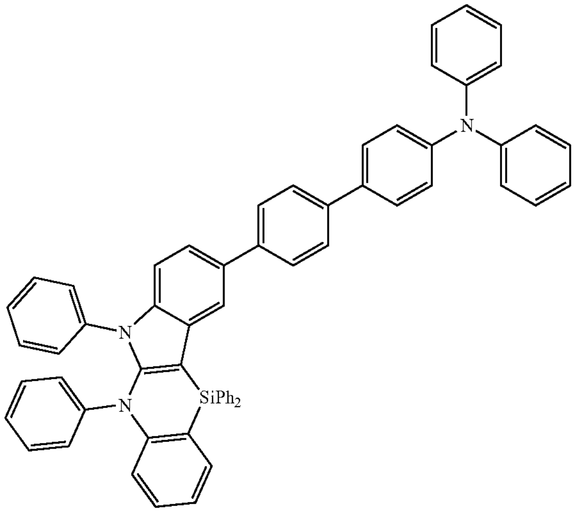

-continued
E38
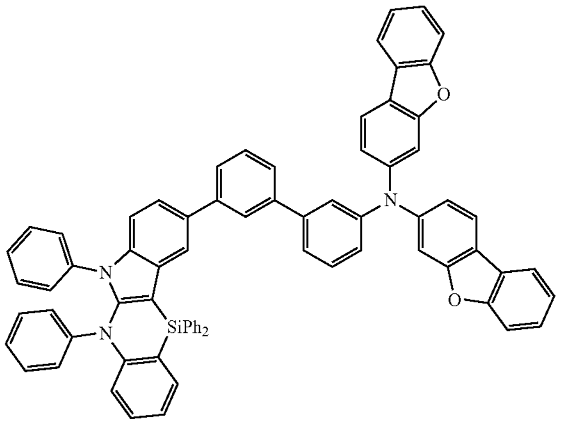
E39
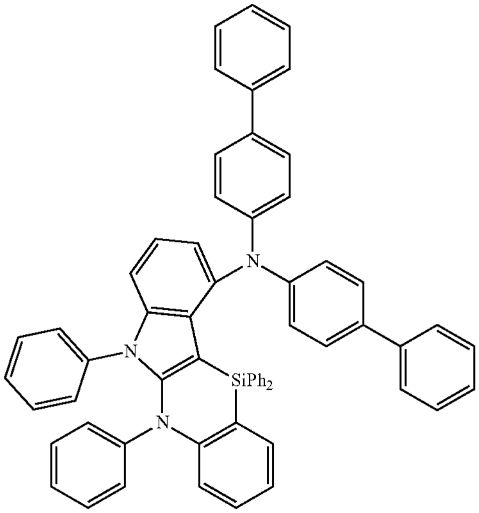
E40
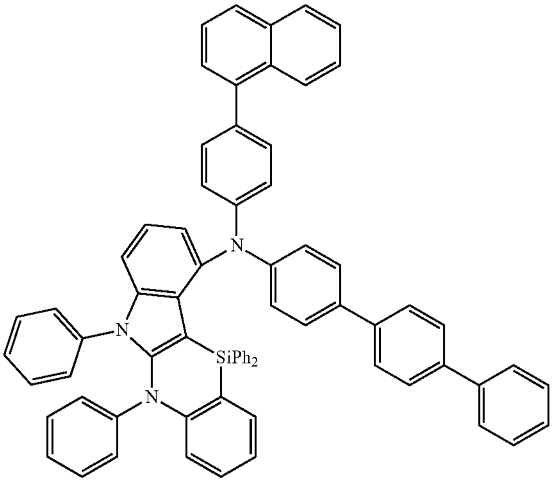
-continued
E41
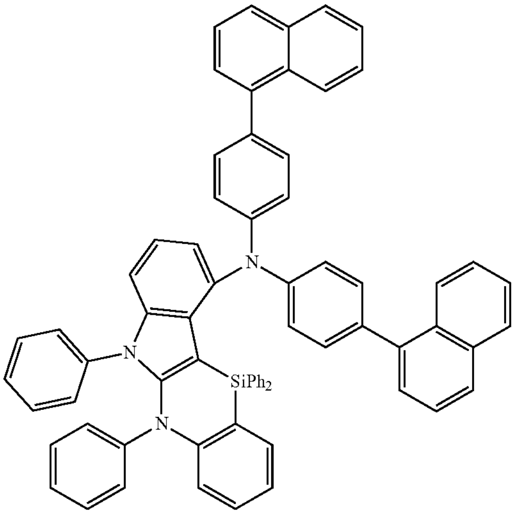
E42
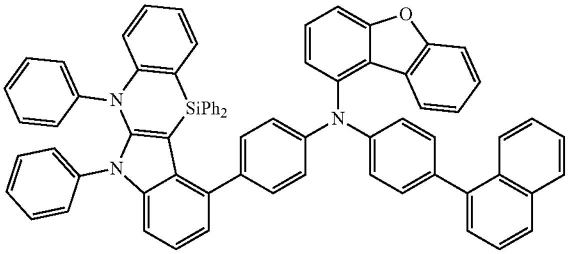
E43
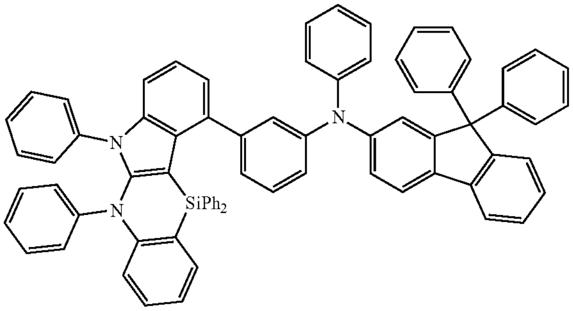
E44
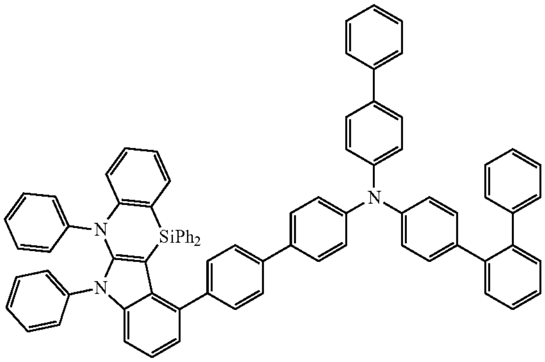

-continued
E45
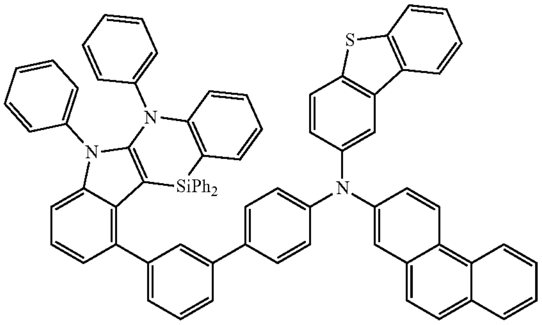
E46
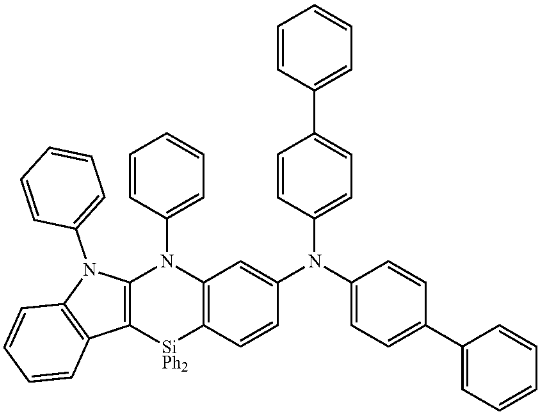
E47
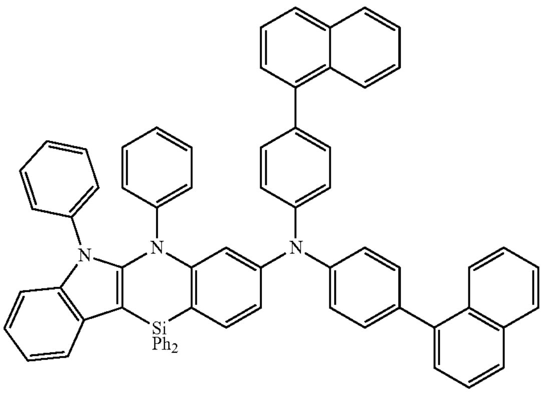
E48
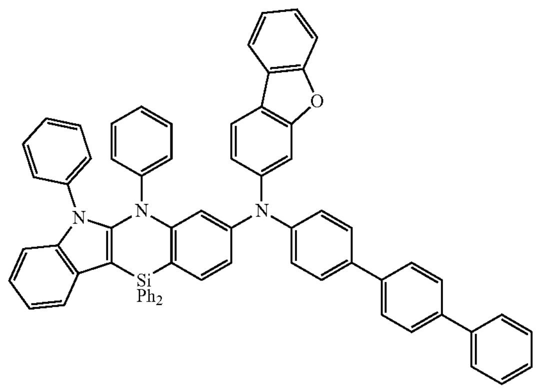
-continued
E49
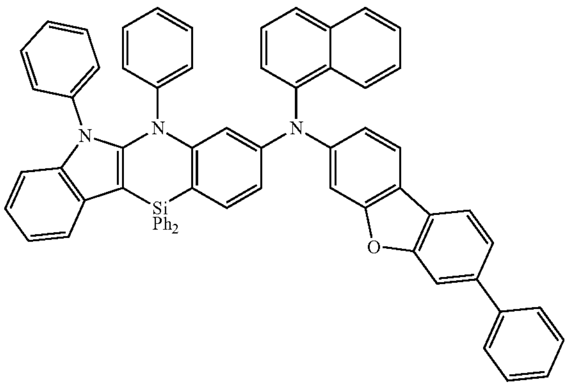
E50
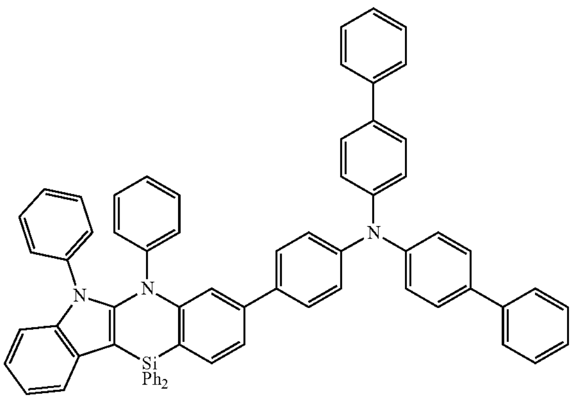
E51
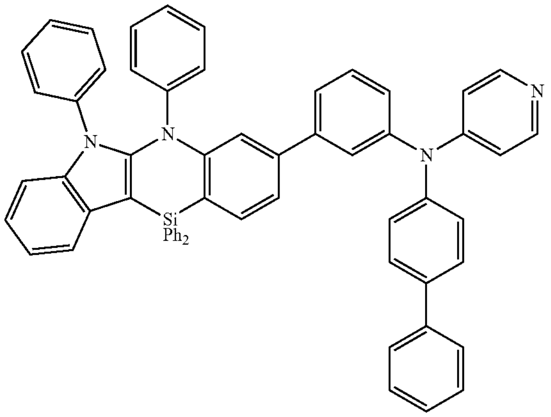
E52
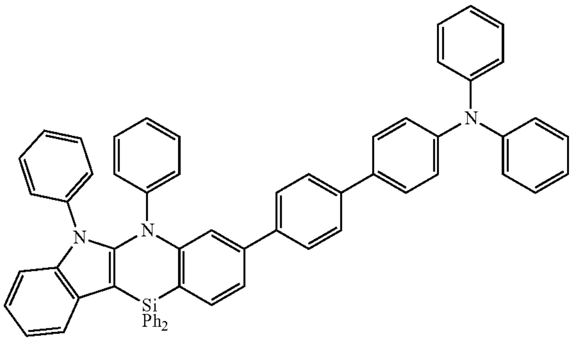

E53
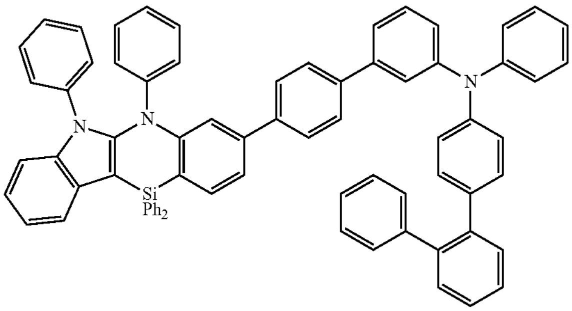
E54
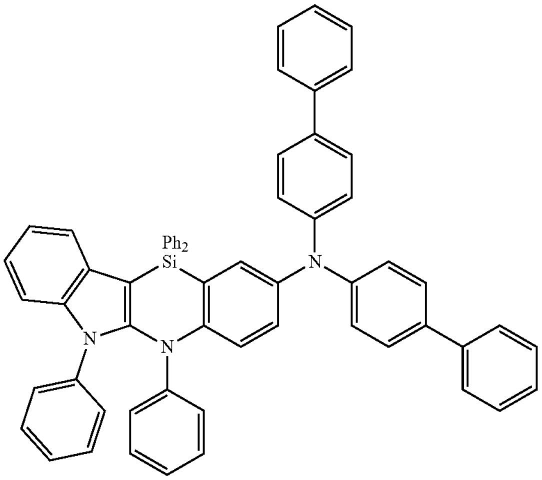
E55
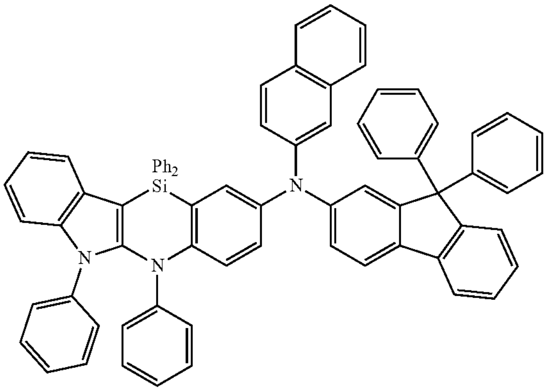
E56
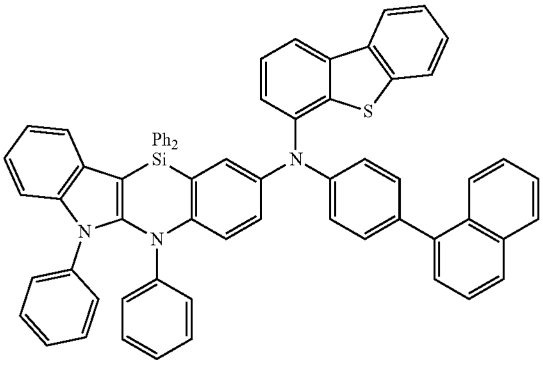
E57
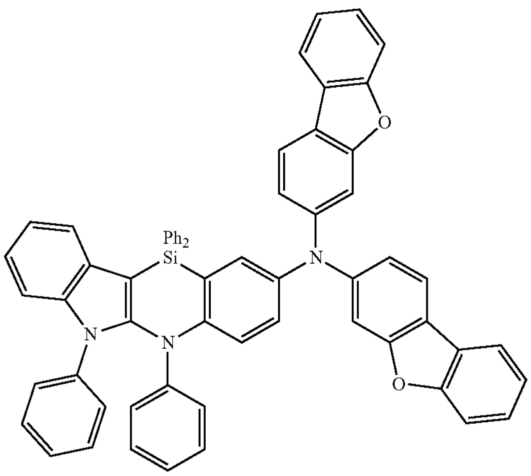
E58
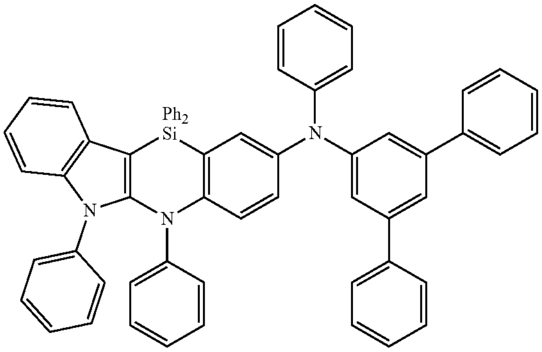
E59
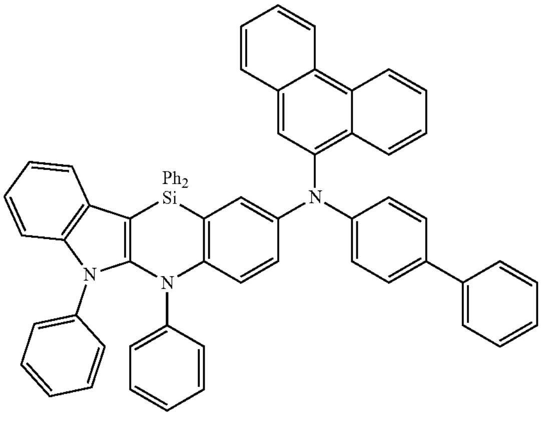

-continued
E60
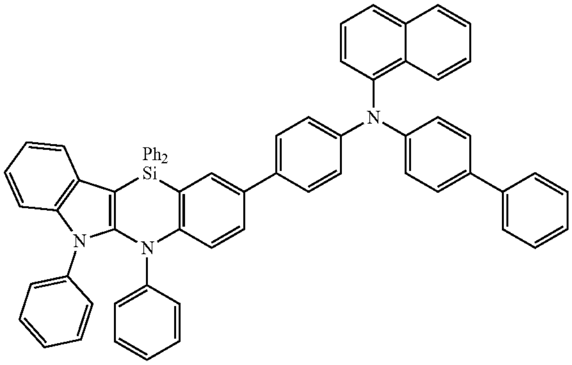
E61
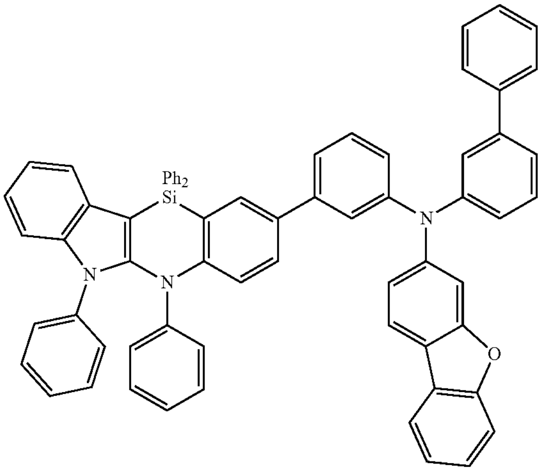
E62
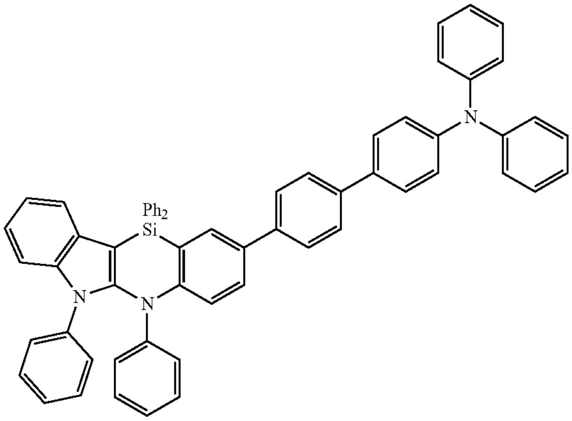
-continued
E63
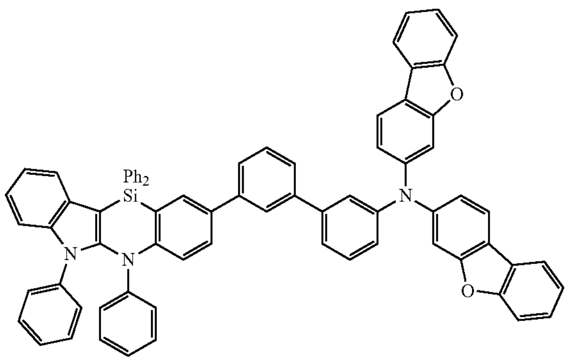
E64
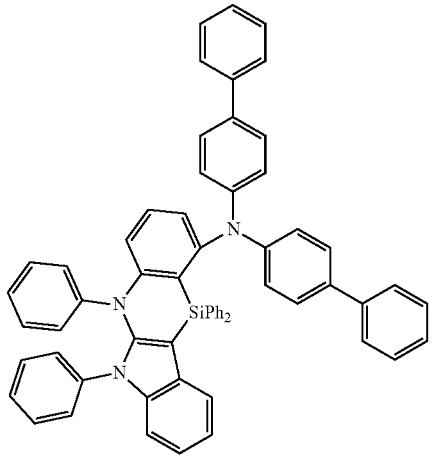
E65
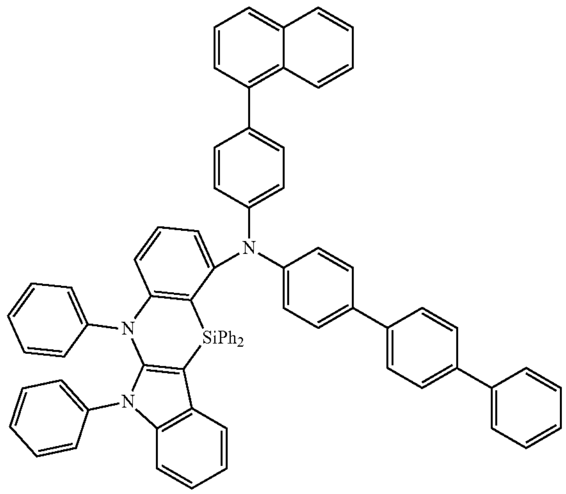

-continued
E66
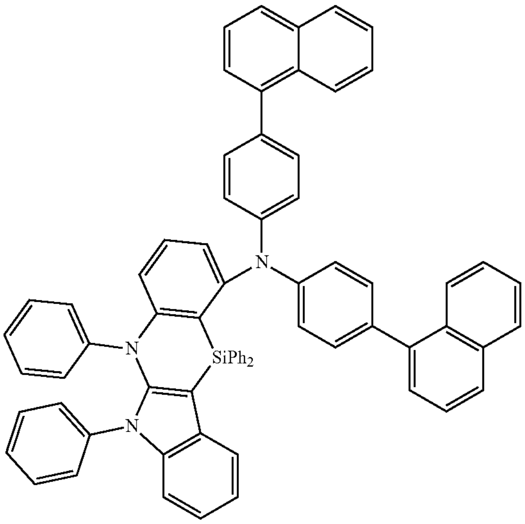
E67
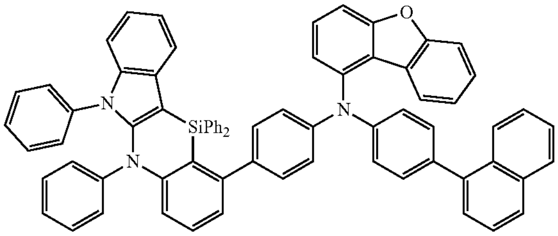
E68
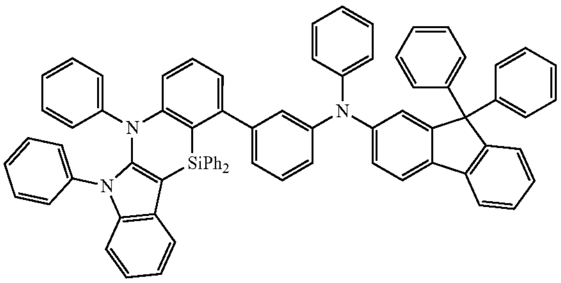
-continued
E69
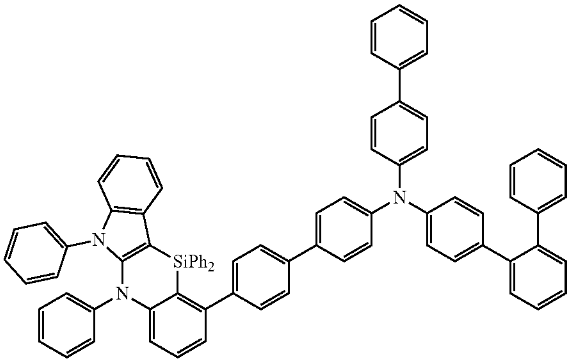
E70
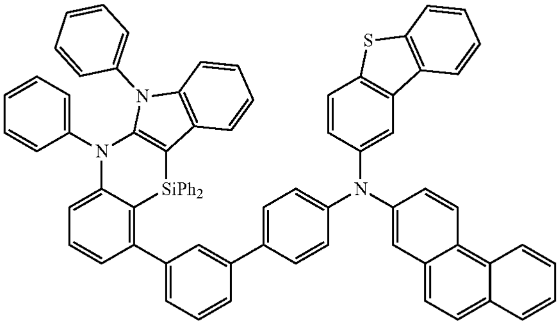
* * * * *

UNITED STATES PATENT AND TRADEMARK OFFICE

CERTIFICATE OF CORRECTION

PATENT NO. : 12,144,251 B2
APPLICATION NO. : 16/443807
DATED : November 12, 2024
INVENTOR(S) : Takuya Uno It is certified that error appears in the above-identified patent and that said Letters Patent is hereby corrected as shown below:

In the Claims

In Column 161, Line 43, in Claim 1, after "is" insert -- a --.

In Column 161, Line 45, in Claim 1, delete "R1 and R2" and insert -- $R_1$ and $R_2$ --.

In Column 161, Line 51, in Claim 1, delete "R5, R6, and R7" and insert -- $R_5$, $R_6$, and $R_7$ --.

In Column 163, Line 65, in Claim 6, delete "quinqphenyl" and insert -- quinquephenyl --.

In Column 255, Line 4, in Claim 14, after "is" delete "independently".

In Column 257, Line 11, in Claim 16, after "Formulae" delete "3-2 and".

Signed and Sealed this
Third Day of June, 2025

Coke Morgan Stewart
*Acting Director of the United States Patent and Trademark Office*

In Column 264, Lines 36-49, in Claim 22, delete
"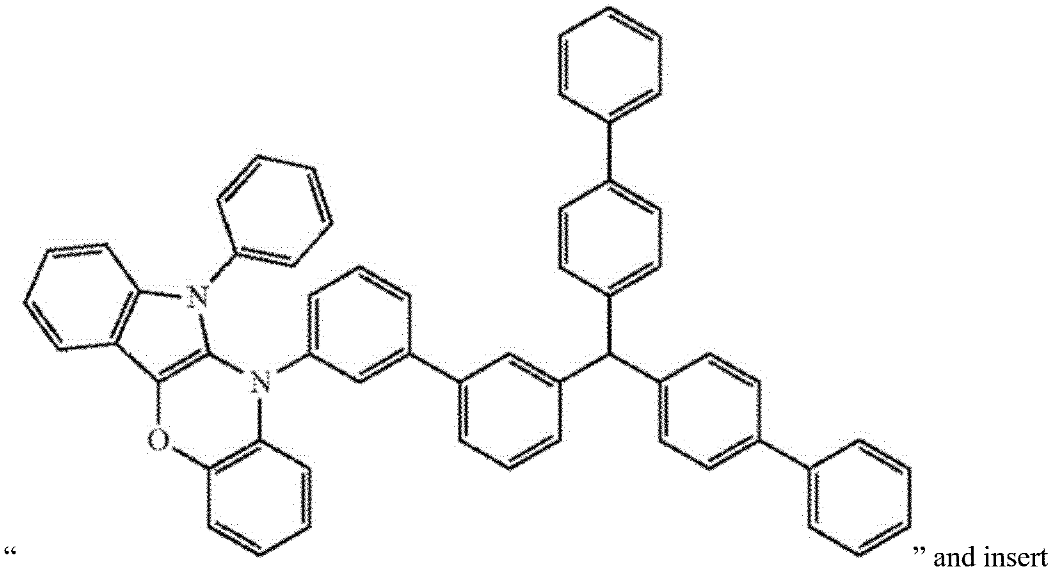" and insert
--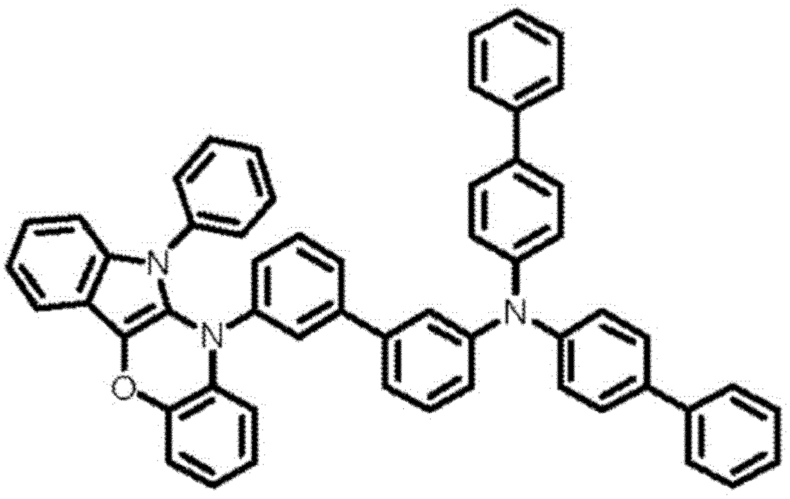--.